(12) United States Patent
Grandi et al.

(10) Patent No.: US 8,481,057 B2
(45) Date of Patent: Jul. 9, 2013

(54) CHLAMYDIAL ANTIGENS

(75) Inventors: Guido Grandi, Milan (IT); Giulio Ratti, Siena (IT); Lehutova Livia, legal representative, Siena (IT)

(73) Assignee: Novartis Vaccines & Diagnostics SRL, Siena (IT)

( * ) Notice: Subject to any disclaimer, the term of this patent is extended or adjusted under 35 U.S.C. 154(b) by 559 days.

(21) Appl. No.: 12/086,571

(22) PCT Filed: Dec. 19, 2006

(86) PCT No.: PCT/IB2006/004121
§ 371 (c)(1),
(2), (4) Date: May 25, 2010

(87) PCT Pub. No.: WO2007/110700
PCT Pub. Date: Oct. 4, 2007

(65) Prior Publication Data
US 2010/0297164 A1   Nov. 25, 2010

Related U.S. Application Data

(60) Provisional application No. 60/753,305, filed on Dec. 22, 2005, provisional application No. 60/795,857, filed on Apr. 28, 2006.

(51) Int. Cl.
*A61K 39/118* (2006.01)
*C07K 14/295* (2006.01)

(52) U.S. Cl.
USPC .............. 424/263.1; 424/192.1; 530/326; 530/350

(58) Field of Classification Search
None
See application file for complete search history.

(56) References Cited

FOREIGN PATENT DOCUMENTS

| WO | WO 00/37494 A | 6/2000 |
|---|---|---|
| WO | WO 02/057784 A | 7/2002 |
| WO | WO 02/095416 A | 11/2002 |
| WO | WO 03/049762 A | 6/2003 |
| WO | WO 2005/002619 A | 1/2005 |

OTHER PUBLICATIONS

Devos et al (Proteins: Structure, Function and Genetics, 2000, vol. 41: 98-107).*
Whisstock et al (Quarterly Reviews of Biophysics 2003, vol. 36 (3): 307-340 ).*
Witkowski et al (Biochemistry 38:11643-11650, 1999).*
Seffernick et al (J. Bacteriol. 183(8): 2405-2410, 2001).*
Clifton, et al., "A Chylamydial Type III Translocated Protein is Tyrosine-Phosphorylated at the Site of Entry and Associated With the Recruitment of Actin," *PNAS USA* 101:10166-10171 (2004).
Dieterle, et al., "Humoral Immune Response to the Chlamydial Heat Shock Proteins HSP60 and HSP 70 in Chylamidia-Associated Chronic Salpingitis With Tubal Occlusion," *Human Reproduction* 11:1352-1356 (1996).
Eko, et al., "A Novel Recombinant Multisubunit Vaccine Against Chlamydia," *Journal of Immunology* 173:3375-3382 (2004).
Finco, et al., "Identification of New Potential Vaccine Candidates Against Chylamdia Pneumoniae by Multiple Screenings," *Vaccine* 23:1178-1188 (2005).
Hessel, et al., "Immune Response to Chylamidial 60-Kilodalton Heat Shock Protein in Tears From Napali Trachoma Patients," *Infection and Immunity* 69:4996-5000 (2001).
Sanchez-Campillo, et al., "Identification of Immunoreactive Proteins of Chlamydia Trachomatis by Western Blot Analysis of a Two-Dimensional Electrophoresis Map With Patient Sera," *Electrophoresis* 20:2269-2279 (1999).
Taylor, et al. , "Chlamydial Heat Shock Proteins and Trachoma," *Infection and Immunity* 58:3061-3063 (1990).

* cited by examiner

*Primary Examiner* — Padma V Baskar
(74) *Attorney, Agent, or Firm* — Roberta L. Robins; Robins Law Group

(57) ABSTRACT

The invention is in the field of immunology and vaccinology. In particular, it relates to antigens derived from *Chlamydia trachomatis* that are expressed on the cell surface and so are ideal for use in immunization as well as combinations of these antigens.

5 Claims, 14 Drawing Sheets

Figure 10

| Antigen | Identified peptide coord - sequence | | PredBALB/c | | | | Rankpep | | | | Proposed peptide for synthesis |
|---|---|---|---|---|---|---|---|---|---|---|---|
| | | | Predicted I-A$^d$ | | Predicted I-E$^d$ | | Predicted I-A$^d$ | | Predicted I-E$^d$ Epitope | | |
| | | | sequence | - | sequence | - | sequence | - | sequence | score | |
| CT823 (htrA) | 475-489 | genvllmvsqgdvvr | NVLLMVSQG | 9.22 | NVLLMVSQG | 5 | | | | | NVLLMVSQG |
| | | | DVVRFIVLK | 3.86 | DVVRFIVLK | 9.9 | | | DVVRFIVLK | 15.6 (top) | DVVRFIVLK or |
| | 365-386 | SGETEDTTIADLAVAFNTGQIK | LSHRSGETE | 6.66 | LSHRSGETE | 9.18 | | | | | LSHRSGETEDTTIADLA VAFNTGQIKTG |
| | | | SGETEDTTI | 5.35 | SGETEDTTI | 0.56 | | | | | QIKTGSL or |
| | | | IADLAVAFN | 9.66 | IADLAVAFN | 4.96 | | | | | LSHRSGETEDTTIADLA VAFNTGQIKTG |
| CT587 (enolase) | | | LAVAFNTGQ | 1.6 | LAVAFNTGQ | 9.46 | | | | | |
| | | | VAFNTGQIK | 5.22 | VAFNTGQIK | 9.26 | | | | | |
| | | | FNTGQIKTG | 1.02 | FNTGQIKTG | 9.28 | | | | | |
| | | | TGQIKTGSL | 9.18 | TGQIKTGSL | 2.62 | | | | | |
| | 402-423 | LMAIEEEMGPEALFQDSNPFSK | YNRLMAIEE | 9.7 | YNRLMAIEE | 5.28 | | | | | RIAKYNRLMAIEE or a more extended one |
| | | | RIAKYNRLM | 0.94 | RIAKYNRLM | 9.9 | | | RIAKYNRLM | 18.75 | |
| | 75-95 | LLEGSMLGGQMAGGGVGVATK | LYEKLLEGS | 2.88 | LYEKLLEGS | 9.16 | | | | | LYEKLLEGSMLGGQMA |
| | | | GSMLGGQMA | 9.5 | GSMLGGQMA | 2.5 | | | | | GGGVGVATK |
| CT043 (hypo) | | | GGGVGVATK | 9.6 | GGGVGVATK | 8.7 | GGVGVATKE | 13 | | | |
| CT153 (hypo) | 23-36 | FSTDSDTYIEEENR | in progress | | in progress | | none | | none | | |

CHLAMYDIAL ANTIGENS

CROSS-REFERENCE TO RELATED APPLICATIONS

This application is a 35 U.S.C. §371 filing of PCT/IB2006/004121, filed Dec. 19, 2006. PCT/IB2006/004121 claims the benefit of U.S. Provisional Patent Application No. 60/753,305, filed Dec. 22, 2005 and U.S. Provisional Patent Application No. 60/795,857, filed Apr. 28, 2006. The disclosures of the aforementioned applications are incorporated by reference in their entireties for all purposes.

All documents cited herein are incorporated by reference in their entirety.

TECHNICAL FIELD

This invention is in the fields of immunology and vaccinology. In particular, it relates to antigens derived from *Chlamydia trachomatis* and their use in immunisation.

BACKGROUND ART

The Chlamydiae are obligate intracellular parasites of eukaryotic cells which are responsible for endemic sexually transmitted infections and various other disease syndromes. They occupy an exclusive eubacterial phylogenic branch, having no close relationship to any other known organisms. A particular characteristic of the Chlamydiae is their unique life cycle, in which the bacterium alternates between two morphologically distinct forms: an extracellular infective form (elementary bodies, EB) and an intracellular non-infective form (reticulate bodies, RB). The life cycle is completed with the re-organization of RB into EB, which leave the disrupted host cell ready to infect further cells.

The genome sequences of at least five *Chlamydia trachomatis* or *chlamydophila* species are currently known—*C. trachomatis, C. pneumoniae, C. muridarum, C. pecorum* and *C. psittaci* [1, 7]. The various *C. trachomatis* strains, of which there are currently at least 18 serovariants (serovars), may be classified according to their serological reactivities with polyclonal or monoclonal antisera. These serological differences are typically detected due to differences in the MOMP (Major Outer Membrane Protein) of *C. trachomatis*.

Although *Chlamydia* infection itself causes disease, it is thought that the severity of symptoms in some patients is actually due to an aberrant or an altered host immune response which may arise from either (i) the nature of the invading *Chlamydia* organism which may vary from serovar to serovar or (ii) the nature of the subject invaded (for example, the nature of the patient profile). The failure to clear the infection results in persistent immune stimulation and, rather than helping the host, this results in chronic infection with severe consequences, including sterility and blindness [8]. In addition, the protection conferred by natural *Chlamydial* infection is usually incomplete, transient, and strain-specific.

Unfortunately the major determinants of *Chlamydia* pathogenesis are complicated and at present still unclear, mostly due to the intrinsic difficulty in working with this pathogen and the lack of adequate methods for its genetic manipulation. In particular very little is known about the antigenic composition of elementary body surface, that is an essential compartment in pathogen-host interactions, and likely to carry antigens able to elicit a protective immune response.

Due to the serious nature of the disease, there is a desire to provide suitable immunogenic compositions, such as vaccines to deal with an aberrant or altered host cell immune response which may result from, for example, allelic variation in the invading *Chlamydia* strain and/or aberrant or altered forms of *Chlamydia* invading strain. These immunogenic compositions may be useful (a) for immunisation against *Chlamydial* infection or against *Chlamydia*-induced disease (prophylactic vaccination) or (b) for the eradication of an established chronic *Chlamydia* infection (therapeutic vaccination). Being an intracellular parasite, however, the bacterium can generally evade antibody-mediated immune responses.

Various antigenic proteins have been described for *C. trachomatis*, and the cell surface in particular has been the target of detailed research [9]. These include, for instance, Pgp3 [10, 11, and 12], MOMP [13], Hsp60 (GroEL) [14] and Hsp70 (DnaK-like) [15]. Not all of these have proved to be effective vaccines, however, and further candidates have been identified [16]. Compositions comprising combinations of *C. trachomatis* antigens are described in reference 17.

Vaccines against pathogens such as hepatitis B virus, diphtheria and tetanus typically contain a single protein antigen (e.g. the HBV surface antigen, or a tetanus toxoid). In contrast, acellular whooping cough vaccines typically have at least three *B. pertussis* proteins, and the Prevnar™ pneumococcal vaccine contains seven separate conjugated saccharide antigens. Other vaccines such as cellular *pertussis* vaccines, the measles vaccine, the inactivated polio vaccine (IPV) and meningococcal OMV vaccines are by their very nature complex mixtures of a large number of antigens. Whether protection can be elicited by a single antigen, a small number of defined antigens, or a complex mixture of undefined antigens, therefore depends on the pathogen in question.

It is an object of the invention to provide further and improved immunogenic compositions for providing immunity against *Chlamydial* disease and/or infection. In particular, it is an object of the invention to provide improved immunogenic compositions for providing immunity against aberrant or altered *Chlamydia* serovar strains (e.g. strains such as allelic variant strains).

It is an object of the invention to provide further and improved compositions for providing immunity against *chlamydial* disease and/or infection. The compositions are based on a newly discovered, surface-exposed *C. trachomatis* antigens.

DISCLOSURE OF THE INVENTION

Within the ~900 proteins described for the *C. trachomatis* genome of reference 4, the applicant has discovered a group of twenty *Chlamydia trachomatis* surface-exposed antigens, surface-associated antigens and fragments thereof that are particularly suitable for immunisation purposes, particularly when used in combinations. These antigens which are exposed on the surface of *Chlamydia trachomatis* have been identified using "surface shaving" techniques. Until now, surface proteins of *Chlamydia trachomatis* have been detected by indirect methods [18], but here we describe the use of a method which identifies one or more surface-exposed and/or surface associated antigens from the surface of a *Chlamydia* Elementary Body (EB) and fragments of these antigens. The invention therefore provides a composition comprising a combination of *Chlamydia trachomatis* antigens, said combination consisting of two or more (i.e. 2, 3, 4, 5, 6, 7, 8, 9, 10, 11, 12, 13, 14, 15, 16, 17, 18, 19 or all 20) *Chlamydia trachomatis* antigens of a first antigen group, said first antigen group consisting of: (1) a GroEL-1 antigen, (2) a DnaK antigen, (3) an Ef-Tu antigen, (4) a Mip-like protein antigen, (5) a Major outer membrane protein (MOMP) antigen, (6) a HctA antigen, (7) a CT577 antigen, (8) a CT223 antigen, (9) a GroeS antigen, (10) a Tarp antigen, (11) a Rs10 antigen, (12) an OmpH-like protein antigen, (13) a Rs13 antigen, (14) a R11 antigen, (15) a CT875 antigen, (16) a HtrA antigen, (17) a RpoA antigen, (18) a PepA antigen, (19) an Alanyl tRNA synthetase antigen, (20) a RpoC antigen, (21) a YaeL antigen, (22) an EF-G antigen, (23) a CT578 antigen, (24) a CT579 antigen, (25) a CT680 antigen and (26) a CT814 antigen. These antigens are referred to herein as the 'first antigen group'.

A preferred subgroup of the first antigen group consists of: (1) a GroEL-1 antigen, (2) a DnaK antigen, (3) an Ef-Tu antigen, (4) a Mip-like protein antigen, (5) a Major outer membrane protein (MOMP) antigen, (6) a HctA antigen, (7) a CT577 antigen, (8) a CT223 antigen, (9) a GroeS antigen, (10) a Tarp antigen, (11) a Rs10 antigen, (12) an OmpH-like protein antigen, (13) a Rs13 antigen, (14) a R11 antigen, (15) a CT875 antigen, (16) a HtrA antigen, (17) a RpoA antigen, (18) a PepA antigen, (19) an Alanyl tRNA synthetase antigen and (20) a RpoC antigen.

A further preferred subgroup of the first antigen group consists of: (1) a GroEL-1 antigen, (3) an Ef-Tu antigen, (6) a HctA antigen, (7) a CT577 antigen, (8) a CT223 antigen, (9) a GroeS antigen, (11) a Rs10 antigen, (13) a Rs13 antigen, (14) a R11 antigen, (15) a CT875 antigen, (17) a RpoA antigen, (19) an Alanyl tRNA synthetase antigen and (20) a RpoC antigen.

A further preferred subgroup of the first antigen group consists of (1) a GroEL-1 antigen, (3) an Ef-Tu antigen, (6) a HctA antigen, (7) a CT577 antigen, (8) a CT223 antigen, (9) a GroeS antigen, (11) a Rs10 antigen, (13) a Rs13 antigen, (14) a R11 antigen, (15) a CT875 antigen, (17) a RpoA antigen, (19) an Alanyl tRNA synthetase antigen, (20) a RpoC antigen, (21) a YaeL antigen, (22) an EF-G antigen, (23) a CT578 antigen, (24) a CT579 antigen, (25) a CT680 antigen and (26) a CT814 antigen.

A further preferred subgroup consists of (7) a CT577 antigen, (8) a CT223 antigen, (15) a CT875 antigen, (9) a GroeS antigen and (13) a Rs13 antigen.

A further preferred subgroup of the first antigen group consists of (21) a YaeL antigen, (22) an EF-G antigen, (23) a CT578 antigen, (24) a CT579 antigen, (25) a CT680 antigen and (26) a CT814 antigen.

Reference to the 'first antigen group' herein includes reference to the first antigen group itself as well as the preferred subgroups.

The efficacy of a composition of *Chlamydia trachomatis* antigens may be improved by combination with one or more *Chlamydia trachomatis* antigens from the first antigen group. Such other known *Chlamydia trachomatis* antigens include a second antigen group consisting of: (1) a LcrE antigen; (2) an ArtJ antigen; and (3) a CT398 antigen. These antigens are referred to herein as the 'second antigen group'.

The invention thus includes a composition comprising a combination of *Chlamydia trachomatis* antigens, said combination selected from the group consisting of one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Chlamydia trachomatis* antigens of the first antigen group and one, two or three *Chlamydia trachomatis* antigens of the second antigen group.

The efficacy of a composition of *Chlamydia trachomatis* antigens may be improved by combination with one or more *Chlamydia trachomatis* antigens from the first antigen group. Such other known *Chlamydia trachomatis* antigens include a third antigen group consisting of: (1) a L7/L12 antigen; (2) an OmcA antigen; (3) an AtoS antigen; (4) a CT547 antigen; (5) an Eno antigen; and (6) a MurG antigen. These antigens are referred to herein as the 'third antigen group'.

The invention thus includes a composition comprising a combination of *Chlamydia trachomatis* antigens, said combination selected from the group consisting of one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Chlamydia trachomatis* antigens of the first antigen group and one, two, three, four, five or six *Chlamydia trachomatis* antigens of the third antigen group.

The efficacy of a composition of *Chlamydia trachomatis* antigens may be improved by combination with one or more *Chlamydia trachomatis* antigens from the first antigen group. Such other known *Chlamydia trachomatis* antigens include a fourth antigen group consisting of: (1) a PGP3 antigen, (2) one or more PMP antigens, (3) a Cap1 antigen (CT529); (4) a GroEL-like hsp60 protein (Omp2) antigen; and (5) a 60 kDa Cysteine rich protein (omcB) antigen. These antigens are referred to herein as the 'fourth antigen group'.

The invention thus includes a composition comprising a combination of *Chlamydia trachomatis* antigens, said combination selected from the group consisting of one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Chlamydia trachomatis* antigens of the first antigen group and one, two, three, four or five *Chlamydia trachomatis* antigens of the fourth antigen group.

The efficacy of a composition of *Chlamydia trachomatis* antigens of known and unknown biological function may be improved by combination with one or more *Chlamydia trachomatis* antigens from the first antigen group. Such other *Chlamydia trachomatis* antigens of known and unknown biological function include a fifth antigen group consisting of: (1) a YscJ antigen; (2) a Pal antigen; (3) a CHLPN 76 kDA homologue antigen; (4) a CT700 antigen; (5) a CT266 antigen; (6) a CT077 antigen; (7) a CT165 antigen and (8) a PorB antigen. These antigens are referred to as the "fifth antigen group".

The invention thus includes a composition comprising a combination of *Chlamydia trachomatis* antigens, said combination selected from the group consisting of one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Chlamydia trachomatis* antigens of the first antigen group and one, two, three, four, five, six, seven or eight *Chlamydia trachomatis* antigens of the fifth antigen group.

The efficacy of a composition of *Chlamydia trachomatis* antigens of known and unknown biological function may be improved by combination with one or more *Chlamydia trachomatis* antigens from the first antigen group. Such other *Chlamydia trachomatis* antigens of known and unknown biological function include a sixth antigen group consisting of: (1) a CT082 antigen; (2) a CT181 antigen; (3) a CT050 antigen; (4) a Phospholipase D superfamily antigen; and (5) an AdK adenylate cyclase antigen. These antigens are referred to as the "sixth antigen group".

The invention thus includes a composition comprising a combination of *Chlamydia trachomatis* antigens, said combination selected from the group consisting of one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Chlamydia trachomatis* antigens of the first antigen group and one, two, three, four or five *Chlamydia trachomatis* antigens of the sixth antigen group.

The efficacy of a composition of *Chlamydia trachomatis* antigens of known and unknown biological function may be improved by combination with one or more *Chlamydia trachomatis* antigens from the first antigen group. Such other *Chlamydia trachomatis* antigens of known and unknown biological function include a seventh antigen group consisting of (1) a CT153 antigen; (2) a CT262 antigen; (3) a CT276 antigen; (4) a CT296 antigen; (5) a CT372 antigen; (6) a PmpA antigen; (7) an OligoPeptide Binding Protein antigen; (8) a CT548 antigen; (9) a CT043 antigen; (10) a CT635 antigen; (11) a CT859 (Metalloprotease) antigen; (12) a CT671 antigen; (13) a CT016 antigen; (14) a CT017 antigen; (15) a PmpD antigen and (16) a PmpE antigen. These antigens are referred to as the "seventh antigen group". The invention thus includes a composition comprising a combination of *Chlamydia trachomatis* antigens, said combination selected from the group consisting of one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Chlamydia trachomatis* antigens of the first antigen group and of one or more (i.e. 1, 2, 3, 4, 5, 6, 7, 8, 9, 10, 11, 12, 13, 14, 15, or all 16) *Chlamydia trachomatis* antigens of the seventh antigen group.

The efficacy of a composition of *Chlamydia trachomatis* antigens of known and unknown biological function may be improved by combination with one or more *Chlamydia trachomatis* antigens from the first antigen group. Such other *Chlamydia trachomatis* antigens of known and unknown biological function include a eighth antigen group consisting of (1) a GatA antigen, (2) a GatB antigen, (3) a CT005 antigen, (4) a CT042 antigen, (5) a sucB1 antigen, (6) a CT113 antigen, (7) an Rs9 antigen, (8) a DhnA antigen, (9) an AcpP antigen, (10) a HimD antigen, (11) a Tal antigen, (12) a DksA antigen, (13) a CT425 antigen, (14) a Ym74 antigen, (15) a Rl15 antigen, (16) a Rs5 antigen, (17) a Rl6 antigen, (18) a Rl24 antigen, (19) a Rl22 antigen, (20) a Rl2 antigen, (21) a Rl4 antigen, (22) a LerH1 antigen, (23) an AhpC antigen, (24) a CT610 antigen, (25) a CT622 antigen, (26) a CT664 antigen, (27) a FliN antigen, (28) a PyrH antigen, (29) a CT741 antigen, (30) a Efp2 antigen, (31) a CT768 antigen, (32) a CT771 antigen, (33) a Ldh antigen, (34) a Rl35 antigen, (35) a FtsH antigen and (36) a Pnp antigen. These antigens are referred to as the "eighth antigen group".

The invention thus includes a composition comprising a combination of *Chlamydia trachomatis* antigens, said combination selected from the group consisting of one or more (i.e. 1, 2, 3, 4, 5, 6, 7, 8, 9, 10, 11, 12, 13, 14, 15, 16, 17, 18, 19, 20, 21, 22, 23, 24, 25 or all 26) *Chlamydia trachomatis* antigens of the first antigen group and of one or more (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or all 36) *Chlamydia trachomatis* antigens of the eighth antigen group.

The invention includes a composition comprising a combination of *Chlamydia trachomatis* antigens, said combination selected from the group consisting of one or more (i.e. 1, 2, 3, 4, 5, 6, 7, 8, 9, 10, 11, 12, 13, 14, 15, 16, 17, 18, 19, 20, 21, 22, 23, 24, 25 or all 26) antigens of the first antigen group and "A" antigens from the second antigen group, "B" antigens from the third antigen group, "C" antigens from the fourth antigen group, "D" antigens from the fifth antigen group, "E" antigens from the sixth antigen group and "F" antigens from the seventh antigen group, wherein
A=0-3, B=0-6, C=0-5, D=0-8, E=0-5 and F=0-16, and A+B+C+D+E+F>1 (i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 or 43).

Such a composition may optionally comprise "G" antigens from the eighth antigen group, wherein G=0-36, and A+B+C+D+E+F+G>1 (i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78 or 79).

Thus the compositions comprise at least one antigen from the first antigen group and at least one antigen from any one or more of the second to seventh groups. The compositions may comprise more than one antigen from a given group or no antigens from one or more of the second to seventh groups. However, where the composition only contains a single antigen from the first group, it must also contain at least one antigen from one or more of the second to seventh, or eighth groups. Preferably, the compositions comprise two, three, four or five *Chlamydia trachomatis* antigens of the first antigen group. Still more preferably, the composition comprises of five *Chlamydia trachomatis* antigens of the first antigen group. Preferably, the composition consists of five *Chlamydia trachomatis* antigens of the first antigen group.

There is an upper limit to the number of *Chlamydia trachomatis* antigens which will be in the compositions of the invention. Preferably, the number of *Chlamydia trachomatis* antigens in a composition of the invention is less than 20, less than 19, less than 18, less than 17, less than 16, less than 15, less than 14, less than 13, less than 12, less than 11, less than 10, less than 9, less than 8, less than 7, less than 6, less than 5, less than 4, or less than 3. Still more preferably, the number of *Chlamydia trachomatis* antigens in a composition of the invention is less than 6, less than 5, or less than 4. The *Chlamydia trachomatis* antigens used in the invention are preferably isolated, i.e., separate and discrete, from the whole organism with which the molecule is found in nature or, when the polynucleotide or polypeptide is not found in nature, is sufficiently free of other biological macromolecules so that the polynucleotide or polypeptide can be used for its intended purpose.

First Antigen Group (1) GroEL-1 One example of "GroEL-1" is disclosed as CT110 in reference 19 (GenBank accession number: AAC67701, GenInfo Identifier: 3328508; Hsp-60; SEQ ID NO: 1 herein). GroEL is a chaparone of the Hsp-60 class, known as chaperonins. GroEL is able to catalyse the unfolding of small proteins.

Preferred GroEL proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 1; and/or (b) which is a fragment of at least n consecutive amino acids of SEQ ID NO: 1, wherein n is 7 or more (e.g. 8, 10, 12, 14, 16, 18, 20, 25, 30, 35, 40, 50, 60, 70, 80, 90, 100, 150, 200, 250 or more). These GroEL-1 proteins include variants (e.g. allelic variants, homologs, orthologs, paralogs, mutants, etc.) of SEQ ID NO: 1. Preferred fragments of (b) comprise an epitope from SEQ ID NO: 1. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 1. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 2-8 and 130-136, which consist of amino acids 85-105, 182-197, 287-308, 309-319, 328-339, 381-390, 485-500, 59-75, 106-117, 143-168, 172-181, 352-362, 463-474 and 475-484 of CT110 respectively.

(2) DnaK One example of a DnaK protein is disclosed as SEQ ID NOs: 107 & 108 in reference 16 (GenBank accession number: AAC67993, GenInfo Identifier:3328822; CT396; Hsp-70; SEQ ID NO: 9 herein). Other DnaK sequences are disclosed in references 20, 21 and 22.

Preferred DnaK proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9; and/or (b) which is a fragment of at least n consecutive amino acids of SEQ ID NO: 9, wherein n is 7 or more (e.g. 8, 10, 12, 14, 16, 18, 20, 25, 30, 35, 40, 50, 60, 70, 80, 90, 100, 150, 200, 250 or more). These DnaK proteins include variants (e.g. allelic variants, homologs, orthologs, paralogs, mutants, etc.) of SEQ ID NO: 9. Preferred fragments of (b) comprise an epitope from SEQ ID NO: 9. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 9. Other fragments omit one or more domains of the protein (e.g. omission of a signal peptide, of a cytoplasmic domain, of a transmembrane domain, or of an extracellular domain). The DnaK may be phosphorylated e.g. at a threonine or a tyrosine. Particularly preferred fragments are those recited in SEQ ID NOs: 10-13 and 149-151, which consist of amino acids 112-125, 269-292, 327-343, 362-385, 81-90, 82-90 and 171-186 of DnaK respectively.

(3) Ef-Tu One example of a "Ef-Tu" protein is disclosed as CT322 in reference 19 (Genbank accession number AAC67915, GenInfo Identifier:3328740; SEQ ID NO: 14 in the attached sequence listing). It is an elongation factor protein that assists aa-tRNAs during protein synthesis.

Preferred Ef-Tu proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 14; and/or (b) which is a fragment of at least n consecutive amino acids of SEQ ID NO: 14, wherein n is 7 or more (e.g. 8, 10, 12, 14, 16, 18, 20, 25, 30, 35, 40, 50, 60, 70, 80, 90, 100, 150, 200, 250 or more). These Ef-Tu proteins include variants (e.g. allelic variants, homologs, orthologs, paralogs, mutants, etc.) of SEQ ID NO: 14. Preferred fragments of (b) comprise an epitope from SEQ ID NO: 14. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 14. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 15, 16 and 143-148, which consist of amino acids 178-188, 191-205, 46-57, 60-75, 137-162, 206-224, 253-263 and 271-280 of CT322 respectively.

(4) Mip-like One example of a "Mip-like" protein is disclosed as SEQ ID NOs: 149 & 150 in reference 16 (GenBank accession number: AAC68143, GenInfo Identifier:3328979; CT541; SEQ ID NO: 17 herein).

Preferred Mip-like proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 17; and/or (b) which is a fragment of at least n consecutive amino acids of SEQ ID NO: 17, wherein n is 7 or more (e.g. 8, 10, 12, 14, 16, 18, 20, 25, 30, 35, 40, 50, 60, 70, 80, 90, 100, 150, 200, 250 or more). These Mip proteins include variants (e.g. allelic variants, homologs, orthologs, paralogs, mutants, etc.) of SEQ ID NO: 17. Preferred fragments of (b) comprise an epitope from SEQ ID NO: 17. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 17. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 18, 19 and 160, which consist of amino acids 34-46, 62-74 and 75-94 of CT541 respectively.

(5) Major Outer Membrane Protein—MOMP One example of a MOMP sequence is disclosed as SEQ ID Nos: 155 and 156 in reference 16 (GenBank accession number AAC68276, GenInfo Identifier:3329133; CT681; SEQ ID NO: 20 herein). This protein is thought to function in vivo as a porin [23], and to be present during the whole life cycle of the bacteria [24]. MOMP displays four variable domains (VD) surrounded by five constant regions that are highly conserved among serovars [25, 26]. In vitro and in vivo neutralizing B-cell epitopes have been mapped on VDs [27-31]. T-cell epitopes have been identified in both variable and constant domains [32, 33].

Preferred MOMP proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 20; and/or (b) which is a fragment of at least n consecutive amino acids of SEQ ID NO: 20, wherein n is 7 or more (e.g. 8, 10, 12, 14, 16, 18, 20, 25, 30, 35, 40, 50, 60, 70, 80, 90, 100, 150, 200, 250 or more). These MOMP proteins include variants (e.g. allelic variants, homologs, orthologs, paralogs, mutants, etc.) of SEQ ID NO: 20. Preferred fragments of (b) comprise an epitope from SEQ ID NO: 20, preferably one or more of the B cell or T cell epitopes identified above. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 20. Other fragments omit one or more domains of the protein (e.g. omission of a signal peptide, of a cytoplasmic domain, of a transmembrane domain, or of an extracellular domain). Other preferred fragments include one or more of the conserved constant regions identified above. A particularly preferred fragment is that recited in SEQ ID NO: 21, which consists of amino acids 309-330 of CT681.

(6) HctA One example of a Histone-like developmental protein is disclosed in reference 4 (GenBank accession number AAC68338, Geninfo Identifier:3329202; CT743; SEQ ID NO: 22 herein).

Preferred HctA proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 22; and/or (b) which is a fragment of at least n consecutive amino acids of SEQ ID NO: 22, wherein n is 7 or more (e.g. 8, 10, 12, 14, 16, 18, 20, 25, 30, 35, 40, 50, 60, 70, 80, 90, 100, 150, 200, 250 or more). These HctA proteins include variants (e.g. allelic variants, homologs, orthologs, paralogs, mutants, etc.) of SEQ ID NO: 22. Preferred fragments of (b) comprise an epitope from SEQ ID NO: 22. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 22. Other fragments omit one or more domains of the protein (e.g. omission of a signal peptide, of a cytoplasmic domain, of a transmembrane domain, or of an extracellular domain). A particularly preferred fragment is that recited in SEQ ID NO: 23, which consists of amino acids 10-23 of CT743.

(7) CT577 CT577 protein is disclosed in reference 7 (GenBank accession number AAC68179, GenInfo Identifier: 3329019; SEQ ID NO: 24 herein). A biological function for CT577 has not previously been described. However, it is postulated that CT577 forms part of a Type Three Secretion System (TTSS).

Preferred CT577 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 24; and/or (b) which is a fragment of at least n consecutive amino acids of SEQ ID NO: 24, wherein n is 7 or more (e.g. 8, 10, 12, 14, 16, 18, 20, 25, 30, 35, 40, 50, 60, 70, 80, 90, 100, 150, 200, 250 or more). These CT577 proteins include variants (e.g. allelic variants, homologs, orthologs, paralogs, mutants, etc.) of SEQ ID NO: 24. Preferred fragments of (b) comprise an epitope from SEQ ID NO: 24. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 24. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 25 and 163, which consist of amino acids 63-81 and 89-105 of CT577 respectively.

(8) CT223 CT223 protein is disclosed in reference 7 (GenBank accession number AAC67815, GenInfo:3328632; SEQ ID NO: 26 herein). A biological function for CT223 has not previously been described.

Preferred CT223 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 26; and/or (b) which is a fragment of at least n consecutive amino acids of SEQ ID NO: 26, wherein n is 7 or more (e.g. 8, 10, 12, 14, 16, 18, 20, 25, 30, 35, 40, 50, 60, 70, 80, 90, 100, 150, 200, 250 or more). These CT223 proteins include variants (e.g. allelic variants, homologs, orthologs, paralogs, mutants, etc.) of SEQ ID NO: 26. Preferred fragments of (b) comprise an epitope from SEQ ID NO: 26. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 26. Other fragments omit one or more domains of the protein (e.g. omission of a signal peptide, of a cytoplasmic domain, of a transmembrane domain, or of an extracellular domain). A particularly preferred fragment is that recited in SEQ ID NO: 27, which consists of amino acids 113-124 of CT223.

(9) GroES One example of a GroES chaperonin protein is disclosed in reference 4 (GenBank accession number AAC67702, GenInfo Identifier:3328509; CT111; SEQ ID NO: 28 herein).

Preferred GroES proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 28; and/or (b) which is a fragment of at least n consecutive amino acids of SEQ ID NO: 28, wherein n is 7 or more (e.g. 8, 10, 12, 14, 16, 18, 20, 25, 30, 35, 40, 50, 60, 70, 80, 90, 100, 150, 200, 250 or more). These CT111 proteins include variants (e.g. allelic variants, homologs, orthologs, paralogs, mutants, etc.) of SEQ ID NO: 28. Preferred fragments of (b) comprise an epitope from SEQ ID NO: 28. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 28. Other fragments omit one or more domains of the protein (e.g. omission of a signal peptide, of a cytoplasmic domain, of a transmembrane domain, or of an extracellular domain). A particularly preferred fragment is that recited in SEQ ID NO: 29, which consists of amino acids 59-76 of CT111.

(10) Tarp One example of a Tarp protein is disclosed as SEQ ID NOs: 255 & 256 in [16] (GenBank accession number AAC68056, GenInfo Identifier:3328889; CT456; SEQ ID NO: 30 herein). Tarp is also known as CT456 [34].

Preferred Tarp proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 30; and/or (b) which is a fragment of at least n consecutive amino acids of SEQ ID NO: 30, wherein n is 7 or more (e.g. 8, 10, 12, 14, 16, 18, 20, 25, 30, 35, 40, 50, 60, 70, 80, 90, 100, 150, 200, 250 or more). These Tarp proteins include variants (e.g. allelic variants, homologs, orthologs, paralogs, mutants, etc.) of SEQ ID NO: 30. Preferred fragments of (b) comprise an epitope from SEQ ID NO: 30. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 30. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 31, 155 and 156, which consist of amino acids 166-178, 179-197 and 279-298 of Tarp respectively.

(11) Rs10 One example of an "RS10" protein (a S10 Ribosomal Protein) is disclosed in reference 4 (GenBank accession number AAC68035, GenInfo Identifier:3328867; CT436; SEQ ID NO: 32 herein).

Preferred Rs10 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 32; and/or (b) which is a fragment of at least n consecutive amino acids of SEQ ID NO: 32, wherein n is 7 or more (e.g. 8, 10, 12, 14, 16, 18, 20, 25, 30, 35, 40, 50, 60, 70, 80, 90, 100, 150, 200, 250 or more). These Rs10 proteins include variants (e.g. allelic variants, homologs, orthologs, paralogs, mutants, etc.) of SEQ ID NO: 32. Preferred fragments of (b) comprise an epitope from SEQ ID NO: 32. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 32. Other fragments omit one or more domains of the protein (e.g. omission of a signal peptide, of a cytoplasmic domain, of a transmembrane domain, or of an extracellular domain). A particularly preferred fragment is that recited in SEQ ID NO: 33, which consists of amino acids 14-32 of Rs10.

(12) OmpH-like One example of 'OmpH-like' protein is disclosed as SEQ ID NOs: 57 & 58 in reference 16 (GenBank accession number: AAC67835, GenInfo Identifier:3328652; CT242; SEQ ID NO: 34 herein).

Preferred OmpH-like proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 34; and/or (b) which is a fragment of at least n consecutive amino acids of SEQ ID NO: 34, wherein n is 7 or more (e.g. 8, 10, 12, 14, 16, 18, 20, 25, 30, 35, 40, 50, 60, 70, 80, 90, 100, 150, 200, 250 or more). These OmpH-like proteins include variants (e.g. allelic variants, homologs, orthologs, paralogs, mutants, etc.) of SEQ ID NO: 34. Preferred fragments of (b) comprise an epitope from SEQ ID NO: 34. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more; preferably 19 or more, to remove the signal peptide) from the N-terminus of SEQ ID NO: 34. Other fragments omit one or more domains of the protein (e.g. omission of a signal peptide as described above, of a cytoplasmic domain, of a transmembrane domain, or of an extracellular domain). Particularly preferred fragments are those recited in SEQ ID NOs: 35 and 138, which consist of amino acids 62-72 and 73-91 of OmpH respectively.

(13) Rs13 One example of an "Rs13" protein (S13 Ribosomal Protein) is disclosed in reference 4 (GenBank accession number AAC68110, Geninfo Identifier:3328946; CT509; SEQ ID NO: 36 herein).

Preferred Rs13 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 36; and/or (b) which is a fragment of at least n consecutive amino acids of SEQ ID NO: 36, wherein n is 7 or more (e.g. 8, 10, 12, 14, 16, 18, 20, 25, 30, 35, 40, 50, 60, 70, 80, 90, 100, 150, 200, 250 or more). These Rs13 proteins include variants (e.g. allelic variants, homologs, orthologs, paralogs, mutants, etc.) of SEQ ID NO: 36. Preferred fragments of (b) comprise an epitope from SEQ ID NO: 36. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 36. Other fragments omit one or more domains of the protein (e.g. omission of a signal peptide, of a cytoplasmic domain, of a transmembrane domain, or of an extracellular domain). A particularly preferred fragment is that recited in SEQ ID NO: 37, which consists of amino acids 45-55 of Rs13.

(14) R11 One example of an "R11" protein is disclosed in reference 4 (GenBank accession number AAC67911, GenInfo Identifier:3328735; CT318; SEQ ID NO: 38 herein).

Preferred R11 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 38; and/or (b) which is a fragment of at least n consecutive amino acids of SEQ ID NO: 38, wherein n is 7 or more (e.g. 8, 10, 12, 14, 16, 18, 20, 25, 30, 35, 40, 50, 60, 70, 80, 90, 100, 150, 200, 250 or more). These R11 proteins include variants (e.g. allelic variants, homologs, orthologs, paralogs, mutants, etc.) of SEQ ID NO: 38. Preferred fragments of (b) comprise an epitope from SEQ ID NO: 38. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 38. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 39 and 142, which consist of amino acids 38-47 and 20-31 of R11 respectively.

(15) CT875 CT875 is disclosed in reference 4 (GenBank accession number AAC68473, GenInfo Identifier:3329351; SEQ ID NO: 40 herein). A biological function for CT875 has not previously been described.

Preferred CT875 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 40; and/or (b) which is a fragment of at least n consecutive amino acids of SEQ ID NO: 40, wherein n is 7 or more (e.g. 8, 10, 12, 14, 16, 18, 20, 25, 30, 35, 40, 50, 60, 70, 80, 90, 100, 150, 200, 250 or more). These CT875 proteins include variants (e.g. allelic variants, homologs, orthologs, paralogs, mutants, etc.) of SEQ ID NO: 40. Preferred fragments of (b) comprise an epitope from SEQ ID NO: 40. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 40. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 41 and 167-172, which consist of amino acids 52-75, 159-176, 293-308, 336-346, 433-447, 556-567 and 521-567 of CT875 respectively.

(16) HtrA One example of an 'HtrA' protein is disclosed as SEQ ID NOs: 229 & 230 in reference 16 (GenBank accession number: AAC68420, GenInfo Identifier:3329293; CT823; DO Serine protease; SEQ ID NO: 42 herein).

Preferred HtrA proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 42; and/or (b) which is a fragment of at least n consecutive amino acids of SEQ ID NO: 42, wherein n is 7 or more (e.g. 8, 10, 12, 14, 16, 18, 20, 25, 30, 35, 40, 50, 60, 70, 80, 90, 100, 150, 200, 250 or more). These HtrA proteins include variants (e.g. allelic variants, homologs, orthologs, paralogs, mutants, etc.) of SEQ ID NO: 42. Preferred fragments of (b) comprise an epitope from SEQ ID NO: 42. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more; preferably at least 16 to remove the signal peptide) from the N-terminus of SEQ ID NO: 42. Other fragments omit one or more domains of the protein (e.g. omission of a signal peptide as described above, of a cytoplasmic domain, of a transmembrane domain, or of an extracellular domain). A particularly preferred fragment is that recited in SEQ ID NO: 43, which consists of amino acids 475-489 of HtrA. The preferred fragment recited in SEQ ID NO: 43 is predicted to comprise two $CD4^+$ Th1 epitopes. These epitopes are NVLLMVSQG (SEQ ID NO: 261) and DVVRFIVLK (SEQ ID NO: 262). See also the examples and FIG. 10.

(17) RpoA (RNA polymerase alpha) One example of an 'RpoA' protein is disclosed as spot 24 in reference 19 (GenBank accession number: AAC68108, GenInfo Identifier: 3328944; CT507; SEQ ID NO: 44 herein).

Preferred RpoA proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 44; and/or (b) which is a fragment of at least n consecutive amino acids of SEQ ID NO: 44, wherein n is 7 or more (e.g. 8, 10, 12, 14, 16, 18, 20, 25, 30, 35, 40, 50, 60, 70, 80, 90, 100, 150, 200, 250 or more). These RpoA proteins include variants (e.g. allelic variants, homologs, orthologs, paralogs, mutants, etc.) of SEQ ID NO: 44. Preferred fragments of (b) comprise an epitope from SEQ ID NO: 44. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more; preferably at least 16 to remove the signal peptide) from the N-terminus of SEQ ID NO: 44. Other fragments omit one or more domains of the protein (e.g. omission of a signal peptide as described above, of a cytoplasmic domain, of a transmembrane domain, or of an extracellular domain). Particularly preferred fragments are those recited in SEQ ID NOs: 45 and 157-159, which consist of amino acids 21-33, 216-224, 225-235 and 342-359 of RpoA respectively.

(18) PepA (Leucyl aminopeptidase) One example of a 'PepA' protein is disclosed as SEQ ID NOs: 71 & 72 in reference 16 (GenBank accession number: AAC67636, GenInfo Identifier:3328437; CT045; SEQ ID NO: 46 herein). It is believed to catalyse the removal of unsubstituted N-terminal amino acids from various polypeptides.

Preferred PepA proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 46; and/or (b) which is a fragment of at least n consecutive amino acids of SEQ ID NO: 46, wherein n is 7 or more (e.g. 8, 10, 12, 14, 16, 18, 20, 25, 30, 35, 40, 50, 60, 70, 80, 90, 100, 150, 200, 250 or more). These PepA proteins include variants (e.g. allelic variants, homologs, orthologs, paralogs, mutants, etc.) of SEQ ID NO: 46. Preferred fragments of (b) comprise an epitope from SEQ ID NO: 46. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 46. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 47 and 129, which consists of amino acids 184-197 and 399-413 of PepA respectively.

The PepA protein may contain manganese ions.

(19) Alanyl tRNA synthetase One example of an alanyl tRNA synthetase is disclosed in reference 4 (GenBank accession number AAC68344, GenInfo Identifier:6578113; CT749; SEQ ID NO: 48 herein).

Preferred Alanyl tRNA synthetase proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 48; and/or (b) which is a fragment of at least n consecutive amino acids of SEQ ID NO: 48, wherein n is 7 or more (e.g. 8, 10, 12, 14, 16, 18, 20, 25, 30, 35, 40, 50, 60, 70, 80, 90, 100, 150, 200, 250 or more). These CT749 proteins include variants (e.g. allelic variants, homologs, orthologs, paralogs, mutants, etc.) of SEQ ID NO: 48. Preferred fragments of (b) comprise an epitope from SEQ ID NO: 48. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 48. Other fragments omit one or more domains of the protein (e.g. omission of a signal peptide, of a cytoplasmic domain, of a transmembrane domain, or of an extracellular domain). A particularly preferred fragment is that recited in SEQ ID NO: 49, which consists of amino acids 600-616 of CT749.

(20) RpoC (RNA polymerase beta) One example of an 'RpoC' protein is disclosed in reference 4 (GenBank accession number AAC67907, GenInfo Identifier:3328731; CT314; SEQ ID NO: 50 herein).

Preferred RpoC proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 50; and/or (b) which is a fragment of at least n consecutive amino acids of SEQ ID NO: 50, wherein n is 7 or more (e.g. 8, 10, 12, 14, 16, 18, 20, 25, 30, 35, 40, 50, 60, 70, 80, 90, 100, 150, 200, 250 or more). These CT314 proteins include variants (e.g. allelic variants, homologs, orthologs, paralogs, mutants, etc.) of SEQ ID NO: 50. Preferred fragments of (b) comprise an epitope from SEQ ID NO: 50. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 50. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 51, 139 and 140, which consist of amino acids 407-420, 263-273 and 347-362 of CT314 respectively.

(21) YaeL (Metalloprotease) One example of a 'YaeL' protein is disclosed in reference 4 (GenBank accession number: AAC67663, GenInfo Identifier: 3328467; CT072; SEQ ID NO: 105 herein).

Preferred YaeL proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 105; and/or (b) which is a fragment of at least n consecutive amino acids of SEQ ID NO: 105, wherein n is 7 or more (e.g. 8, 10, 12, 14, 16, 18, 20, 25, 30, 35, 40, 50, 60, 70, 80, 90, 100, 150, 200, 250 or more). These YaeL proteins include variants (e.g. allelic variants, homologs, orthologs, paralogs, mutants, etc.) of SEQ ID NO: 105. Preferred fragments of (b) comprise an epitope from SEQ ID NO: 105. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6; 7, 8, 9, 10, 15, 20, 25 or more) from the N-terminus of SEQ ID NO: 105. Other fragments omit one or more domains of the protein (e.g. omission of a signal peptide, of a cytoplasmic domain, of a transmembrane domain, or of an extracellular domain). A particularly preferred fragment is that recited in SEQ ID NO: 106, which consists of amino acids 232-244 of YaeL.

(22) EF-G (Elongation factor G) One example of an 'EF-G' protein is disclosed in reference 4 (GenBank accession number: AAC68036, GenInfo Identifier: 3328868; CT437; SEQ ID NO: 107 herein).

Preferred EF-G proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 107; and/or (b) which is a fragment of at least n consecutive amino acids of SEQ ID NO: 107, wherein n is 7 or more (e.g. 8, 10, 12, 14, 16, 18, 20, 25, 30, 35, 40, 50, 60, 70, 80, 90, 100, 150, 200, 250 or more). These EF-G proteins include variants (e.g. allelic variants, homologs, orthologs, paralogs, mutants, etc.) of SEQ ID NO: 107. Preferred fragments of (b) comprise an epitope from SEQ ID NO: 107. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 107. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 108, 109, 110 and 111, which consist of amino acids 141-153, 300-310, 428-443 and 234-251 of EF-G respectively.

(23) CT578 CT578 is disclosed in reference 4 (GenBank accession number AAC68180, GenInfo Identifier: 3329020; SEQ ID NO: 112 herein). A biological function for CT578 has not previously been described. However, it is postulated that CT576 forms part of a Type Three Secretion System (TTSS).

Preferred CT578 proteins for use with the invention comprise an amino acid sequence: (a) having 50% or more identity (e.g. 60%, 65%, 70%, 75%, 80%, 85%; 90%, 91%, 92%, 93%, 94%, 95%, 96%, 97%, 98%, 99%, 99.5% or more) to SEQ ID NO: 112; and/or (b) which is a fragment of at least n consecutive amino acids of SEQ ID NO: 112, wherein n is 7 or more (e.g. 8, 10, 12, 14, 16, 18, 20, 25, 30, 35, 40, 50, 60, 70, 80, 90, 100, 150, 200, 250 or more). These CT578 proteins include variants (e.g. allelic variants, homologs, orthologs, paralogs, mutants, etc.) of SEQ ID NO: 112. Preferred fragments of (b) comprise an epitope from SEQ ID NO: 112. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 112. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 113, 114, 115 and 116, which consists of amino acids 70-91, 92-107, 108-120 and 454-467 of CT578 respectively.

(24) CT579 CT579 is disclosed in reference 4 (GenBank accession number AAC68181, GenInfo Identifier: 3329021; SEQ ID NO: 117 herein). A biological function for CT579 has not previously been described. However, it is postulated that CT576 forms part of a Type Three Secretion System.

Preferred CT579 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 117; and/or (b) which is a fragment of at least n consecutive amino acids of SEQ ID NO: 117, wherein n is 7 or more (e.g. 8, 10, 12, 14, 16, 18, 20, 25, 30, 35, 40, 50, 60, 70, 80, 90, 100, 150, 200, 250 or more). These CT579 proteins include variants (e.g. allelic variants, homologs, orthologs, paralogs, mutants, etc.) of SEQ ID NO: 117. Preferred fragments of (b) comprise an epitope from SEQ ID NO: 117. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 117. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 118, 119, 120, 121, 122 and 123, which consists of amino acids 108-133, 231-251, 271-285, 252-270, 286-296 and 305-322 of CT579 respectively.

(25) Rs2 (S2 ribosomal protein) One example of an 'Rs2' protein is disclosed in reference 4 (GenBank accession number: AAC68275, GenInfo Identifier: 3329132; CT680; SEQ ID NO: 124 herein).

Preferred Rs2 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 124; and/or (b) which is a fragment of at least n consecutive amino acids of SEQ ID NO: 124, wherein n is 7 or more (e.g. 8, 10, 12, 14, 16, 18, 20, 25, 30, 35, 40, 50, 60, 70, 80, 90, 100, 150, 200, 250 or more). These Rs2 proteins include variants (e.g. allelic variants, homologs, orthologs, paralogs, mutants, etc.) of SEQ ID NO: 124. Preferred fragments of (b) comprise an epitope from SEQ ID NO: 124. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 124. Other fragments omit one or more domains of the protein (e.g. omission of a signal peptide, of a cytoplasmic domain, of a transmembrane domain, or of an extracellular domain). A particularly preferred fragment is that recited in SEQ ID NO: 125, which consists of amino acids 120-133 of Rs2.

(26) CT814 CT814 is disclosed in reference 4 (GenBank accession number AAC68410, GenInfo Identifier: 3329282; SEQ ID NO: 126 herein). A biological function for CT814 has not previously been described.

Preferred CT814 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 126; and/or (b) which is a fragment of at least n consecutive amino acids of SEQ ID NO: 126, wherein n is 7 or more (e.g. 8, 10, 12, 14, 16, 18, 20, 25, 30, 35, 40, 50, 60, 70, 80, 90, 100, 150, 200, 250 or more). These CT814 proteins include variants (e.g. allelic variants, homologs, orthologs, paralogs, mutants, etc.) of SEQ ID NO: 126. Preferred fragments of (b) comprise an epitope from SEQ ID NO: 126. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 126. Other fragments omit one or more domains of the protein (e.g. omission of a signal peptide, of a cytoplasmic domain, of a transmembrane domain, or of an extracellular domain). A particularly preferred fragment is that recited in SEQ ID NO: 127, which consists of amino acids 118-131 of CT814.

Second Antigen Group (1) LcrE low calcium response E protein (CT089) One example of a 'LcrE' protein is disclosed as SEQ ID NOs: 61 & 62 in WO 03/049762 (GenBank accession number: AAC67680, GenInfo Identifier:3328485; 'CT089'; SEQ ID NO: 52 herein). Preferred LcrE proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 52; and/or (b) which is a fragment of at least n consecutive amino acids of SEQ ID NO: 52, wherein n is 7 or more (e.g. 8, 10, 12, 14, 16, 18, 20, 25, 30, 35, 40, 50, 60, 70, 80, 90, 100, 150, 200, 250 or more). These LcrE proteins include variants (e.g. allelic variants, homologs, orthologs, paralogs, mutants, etc.) of SEQ ID NO: 52. Preferred fragments of (b) comprise an epitope from SEQ ID NO: 52. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 52. Other fragments omit one or more domains of the protein (e.g. omission of a signal peptide, of a cytoplasmic domain, of a transmembrane domain, or of an extracellular domain).

(2) ArtJ arginine-binding protein (CT381) One example of an 'ArtJ' protein is disclosed as SEQ ID NOs: 105 & 106 in WO 03/049762 (GenBank accession number: AAC67977, GenInfo Identifier:3328806; 'CT381'; SEQ ID NO: 53 herein). Preferred ArtJ proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 53; and/or (b) which is a fragment of at least n consecutive amino acids of SEQ ID NO: 53, wherein n is 7 or more (e.g. 8, 10, 12, 14, 16, 18, 20, 25, 30, 35, 40, 50, 60, 70, 80, 90, 100, 150, 200, 250 or more). These ArtJ proteins include variants (e.g. allelic variants, homologs, orthologs, paralogs, mutants, etc.) of SEQ ID NO: 53. Preferred fragments of (b) comprise an epitope from SEQ ID NO: 53. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 53. Other fragments omit one or more domains of the protein (e.g. omission of a signal peptide, of a cytoplasmic domain, of a transmembrane domain, or of an extracellular domain). The ArtJ protein may be bound to a small molecule like arginine or another amino acid.

(3) CT398 protein One example of a 'CT398' protein is disclosed as SEQ ID NOS: 111 & 112 in WO 03/049762 (GenBank accession number: AAC67995, GenInfo Identifier:3328825; SEQ ID NO: 54 herein). A biological function for CT398 has not previously been described.

Preferred CT398 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 54; and/or (b) which is a fragment of at least n consecutive amino acids of SEQ ID NO: 54, wherein n is 7 or more (e.g. 8, 10, 12, 14, 16, 18, 20, 25, 30, 35, 40, 50, 60, 70, 80, 90, 100, 150, 200, 250 or more). These CT398 proteins include variants (e.g. allelic variants, homologs, orthologs, paralogs, mutants, etc.) of SEQ ID NO: 54. Preferred fragments of (b) comprise an epitope from SEQ ID NO: 54. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 54. Other fragments omit one or more domains of the protein (e.g. omission of a signal peptide, of a cytoplasmic domain, of a transmembrane domain, or of an extracellular domain). A particularly preferred fragment is that recited in SEQ ID NO: 152, which consists of amino acids 130-151 of CT398.

Third Antigen Group (1) L7/L12 ribosomal protein (CT316) One example of an 'L7/L12' protein is deposited in GenBank under accession number AAC67909 (GenInfo Identifier:3328733; 'CT316'; SEQ ID NO: 55 herein).

Preferred L7/L12 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 55; and/or (b) which is a fragment of at least n consecutive amino acids of SEQ ID NO: 55, wherein n is 7 or more (e.g. 8, 10, 12, 14, 16, 18, 20, 25, 30, 35, 40, 50, 60, 70, 80, 90, 100, 150, 200, 250 or more). These L7/L12 proteins include variants (e.g. allelic variants, homologs, orthologs, paralogs, mutants, etc.) of SEQ ID NO: 55. Preferred fragments of (b) comprise an epitope from SEQ ID NO 55. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 55. Other fragments omit one or more domains of the protein (e.g. omission of a signal peptide, of a cytoplasmic domain, of a transmembrane domain, or of an extracellular domain). The L7/L12 protein may be N-terminally modified. A particularly preferred fragment is that recited in SEQ ID NO: 141, which consists of amino acids 32-73 of CT316.

(2) OmcA cysteine-rich lipoprotein (CT444) One example of an 'OmcA' protein is disclosed as SEQ ID NOs: 127 & 128 in WO 03/049762 (GenBank accession number: AAC68043, GenInfo Identifier:3328876; 'CT444', 'Omp2A', 'Omp3'; SEQ ID NO: 56 herein). A variant sequence is disclosed in reference 35.

Preferred OmcA proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 56; and/or (b) which is a fragment of at least n consecutive amino acids of SEQ ID NO: 56, wherein n is 7 or more (e.g. 8, 10, 12, 14, 16, 18, 20, 25, 30, 35, 40, 50, 60, 70, 80, 90, 100, 150, 200, 250 or more). These OmcA proteins include variants (e.g. allelic variants, homologs, orthologs, paralogs, mutants, etc.) of SEQ ID NO: 56. Preferred fragments of (b) comprise an epitope from SEQ ID NO: 8. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more; preferably 18 or more to remove the signal peptide) from the N-terminus of SEQ ID NO: 56. Other fragments omit one or more domains of the protein (e.g. omission of a signal peptide as described above, of a cytoplasmic domain, of a transmembrane domain, or of an extracellular domain). The protein may be lipidated (e.g. by a N-acyl diglyceride), and may thus have a N-terminal cysteine.

(3) AtoS two-component regulatory system sensor histidine kinase protein (CT467) One example of an 'AtoS' protein is disclosed as SEQ ID NOs: 129 & 130 in reference 36 (GenBank accession number: AAC68067, GenInfo Identifier:3328901; 'CT467'; SEQ ID NO: 57 herein).

Preferred AtoS proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 57; and/or (b) which is a fragment of at least n consecutive amino acids of SEQ ID NO: 57, wherein n is 7 or more (e.g. 8, 10, 12, 14, 16, 18, 20, 25, 30, 35, 40, 50, 60, 70, 80, 90, 100, 150, 200, 250 or more). These AtoS proteins include variants (e.g. allelic variants, homologs, orthologs, paralogs, mutants, etc.) of SEQ ID NO: 57. Preferred fragments of (b) comprise an epitope from SEQ ID NO: 57. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 57. Other fragments omit one or more domains of the protein (e.g.

omission of a signal peptide, of a cytoplasmic domain, of a transmembrane domain, or of an extracellular domain).

(4) CT547 protein (Hypothetical Protein) One example of 'CT547' protein is disclosed as SEQ ID NOs: 151 & 152 in reference 36 (GenBank accession number: AAC68149, GenInfo Identifier:3328986; SEQ ID NO: 58 herein).

Preferred CT547 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 58; and/or (b) which is a fragment of at least n consecutive amino acids of SEQ ID NO: 58, wherein n is 7 or more (e.g. 8, 10, 12, 14, 16, 18, 20, 25, 30, 35, 40, 50, 60, 70, 80, 90, 100, 150, 200, 250 or more). These CT547 proteins include variants (e.g. allelic variants, homologs, orthologs, paralogs, mutants, etc.) of SEQ ID NO: 58. Preferred fragments of (b) comprise an epitope from SEQ ID NO: 58. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 58. Other fragments omit one or more domains of the protein (e.g. omission of a signal peptide, of a cytoplasmic domain, of a transmembrane domain, or of an extracellular domain).

(5) Enolase (2-phosphoglycerate dehydratase) protein (CT587) One example of an 'Eno' protein is disclosed as SEQ ID NOs: 189 & 190 in reference 36 (GenBank accession number: AAC68189, GenInfo Identifier:3329030; 'CT587'; SEQ ID NO: 59 herein).

Preferred Eno proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 59; and/or (b) which is a fragment of at least n consecutive amino acids of SEQ ID NO: 59, wherein n is 7 or more (e.g. 8, 10, 12, 14, 16, 18, 20, 25, 30, 35, 40, 50, 60, 70, 80, 90, 100, 150, 200, 250 or more). These Eno proteins include variants (e.g. allelic variants, homologs, orthologs, paralogs, mutants, etc.) of SEQ ID NO: 59. Preferred fragments of (b) comprise an epitope from SEQ ID NO: 59. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 59. Other fragments omit one or more domains of the protein (e.g. omission of a signal peptide, of a cytoplasmic domain, of a transmembrane domain, or of an extracellular domain). The Eno protein may contain magnesium ions, and may be in the form of a homodimer. Particularly preferred fragments are those recited in SEQ ID NOs: 164 and 165, which consist of amino acids 365-386 and 402-423 of CT587 respectively.

The preferred fragments recited in SEQ ID NOs: 164 and 165 are predicted to comprise seven and two CD4+ Th1 epitopes respectively. These epitopes are LSHRSGETE (SEQ ID NO: 263), SGETEDTTI (SEQ ID NO: 264), IADLAVAFN (SEQ ID NO: 265), LAVAFNTGQ (SEQ ID NO: 266), VAFNTGQIK (SEQ ID NO: 267), FNTGQIKTG (SEQ ID NO: 268) and TGQIKTGSL (SEQ ID NO: 269) for SEQ ID NO: 164 and YNRLMAIEE (SEQ ID NO: 270) and RIAKYNRLM (SEQ ID NO: 271) for SEQ ID NO: 165. See also the examples and FIG. 10.

(6) MurG peptidoglycan transferase protein (CT761) One example of a 'MurG' protein is disclosed as SEQ ID NOs: 217 & 218 in reference 36 (GenBank accession number: AAC68356, GenInfo Identifier:3329223; 'CT761'; SEQ ID NO: 60 herein). It is a UDP-N-acetylglucosamine-N-acetylmuramyl(pentapeptide)pyrophosphoryl undecaprenol-N-acetylglucosamine transferase.

Preferred MurG proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 60; and/or (b) which is a fragment of at least n consecutive amino acids of SEQ ID NO: 60, wherein n is 7 or more (e.g. 8, 10, 12, 14, 16, 18, 20, 25, 30, 35, 40, 50, 60, 70, 80, 90, 100, 150, 200, 250 or more). These MurG proteins include variants (e.g. allelic variants, homologs, orthologs, paralogs, mutants, etc.) of SEQ ID NO: 60. Preferred fragments of (b) comprise an epitope from SEQ ID NO: 60. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 60. Other fragments omit one or more domains of the protein (e.g. omission of a signal peptide as described above, of a cytoplasmic domain, of a transmembrane domain, or of an extracellular domain). The MurG may be lipidated e.g. with undecaprenyl.

Fourth Antigen Group (1) Plasmid Encoded Protein (PGP3, P-glycoprotein) One example of PGP3 sequence is disclosed in, for example, at Genbank entry GenInfo Identifier: 121541. Immunization with PGP3 is discussed in [37] and [38]. One example of a PGP3 protein is described herein as SEQ ID NO: 61.

Preferred PGP3 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 61; and/or (b) which is a fragment of at least n consecutive amino acids of SEQ ID NO: 61, wherein n is 7 or more (e.g. 8, 10, 12, 14, 16, 18, 20, 25, 30, 35, 40, 50, 60, 70, 80, 90, 100, 150, 200, 250 or more). These PGP3 proteins include variants (e.g. allelic variants, homologs, orthologs, paralogs, mutants, etc.) of SEQ ID NO: 61. Preferred fragments of (b) comprise an epitope from SEQ ID NO: 61. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 61. Other fragments omit one or more domains of the protein (e.g. omission of a signal peptide, of a cytoplasmic domain, of a transmembrane domain, or of an extracellular domain).

(2) Polymorphic Membrane Proteins (PMP) A family of nine *Chlamydia trachomatis* genes encoding predicted polymorphic membrane proteins (PMP) have been identified (pmpA to pmpI). See reference 4, specifically FIG. 1. Examples of amino acid sequences of the PMP genes are set forth as SEQ ID NOS: 62-70. (These sequences can also be found in Genbank—GenInfo Identifier nos. 15605137 (pmpA), 15605138 (pmpB—CT413), 15605139 (pmpC—CT414), 15605546 (pmpD), 15605605 (pmpE), 15605606 (pmpF), 15605607 (pmpG), 15605608 (pmpH), and 15605610 (pmpI)). These PMP genes encode relatively large proteins (90 to 187 kDa in mass). The majority of these PMP proteins are predicted to be outer membrane proteins, and are thus also referred to as Predicted Outer Membrane Proteins. As used herein, PMP refers to one or more of the *Chlamydia trachomatis* pmp proteins (pmpA to pmpI) or an immunogenic fragment thereof. Preferably, the PMP protein used in the invention is pmpE or pmpI. Preferably, the PMP protein used in the invention comprises one or more of the fragments of pmpE or pmpI identified in International Patent Application PCT/US01/30345 (WO 02/28998) in Table 1 on page 20 (preferred fragments of pmpE) or Table 2 on page 21 (preferred fragments of pmpI).

Preferred PMP proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to one of the polypeptide sequences set forth as SEQ ID NOS: 62-70; and/or (b) which is a fragment of at least n consecutive amino acids of one of the polypeptide sequences set forth as SEQ ID NOS: 62-70, wherein n is 7 or more (e.g. 8, 10, 12, 14, 16, 18, 20, 25, 30, 35, 40, 50, 60, 70, 80, 90, 100, 150, 200, 250 or more). These PMP proteins include variants (e.g. allelic variants, homologs, orthologs, paralogs, mutants, etc.) of the polypeptide sequences set forth as SEQ ID NOS: 62-70. Preferred fragments of (b) comprise an epitope from one of the polypeptide sequences set forth as SEQ ID NOS: 62-70. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of one of the polypeptide sequences set forth as SEQ ID NOS: 62-70. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 257 and 258, which consist of amino acids 208-233 of CT413 and 1377-1392 of CT414 respectively.

(3) Cap1 (CT529) The *Chlamydia trachomatis* Cap1 protein corresponds with the hypothetical open reading frame CT529 and refers to Class I Accessible Protein-1 [39] (see also GenBank accession number NP_220044; GI:15605258. One example of a Cap1 protein is referred to herein as SEQ ID NO: 71. Predicted T-cell epitopes of Cap1 are identified in this reference as SEQ ID NO: 72 CSFIGGITYL, preferably SEQ ID NO: 73 SFIGGITYL, and SEQ ID NO: 74 SIIGGITYL.

Preferred Cap1 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 71; and/or (b) which is a fragment of at least n consecutive amino acids of SEQ ID NO: 71, wherein n is 7 or more (e.g. 8, 10, 12, 14, 16, 18, 20, 25, 30, 35, 40, 50, 60, 70, 80, 90, 100, 150, 200, 250 or more). These Cap1 proteins include variants (e.g. allelic variants, homologs, orthologs, paralogs, mutants, etc.) of SEQ ID NO: 71. Preferred fragments of (b) comprise an epitope from SEQ ID NO: 71. Preferred T-cell epitopes include one or more of the T-cell epitopes identified above. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 71. Other fragments omit one or more domains of the protein (e.g. omission of a signal peptide, of a cytoplasmic domain, of a transmembrane domain, or of an extracellular domain).

(4) GroEL-like hsp60 protein One example of a *Chlamydia trachomatis* GroEL-like hsp60 protein is set forth herein as SEQ ID NO: 75 (see also GenBank accession number NP_219613; GenInfo Identifier: 15604829). The role of Hsp60 in *chlamydial* infection is further described in, for example, [40-44]. Immunization of guinea pig models with recombinant Hsp60 is described in reference 45. B-cell epitopes of Hsp60 are identified in reference 46.

Preferred hsp60 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 75; and/or (b) which is a fragment of at least n consecutive amino acids of SEQ ID NO: 75, wherein n is 7 or more (e.g. 8, 10, 12, 14, 16, 18, 20, 25, 30, 35, 40, 50, 60, 70, 80, 90, 100, 150, 200, 250 or more). These hsp60 proteins include variants (e.g. allelic variants, homologs, orthologs, paralogs, mutants, etc.) of SEQ ID NO: 75. Preferred fragments of (b) comprise an epitope from SEQ ID NO: 75, including one or more of the epitopes identified in the references discussed above. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 75. Other fragments omit one or more domains of the protein (e.g. omission of a signal peptide, of a cytoplasmic domain, of a transmembrane domain, or of an extracellular domain). Other preferred fragments comprise a polypeptide sequence which does not cross-react with related human proteins.

(5) 60 kDa Cysteine rich protein (OmcB) (CT443) One example of a *Chlamydia trachomatis* 60 kDa Cysteine rich protein is referred to herein as SEQ ID NO: 76 (see also GenBank accession number CAA39396; GenInfo Identifier: 40725). This protein is also generally referred to as OmcB, Omp2 or CT 443. The role of OmcB in *chlamydial* infection is further described in, for example, references 47-51.

Preferred OmcB proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 76; and/or (b) which is a fragment of at least n consecutive amino acids of SEQ ID NO: 76, wherein n is 7 or more (e.g. 8, 10, 12, 14, 16, 18, 20, 25, 30, 35, 40, 50, 60, 70, 80, 90, 100, 150, 200, 250 or more). These OmcB proteins include variants (e.g. allelic variants, homologs, orthologs, paralogs, mutants, etc.) of SEQ ID NO: 76. Preferred fragments of (b) comprise an epitope from SEQ ID NO: 76, including one or more of the epitopes identified in the references discussed above. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 76. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 153 and 154, which consist of amino acids 77-85 and 155-166 of OmcB respectively.

Fifth Antigen Group (1) YscJ (CT559) One example of a 'YscJ' protein is disclosed as SEQ ID NOs: 199 & 200 in reference 36 (GenBank accession number: AAC68161.1; GenInfo Identifier: 3329000; 'CT559'; SEQ ID NO: 77 herein).

Preferred YscJ proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 77; and/or (b) which is a fragment of at least n consecutive amino acids of SEQ ID NO: 77, wherein n is 7 or more (e.g. 8, 10, 12, 14, 16, 18, 20, 25, 30, 35, 40, 50, 60, 70, 80, 90, 100, 150, 200, 250 or more). These YscJ proteins include variants (e.g. allelic variants, homologs, orthologs, paralogs, mutants, etc.) of SEQ ID NO: 77. Preferred fragments of (b) comprise an epitope from SEQ ID NO: 77. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 77. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 161 and 162, which consist of amino acids 118-131 and 294-313 of CT559 respectively.

(2) Pal (CT600) One example of a 'Pal' protein is disclosed as SEQ ID NOs: 173 & 174 in reference 36 (GenBank accession number: AAC68202.1; GenInfo Identifier:3329044 'CT600'; SEQ ID NO: 78 herein).

Preferred Pal proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 78; and/or (b) which is a fragment of at least n consecutive amino acids of SEQ ID NO: 78, wherein n is 7 or more (e.g. 8, 10, 12, 14, 16, 18, 20, 25, 30, 35, 40, 50, 60, 70, 80, 90, 100, 150, 200, 250 or more). These Pal proteins include variants (e.g. allelic variants, homologs, orthologs, paralogs, mutants, etc.) of SEQ ID NO: 78. Preferred fragments of (b) comprise an epitope from SEQ ID NO: 78. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 78. Other fragments omit one or more domains of the protein (e.g. omission of a signal peptide, of a cytoplasmic domain, of a transmembrane domain, or of an extracellular domain).

(3) CHLPN (76 kDa) (CT623) One example of a CHLPN (76 kDa protein) is disclosed as SEQ ID NOs: 163 & 164 in reference 36 (GenBank accession number: AAC68227.2; GenInfo Identifier:6578109 'CT623'; SEQ ID NO: 79 herein).

Preferred CHLPN (76 kDa protein proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 79; and/or (b) which is a fragment of at least n consecutive amino acids of SEQ ID NO: 79, wherein n is 7 or more (e.g. 8, 10, 12, 14, 16, 18, 20, 25, 30, 35, 40, 50, 60, 70, 80, 90, 100, 150, 200, 250 or more). These CHLPN (76 kDa protein) proteins include variants (e.g. allelic variants, homologs, orthologs, paralogs, mutants, etc.) of SEQ ID NO: 79. Preferred fragments of (b) comprise an epitope from SEQ ID NO: 79. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 79. Other fragments omit one or more domains of the protein (e.g. omission of a signal peptide, of a cytoplasmic domain, of a transmembrane domain, or of an extracellular domain).

(4) CT700 One example of a CT700 Hypothetical Protein is disclosed as SEQ ID NOs 261 & 262 in reference 36 (GenBank accession number: AAC68295.1; Geninfo Identifier:3329154 'CT700'; SEQ ID NO: 80 herein). A biological function for CT700 has not previously been described.

Preferred CT700 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 80; and/or (b) which is a fragment of at least n consecutive amino acids of SEQ ID NO: 80, wherein n is 7 or more (e.g. 8, 10, 12, 14, 16, 18, 20, 25, 30, 35, 40, 50, 60, 70, 80, 90, 100, 150, 200, 250 or more). These CT700 Hypothetical proteins include variants (e.g. allelic variants, homologs, orthologs, paralogs, mutants, etc.) of SEQ ID NO: 80. Preferred fragments of (b) comprise an epitope from SEQ ID NO: 80. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 80. Other fragments omit one or more domains of the protein (e.g. omission of a signal peptide, of a cytoplasmic domain, of a transmembrane domain, or of an extracellular domain).

(5) CT266 One example of a CT266 Hypothetical Protein is disclosed as SEQ ID NOs 77 & 78 in reference 36 (GenBank accession number: AAC67859.1; Geninfo Identifier: 3328678 'CT266'; SEQ ID NO: 81 herein). A biological function for CT266 has not previously been described.

Preferred CT266 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 81; and/or (b) which is a fragment of at least n consecutive amino acids of SEQ ID NO: 81, wherein n is 7 or more (e.g. 8, 10, 12, 14, 16, 18, 20, 25, 30, 35, 40, 50, 60, 70, 80, 90, 100, 150, 200, 250 or more). These CT266 Hypothetical proteins include variants (e.g. allelic variants, homologs, orthologs, paralogs, mutants, etc.) of SEQ ID NO: 81. Preferred fragments of (b) comprise an epitope from SEQ ID NO: 81. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 81. Other fragments omit one or more domains of the protein (e.g. omission of a signal peptide, of a cytoplasmic domain, of a transmembrane domain, or of an extracellular domain).

(6) CT077 One example of a CT077 Hypothetical Protein is disclosed as SEQ ID NOs 65 & 66 in reference 36 (GenBank accession number: AAC67668.1; GenInfo Identifier: 3328472 'CT077'; SEQ ID NO: 82 herein). A biological function for CT077 has not previously been described.

Preferred CT077 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 82; and/or (b) which is a fragment of at least n consecutive amino acids of SEQ ID NO: 82, wherein n is 7 or more (e.g. 8, 10, 12, 14, 16, 18, 20, 25, 30, 35, 40, 50, 60, 70, 80, 90, 100, 150, 200, 250 or more). These CT077 Hypothetical proteins include variants (e.g. allelic variants, homologs, orthologs, paralogs, mutants, etc.) of SEQ ID NO: 82. Preferred fragments of (b) comprise an epitope from SEQ ID NO: 82. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 82. Other fragments omit one or more domains of the protein (e.g. omission of a signal peptide, of a cytoplasmic domain, of a transmembrane domain, or of an extracellular domain).

(7) CT165 One example of a CT165 protein is disclosed in [4] (GenBank accession number: AAC67756.1; GenInfo Identifier:3328568; 'CT165'; SEQ ID NO: 83 herein). A biological function for CT165 has not previously been described.

Preferred CT165 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 83; and/or (b) which is a fragment of at least n consecutive amino acids of SEQ ID NO: 83, wherein n is 7 or more (e.g. 8, 10, 12, 14, 16, 18, 20, 25, 30, 35, 40, 50, 60, 70, 80, 90, 100, 150, 200, 250 or more). These CT165 Hypothetical proteins include variants (e.g. allelic variants, homologs, orthologs, paralogs, mutants, etc.) of SEQ ID NO: 83. Preferred fragments of (b) comprise an epitope from SEQ ID NO: 83. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 83. Other fragments omit one or more domains of the protein (e.g. omission of a signal peptide, of a cytoplasmic domain, of a transmembrane domain, or of an extracellular domain).

(8) PorB (CT713) One example of a PorB protein is disclosed as SEQ ID NOs 201 & 202 in reference 36 (GenBank accession number: AAC68308.1; GenInfo Identifier: 3329169; 'CT713'; SEQ ID NO: 84 herein).

Preferred PorB proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 84; and/or (b) which is a fragment of at least n consecutive amino acids of SEQ ID NO: 84, wherein n is 7 or more (e.g. 8, 10, 12, 14, 16, 18, 20, 25, 30, 35, 40, 50, 60, 70, 80, 90, 100, 150, 200, 250 or more). These PorB proteins include variants (e.g. allelic variants, homologs, orthologs, paralogs, mutants, etc.) of SEQ ID NO: 84. Preferred fragments of (b) comprise an epitope from SEQ ID NO: 84. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 84. Other fragments omit one or more domains of the protein (e.g. omission of a signal peptide, of a cytoplasmic domain, of a transmembrane domain, or of an extracellular domain).

Sixth Antigen Group (1) CT082 One example of a CT082 protein is disclosed in reference 4 (GenBank accession number: AAC67673.1; GenInfo Identifier:3328477; 'CT082'; SEQ ID NO: 85 herein): A biological function for CT082 has not previously been described.

Preferred CT082 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 85; and/or (b) which is a fragment of at least n consecutive amino acids of SEQ ID NO: 85, wherein n is 7 or more (e.g. 8, 10, 12, 14, 16, 18, 20, 25, 30, 35, 40, 50, 60, 70, 80, 90, 100, 150, 200, 250 or more). These CT082 Hypothetical proteins include variants (e.g. allelic variants, homologs, orthologs, paralogs, mutants, etc.) of SEQ ID NO: 85. Preferred fragments of (b) comprise an epitope from SEQ ID NO: 85. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 85. Other fragments omit one or more domains of the protein (e.g. omission of a signal peptide, of a cytoplasmic domain, of a transmembrane domain, or of an extracellular domain).

(2) CT181 One example of a CT181 protein is disclosed as SEQ ID NOs 245 & 246 in reference 36 (GenBank accession number: AAC67772.1; GenInfo Identifier:3328585; 'CT181'; SEQ ID NO: 86 herein). A biological function for CT181 proteins has not previously been described.

Preferred CT181 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 86; and/or (b) which is a fragment of at least n consecutive amino acids of SEQ ID NO: 86, wherein n is 7 or more (e.g. 8, 10, 12, 14, 16, 18, 20, 25, 30, 35, 40, 50, 60, 70, 80, 90, 100, 150, 200, 250 or more). These CT181 Hypothetical proteins include variants (e.g. allelic variants, homologs, orthologs, paralogs, mutants, etc.) of SEQ ID NO: 86. Preferred fragments of (b) comprise an epitope from SEQ ID NO: 86. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 86. Other fragments omit one or more domains of the protein (e.g. omission of a signal peptide, of a cytoplasmic domain, of a transmembrane domain, or of an extracellular domain).

(3) CT050 One example of a CT050 protein is disclosed in reference 4 (GenBank accession number: AAC67641.1; GenInfo Identifier:3328442; 'CT050'; SEQ ID NO: 87 herein). A biological function for CT050 proteins has not previously been described.

Preferred CT050 hypothetical proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 87; and/or (b) which is a fragment of at least n consecutive amino acids of SEQ ID NO: 87, wherein n is 7 or more (e.g. 8, 10, 12, 14, 16, 18, 20, 25, 30, 35, 40, 50, 60, 70, 80, 90, 100, 150, 200, 250 or more). These CT050 Hypothetical proteins include variants (e.g. allelic variants, homologs, orthologs, paralogs, mutants, etc.) of SEQ ID NO: 87. Preferred fragments of (b) comprise an epitope from SEQ ID NO: 87. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 87. Other fragments omit one or more domains of the protein (e.g. omission of a signal peptide, of a cytoplasmic domain, of a transmembrane domain, or of an extracellular domain).

(4) Phospholipase D SuperFamily (CT157) One example of a Phospholipase D SuperFamily Protein is disclosed as (GenBank accession number: AAC67748.1; GenInfo Identifier:3328559; 'CT157'; SEQ ID NO: 88 herein).

Preferred Phospholipase D SuperFamily proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 88; and/or (b) which is a fragment of at least n consecutive amino acids of SEQ ID NO: 88, wherein n is 7 or more (e.g. 8, 10, 12, 14, 16, 18, 20, 25, 30, 35, 40, 50, 60, 70, 80, 90, 100, 150, 200, 250 or more). These Phospholipase D SuperFamily proteins include variants (e.g. allelic variants, homologs, orthologs, paralogs, mutants, etc.) of SEQ ID NO: 88. Preferred fragments of (b) comprise an epitope from SEQ ID NO: 88. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 88. Other fragments omit one or more domains of the protein (e.g.

omission of, a signal peptide, of a cytoplasmic domain, of a transmembrane domain, or of an extracellular domain).

(5) AdK (Adenylate Kinase) (CT128) One example of an Adenylate Kinase Protein is disclosed as (GenBank accession number: AAC67719.1 GenInfo Identifier:3328527; 'CT128'; SEQ ID NO: 89 herein).

Preferred Adenylate Kinase proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 89; and/or (b) which is a fragment of at least n consecutive amino acids of SEQ ID NO: 89, wherein n is 7 or more (e.g. 8, 10, 12, 14, 16, 18, 20, 25, 30, 35, 40, 50, 60, 70, 80, 90, 100, 150, 200, 250 or more). These Adenylate Kinase proteins include variants (e.g. allelic variants, homologs, orthologs, paralogs, mutants, etc.) of SEQ ID NO: 89. Preferred fragments of (b) comprise an epitope from SEQ ID NO: 89. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 89. Other fragments omit one or more domains of the protein (e.g. omission of a signal peptide, of a cytoplasmic domain, of a transmembrane domain, or of an extracellular domain).

Seventh Antigen Group (1) CT153 One example of a CT153 Protein is disclosed in reference 4 (GenBank accession number: AAC67744.1; GenInfo Identifier:3328555; 'CT153'; SEQ ID NO: 90 herein). A biological function for CT153 proteins has not previously been described.

Preferred CT153 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 90; and/or (b) which is a fragment of at least n consecutive amino acids of SEQ ID NO: 90, wherein n is 7 or more (e.g. 8, 10, 12, 14, 16, 18, 20, 25, 30, 35, 40, 50, 60, 70, 80, 90, 100, 150, 200, 250 or more). These CT153 Hypothetical proteins include variants (e.g. allelic variants, homologs, orthologs, paralogs, mutants, etc.) of SEQ ID NO: 90. Preferred fragments of (b) comprise an epitope from SEQ ID NO: 90. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 90. Other fragments omit one or more domains of the protein (e.g. omission of a signal peptide, of a cytoplasmic domain, of a transmembrane domain, or of an extracellular domain). A particularly preferred fragment is that recited in SEQ ID NO: 137, which consists of amino acids 23-36 of CT153.

(2) CT262 One example of a CT262 protein is disclosed in reference 4 (GenBank accession number: AAC67855.1; GenInfo Identifier: 3328674; CT262'; SEQ ID NO: 91 herein). A biological function for CT262 proteins has not previously been described.

Preferred CT262 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 91; and/or (b) which is a fragment of at least n consecutive amino acids of SEQ ID NO: 91, wherein n is 7 or more (e.g. 8, 10, 12, 14, 16, 18, 20, 25, 30, 35, 40, 50, 60, 70, 80, 90, 100, 150, 200, 250 or more). These CT262 Hypothetical proteins include variants (e.g. allelic variants, homologs, orthologs, paralogs, mutants, etc.) of SEQ ID NO: 91. Preferred fragments of (b) comprise an epitope from SEQ ID NO: 91. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 91. Other fragments omit one or more domains of the protein (e.g. omission of a signal peptide, of a cytoplasmic domain, of a transmembrane domain, or of an extracellular domain).

(3) CT276 One example of a CT276 protein is disclosed in reference 4 (GenBank accession number: AAC67869.1; GenInfo Identifier:3328689; 'CT276'; SEQ ID NO: 92 herein). A biological function for CT276 proteins has not previously been described.

Preferred CT276 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 92; and/or (b) which is a fragment of at least n consecutive amino acids of SEQ ID NO: 92, wherein n is 7 or more (e.g. 8, 10, 12, 14, 16, 18, 20, 25, 30, 35, 40, 50, 60, 70, 80, 90, 100, 150, 200, 250 or more). These CT276 Hypothetical proteins include variants (e.g. allelic variants, homologs, orthologs, paralogs, mutants, etc.) of SEQ ID NO: 92. Preferred fragments of (b) comprise an epitope from SEQ ID NO: 92. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 92. Other fragments omit one or more domains of the protein (e.g. omission of a signal peptide, of a cytoplasmic domain, of a transmembrane domain, or of an extracellular domain).

(4) CT296 One example of a CT296 protein is disclosed in reference 4 (GenBank accession number: AAC67889.1; GenInfo Identifier:3328711; 'CT296'; SEQ ID NO: 93 herein). A biological function for CT296 proteins has not previously been described.

Preferred CT296 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 93; and/or (b) which is a fragment of at least n consecutive amino acids of SEQ ID NO: 93, wherein n is 7 or more (e.g. 8, 10, 12, 14, 16, 18, 20, 25, 30, 35, 40, 50, 60, 70, 80, 90, 100, 150, 200, 250 or more). These CT296 Hypothetical proteins include variants (e.g. allelic variants, homologs, orthologs, paralogs, mutants, etc.) of SEQ ID NO: 93. Preferred fragments of (b) comprise an epitope from SEQ ID NO: 93. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 93. Other fragments omit one or more domains of the protein (e.g. omission of a signal peptide, of a cytoplasmic domain, of a transmembrane domain, or of an extracellular domain).

(5) CT372 One example of a CT372 protein is disclosed as SEQ ID NOs 187 & 188 in reference 36 (GenBank accession number: AAC67968.1; GenInfo Identifier:3328796; 'CT372'; SEQ ID NO: 94 herein). A biological function for CT372 proteins has not previously been described.

Preferred CT372 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 94; and/or (b) which is a fragment of at least n consecutive amino acids of SEQ ID NO: 94, wherein n is 7 or more (e.g. 8, 10, 12, 14, 16, 18, 20, 25, 30, 35, 40, 50, 60, 70, 80, 90, 100, 150, 200, 250 or more). These CT372 Hypothetical proteins include variants (e.g. allelic variants, homologs, orthologs, paralogs, mutants, etc.) of SEQ ID NO: 94. Preferred fragments of (b) comprise an epitope from SEQ ID NO: 94. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 94. Other fragments omit one or more domains of the protein (e.g. omission of a signal peptide, of a cytoplasmic domain, of a transmembrane domain, or of an extracellular domain).

(6) Putative Outer Membrane Protein A (PmpA) (CT412) One example of a PmpA protein is disclosed as SEQ ID NOs 89 & 90 in reference 36 (GenBank accession number: AAC68009.1; GenInfo Identifier:3328840; 'CT412'; SEQ ID NO: 95 herein and also SEQ ID NO: 61 above).

Preferred PmpA proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 95; and/or (b) which is a fragment of at least n consecutive amino acids of SEQ ID NO: 95, wherein n is 7 or more (e.g. 8, 10, 12, 14, 16, 18, 20, 25, 30, 35, 40, 50, 60, 70, 80, 90, 100, 150, 200, 250 or more). These PmpA proteins include variants (e.g. allelic variants, homologs, orthologs, paralogs, mutants, etc.) of SEQ ID NO: 95. Preferred fragments of (b) comprise an epitope from SEQ ID NO: 95. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 95. Other fragments omit one or more domains of the protein (e.g. omission of a signal peptide, of a cytoplasmic domain, of a transmembrane domain, or of an extracellular domain).

(7) Oligopeptide Binding Lipoprotein (CT480) One example of an Oligopeptide binding lipoprotein is disclosed as SEQ ID NOs 141 & 142 in reference 36 (GenBank accession number: AAC68080.1; GenInfo Identifier:3328915; 'CT480'; SEQ ID NO: 96 herein).

Preferred Oligopeptide Binding Lipoproteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 96; and/or (b) which is a fragment of at least n consecutive amino acids of SEQ ID NO: 96, wherein n is 7 or more (e.g. 8, 10, 12, 14, 16, 18, 20, 25, 30, 35, 40, 50, 60, 70, 80, 90, 100, 150, 200, 250 or more). These OligoPeptide Binding proteins include variants (e.g. allelic variants, homologs, orthologs, paralogs, mutants, etc.) of SEQ ID NO: 96. Preferred fragments of (b) comprise an epitope from SEQ ID NO: 96. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 96. Other fragments omit one or more domains of the protein (e.g. omission of a signal peptide, of a cytoplasmic domain, of a transmembrane domain, or of an extracellular domain).

(8) CT548 One example of a CT548 protein is disclosed as SEQ ID NOs 153 & 154 in reference 36 (GenBank accession number: AAC68150.1; GenInfo Identifier:3328987; 'CT548'; SEQ ID NO: 97 herein). A biological function for CT548 proteins has not previously been described.

Preferred CT548 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 97; and/or (b) which is a fragment of at least n consecutive amino acids of SEQ ID NO: 97, wherein n is 7 or more (e.g. 8, 10, 12, 14, 16, 18, 20, 25, 30, 35, 40, 50, 60, 70, 80, 90, 100, 150, 200, 250 or more). These CT548 Hypothetical proteins include variants (e.g. allelic variants, homologs, orthologs, paralogs, mutants, etc.) of SEQ ID NO: 97. Preferred fragments of (b) comprise an epitope from SEQ ID NO: 97. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 97. Other fragments omit one or more domains of the protein (e.g. omission of a signal peptide, of a cytoplasmic domain, of a transmembrane domain, or of an extracellular domain).

(9) CT043 One example of a CT043 protein is disclosed in reference 4 (GenBank accession number: AAC67634.1; GenInfo Identifier:3328435; 'CT043'; SEQ ID NO: 98 herein). A biological function for CT043 proteins has not previously been described. It is postulated here that CT043 is a type three secretion system (TTSS) chaperone.

Preferred CT043 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 98; and/or (b) which is a fragment of at least n consecutive amino acids of SEQ ID NO: 98, wherein n is 7 or more (e.g. 8, 10, 12, 14, 16, 18, 20, 25, 30, 35, 40, 50, 60, 70, 80, 90, 100, 150, 200, 250 or more). These CT043 Hypothetical proteins include variants (e.g. allelic variants, homologs, orthologs, paralogs, mutants, etc.) of SEQ ID NO: 98. Preferred fragments of (b) comprise an epitope from SEQ ID NO: 98. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 98. Other fragments omit one or more domains of the protein (e.g. omission of a signal peptide, of a cytoplasmic domain, of a transmembrane domain, or of an extracellular domain). A particularly preferred fragment is that recited in SEQ ID NO: 128, which consists of amino acids 75-95 of CT043.

The preferred fragment recited in SEQ ID NO: 128 is predicted to comprise three $CD4^+$ Th1 epitopes. These epitopes are LYEKLLEGS (SEQ ID NO: 272), GSMLGGQMA (SEQ ID NO: 273) and GGGVGVATK (SEQ ID NO: 274). An optional variant of the third epitope is GGVGVATKE (SEQ ID NO: 275). See also the examples and FIG. 10.

(10) CT635 One example of a CT635 protein is disclosed in reference 4 (GenBank accession number: AAC68239.1; GenInfo Identifier:3329083; 'CT635'; SEQ ID NO: 99 herein). A biological function for CT635 proteins has not previously been described.

Preferred CT635 Hypothetical proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 99; and/or (b) which is a fragment of at least n consecutive amino acids of SEQ ID NO: 99, wherein n is 7 or more (e.g. 8, 10, 12, 14, 16, 18, 20, 25, 30, 35, 40, 50, 60, 70, 80, 90, 100, 150, 200, 250 or more). These CT635 Hypothetical proteins include variants (e.g. allelic variants, homologs, orthologs, paralogs, mutants, etc.) of SEQ ID NO: 99. Preferred fragments of (b) comprise an epitope from SEQ ID NO: 99. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 99. Other fragments omit one or more domains of the protein (e.g. omission of a signal peptide, of a cytoplasmic domain, of a transmembrane domain, or of an extracellular domain). A particularly preferred fragment is that recited in SEQ ID NO: 166, which consists of amino acids 70-88 of CT635 respectively.

(11) Metalloprotease (CT859) One example of a Metalloproease Protein is disclosed in reference 4 (GenBank accession number: AAC68457.1; GenInfo Identifier:3329333; 'CT859'; SEQ ID NO: 100 herein).

Preferred Metalloprotease proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 100; and/or (b) which is a fragment of at least n consecutive amino acids of SEQ ID NO: 100, wherein n is 7 or more (e.g. 8, 10, 12, 14, 16, 18, 20, 25, 30, 35, 40, 50, 60, 70, 80, 90, 100, 150, 200, 250 or more). These Metalloprotease proteins include variants (e.g. allelic variants, homologs, orthologs, paralogs, mutants, etc.) of SEQ ID NO: 100. Preferred fragments of (b) comprise an epitope from SEQ ID NO: 100. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 100. Other fragments omit one or more domains of the protein (e.g. omission of a signal peptide, of a cytoplasmic domain, of a transmembrane domain, or of an extracellular domain).

(12) CT671 One example of a CT671 protein is disclosed in reference 4 (GenBank accession number: AAC68266.1; GenInfo Identifier:3329122; 'CT671'; SEQ ID NO: 101 herein). A biological function for CT671 proteins has not previously been described.

Preferred CT671 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 101; and/or (b) which is a fragment of at least n consecutive amino acids of SEQ ID NO: 101, wherein n is 7 or more (e.g. 8, 10, 12, 14, 16, 18, 20, 25, 30, 35, 40, 50, 60, 70, 80, 90, 100, 150, 200, 250 or more). These CT671 Hypothetical proteins include variants (e.g. allelic variants, homologs, orthologs, paralogs, mutants, etc.) of SEQ ID NO: 101. Preferred fragments of (b) comprise an epitope from SEQ ID NO: 101. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 101. Other fragments omit one or more domains of the protein (e.g. omission of a signal peptide, of a cytoplasmic domain, of a transmembrane domain, or of an extracellular domain).

(13) CT016 One example of a CT016 protein is disclosed in reference 4 (GenBank accession number: AAC67606.1; GenInfo Identifier:3328405; 'CT016'; SEQ ID NO: 102 herein). A biological function for CT016 proteins has not previously been described.

Preferred CT016 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 102; and/or (b) which is a fragment of at least n consecutive amino acids of SEQ ID NO: 102, wherein n is 7 or more (e.g. 8, 10, 12, 14, 16, 18, 20, 25, 30, 35, 40, 50, 60, 70, 80, 90, 100, 150, 200, 250 or more). These CT016 Hypothetical proteins include variants (e.g. allelic variants, homologs, orthologs, paralogs, mutants, etc.) of SEQ ID NO: 102. Preferred fragments of (b) comprise an epitope from SEQ ID NO: 102. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 102. Other fragments omit one or more domains of the protein (e.g. omission of a signal peptide, of a cytoplasmic domain, of a transmembrane domain, or of an extracellular domain).

(14) CT017 One example of a CT017 protein is disclosed in reference 4 (GenBank accession number: AAC67607.1; GenInfo Identifier:3328406; 'CT017'; SEQ ID NO: 103 herein). A function for CT017 proteins has not previously been identified.

Preferred CT017 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 103; and/or (b) which is a fragment of at least n consecutive amino acids of SEQ ID NO: 103, wherein n is 7 or more (e.g. 8, 10, 12, 14, 16, 18, 20, 25, 30, 35, 40, 50, 60, 70, 80, 90, 100, 150, 200, 250 or more). These CT017 Hypothetical proteins include variants (e.g. allelic variants, homologs, orthologs, paralogs, mutants, etc.) of SEQ ID NO: 103. Preferred fragments of (b) comprise an epitope from SEQ ID NO: 103. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 103. Other fragments omit one or more domains of the protein (e.g. omission of a signal peptide, of a cytoplasmic domain, of a transmembrane domain, or of an extracellular domain).

(15) PmpD (CT812) This polymorphic membrane protein D is discussed above as SEQ ID NO: 64 (CT812).

(16) PmpE (CT869) This polymorphic membrane protein E is discussed above as SEQ ID NO: 65.

Eighth Antigen Group (1) GatA One example of a GatA protein is disclosed in reference 4 (GenBank accession number: AAC67593; GenInfo Identifier: 3328391; 'CT003'; SEQ ID NO: 173 herein).

Preferred GatA proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 173; and/or (b) which is a fragment of at least n consecutive amino acids of SEQ ID NO: 173, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 173. Preferred fragments of (b) comprise an epitope from SEQ ID NO: 173. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 173. Other fragments omit one or more domains of the protein (e.g. omission of a signal peptide, of a cytoplasmic domain, of a transmembrane domain, or of an extracellular domain). A particularly preferred fragment is that recited in SEQ ID NO: 174, which consists of amino acids 148-163 of GatA.

(2) GatB One example of a GatB protein is disclosed in reference 4 (GenBank accession number: AAC67594; GenInfo Identifier: 3328392; 'CT004'; SEQ ID NO: 175 herein).

Preferred GatB proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 175; and/or (b) which is a fragment of at least n consecutive amino acids of SEQ ID NO: 175, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 175. Preferred fragments of (b) comprise an epitope from SEQ ID NO: 175. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 175. Other fragments omit one or more domains of the protein (e.g. omission of a signal peptide, of a cytoplasmic domain, of a transmembrane domain, or of an extracellular domain). A particularly preferred fragment is that recited in SEQ ID NO: 176, which consists of amino acids 437-450 of GatB.

(3) CT005 One example of a CT005 protein is disclosed in reference 4 (GenBank accession number: AAC67595; GenInfo Identifier: 3328393; 'CT005'; SEQ ID NO: 177 herein). A function for CT005 proteins has not previously been identified.

Preferred CT005 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 177; and/or (b) which is a fragment of at least n consecutive amino acids of SEQ ID NO: 177, wherein n is 7 or more (e.g. 8, 10, 12, 14, 16, 18, 20, 25, 30, 35, 40, 50, 60, 70, 80, 90, 100, 150, 200, 250 or more). These CT005 Hypothetical proteins include variants (e.g. allelic variants, homologs, orthologs, paralogs, mutants, etc.) of SEQ ID NO: 177. Preferred fragments of (b) comprise an epitope from SEQ ID NO: 177. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 177. Other fragments omit one or more domains of the protein (e.g. omission of a signal peptide, of a cytoplasmic domain, of a transmembrane domain, or of an extracellular domain). A particularly preferred fragment is that recited in SEQ ID NO: 178, which consists of amino acids 340-357 of CT005.

(4) CT042 One example of a CT042 protein is disclosed in reference 4 (GenBank accession number: AAC67632; GenInfo Identifier: 3328433; 'CT042'; SEQ ID NO: 179 herein). CT042 is predicted to be a metalloprotease protein.

Preferred CT042 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 179; and/or (b) which is a fragment of at least n consecutive amino acids of SEQ ID NO: 179, wherein n is 7 or more (e.g. 8, 10, 12, 14, 16, 18, 20, 25, 30, 35, 40, 50, 60, 70, 80, 90, 100, 150, 200, 250 or more). These CT042 proteins include variants (e.g. allelic variants, homologs, orthologs, paralogs, mutants, etc.) of SEQ ID NO: 179. Preferred fragments of (b) comprise an epitope from SEQ ID NO: 179. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 179. Other fragments omit one or more domains of the protein (e.g. omission of a signal peptide, of a cytoplasmic domain, of a transmembrane domain, or of an extracellular domain). A particularly preferred fragment is that recited in SEQ ID NO: 180, which consists of amino acids 396-412 of CT042.

(5) SucB1 One example of a SucB1 protein is disclosed in reference 4 (GenBank accession number: AAC67646; GenInfo Identifier: 3328448; 'CT055'; SEQ ID NO: 181 herein).

Preferred SucB 1 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 181; and/or (b) which is a fragment of at least n consecutive amino acids of SEQ ID NO: 181, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 181. Preferred fragments of (b) comprise an epitope from SEQ ID NO: 181. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 181. Other fragments omit one or more domains of the protein (e.g. omission of a signal peptide, of a cytoplasmic domain, of a transmembrane domain, or of an extracellular domain). A particularly preferred fragment is that recited in SEQ ID NO: 182, which consists of amino acids 213-225 of SucB1.

(6) ClpB One example of a ClpB protein is disclosed in reference 4 (GenBank accession number: AAC67704; GenInfo Identifier: 3328511; 'CT113'; SEQ ID NO: 256 herein).

Preferred ClpB proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 256; and/or (b) which is a fragment of at least n consecutive amino acids of SEQ ID NO: 256, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 256. Preferred fragments of (b) comprise an epitope from SEQ ID NO: 256. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 256. Other fragments omit one or more domains of the protein (e.g. omission of a signal peptide, of a cytoplasmic domain, of a transmembrane domain, or of an extracellular domain).

(7) Rs9 One example of a Rs9 protein is disclosed in reference 4 (GenBank accession number: AAC67717; GenInfo Identifier: 3328525; 'CT126'; SEQ ID NO: 183 herein).

Preferred Rs9 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 183; and/or (b) which is a fragment of at least n consecutive amino acids of SEQ ID NO: 183, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 183. Preferred fragments of (b) comprise an epitope from SEQ ID NO: 183. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 183. Other fragments omit one or more domains of the protein (e.g. omission of a signal peptide, of a cytoplasmic domain, of a transmembrane domain, or of an extracellular domain). A particularly preferred fragment is that recited in SEQ ID NO: 184, which consists of amino acids 66-79 of Rs9.

(8) DhnA One example of a DhnA protein is disclosed in reference 4 (GenBank accession number: AAC67807; GenInfo Identifier: 3328623; 'CT215'; SEQ ID NO: 185 herein).

Preferred DhnA proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 185; and/or (b) which is a fragment of at least n consecutive amino acids of SEQ ID NO: 185, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 185. Preferred fragments of (b) comprise an epitope from SEQ ID NO: 185. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 185. Other fragments omit one or more domains of the protein (e.g. omission of a signal peptide, of a cytoplasmic domain, of a transmembrane domain, or of an extracellular domain). A particularly preferred fragment is that recited in SEQ ID NO: 186, which consists of amino acids 283-302 of DhnA.

(9) AcpP One example of a AcpP protein is disclosed in reference 4 (GenBank accession number: AAC67828; GenInfo Identifier: 3328645; 'CT236'; SEQ ID NO: 187 herein).

Preferred AcpP proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 187; and/or (b) which is a fragment of at least n consecutive amino acids of SEQ ID NO: 187, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 187. Preferred fragments of (b) comprise an epitope from SEQ ID NO: 187. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 187. Other fragments omit one or more domains of the protein (e.g. omission of a signal peptide, of a cytoplasmic domain, of a transmembrane domain, or of an extracellular domain). A particularly preferred fragment is that recited in SEQ ID NO: 188, which consists of amino acids 9-23 of AcpP.

(10) HimD One example of a HimD protein is disclosed in reference 4 (GenBank accession number: AAC67860; GenInfo Identifier: 3328679; 'CT267'; SEQ ID NO: 189 herein).

Preferred HimD proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 189; and/or (b) which is a fragment of at least n consecutive amino acids of SEQ ID NO: 189, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 189. Preferred fragments of (b) comprise an epitope from SEQ ID NO: 189. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 189. Other fragments omit one or more domains of the protein (e.g. omission of a signal peptide, of a cytoplasmic domain, of a transmembrane domain, or of an extracellular domain). A particularly preferred fragment is that recited in SEQ ID NO: 190, which consists of amino acids 35-44 of HimD.

(11) Tal One example of a Tal (transaldolase) protein is disclosed in reference 4 (GenBank accession number: AAC67906; GenInfo Identifier: 3328729; 'CT313'; SEQ ID NO: 191 herein).

Preferred Tal proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 191; and/or (b) which is a fragment of at least n consecutive amino acids of SEQ ID NO: 191, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 191. Preferred fragments of (b) comprise an epitope from SEQ ID NO: 191. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 191. Other fragments omit one or more domains of the protein (e.g. omission of a signal peptide, of a cytoplasmic domain, of a transmembrane domain, or of an extracellular domain). A particularly preferred fragment is that recited in SEQ ID NO: 192, which consists of amino acids 10-25 of Tal.

(12) DksA One example of a DksA protein is disclosed in reference 4 (GenBank accession number: AAC68004; GenInfo Identifier: 3328835; 'CT407'; SEQ ID NO: 193 herein).

Preferred DksA proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 193; and/or (b) which is a fragment of at least n consecutive amino acids of SEQ ID NO: 193, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 193. Preferred fragments of (b) comprise an epitope from SEQ ID NO: 193. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 193. Other fragments omit one or more domains of the protein (e.g. omission of a signal peptide, of a cytoplasmic domain, of a transmembrane domain, or of an extracellular domain). A particularly preferred fragment is that recited in SEQ ID NO: 194, which consists of amino acids 2-12 of DksA.

(13) CT425 One example of a CT425 protein is disclosed in reference 4 (GenBank accession number: AAC68022; GenInfo Identifier: 3328855; 'CT425'; SEQ ID NO: 195 herein). A biological function for CT425 proteins has not previously been described.

Preferred CT425 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 195; and/or (b) which is a fragment of at least n consecutive amino acids of SEQ ID NO: 195, wherein n is 7 or more (e.g. 8, 10, 12, 14, 16, 18, 20, 25, 30, 35, 40, 50, 60, 70, 80, 90, 100, 150, 200, 250 or more). These CT425 proteins include variants (e.g. allelic variants, homologs, orthologs, paralogs, mutants, etc.) of SEQ ID NO: 195. Preferred fragments of (b) comprise an epitope from SEQ ID NO: 195. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 195. Other fragments omit one or more domains of the protein (e.g. omission of a signal peptide, of a cytoplasmic domain, of a transmembrane domain, or of an extracellular domain). A particularly preferred fragment is that recited in SEQ ID NO: 196, which consists of amino acids 143-156 of CT425.

(14) Ym74 One example of a Ym74 protein is disclosed in reference 4 (GenBank accession number: AAC68060; GenInfo Identifier: 3328894; 'CT460'; SEQ ID NO: 197 herein).

Preferred Ym74 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 197; and/or (b) which is a fragment of at least n consecutive amino acids of SEQ ID NO: 197, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 197. Preferred fragments of (b) comprise an epitope from SEQ ID NO: 197. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 197. Other fragments omit one or more domains of the protein (e.g. omission of a signal peptide, of a cytoplasmic domain, of a transmembrane domain, or of an extracellular domain). A particularly preferred fragment is that recited in SEQ ID NO: 198, which consists of amino acids 44-53 of Ym74.

(15) Rl15 One example of a Rl15 protein is disclosed in reference 4 (GenBank accession number: AAC68112; GenInfo Identifier: 3328948; 'CT511'; SEQ ID NO: 199 herein).

Preferred Rl15 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 199; and/or (b) which is a fragment of at least n consecutive amino acids of SEQ ID NO: 199, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 199. Preferred fragments of (b) comprise an epitope from SEQ ID NO: 199. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 199. Other fragments omit one or more domains of the protein (e.g. omission of a signal peptide, of a cytoplasmic domain, of a transmembrane domain, or of an extracellular domain). A particularly preferred fragment is that recited in SEQ ID NO: 200, which consists of amino acids 84-100 of Rl15.

(16) Rs5 One example of a Rs5 protein is disclosed in reference 4 (GenBank accession number: AAC68113; GenInfo Identifier: 3328949; 'CT512'; SEQ ID NO: 201 herein).

Preferred Rs5 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 201; and/or (b) which is a fragment of at least n consecutive amino acids of SEQ ID NO: 201, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 201. Preferred fragments of (b) comprise an epitope from SEQ ID NO: 201. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 201. Other fragments omit one or more domains of the protein (e.g. omission of a signal peptide, of a cytoplasmic domain, of a transmembrane domain, or of an extracellular domain). A particularly preferred fragment is that recited in SEQ ID NO: 202, which consists of amino acids 130-141 of Rs5.

(17) Rl6 One example of a Rl6 protein is disclosed in reference 4 (GenBank accession number: AAC68115; GenInfo Identifier: 3328951; 'CT514'; SEQ ID NO: 203 herein).

Preferred Rl6 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 203; and/or (b) which is a fragment of at least n consecutive amino acids of SEQ ID NO: 203, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 203. Preferred fragments of (b) comprise an epitope from SEQ ID NO: 203. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 203. Other fragments omit one or more domains of the protein (e.g. omission of a signal peptide, of a cytoplasmic domain, of a transmembrane domain, or of an extracellular domain). A particularly preferred fragment is that recited in SEQ ID NO: 204, which consists of amino acids 116-128 of Rl6.

(18) Rl24 One example of a Rl24 protein is disclosed in reference 4 (GenBank accession number: AAC68118; GenInfo Identifier: 3328954; 'CT517'; SEQ ID NO: 205 herein).

Preferred Rl24 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 205; and/or (b) which is a fragment of at least n consecutive amino acids of SEQ ID NO: 205, wherein n is 7 or more (e.g. 8, 10, 12, 14, 16, 18, 20, 25, 30, 35, 40, 50, 60, 70, 80; 90, 100, 150, 200, 250 or more). These proteins include variants (e.g. allelic variants, homologs, orthologs, paralogs, mutants, etc.) of SEQ ID NO: 205. Preferred fragments of (b) comprise an epitope from SEQ ID NO: 205. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 205. Other fragments omit one or more domains of the protein (e.g. omission of a signal peptide, of a cytoplasmic domain, of a transmembrane domain, or of an extracellular domain). A particularly preferred fragment is that recited in SEQ ID NO: 206, which consists of amino acids 95-104 of Rl24.

(19) Rl22 One example of a Rl22 protein is disclosed in reference 4 (GenBank accession number: AAC68124; GenInfo Identifier: 3328960; 'CT523'; SEQ ID NO: 207 herein).

Preferred Rl22 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 207; and/or (b) which is a fragment of at least n consecutive amino acids of SEQ ID NO: 207, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 207. Preferred fragments of (b) comprise an epitope from SEQ ID NO: 207. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 207. Other fragments omit one or more domains of the protein (e.g. omission of a signal peptide, of a cytoplasmic domain, of a transmembrane domain, or of an extracellular domain). A particularly preferred fragment is that recited in SEQ ID NO: 208, which consists of amino acids 49-64 of Rl22.

(20) Rl2 One example of a Rl2 protein is disclosed in reference 4 (GenBank accession number: AAC68126; GenInfo Identifier: 3328962; 'CT525'; SEQ ID NO: 209 herein).

Preferred Rl2 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 209; and/or (b) which is a fragment of at least n consecutive amino acids of SEQ ID NO: 209, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 209. Preferred fragments of (b) comprise an epitope from SEQ ID NO: 209. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 209. Other fragments omit one or more domains of the protein (e.g. omission of a signal peptide, of a cytoplasmic domain, of a transmembrane domain, or of an extracellular domain). A particularly preferred fragment is that recited in SEQ ID NO: 210, which consists of amino acids 233-249 of Rl2.

(21) Rl4 One example of a Rl4 protein is disclosed in reference 4 (GenBank accession number: AAC68128; GenInfo Identifier: 3328964; 'CT527'; SEQ ID NO: 211 herein).

Preferred Rl4 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 211; and/or (b) which is a fragment of at least n consecutive amino acids of SEQ ID NO: 211, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 211. Preferred fragments of (b) comprise an epitope from SEQ ID NO: 211. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 211. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 212 and 213, which consist of amino acids 123-139 and 184-200 of Rl4 respectively.

(22) LcrH1 One example of a LcrH1 protein is disclosed in reference 4 (GenBank accession number: AAC68178; GenInfo Identifier: 3329018; 'CT576'; SEQ ID NO: 214 herein). It is postulated that CT576 forms part of a Type Three Secretion System (TTSS).

Preferred LcrH1 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 214; and/or (b) which is a fragment of at least n consecutive amino acids of SEQ ID NO: 214, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 214. Preferred fragments of (b) comprise an epitope from SEQ ID NO: 214. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 214. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 215 and 216, which consist of amino acids 42-51 and 159-177 of LcrH1 respectively.

(23) AhpC One example of an AhpC protein is disclosed in reference 4 (GenBank accession number: AAC67809; GenInfo Identifier: 3328625; 'CT603'; SEQ ID NO: 217 herein).

Preferred AhpC proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 217; and/or (b) which is a fragment of at least n consecutive amino acids of SEQ ID NO: 217, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 217. Preferred fragments of (b) comprise an epitope from SEQ ID NO: 217. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 217. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 218, 219 and 220, which consist of amino acids 89-107, 108-124 and 137-147 of AhpC respectively.

(24) CT610 One example of a CT610 protein is disclosed in reference 4 (GenBank accession number: AAC68213; GenInfo Identifier: 3329055; 'CT610'; SEQ ID NO: 221 herein). A biological function for CT610 proteins has not previously been described.

Preferred CT610 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 221; and/or (b) which is a fragment of at least n consecutive amino acids of SEQ ID NO: 221, wherein n is 7 or more (e.g. 8, 10, 12, 14, 16, 18, 20, 25, 30, 35, 40, 50, 60, 70, 80, 90, 100, 150, 200, 250 or more). These CT610 Hypothetical proteins include variants (e.g. allelic variants, homologs, orthologs, paralogs, mutants, etc.) of SEQ ID NO: 221. Preferred fragments of (b) comprise an epitope from SEQ ID NO: 221. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 221. Other fragments omit one or more domains of the protein (e.g. omission of a signal peptide, of a cytoplasmic domain, of a transmembrane domain, or of an extracellular domain). A particularly preferred fragment is that recited in SEQ ID NO: 222, which consists of amino acids 94-116 of CT610.

(25) CT622 One example of a CT622 protein is disclosed in reference 4 (GenBank accession number: AAS90241; GenInfo Identifier: 46370936; 'CT622'; SEQ ID NO: 223 herein). CT622 is predicted to be a CHLPN 76 kD homologue.

Preferred CT622 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 223; and/or (b) which is a fragment of at least n consecutive amino acids of SEQ ID NO: 223, wherein n is 7 or more (e.g. 8, 10, 12, 14, 16, 18, 20, 25, 30, 35, 40, 50, 60, 70, 80, 90, 100, 150, 200, 250 or more). These CT622 proteins include variants (e.g. allelic variants, homologs, orthologs, paralogs, mutants, etc.) of SEQ ID NO: 223. Preferred fragments of (b) comprise an epitope from SEQ ID NO: 223. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 223. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 224, 225 and 259, which consist of amino acids 70-91, 109-123 and 443-459 of CT622 respectively.

(26) CT664 One example of a CT664 protein is disclosed in reference 4 (GenBank accession number: AAC68259; GenInfo Identifier: 3329115; 'CT664'; SEQ ID NO: 226 herein). CT664 is predicted to be a FHA domain with homology to adenylate cyclase.

Preferred CT664 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%; 98%, 99%, 99.5% or more) to SEQ ID NO: 226; and/or (b) which is a fragment of at least n consecutive amino acids of SEQ ID NO: 226, wherein n is 7 or more (e.g. 8, 10, 12, 14, 16, 18, 20, 25, 30, 35, 40, 50, 60, 70, 80, 90, 100, 150, 200, 250 or more). These CT664 proteins include variants (e.g. allelic variants, homologs, orthologs, paralogs, mutants, etc.) of SEQ ID NO: 226. Preferred fragments of (b) comprise an epitope from SEQ ID NO: 226. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 226. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 227-231 and 232, which consist of amino acids 186-200, 343-356, 297-312, 313-330, 357-372 and 405-426 of CT664 respectively.

(27) FliN One example of a FliN protein is disclosed in reference 4 (GenBank accession number: AAC68267; GenInfo Identifier: 3329123; 'CT672'; SEQ ID NO: 233 herein). This protein is a flagellar motor switch domain of the YscQ family.

Preferred FliN proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 233; and/or (b) which is a fragment of at least n consecutive amino acids of SEQ ID NO: 233, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 233. Preferred fragments of (b) comprise an epitope from SEQ ID NO: 233. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 233. Other fragments omit one or more domains of the protein (e.g. omission of a signal peptide, of a cytoplasmic domain, of a transmembrane domain, or of an extracellular domain). A particularly preferred fragment is that recited in SEQ ID NO: 234, which consists of amino acids 90-105 of FliN.

(28) PyrH One example of a PyrH protein is disclosed in reference 4 (GenBank accession number: AAC68273; GenInfo Identifier: 3329130; 'CT678'; SEQ ID NO: 235 herein). This protein is a UMP kinase.

Preferred PyrH proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 235; and/or (b) which is a fragment of at least n consecutive amino acids of SEQ ID NO: 235, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 235. Preferred fragments of (b) comprise an epitope from SEQ ID NO: 235. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 235. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 236 and 237, which consist of amino acids 13-26 and 61-72 of PyrH.

(29) CT741 One example of a CT741 protein is disclosed in reference 4 (GenBank accession number: AAC68336; GenInfo Identifier: 3329200; 'CT741'; SEQ ID NO: 238 herein). A biological function for CT741 proteins has not previously been described.

Preferred CT741 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 238; and/or (b) which is a fragment of at least n consecutive amino acids of SEQ ID NO: 238, wherein n is 7 or more (e.g. 8, 10, 12, 14, 16, 18, 20, 25, 30, 35, 40, 50, 60, 70, 80, 90, 100, 150, 200, 250 or more). These CT741 hypothetical proteins include variants (e.g. allelic variants, homologs, orthologs, paralogs, mutants, etc.) of SEQ ID NO: 238. Preferred fragments of (b) comprise an epitope from SEQ ID NO: 238. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 238. Other fragments omit one or more domains of the protein (e.g. omission of a signal peptide, of a cytoplasmic domain, of a transmembrane domain, or of an extracellular domain). A particularly preferred fragment is that recited in SEQ ID NO: 239, which consists of amino acids 73-86 of CT741.

(30) Efp2 One example of an Efp2 (elongation factor P) protein is disclosed in reference 4 (GenBank accession number: AAC68347; GenInfo Identifier: 3329213; 'CT752'; SEQ ID NO: 240 herein).

Preferred Efp2 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 240; and/or (b) which is a fragment of at least n consecutive amino acids of SEQ ID NO: 240, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 240. Preferred fragments of (b) comprise an epitope from SEQ ID NO: 240. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 240. Other fragments omit one or more domains of the protein (e.g. omission of a signal peptide, of a cytoplasmic domain, of a transmembrane domain, or of an extracellular domain). A particularly preferred fragment is that recited in SEQ ID NO: 241, which consists of amino acids 163-176 of Efp2.

(31) CT768 One example of a CT768 protein is disclosed in reference 4 (GenBank accession number: AAC68363; GenInfo Identifier: 3329231; 'CT768'; SEQ ID NO: 242 herein). A biological function for CT768 proteins has not previously been described.

Preferred CT768 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 242; and/or (b) which is a fragment of at least n consecutive amino acids of SEQ ID NO: 242, wherein n is 7 or more (e.g. 8, 10, 12, 14, 16, 18, 20, 25, 30, 35, 40, 50, 60, 70, 80, 90, 100, 150, 200, 250 or more). These CT768 hypothetical proteins include variants (e.g. allelic variants, homologs, orthologs, paralogs, mutants, etc.) of SEQ ID NO: 242. Preferred fragments of (b) comprise an epitope from SEQ ID NO: 242. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 242. Other fragments omit one or more domains of the protein (e.g. omission of a signal peptide, of a cytoplasmic domain, of a transmembrane domain, or of an extracellular domain). A particularly preferred fragment is that recited in SEQ ID NO: 243, which consists of amino acids 461-472 of CT768.

(32) CT771 One example of a CT771 protein is disclosed in reference 4 (GenBank accession number: AAC68366; GenInfo Identifier: 3329234; 'CT771'; SEQ ID NO: 244 herein). CT771 is predicted to be a hydrolase/phosphatase homologue.

Preferred CT771 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 244; and/or (b) which is a fragment of at least n consecutive amino acids of SEQ ID NO: 244, wherein n is 7 or more (e.g. 8, 10, 12, 14, 16, 18, 20, 25, 30, 35, 40, 50, 60, 70, 80, 90, 100, 150, 200, 250 or more). These CT771 proteins include variants (e.g. allelic variants, homologs, orthologs, paralogs, mutants, etc.) of SEQ ID NO: 244. Preferred fragments of (b) comprise an epitope from SEQ ID NO: 244. Other preferred fragments lack one or more amino acids (e.g. 1, 2, 3, 4, 5, 6, 7, 8, 9, 10; 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 244. Other fragments omit one or more domains of the protein (e.g. omission of a signal peptide, of a cytoplasmic domain, of a transmembrane domain, or of an extracellular domain). A particularly preferred fragment is that recited in SEQ ID NO: 245, which consist of amino acids 59-74 of CT771 respectively.

(33) Ldh One example of a Ldh (leucine dehydrogenase) protein is disclosed in reference 4 (GenBank accession number: AAC68368; GenInfo Identifier: 3329236; 'CT773'; SEQ ID NO: 246 herein).

Preferred Ldh proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 246; and/or (b) which is a fragment of at least n consecutive amino acids of SEQ ID NO: 246, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 246. Preferred fragments of (b) comprise an epitope from SEQ ID NO: 246. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 246. Other fragments omit one or more domains of the protein (e.g. omission of a signal peptide, of a cytoplasmic domain, of a transmembrane domain, or of an extracellular domain). A particularly preferred fragment is that recited in SEQ ID NO: 247, which consists of amino acids 253-269 of Ldh.

(34) Rl35 One example of a 8135 (L35 ribosomal) protein is disclosed in reference 4 (GenBank accession number: AAC68431; Geninfo Identifier: 3329305; 'CT834'; SEQ ID NO: 248 herein).

Preferred Rl35 proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 248; and/or (b) which is a fragment of at least n consecutive amino acids of SEQ ID NO: 248, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 248. Preferred fragments of (b) comprise an epitope from SEQ ID NO: 248. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 248. Other fragments omit one or more domains of the protein (e.g. omission of a signal peptide, of a cytoplasmic domain, of a transmembrane domain, or of an extracellular domain). A particularly preferred fragment is that recited in SEQ ID NO: 249, which consists of amino acids 47-59 of Rl35.

(35) FtsH One example of a FtsH (ATP-dependent zinc protease) protein is disclosed in reference 4 (GenBank accession number: AAC68438; GenInfo Identifier: 3329313; 'CT841'; SEQ ID NO: 250 herein).

Preferred FtsH proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 250; and/or (b) which is a fragment of at least n consecutive amino acids of SEQ ID NO: 250, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 250. Preferred fragments of (b) comprise an epitope from SEQ ID NO: 250. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 250. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 251 and 252, which consist of amino acids 252-264 and 626-632 of FtsH.

(36) Pnp One example of a Pnp (polynucleotide transferase) protein is disclosed in reference 4 (GenBank accession number: AAC68439; GenInfo Identifier: 3329314; 'CT842'; SEQ ID NO: 253 herein).

Preferred Pnp proteins for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 253; and/or (b) which is a fragment of at least n consecutive amino acids of SEQ ID NO: 253, wherein n is 7 or more (e.g. 8, 10, 12, 14, 16, 18, 20, 25, 30, 35, 40, 50, 60, 70, 80, 90, 100, 150, 200, 250 or more). These proteins include variants (e.g. allelic variants, homologs, orthologs, paralogs, mutants, etc.) of SEQ ID NO: 253. Preferred fragments of (b) comprise an epitope from SEQ ID NO: 253. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 253. Other fragments omit one or more domains of the protein (e.g. omission of a signal peptide, of a cytoplasmic domain, of a transmembrane domain, or of an extracellular domain). Particularly preferred fragments are those recited in SEQ ID NOs: 254 and 255, which consist of amino acids 261-270 and 271-294 of Pnp.

Preferably, a composition according to the invention comprises one or more (i.e. 1, 2, 3, 4, 5, 6, 7, 8, 9, 10, 11, 12, 13, 14, 15, 16, 17, 18, 19 or all 20) Chlamydia trachomatis antigens of the first antigen group combined with one of the following combinations of Chlamydia trachomatis antigens: (1) CT016 and CT128 and CT671 and CT262; (2) CT296 and CT372 and CT635 and CT859; (3) CT412 and CT480 and CT869 and CT871; (4) CT050 and CT153 and CT157 and CT165; (5) CT276 and CT296 and CT456 and CT480; (6) CT089 and CT381 and CT396 and CT548; (7) CT635 and CT700 and CT711 and CT859; (8) CT812 and CT869 and CT552 and CT671; (9) CT713 and CT017 and CT043 and CT082; (10)'CT266 and CT443 and CT559 a CT597; and (11) CT045 and CT089 and CT396 and CT398 and CT39 (12) CT681 and CT547; (13) CT623 and CT414.

Preferably, a composition according to the invention comprises or consists of a) CT587, CT823, CT043, CT396 and CT381; and/or b) CT467, CT153, CT398 and CT480.

Preferably, a composition according to the invention comprises one or more of the epitopes recited in SEQ ID NOs: 261-275.

Preferably a composition according to the invention comprises one or more (i.e. 1, 2, 3, 4, 5, 6, 7, 8, 9, 10, 11, 12, 13, 14, 15, 16, 17, 18, 19, 20, 21, 22, 23, 24, 25 or all 26) Chlamydia trachomatis antigens of the first antigen group combined with the Chlamydia pneumoniae polypeptide referred to as SEQ ID NO: 2 in WO01/75114 or the polypeptide referred to as SEQ ID NO: 2 in WO01/075113 or a fragment thereof or a polypeptide holmologous thereto. Such polypeptide fragments preferably are at least 12 amino acids in length. Advantageously, they are at least 15 amino acids, preferably at least 20, 25, 30, 35, 40, 45, 50 amino acids, more preferably at least 55, 60, 65, 70, 75 amino acids, and most preferably at least 80, 85, 90, 95, 100 amino acids in length. Preferably the fragment comprises a T- and/or B-cell epitope.

Alternatively, a composition according to the invention comprises one or more (i.e. 1, 2, 3, 4, 5, 6, 7, 8, 9, 10, 11, 12, 13, 14, 15, 16, 17, 18, 19, 20, 21, 22, 23, 24, 25 or all 26) Chlamydia trachomatis antigens of the first antigen group combined with the Chlamydia pneumoniae polypeptide referred to as SEQ ID NO: 1 in U.S. Pat. No. 6,491,924 or a fragment thereof or a polypeptide holmologous thereto. Such polypeptide fragments preferably are at least 12 amino acids in length. Advantageously, they are at least 15 amino acids, preferably at least 20, 25, 30, 35, 40, 45, 50 amino acids, more preferably at least 55, 60, 65, 70, 75 amino acids, and most preferably at least 80, 85, 90, 95, 100 amino acids in length. Preferably the fragment comprises a T- and/or B-cell epitope.

Type Three Secretion System

CT576, CT577, CT578 and CT579 are postulated to form part of a Type Three Secretion System (TTSS). CT576 is predicted to be a low calcium responsive protein H (lcrH1) similar to the lcrH encoded in the lcrGVH-yopBD operon of Yersinia, in proximity to YopBD. It therefore appears that CT579 is the Chlamydial equivalent of LcrV. LcrV is known to be an important virulence determinant (the V antigen) in Yersinia [52], and antibodies against this protein have been shown to be protective in a mouse model of plague [53].

Thus particularly preferred compositions of the invention comprise one or more CT579 antigens.

Fusion Proteins

The Chlamydia trachomatis antigens used in the invention may be present in the composition as individual separate polypeptides. Generally, the recombinant fusion proteins of the present invention are prepared as a GST-fusion protein and/or a His-tagged fusion protein.

Where more than one antigen is used, however, they do not have to be present as separate polypeptides. Instead, at least two (i.e. 2, 3, 4, 5, 6, 7, 8, 9, 10, 11, 12, 13, 14, 15, 16, 17, 18, 19, 20 or more) of the antigens can be expressed as a single polypeptide chain (a 'hybrid' polypeptide). Hybrid polypeptides offer two principal advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful.

The hybrid polypeptide may comprise two or more polypeptide sequences from the first antigen group. Accordingly, the invention includes a composition comprising a first amino acid sequence and a second amino acid sequence, wherein said first and second amino acid sequences are selected from a *Chlamydia trachomatis* antigen or a fragment thereof of the first antigen group. Preferably, the first and second amino acid sequences in the hybrid polypeptide comprise different epitopes.

The hybrid polypeptide may comprise one or more polypeptide sequences from the first antigen group and one or more polypeptide sequences from the second antigen group. Accordingly, the invention includes a composition comprising a first amino acid sequence and a second amino acid sequence, said first amino acid sequence selected from a *Chlamydia trachomatis* antigen or a fragment thereof from the first antigen group and said second amino acid sequence selected from a *Chlamydia trachomatis* antigen or a fragment thereof from the second antigen group. Preferably, the first and second amino acid sequences in the hybrid polypeptide comprise different epitopes.

The hybrid polypeptide may comprise one or more polypeptide sequences from the first antigen group and one or more polypeptide sequences from the third antigen group. Accordingly, the invention includes a composition comprising a first amino acid sequence and a second amino acid sequence, said first amino acid sequence selected from a *Chlamydia trachomatis* antigen or a fragment thereof from the first antigen group and said second amino acid sequence selected from a *Chlamydia trachomatis* antigen or a fragment thereof from the third antigen group.

Preferably, the first and second amino acid sequences in the hybrid polypeptide comprise different epitopes.

The hybrid polypeptide may comprise one or more polypeptide sequences from the first antigen group and one or more polypeptide sequences from the fourth antigen group. Accordingly, the invention includes a composition comprising a first amino acid sequence and a second amino acid sequence, said first amino acid sequence selected from a *Chlamydia trachomatis* antigen or a fragment thereof from the first antigen group and said second amino acid sequence selected from a *Chlamydia trachomatis* antigen or a fragment thereof from the fourth antigen group. Preferably, the first and second amino acid sequences in the hybrid polypeptide comprise different epitopes.

The hybrid polypeptide may comprise one or more polypeptide sequences from the first antigen group and one or more polypeptide sequences from the fifth antigen group. Accordingly, the invention includes a composition comprising a first amino acid sequence and a second amino acid sequence, said first amino acid sequence selected from a *Chlamydia trachomatis* antigen or a fragment thereof from the first antigen group and said second amino acid sequence selected from a *Chlamydia trachomatis* antigen or a fragment thereof from the fifth antigen group. Preferably, the first and second amino acid sequences in the hybrid polypeptide comprise different epitopes.

The hybrid polypeptide may comprise one or more polypeptide sequences from the first antigen group and one or more polypeptide sequences from the sixth antigen group. Accordingly, the invention includes a composition comprising a first amino acid sequence and a second amino acid sequence, said first amino acid sequence selected from a *Chlamydia trachomatis* antigen or a fragment thereof from the first antigen group and said second amino acid sequence selected from a *Chlamydia trachomatis* antigen or a fragment thereof from the sixth antigen group. Preferably, the first and second amino acid sequences in the hybrid polypeptide comprise different epitopes.

The hybrid polypeptide may comprise one or more polypeptide sequences from the first antigen group and one or more polypeptide sequences from the seventh antigen group. Accordingly, the invention includes a composition comprising a first amino acid sequence and a second amino acid sequence, said first amino acid sequence selected from a *Chlamydia trachomatis* antigen or a fragment thereof from the first antigen group and said second amino acid sequence selected from a *Chlamydia trachomatis* antigen or a fragment thereof from the seventh antigen group. Preferably, the first and second amino acid sequences in the hybrid polypeptide comprise different epitopes.

The hybrid polypeptide may comprise one or more polypeptide sequences from the first antigen group and one or more polypeptide sequences from the eighth antigen group. Accordingly, the invention includes a composition comprising a first amino acid sequence and a second amino acid sequence, said first amino acid sequence selected from a *Chlamydia trachomatis* antigen or a fragment thereof from the first antigen group and said second amino acid sequence selected from a *Chlamydia trachomatis* antigen or a fragment thereof from the eighth antigen group. Preferably, the first and second amino acid sequences in the hybrid polypeptide comprise different epitopes.

Hybrids consisting of amino acid sequences from two, three, four, five, six, seven, eight, nine, or ten *Chlamydia trachomatis* antigens are preferred. In particular, hybrids consisting of amino acid sequences from two, three, four, or five *Chlamydia trachomatis* antigens are preferred. Particularly preferred are hybrids consisting of amino acid sequences from two or three *Chlamydia trachomatis* antigens.

Different hybrid polypeptides may be mixed together in a single formulation. Within such combinations, a *Chlamydia trachomatis* antigen may be present in more than one hybrid polypeptide and/or as a non-hybrid polypeptide. It is preferred, however, that an antigen is present either as a hybrid or as a non-hybrid, but not as both.

Two antigen hybrids for use in the present invention may also comprise combinations of antigens selected from the second, third, fourth, fifth, sixth, seventh and eighth antigen groups.

Hybrid polypeptides can be represented by the formula $NH_2$-A-$\{$-X-L-$\}_n$-B—COOH, wherein: X is an amino acid sequence of a *Chlamydia trachomatis* antigen or a fragment thereof from the first antigen group, the second antigen group, the third antigen group, the fourth antigen group, the fifth antigen group, the sixth antigen group or the seventh antigen group; L is an optional linker amino acid sequence; A is an optional N-terminal amino acid sequence; B is an optional C-terminal amino acid sequence; and n is 2, 3, 4, 5, 6, 7, 8, 9, 10, 11, 12, 13, 14 or 15. At least one —X— moiety is from the first antigen group and (n-1) —X— moieties are from the first antigen group, the second antigen group, the third antigen group, the fourth antigen group, the fifth antigen group, the sixth antigen group or the seventh antigen group.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of {—X-L-}, linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG (SEQ ID NO: 104), with the Gly-Ser dipeptide being formed from a BamHI restriction site, thus aiding cloning and manipulation, and the $(Gly)_4$ tetrapeptide being a typical poly-glycine linker. The same variants apply to {—Y-L-}. Therefore, for each m instances of {—Y-L-}, linker amino acid sequence -L- may be present or absent.

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more), or sequences which enhance protein stability. Other suitable C-terminal amino acid sequences will be apparent to those skilled in the art. Most preferably, n is 2 or 3.

Preferred fusion protein compositions of the invention comprise one or more (i.e. 1, 2, 3, 4, 5, 6, 7, 8, 9, 10 or more) of CT587, 587his, gst587, CT823, 823his, gst823, CT043, 043his, gst043, CT396, 396his, gst396, CT381, 381his, gst381, CT467, 467his, gst467, CT153, 153his, gst153, CT398, 398his, gst398, CT480, 480his and/or gst480. According to this nomenclature, each antigen may have a N-terminal GST tag or a C-terminal his tag. Therefore, for example, 587his is CT587 with a C-terminal his tag and gst587 is CT587 with a N-terminal gst tag.

Preferably, a fusion protein composition according to the invention comprises one or more of the epitopes recited in SEQ ID NOs: 261-275.

The invention also provides nucleic acid encoding hybrid polypeptides of the invention. Furthermore, the invention provides nucleic acid which can hybridize to this nucleic acid, preferably under "high stringency" conditions (e.g. 65° C. in a 0.1×SSC, 0.5% SDS solution).

Polypeptides of the invention can be prepared by various means (e.g. recombinant expression, purification from cell culture, chemical synthesis, etc.) and in various forms (e.g. native, fusions, non-glycosylated, lipidated, etc.). They are preferably prepared in substantially pure form (i.e. substantially free from other chlamydial or host cell proteins).

Nucleic acid according to the invention can be prepared in many ways (e.g. by chemical synthesis, from genomic or cDNA libraries, from the organism itself, etc.) and can take various forms (e.g. single stranded, double stranded, vectors, probes, etc.). They are preferably prepared in substantially pure form (i.e. substantially free from other chlamydial or host cell nucleic acids).

The term "nucleic acid" includes DNA and RNA, and also their analogues, such as those containing modified backbones (e.g. phosphorothioates, etc.), and also peptide nucleic acids (PNA), etc. The invention includes nucleic acid comprising sequences complementary to those described above (e.g. for antisense or probing purposes).

The invention also provides a process for producing a polypeptide of the invention, comprising the step of culturing a host cell transformed with nucleic acid of the invention under conditions which induce polypeptide expression.

The invention provides a process for producing a polypeptide of the invention, comprising the step of synthesizing at least part of the polypeptide by chemical means.

The invention provides a process for producing nucleic acid of the invention, comprising the step of amplifying nucleic acid using a primer-based amplification method (e.g. PCR).

The invention provides a process for producing nucleic acid of the invention, comprising the step of synthesizing at least part of the nucleic acid by chemical means.

Polypeptides Used With the Invention

Polypeptides used with the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). F1, for instance, is known to exist in various forms, including a multimeric glycoprotein form. Lipoproteins are particularly preferred for use as immunogens.

Polypeptides used with the invention can be prepared by various means (e.g. recombinant expression, purification from cell culture, chemical synthesis, etc.). Recombinantly-expressed proteins are preferred, particularly for hybrid polypeptides.

Polypeptides used with the invention are preferably provided in purified or substantially purified form i.e. substantially free from other polypeptides (e.g. free from naturally-occurring polypeptides), particularly from other *Chlamydia* or host cell polypeptides, and are generally at least about 50% pure (by weight), and usually at least about 90% pure i.e. less than about 50%, and more preferably less than about 10% (e.g. 5%) of a composition is made up of other expressed polypeptides. Thus the antigens in the compositions are separated from the whole organism with which the molecule is expressed.

Polypeptides used with the invention are preferably *C. trachomatis* polypeptides.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included are, for example, polypeptides containing one or more analogs of an amino acid (including, for example, unnatural amino acids, etc.), as well as other modifications known in the art. Polypeptides can occur as single chains or associated chains.

The invention provides polypeptides comprising a sequence —P-Q- or -Q-P—, wherein: —P— is an amino acid sequence as defined above and -Q- is not a sequence as defined above i.e. the invention provides fusion proteins. Where the N-terminus codon of —P— is not ATG, but this codon is not present at the N-terminus of a polypeptide, it will be translated as the standard amino acid for that codon rather than as a Met. Where this codon is at the N-terminus of a polypeptide, however, it will be translated as Met. Polypeptides used with the invention may be prepared as a GST-fusion protein and/or a His-tagged fusion protein.

Strains

The human serovars of *C. trachomatis* are divided into two biovariants ("biovars"). Serovars L1, L2 and L3 are the agents of invasive lymphogranuloma venereum (LGV) which is a sexually transmitted systemic infection. LGV is uncommon in industrialized countries but frequent in Africa, Asia, Australian and South America. It predominantly affects lymphatic tissue but may also occur as an acute symptomatic infection without apparent lymph node involvement or tissue reaction at the point of infection. Acute LGV is reported over five times more frequent in men than in women. Other biotypes of *C. trachomatis* include serovars A, B, Ba, and C which are associated with trachoma, a transmissible condition of the eye.

Serovars A-K (D, E, F, G, H, I, J and K) are typically associated with genital tract disease.

In particular, Serovars D, E, F, H and K account for nearly 85% of genital tract infections (see, for example, reference 54). Serovars A-K elicit epithelial infections primarily in the ocular tissue (A-C) or urogenital tract (D-K). Research to date also indicates that the 4 Serovars (or serotypes) responsible for Sexually Transmitted Infections or Diseases (STIs or STDs) in the US and Europe are D-K, preferably D, E, F and I.

Preferred polypeptides of the invention comprise an amino acid sequence found in *C. trachomatis* serovar A, B, C, D, E, K, L1, L2 or L3 or in one or more of an epidemiologically prevalent serovar. More preferably, the polypeptides of the invention comprise an amino acid sequence found in *C. trachomatis* serovar D, E or K. More preferably, the polypeptides of the invention comprise an amino acid sequence found in *C. trachomatis* serovar D.

Preferably, polypeptides of the invention comprise an amino acid sequence from a trachoma biovar of *C. trachomatis*.

Preferred polypeptides of the invention comprise an amino acid sequence found in *C. trachomatis* strains D/UW-3/CX or L2/434/BU [4].

The polypeptides of the invention may also be obtained from *C. pneumoniae*.

Where hybrid polypeptides are used, the individual antigens within the hybrid (i.e. individual —X— moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2 \neq X_3$ (iii) $X_1 \neq X_2 = X_3$ (iv) $X_1 = X_2 \neq X_3$ or (v) $X_1 \neq X_3 \neq X_2$, etc.

Heterologous Hosts

Whilst expression of the polypeptides of the invention may take place in *Chlamydia*, the invention preferably utilizes a heterologous host. The heterologous host may be prokaryotic (e.g. a bacterium) or eukaryotic. It is preferably *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc.

Immunogenic Compositions and Medicaments

Compositions of the invention are preferably immunogenic compositions, and are more preferably vaccine compositions. The pH of the composition is preferably between 6 and 8, preferably about 7. The pH may be maintained by the use of a buffer. A phosphate buffer is typical. The composition may be sterile and/or pyrogen-free. The composition may be isotonic with respect to humans.

Vaccines according to the invention may either be prophylactic (i.e. to prevent infection) or therapeutic (i.e. to treat infection), but will typically be prophylactic. Accordingly, the invention includes a method for the therapeutic or prophylactic treatment of *Chlamydia trachomatis* infection in an animal susceptible to chlamydial infection comprising administering to said animal a therapeutic or prophylactic amount of the immunogenic compositions of the invention.

Compositions may include an antimicrobial, particularly if packaged in a multiple dose format.

Compositions may comprise detergent e.g. a Tween (polysorbate), such as Tween 80. Detergents are generally present at low levels e.g. <0.01%.

Compositions may include sodium salts (e.g. sodium chloride) to give tonicity. A concentration of 10±2 mg/ml NaCl is typical.

Compositions may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilization may be adjusted to around 6.1 prior to lyophilization.

The compositions of the invention may also comprise one or more immunoregulatory agents. Preferably, one or more of the immunoregulatory agents include(s) an adjuvant. The adjuvant may be selected from one or more of the group consisting of a TH1 adjuvant and TH2 adjuvant, further discussed below.

Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 55], or mixtures of different mineral compounds, with the compounds taking any suitable form (e.g. gel, crystalline, amorphous, etc.), and with adsorption being preferred. The mineral containing compositions may also be formulated as a particle of metal salt [56].

A typical aluminium phosphate adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

B. Oil Emulsions

Oil emulsion compositions suitable for use as adjuvants in the invention include oil-in-water emulsions and water-in-oil emulsions.

A submicron oil-in-water emulsion may include squalene, Tween 80, and Span 85 e.g. with a composition by volume of about 5% squalene, about 0.5% polysorbate 80 and about 0.5% Span 85 (in weight terms, 4.3% squalene, 0.5% polysorbate 80 and 0.48% Span 85), known as 'MF59' [57-59 chapter 10 of ref. 55; chapter 12 of ref. 60]. The MF59 emulsion advantageously includes citrate ions e.g. 10 mM sodium citrate buffer.

An emulsion of squalene, a tocopherol, and Tween 80 can be used The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≦1 as this provides a more stable emulsion. One such emulsion can be made by dissolving Tween 80 in PBS to give a 2% solution, then mixing 90 ml of this solution with a mixture of (5 g of DL-α-tocopherol and 5 ml squalene), then microfluidizing the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100) can be used.

An emulsion of squalane, polysorbate 80 and poloxamer 401 ("Pluronic™ L121") can be used. The emulsion can be formulated in phosphate buffered saline, pH 7.4. This emulsion is a useful delivery vehicle for muramyl dipeptides, and has been used with threonyl-MDP in the "SAF-1" adjuvant [61] (0.05-1% Thr-MDP, 5% squalane, 2.5% Pluronic L121 and 0.2% polysorbate 80). It can also be used without the Thr-MDP, as in the "AF" adjuvant [62] (5% squalane, 1.25% Pluronic L121 and 0.2% polysorbate 80). Microfluidisation is preferred.

Complete Freund's adjuvant (CFA) and incomplete Freund's adjuvant (IFA) may also be used.

C. Saponin Formulations [Chapter 22 of Ref 55]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 63. Saponin formulations may also comprise a sterol, such as cholesterol [64].

Combinations of saponins and cholesterols can be used to form unique particles called immunostimulating complexes (ISCOMs) [chapter 23 of ref. 55]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 64-66]. Optionally, the ISCOMS may be devoid of additional detergent [67].

A review of the development of saponin based adjuvants can be found in refs. 68 & 69.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in [70-75]. Virosomes are discussed further in, for example [76].

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 77. Such "small particles" of 3dMPL are small enough to be sterile filtered through a 0.22 μm membrane [77]. Other non-toxic LPS derivatives include monophosphoryl lipid A mimics, such as aminoalkyl glucosaminide phosphate derivatives e.g. RC-529 [78,79].

Lipid A derivatives include derivatives of lipid A from *Escherichia coli* such as OM-174. OM-174 is described for example in refs. 80 & 81.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 82, 83 and 84 disclose possible analog substitutions e.g. replacement of guanosine with 2'-deoxy-7-deazaguanosine. The adjuvant effect of CpG oligonucleotides is further discussed in refs. 85-90.

The CpG sequence may be directed to TLR9, such as the motif GTCGTT or TTCGTT [91]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 92-94. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 91 & 95-97.

Other immunostimulatory oligonucleotides include a double-stranded RNA, or an oligonucleotide containing a palindromic sequence, or an oligonucleotide containing a poly(dG) sequence.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 98 and as parenteral adjuvants in ref. 99. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 100-107. Numerical reference for amino acid substitutions is preferably based on the alignments of the A and B subunits of ADP-ribosylating toxins set forth in ref. 108, specifically incorporated herein by reference in its entirety.

Compounds of formula I, II or III (FIGS. 11A, 11B and 11C, respectively), can also be used as adjuvants:
as defined in reference 109, such as 'ER 803058', 'ER 803732', 'ER 804053', ER 804058', 'ER 804059', 'ER 804442', 'ER 804680', 'ER 804764', ER 803022 or 'ER 804057' e.g.:

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to

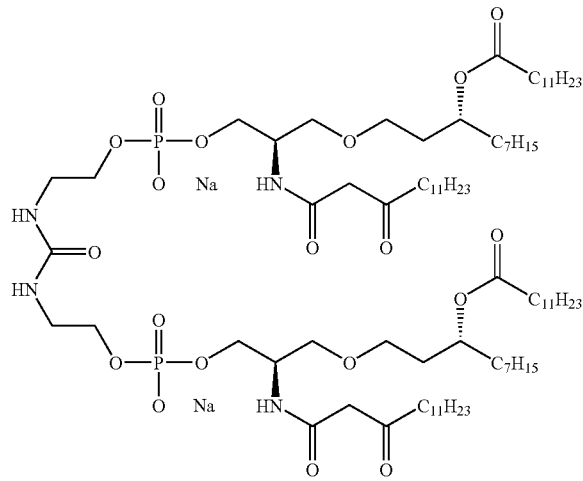

ER-803022:

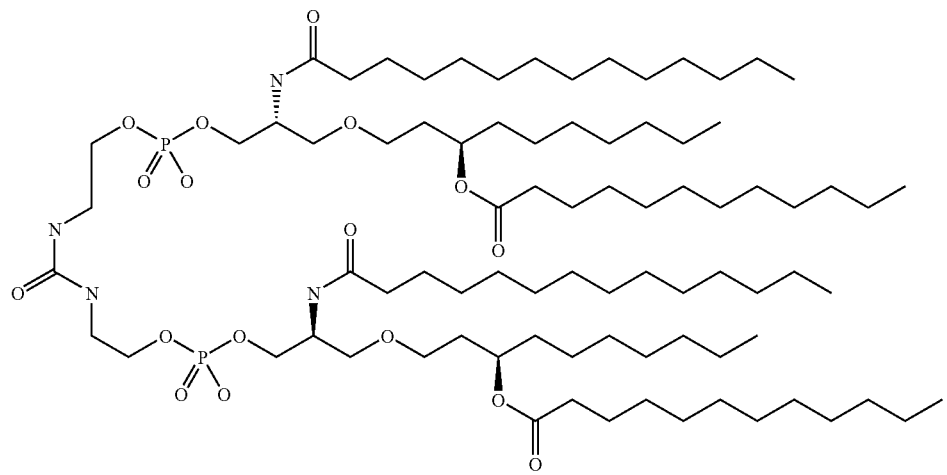

ER804057

F. Human Immunomodulators

Human immunomodulators suitable for use as adjuvants in the invention include cytokines, such as interleukins (e.g. IL-1, IL-2, IL-4, IL-5, IL-6, IL-7, IL-12 [110], IL-17, IL-18 [111], IL-23, IL27 [112] etc.) [113], interferons (e.g. interferon-γ), macrophage colony stimulating factor, tumor necrosis factor and macrophage inflammatory protein-1 alpha (MTP-1alpha) and MIP-1beta [114].

G. Bioadhesives and Mucoadhesives

Bioadhesives and mucoadhesives may also be used as adjuvants in the invention. Suitable bioadhesives include esterified hyaluronic acid microspheres [115] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [116].

have a negatively-charged surface (e.g. with SDS) or a positively-charged surface (e.g. with a cationic detergent, such as CTAB).

I. Liposomes (Chapters 13 & 14 of Ref 55)

Examples of liposome formulations suitable for use as adjuvants are described in refs. 117-119.

J. Polyoxyethylene Ether and Polyoxyethylene Ester Formulations

Adjuvants suitable for use in the invention include polyoxyethylene ethers and polyoxyethylene esters [120]. Such formulations further include polyoxyethylene sorbitan ester surfactants in combination with an octoxynol [121] as well as polyoxyethylene alkyl ethers or ester surfactants in combination with at least one additional non-ionic surfactant such as an octoxynol [122]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Phosphazenes (e.g. PCPP)

Phosphazene adjuvants include poly[di(carboxylatophenoxy)phosphazene] ("PCPP") as described, for example, in references 123 and 124.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolines

Imidazoquinoline adjuvants include Imiquimod ("R-837") [125,126], Resiquimod ("R-848") [127], and their analogs; and salts thereof (e.g. the hydrochloride salts). Further details about immunostimulatory imidazoquinolines can be found in references 128 to 132.

N. Thiosemicarbazones

Thiosemicarbazone adjuvants include those disclosed in reference 133. Methods of formulating, manufacturing, and screening for active compounds are also described in reference 131. The thiosemicarbazones are particularly effective in the stimulation of human peripheral blood mononuclear cells for the production of cytokines, such as TNF-α.

O. Tryptanthrins

Tryptanthrin adjuvants include those disclosed in reference 134. Methods of formulating, manufacturing, and screening for active compounds are also described in reference 134. The thiosemicarbazones are particularly effective in the stimulation of human peripheral blood mononuclear cells for the production of cytokines, such as TNF-α.

P. Nucleoside Analogs

Various nucleoside analogs can be used as adjuvants, such as (a) Isatorabine (ANA-245; 7-thia-8-oxoguanosine):

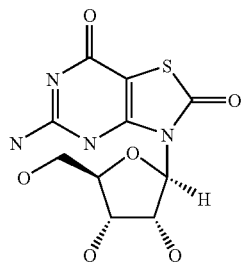 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 135 to 137; (f) a compound having the formula:

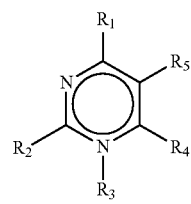

wherein:

$R_1$ and $R_2$ are each independently H, halo, —$NR_aR_b$, —OH, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;

$R_3$ is absent, H, $C_{1-6}$ alkyl, substituted $C_{1-6}$ alkyl, $C_{6-10}$ aryl, substituted $C_{6-10}$ heterocyclyl, or substituted heterocyclyl;

$R_4$ and $R_5$ are each independently H, halo, heterocyclyl, substituted heterocyclyl, —C(O)—$R_d$, $C_{1-6}$ alkyl, substituted $C_{1-6}$ alkyl, or bound together to form a 5 membered ring as in $R_{4-5}$:

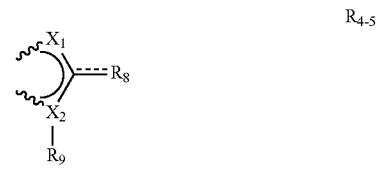

the binding being achieved at the bonds indicated by a ⁓

$X_1$ and $X_2$ are each independently N, C, O, or S;

$R_8$ is H, halo, —OH, $C_{1-6}$ alkyl, $C_{2-6}$ alkenyl, $C_{2-6}$ alkynyl, —OH, —$NR_aR_b$, —$(CH_2)_n$—O—$R_c$, —O—($C_{1-6}$ alkyl), —$S(O)_pR_e$, or —C(O)—$R_d$;

$R_9$ is H, $C_{1-6}$ alkyl, substituted $C_{1-6}$ alkyl, heterocyclyl, substituted heterocyclyl or $R_{9a}$, wherein $R_{9a}$ is:

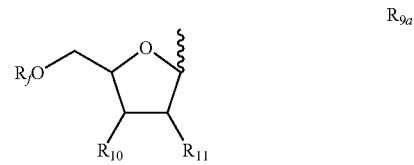

the binding being achieved at the bond indicated by a ⁓

$R_{10}$ and $R_{11}$ are each independently H, halo, $C_{1-6}$ alkoxy, substituted $C_{1-6}$ alkoxy, —$NR_aR_b$, or —OH;

each $R_a$ and $R_b$ is independently H, $C_{1-6}$ alkyl, substituted $C_{1-6}$ alkyl, —$C(O)R_d$, $C_{6-10}$ aryl;

each $R_c$ is independently H, phosphate, diphosphate, triphosphate, $C_{1-6}$ alkyl, or substituted $C_{1-6}$ alkyl;

each $R_d$ is independently H, halo, $C_{1-6}$ alkyl, substituted $C_{1-6}$ alkyl, $C_{1-6}$ alkoxy, substituted $C_{1-6}$ alkoxy, —$NH_2$, —$NH(C_{1-6}$ alkyl), —NH(substituted $C_{1-6}$ alkyl), —$N(C_{1-6}$ alkyl)$_2$, —N(substituted $C_{1-6}$ alkyl)$_2$, $C_{6-10}$ aryl, or heterocyclyl;

each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;

each $R_f$ is independently H, $C_{1-6}$ alkyl, substituted $C_{1-6}$ alkyl, —$C(O)R_d$, phosphate, diphosphate, or triphosphate;

each n is independently 0, 1, 2, or 3;

each p is independently 0, 1, or 2; or or (g) a pharmaceutically acceptable salt of any of (a) to (f), a tautomer of any of (a) to (f), or a pharmaceutically acceptable salt of the tautomer.

Q. Lipids Linked to a Phosphate-Containing Acyclic Backbone

Adjuvants containing lipids linked to a phosphate-containing acyclic backbone include the TLR4 antagonist E5564 [138,139]:

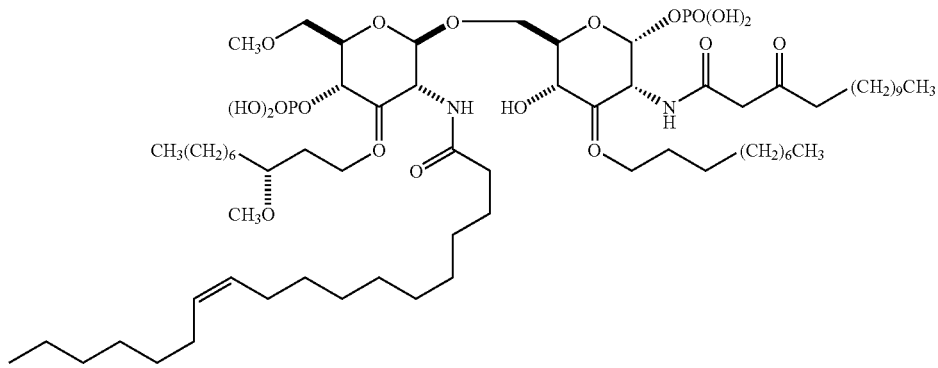

R. Small Molecule Immunopotentiators (SMIPs)
SMIPs include:
N2-methyl-1-(2-methylpropyl)-1H-imidazo[4,5-c]quinoline-2,4-diamine;
N2,N2-dimethyl-1-(2-methylpropyl)-1H-imidazo[4,5-c]quinoline-2,4-diamine;
N2-ethyl-N2-methyl-1-(2-methylpropyl)-1H-imidazo[4,5-c]quinoline-2,4-diamine;
N2-methyl-1-(2-methylpropyl)-N2-propyl-1H-imidazo[4,5-c]quinoline-2,4-diamine;
1-(2-methylpropyl)-N2-propyl-1H-imidazo [4,5-c]quinoline-2,4-diamine;
N2-butyl-1-(2-methylpropyl)-1H-imidazo[4,5-c]quinoline-2,4-diamine;
N2-butyl-N2-methyl-1-(2-methylpropyl)-1H-imidazo[4,5-c]quinoline-2,4-diamine;
N2-methyl-1-(2-methylpropyl)-N2-pentyl-1H-imidazo[4,5-c]quinoline-2,4-diamine;
N2-methyl-1-(2-methylpropyl)-N2-prop-2-enyl-1H-imidazo [4,5-c] quinoline-2,4-diamine;
1-(2-methylpropyl)-2-[(phenylmethyl)thio]-1H-imidazo[4,5-c]quinolin-4-amine;
1-(2-methylpropyl)-2-(propylthio)-1H-imidazo[4,5-c]quinolin-4-amine;
2-[[4-amino-1-(2-methylpropyl)-1H-imidazo[4,5-c]quinolin-2-yl](methyl)amino]ethanol;
2-[[4-amino-1-(2-methylpropyl)-1H-imidazo [4,5-c]quinolin-2-yl](methyl)amino]ethyl acetate;
4-amino-1-(2-methylpropyl)-1,3-dihydro-2H-imidazo[4,5-c]quinolin-2-one;
N2-butyl-1-(2-methylpropyl)-N4,N4-bis(phenylmethyl)-1H-imidazo[4,5-c]quinoline-2,4-diamine;
N2-butyl-N2-methyl-1-(2-methylpropyl)-N4,N4-bis(phenylmethyl)-1H-imidazo[4,5-c]quinoline-2,4-diamine;
N2-methyl-1-(2-methylpropyl)-N4,N4-bis(phenylmethyl)-1H-imidazo[4,5-c]quinoline-2,4-diamine;
N2,N2-dimethyl-1-(2-methylpropyl)-N4,N4-bis(phenylmethyl)-1H-imidazo[4,5-c]quinoline-2,4-diamine;
1-{4-amino-2-[methyl(propyl)amino]-1H-imidazo[4,5-c]quinolin-1-yl}-2-methylpropan-2-ol;
1-[4-amino-2-(propylamino)-1H-imidazo[4,5-c]quinolin-1-yl]-2-methylpropan-2-ol;
N4,N4-dibenzyl-1-(2-methoxy-2-methylpropyl)-N2-propyl-1H-imidazo[4,5-c]quinoline-2,4-diamine.

S. Proteosomes
One adjuvant is an outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of *Neisseria meningitidis* outer membrane and lipopolysaccharides. They have been used as adjuvants for influenza vaccines [140].

T. Other Adjuvants
Other substances that act as immunostimulating agents are disclosed in references 55 and 60. Further useful adjuvant substances include:
Methyl inosine 5'-monophosphate ("MIMP") [141].
A polyhydroxlated pyrrolizidine compound [142], such as one having formula:

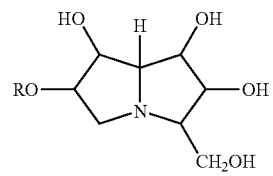

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepicasuarine, etc.

A gamma inulin [143] or derivative thereof, such as algammulin.
Compounds disclosed in reference 144.
Compounds disclosed in reference 145, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [146,147], Hydrapthalamide compounds, Benzophenone compounds, Isoxazole compounds, Sterol compounds, Quinazilinone compounds, Pyrrole compounds [148], Anthraquinone compounds, Quinoxaline compounds, Triazine compounds, Pyrazalopyrimidine compounds, and Benzazole compounds [149].
Loxoribine (7-allyl-8-oxoguanosine) [150].
A formulation of a cationic lipid and a (usually neutral) co-lipid, such as aminopropyl-dimethyl-myristoleyloxy-propanaminium bromide-diphytanoylphosphatidyl-ethanolamine ("Vaxfectin™") or aminopropyl-dimethyl-bis-dodecyloxy-propanaminium bromide-dioleoylphosphatidyl-ethanolamine ("GAP-DLRIE:

DOPE"). Formulations containing (±)-N-(3-aminopropyl)-N,N-dimethyl-2,3-bis(syn-9-tetradeceneyloxy)-1-propanaminium salts are preferred [151].

The invention may also comprise combinations of aspects of one or more of the adjuvants identified above. For example, the following adjuvant compositions may be used in the invention: (1) a saponin and an oil-in-water emulsion [152]; (2) a saponin (e.g. QS21)+a non-toxic LPS derivative (e.g. 3dMPL) [153]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [154]; (5) combinations of 3dMPL with, for example, QS21 and/or oil-in-water emulsions [155]; (6) Ribi™ adjuvant system (RAS), (Bibi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (7) one or more mineral salts (such as an aluminum salt)+a non-toxic derivative of LPS (such as 3dMPL).

The compositions of the invention will preferably elicit both a cell mediated immune response as well as a humoral immune response in order to effectively address a *Chlamydia* intracellular infection. This immune response will preferably induce long lasting (e.g. neutralizing) antibodies and a cell mediated immunity that can quickly respond upon exposure to *Chlamydia*.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class H molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-gamma, and TNF-beta. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TI-11 immune response and a TH2 immune response.

An enhanced TH1 immune response may include one or more of an increase in CTLs, an increase in one or more of the cytokines associated with a TH1 immune response (such as IL-2, IFN-gamma, and TNF-beta), an increase in activated macrophages, an increase in NK activity, or an increase in the production of IgG2a. Preferably, the enhanced Till immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

An enhanced TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

Preferably, the invention includes a composition comprising a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response. The TH1/TH2 response in mice may be measured by comparing IgG2a and IgG1 titers, while the TH1/TH2 response in man may be measured by comparing the levels of cytokines specific for the two types of response (e.g. the IFN-γ/IL-4 ratio).

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

A mineral salt, such as an aluminium salt, and an oligonucleotide containing a CpG motif may be combined to provide for an enhanced immune response. The invention therefore includes an oligonucleotide containing a CpG motif, a mineral salt such as an aluminium salt, and an antigen associated with a sexually transmissible disease, such as a *Chlamydia trachomatis* antigen. Further examples of antigens associated with a sexually transmissible disease are discussed further below.

The use of an aluminium hydroxide and/or aluminium phosphate adjuvant is particularly preferred, and antigens are generally adsorbed to these salts. Calcium phosphate is another preferred adjuvant. Other preferred adjuvant combinations include combinations of TH1 and TH2 adjuvants such as CpG & alum or resiquimod & alum.

The adjuvant may be selected from the group consisting of a mineral salt, such as an aluminium salt and an oligonucleotide containing a CpG motif. Most preferably, the immunogenic composition includes both an aluminium salt and an oligonucleotide containing a CpG motif.

Alternatively, the immunogenic composition includes an ADP ribosylating toxin, such as a detoxified ADP ribosylating toxin and an oligonucleotide containing a CpG motif.

Methods of Treatment and Medical Uses

The invention also provides a composition of the invention for use as a medicament. The medicament is preferably able to raise an immune response in a mammal (i.e. it is an immunogenic composition) and is more preferably a vaccine. The invention also provides the use of the compositions of the invention in the manufacture of a medicament for raising an immune response in a mammal. The medicament is preferably a vaccine.

The invention also provides one or more of (1) a GroEL-1 antigen, (3) a Ef-Tu antigen, (6) a HctA antigen, (7) a CT577 antigen, (8) a CT223 antigen, (9) a GroeS antigen, (11) a Rs10 antigen, (13) a Rs13 antigen, (14) a Rl1 antigen, (15) a CT875 antigen, (17) a RpoA antigen, (19) an Alanyl tRNA synthetase antigen, (20) a RpoC antigen, (21) a YaeL antigen, (22) an EF-G antigen, (23) a CT578 antigen, (24) a CT579 antigen, (25) a CT680 antigen and/or (26) a CT814 antigen for use (i) as an immunogen, (ii) in therapy, and/or (iii) in the manufacture of a medicament for raising an immune response in a mammal.

The invention also provides the use of one or more of (1) a GroEL-1 antigen, (3) a Ef-Tu antigen, (6) a HctA antigen, (7) a CT577 antigen, (8) a CT223 antigen, (9) a GroeS antigen, (11) a Rs10 antigen, (13) a Rs13 antigen, (14) a Rl1 antigen, (15) a CT875 antigen, (17) a RpoA antigen, (19) an Alanyl tRNA synthetase antigen, (20) a RpoC antigen, (21) a YaeL antigen, (22) an EF-G antigen, (23) a CT578 antigen, (24) a CT579 antigen, (25) a CT680 antigen and/or (26) a CT814 antigen in the manufacture of a medicament for raising an immune response in a mammal.

The invention also provides the use of one or more of (1) a GroEL-1 antigen, (3) a Ef-Tu antigen, (6) a HctA antigen, (7) a CT577 antigen, (8) a CT223 antigen, (9) a GroeS antigen, (11) a Rs10 antigen, (13) a Rs13 antigen, (14) a Rl1 antigen, (15) a CT875 antigen, (17) a RpoA antigen, (19) an Alanyl tRNA synthetase antigen, (20) a RpoC antigen, (21) a YaeL antigen, (22) an EF-G antigen, (23) a CT578 antigen, (24) a CT579 antigen, (25) a CT680 antigen and/or (26) a CT814 antigen in the manufacture of a medicament for the treatment of chlamydial infection.

The invention also provides one or more of the polypeptides recited in SEQ ID NOs: 2, 3, 4, 5, 6, 7, 8, 10, 11, 12, 13, 15, 16, 18, 19, 21, 23, 25, 27, 29, 31, 33, 35, 37, 39, 41, 43, 45, 47, 49, 51, 105, 106, 107, 108, 109, 110, 111, 112, 113, 114, 115, 116, 117, 118, 119, 120, 121, 122, 123, 124, 125, 126, 127, 129, 130, 131, 132, 133, 134, 135, 136, 138, 139, 140, 142, 143, 144, 145, 146, 147, 148, 149, 150, 151, 155, 156, 157, 158, 159, 160, 163, 167, 168, 169, 170, 171 and/or 172 for use (i) as an immunogen, (ii) in therapy, and/or (iii) in the manufacture of a medicament for raising an immune response in a mammal.

The invention also provides the use of one or more of the polypeptides recited in SEQ ID NOs: 2, 3, 4, 5, 6, 7, 8, 10, 11, 12, 13, 15, 16, 18, 19, 21, 23, 25, 27, 29, 31, 33, 35, 37, 39, 41, 43, 45, 47, 49, 51, 105, 106, 107, 108, 109, 110, 111, 112, 113, 114, 115, 116, 117, 118, 119, 120, 121, 122, 123, 124, 125, 126, 127, 129, 130, 131, 132, 133, 134, 135, 136, 138, 139, 140, 142, 143, 144, 145, 146, 147, 148, 149, 150, 151, 155, 156, 157, 158, 159, 160, 163, 167, 168, 169, 170, 171 and/or 172 in the manufacture of a medicament for raising an immune response in a mammal.

The invention also provides the use of one or more of the polypeptides recited in SEQ ID NOs: 2, 3, 4, 5, 6, 7, 8, 10, 11, 12, 13, 15, 16, 18, 19, 21, 23, 25, 27, 29, 31, 33, 35, 37, 39, 41, 43, 45, 47, 49, 51, 105, 106, 107, 108, 109, 110, 111, 112, 113, 114, 115, 116, 117, 118, 119, 120, 121, 122, 123, 124, 125, 126, 127, 129, 130, 131, 132, 133, 134, 135, 136, 138, 139, 140, 142, 143, 144, 145, 146, 147, 148, 149, 150, 151, 155, 156, 157, 158, 159, 160, 163, 167, 168, 169, 170, 171 and/or 172 in the manufacture of a medicament for the treatment of chlamydial infection.

The phrase "one or more" in these uses includes, for example, 1, 2, 3, 4, 5, 6, 7, 8, 9, 10 or more.

The medicaments are preferably vaccines.

The invention also provides for a kit comprising a first component comprising a combination of *Chlamydia trachomatis* antigens. The combination of *Chlamydia trachomatis* antigens may be one or more of the immunogenic compositions of the invention. The kit may further include a second component comprising one or more of the following: instructions, syringe or other delivery device, adjuvant, or pharmaceutically acceptable formulating solution.

The invention also provides a delivery device pre-filled with the immunogenic compositions of the invention.

The invention also provides a method for raising an immune response in a mammal comprising the step of administering an effective amount of a composition of the invention. The immune response is preferably protective (such as an immunoprotective response) and preferably involves antibodies and/or cell-mediated immunity. Preferably, the immune response includes one or both of a TH1 immune response and a TH2 immune response. The method may raise a booster response.

Compositions of the invention can preferably protect against *C. trachomatis* biovars including one or both of trachoma and/or LGV.

Compositions of the invention can preferably protect against *C. trachomatis* serovars including one or more of A, B, C, D, E and K.

Compositions of the invention can preferably protect against *C. trachomatis* strains including one or both of D/UW-3/CX and L2/434/BU.

The mammal is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

One way of checking efficacy of therapeutic treatment involves monitoring *C. trachomatis* infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the *Chlamydia trachomatis* antigens in the compositions of the invention after administration of the composition. Typically, serum *Chlamydia* specific antibody responses are determined post-immunization but pre-challenge whereas mucosal *Chlamydia* specific antibody body responses are determined post-immunization and post-challenge.

These uses and methods are preferably for the prevention and/or treatment of a disease caused by a *Chlamydia* (e.g. trachoma, pelvic inflammatory disease, epididymitis, infant pneumonia, etc.). The compositions may also be effective against *C. pneumoniae*.

The vaccine compositions (or immunogenic/immunoprotective compositions) of the present invention can be evaluated in in vitro and in vivo animal models prior to host, e.g., human, administration. For example, in vitro neutralization is suitable for testing vaccine compositions (such as immunogenic/immunoprotective compositions) directed toward *Chlamydia trachomatis* [156].

One example of such an in vitro test is described as follows. Hyper-immune antisera is diluted in PBS containing 5% guinea pig serum, as a complement source. *Chlamydia trachomatis* ($10^4$ IFU; inclusion forming units) are added to the antisera dilutions. The antigen-antibody mixtures are incubated at 37° C. for 45 minutes and inoculated into duplicate confluent Hep-2 or HeLa cell monolayers contained in glass vials (e.g., 15 by 45 mm), which have been washed twice with PBS prior to inoculation. The monolayer cells are infected by centrifugation at 1000×g for 1 hour followed by stationary incubation at 37° C. for 1 hour. Infected monolayers are incubated for 48 or 72 hours, fixed and stained with Chlamydia specific antibody, such as anti-MOMP. Inclusion-bearing cells are counted in ten fields at a magnification of 200×. Neutralization titer is assigned on the dilution that gives 50% inhibition as compared to control monolayers/IFU.

The efficacy of vaccine compositions (such as immunogenic/immunoprotective compositions) can also be determined in vivo by challenging animal models of *Chlamydia trachomatis* infection, e.g., guinea pigs or mice, with the vaccine compositions. For example, in vivo vaccine composition challenge studies in the guinea pig model of *Chlamydia trachomatis* infection can be performed. A description of one example of this type of approach follows. Female guinea pigs weighing 450-500 g are housed in an environmentally controlled room with a 12 hour light-dark cycle and immunized with vaccine compositions via a variety of immunization routes. Post-vaccination, guinea pigs are infected in the genital tract with the agent of guinea pig inclusion conjunctivitis (GPIC), which has been grown in HeLa or McCoy cells [157]. Each animal receives approximately $1.4\times10^7$ inclusion forming units (IFU) contained in 0.05 ml of sucrose-phosphate-glutamate buffer, pH 7.4 (Schacter, 1980). The course of infection monitored by determining the percentage of inclusion-bearing cells by indirect immunofluorescence with GPIC specific antisera, or by Giemsa-stained smear from a scraping from the genital tract [157]. Antibody titers in the serum are determined by an enzyme-linked immunosorbent assay.

Alternatively, in vivo vaccine compositions (such as immunogenic/immunoprotective compositions) challenge studies can be performed in the murine model of *Chlamydia trachomatis [*158]. A description of one example of this type of approach is as follows. Female mice 7 to 12 weeks of age receive 2.5 mg of depoprovera subcutaneously at 10 and 3 days before vaginal infection. Post-vaccination, mice are infected in the genital tract with 1,500 inclusion-forming units of *Chlamydia trachomatis* contained in 5 ml of sucrose-phosphate-glutamate buffer, pH 7.4. The course of infection is monitored by determining the percentage of inclusion-bearing cells by indirect immunofluorescence with *Chlamydia trachomatis* specific antisera, or by a Giemsa-stained smear from a scraping from the genital tract of an infected mouse. The presence of antibody titers in the serum of a mouse is determined by an enzyme-linked immunosorbent assay.

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal (See e.g. reference 159) or transcutaneous (See e.g. references 160 and 161), intranasal (See e.g. reference 162), ocular, aural, pulmonary or other mucosal administration.

The invention may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA and/or IFN-γ/IL-4 ratio.

Dosage treatment can be a single dose schedule or a multiple dose schedule. Multiple doses may be used in a primary immunization schedule and/or in a booster immunization schedule. In a multiple dose schedule the various doses may be given by the same or different routes e.g. a parenteral prime and mucosal boost, a mucosal prime and parenteral boost, etc.

Chlamydial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The invention further provides a method for preparing a pharmaceutical product, comprising the steps of: (a) preparing a composition as described above; (b) mixing the composition with one or more pharmaceutically acceptable carriers; and (c) packaging the composition/carrier mixture into a container, such as a vial or a syringe, to give a pharmaceutical product. Insertion into a syringe may be performed in a factory or in a surgery.

Methods of Activating *Chlamydia*-Specific T Cells

The polynucleotides and/or immunogenic polypeptides of the present invention can be used to activate *Chlamydia*-specific T cells either in vitro or in vivo. Activation of *Chlamydia*-specific T cells can be used, inter alia, to provide model systems to optimize CTL responses to *Chlamydia* and to provide prophylactic or therapeutic treatment against *Chlamydia* infection.

Polyclonal populations of T cells can be derived from the blood, and preferably from peripheral lymphoid organs, such as lymph nodes, spleen, or thymus, of mammals that have been infected with *Chlamydia*. Preferred mammals include mice, chimpanzees, baboons, and humans. Infection with *Chlamydia* serves to expand the number of activated *Chlamydia*-specific T cells in the mammal. The *Chlamydia*-specific T cells derived from the mammal can then be restimulated in vitro by adding, a *Chlamydia* immunogenic polypeptide, polyprotein, and/or multiepitope fusion protein. The *Chlamydia*-specific T cells can then be tested for, inter alia, proliferation, the production of IFN-γ, and the ability to lyse target cells displaying, for example, the polypeptides of the present invention.

In a lymphoproliferation assay, *Chlamydia*-activated CD4$^+$ T cells proliferate when cultured with a *Chlamydia* immunogenic polypeptide, polyprotein, and/or multiepitope fusion protein, but not in the absence of such an immunogenic polypeptide. Thus, particular *Chlamydia* polypeptides and fusions of these polypeptides that are recognized by *Chlamydia*-specific CD4$^+$ T cells can be identified using a lymphoproliferation assay.

Similarly, detection of IFN-γ in *Chlamydia*-specific CD4+ and/or CD8$^+$ T cells after in vitro stimulation with the above-described immunogenic polypeptides, can be used to identify, for example, epitopes and fusions of these epitopes that are particularly effective at stimulating CD4$^+$ and/or CD8$^+$ T cells to produce IFN-γ.

Further, $^{51}$Cr release assays are useful for determining the level of CTL response to *Chlamydia* [163]. For example, *Chlamydia*-specific CD8$^+$ T cells can be derived from a *Chlamydia* infected mammal. These T cells can be tested in $^{51}$Cr release assays against target cells displaying one or more of the polypeptides of the present invention. Several target cell populations expressing different polypeptides epitopes can be constructed so that each target cell population displays different epitopes and polypeptides. The *Chlamydia*-specific CD8$^+$ cells can be assayed against each of these target cell populations. The results of the $^{51}$Cr release assays can be used to determine which epitopes and polypeptides are responsible for the strongest CTL response to *Chlamydia*.

A composition of the invention comprising a *Chlamydia* immunogenic polypeptide, or polynucleotide encoding such a polypeptide is administered in a manner compatible with the particular composition used and in an amount which is effective to activate *Chlamydia*-specific T cells as measured by, inter alia, a $^{51}$Cr release assay, a lymphoproliferation assay, or by intracellular staining for IFN-γ. The proteins and/or polynucleotides can be administered either to a mammal which is not infected with *Chlamydia* or can be administered to a *Chlamydia*-infected mammal.

Immune responses of a mammal generated by the delivery of a composition of the invention, including activation of *Chlamydia*-specific T cells, can be enhanced by varying the dosage, route of administration, or boosting regimens. Compositions of the invention may be given in a single dose schedule, or preferably in a multiple dose schedule in which a primary course of vaccination includes 1-10 separate doses, followed by other doses given at subsequent time intervals required to maintain and/or reinforce an immune response, for example, at 1-4 months for a second dose, and if needed, a subsequent dose or doses after several months.

Further Components of the Composition

Compositions of the invention can be combined with pharmaceutically acceptable carriers. Such carriers include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 164.

Preferred compositions may further contain one or more antigens from another sexually transmitted disease causing organism, other disease causing organisms or antibiotics used to treat *Chlamydia* infections.

Antigens which may be included in compositions of the invention include, but are not limited to:

an outer-membrane vesicle (OMV) preparation from *N. meningitidis* serogroup B, such as those disclosed in refs. 165-168 etc.

a saccharide antigen from *N. meningitidis* serogroup A, C, W135 and/or Y, such as the oligosaccharide disclosed in ref. 169 from serogroup C [see also ref. 170] or the oligosaccharides of ref. 171.

a protein antigen from *N. meningitidis* serogroup B, such as those disclosed in refs. 172-180, etc.

antigens from *Helicobacter pylori* such as CagA [181 to 184], VacA [185, 186], NAP [187, 188, 189], HopX [e.g. 190], HopY [e.g. 190] and/or urease.

a saccharide antigen from *Streptococcus pneumoniae* [e.g. 191, 192, 193].

an antigen from hepatitis A virus, such as inactivated virus [e.g. 194, 195].

an antigen from hepatitis B virus, such as the surface and/or core antigens [e.g. 195, 196].

an antigen from hepatitis C virus [e.g. 197].

an antigen from HIV [198]

a diphtheria antigen, such as a diphtheria toxoid [e.g. chapter 3 of ref. 199].

a tetanus antigen, such as a tetanus toxoid [e.g. chapter 4 of ref. 199].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 200 & 201].

a saccharide antigen from *Haemophilus influenzae* B [e.g. 170].

polio antigen(s) [e.g. 202, 203] such as IPV.

an antigen from *N. gonorrhoeae* [e.g. 204, 205, 206, 207].
an antigen from *Chlamydia pneumoniae* [e.g. refs. 208 to 214].
an antigen from *Porphyromonas gingivalis* [e.g. 215].
rabies antigen(s) [e.g. 216] such as lyophilised inactivated virus [e.g. 217, RabAvert™].
measles, mumps and/or rubella antigens [e.g. chapters 9, 10 & 11 of ref. 199].
influenza antigen(s) [e.g. chapter 19 of ref. 199], such as the haemagglutinin and/or neuraminidase surface proteins. The flu antigen may be selected from a pandemic strain.
antigen(s) from a paramyxovirus such as respiratory syncytial virus (RSV [218, 219]) and/or parainfluenza virus (PIV3 [220]).
an antigen from *Moraxella catarrhalis* [e.g. 221].
an antigen from *Streptococcus pyogenes* (group A *streptococcus*) [e.g. 222, 223, 224].
an antigen from *Staphylococcus aureus* [e.g. 225].
an antigen from *Bacillus anthracis* [e.g. 226, 227, 228].
an antigen from a virus in the flaviviridae family (genus flavivirus), such as from yellow fever virus, Japanese encephalitis virus, four serotypes of Dengue viruses, tick-borne encephalitis virus, West Nile virus.
a pestivirus antigen, such as from classical porcine fever virus, bovine viral diarrhoea virus, and/or border disease virus.
a parvovirus antigen e.g. from parvovirus B19.
a prion protein (e.g. the CJD prion protein)
an amyloid protein, such as a beta peptide [229]
a cancer antigen, such as those listed in Table 1 of ref. 230 or in tables 3 & 4 of ref. 231
an allergen that triggers an allergic or asthmatic response
a Human Papilloma Virus (HPV) antigen (see WO 00/09699)

Preferred gonococcal antigens include ngs13 (OmpA), OmpH, ngs576 (peptidyl-prolyl cis/trans isomerase (PPIase) protein), ngs41 and ngs117.

Preferred HPV antigens include one or more of HPV 16, HPV 18, HPV 6 and HPV 11.

The composition may further comprise an antibiotic that is useful for the treatment of chlamydial infection. Preferred antibiotics for use in the compositions include the tetracyclines, azithromycin and erythromycin. A particular preferred antibiotic is rifalazil.

Nucleic Acid Immunisation

The immunogenic compositions described above include polypeptide antigens from *C. trachomatis*. In all cases, however, the polypeptide antigens can be replaced by nucleic acids (typically DNA) encoding those polypeptides, to give compositions, methods and uses based on nucleic acid immunisation. Nucleic acid immunisation is now a developed field (e.g. see references 232 to 239 etc.), and has been applied to *C. trachomatis* vaccines [240-245].

The nucleic acid encoding the immunogen is expressed in vivo after delivery to a patient and the expressed immunogen then stimulates the immune system. The active ingredient will typically take the form of a nucleic acid vector comprising: (i) a promoter; (ii) a sequence encoding the immunogen, operably linked to the promoter; and optionally (iii) a selectable marker. Preferred vectors may further comprise (iv) an origin of replication; and (v) a transcription terminator downstream of and operably linked to (ii). In general, (i) & (v) will be eukaryotic and (iii) & (iv) will be prokaryotic.

Preferred promoters are viral promoters e.g. from cytomegalovirus (CMV). The vector may also include transcriptional regulatory sequences (e.g. enhancers) in addition to the promoter and which interact functionally with the promoter. Preferred vectors include the immediate-early CMV enhancer/promoter, and more preferred vectors also include CMV intron A. The promoter is operably linked to a downstream sequence encoding an immunogen, such that expression of the immunogen-encoding sequence is under the promoter's control.

Where a marker is used, it preferably functions in a microbial host (e.g. in a prokaryote, in a bacteria, in a yeast). The marker is preferably a prokaryotic selectable marker (e.g. transcribed under the control of a prokaryotic promoter). For convenience, typical markers are antibiotic resistance genes.

The vector of the invention is preferably an autonomously replicating episomal or extrachromosomal vector, such as a plasmid.

The vector of the invention preferably comprises an origin of replication. It is preferred that the origin of replication is active in prokaryotes but not in eukaryotes.

Preferred vectors thus include a prokaryotic marker for selection of the vector, a prokaryotic origin of replication, but a eukaryotic promoter for driving transcription of the immunogen-encoding sequence. The vectors will therefore (a) be amplified and selected in prokaryotic hosts without polypeptide expression, but (b) be expressed in eukaryotic hosts without being amplified. This arrangement is ideal for nucleic acid immunization vectors.

The vector of the invention may comprise a eukaryotic transcriptional terminator sequence downstream of the coding sequence. This can enhance transcription levels. Where the coding sequence does not have its own, the vector of the invention preferably comprises a polyadenylation sequence. A preferred polyadenylation sequence is from bovine growth hormone.

The vector of the invention may comprise a multiple cloning site.

In addition to sequences encoding the immunogen and a marker, the vector may comprise a second eukaryotic coding sequence. The vector may also comprise an IRES upstream of said second sequence in order to permit translation of a second eukaryotic polypeptide from the same transcript as the immunogen. Alternatively, the immunogen-coding sequence may be downstream of an IRES.

The vector of the invention may comprise unmethylated CpG motifs e.g. unmethylated DNA sequences which have in common a cytosine preceding a guanosine, flanked by two 5' purines and two 3' pyrimidines. In their unmethylated form these DNA motifs have been demonstrated to be potent stimulators of several types of immune cell.

Vectors may be delivered in a targeted way. Receptor-mediated DNA therapy techniques are described in, for example, references 246 to 251. Therapeutic compositions containing a nucleic acid are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. Factors such as method of action (e.g. for enhancing or inhibiting levels of the encoded gene product) and efficacy of transformation and expression are considerations which will affect the dosage required for ultimate efficacy. Where greater expression is desired over a larger area of tissue, larger amounts of vector or the same amounts re-administered in a successive protocol of administrations, or several administrations to different adjacent or close tissue portions may be required to effect a positive therapeutic outcome. In all cases, routine experimentation in clinical trials will determine specific ranges for optimal therapeutic effect.

Vectors can be delivered using gene delivery vehicles. The gene delivery vehicle can be of viral or non-viral origin (see generally references 252 to 255).

Viral-based vectors for delivery of a desired nucleic acid and expression in a desired cell are well known in the art. Exemplary viral-based vehicles include, but are not limited to, recombinant retroviruses (e.g. references 256 to 266), alphavirus-based vectors (e.g. Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532); hybrids or chimeras of these viruses may also be used), poxvirus vectors (e.g. vaccinia, fowlpox, canarypox, modified vaccinia Ankara, etc.), adenovirus vectors, and adeno-associated virus (AAV) vectors (e.g. see refs. 267 to 272). Administration of DNA linked to killed adenovirus [273] can also be employed.

Non-viral delivery vehicles and methods can also be employed, including, but not limited to, polycationic condensed DNA linked or unlinked to killed adenovirus alone [e.g. 273], ligand-linked DNA [274], eukaryotic cell delivery vehicles cells [e.g. refs. 275 to 279] and nucleic charge neutralization or fusion with cell membranes. Naked DNA can also be employed. Exemplary naked DNA introduction methods are described in refs. 280 and 281. Liposomes (e.g. immunoliposomes) that can act as gene delivery vehicles are described in refs. 282 to 286. Additional approaches are described in references 287 & 288.

Further non-viral delivery suitable for use includes mechanical delivery systems such as the approach described in ref. 288. Moreover, the coding sequence and the product of expression of such can be delivered through deposition of photopolymerized hydrogel materials or use of ionizing radiation [e.g. refs. 289 & 290]. Other conventional methods for gene delivery that can be used for delivery of the coding sequence include, for example, use of hand-held gene transfer particle gun [291] or use of ionizing radiation for activating transferred genes [289 & 292].

Delivery DNA using PLG {poly(lactide-co-glycolide)} microparticles is a particularly preferred method e.g. by adsorption to the microparticles, which are optionally treated to have a negatively-charged surface (e.g. treated with SDS) or a positively-charged surface (e.g. treated with a cationic detergent, such as CTAB).

Antibodies

Antibodies can be generated to bind specifically to a surface-exposed and/or surface-associated antigen of the invention. The invention therefore provides an antibody that is specific for (1) a GroEL-1 antigen, (3) an Ef-Tu antigen, (6) a HctA antigen, (7) a CT577 antigen, (8) a CT223 antigen, (9) a GroeS antigen, (11) an Rs10 antigen, (13) an Rs13 antigen, (14) an R11 antigen, (15) a CT875 antigen, (17) an RpoA antigen, (19) an Alanyl tRNA synthetase antigen, (20) an RpoC antigen, (21) a YaeL antigen, (22) an EF-G antigen, (23) a CT578 antigen, (24) a CT579 antigen, (25) a CT680 antigen or (26) a CT814 antigen. Preferably an antibody according to the invention binds one of these 20 antigens with substantially greater affinity than antibodies known in the art. Preferably, the affinity is at least 1.5-fold, 2-fold, 5-fold 10-fold, 100-fold, $10^3$-fold, $10^4$-fold, $10^5$-fold, $10^6$-fold stronger than antibodies known in the art or greater.

The term "antibody" includes intact immunoglobulin molecules, as well as fragments thereof which are capable of binding an antigen. These include hybrid (chimeric) antibody molecules [293, 294]; F(ab')2 and F(ab) fragments and Fv molecules; non-covalent heterodimers [295, 296]; single-chain Fv molecules (sFv) [297]; dimeric and trimeric antibody fragment constructs; minibodies [298, 299]; humanized antibody molecules [300-302]; and any functional fragments obtained from such molecules, as well as antibodies obtained through non-conventional processes such as phage display. Preferably, the antibodies are monoclonal antibodies. Methods of obtaining monoclonal antibodies are well known in the art.

Typically, at least 6, 7, 8, 10, or 12 contiguous amino acids are required to form an epitope. However, epitopes which involve non-contiguous amino acids may require more, e.g., at least 15, 25, or 50 amino acids. Various immunoassays (e.g., Western blots, ELISAs, radioimmunoassays, immunohistochemical assays, immunoprecipitations, or other immunochemical assays known in the art) can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen. A preparation of antibodies which specifically bind to a particular antigen typically provides a detection signal at least 5-, 10-, or 20-fold higher than a detection signal provided with other proteins when used in an immunochemical assay. Preferably, the antibodies do not detect other proteins in immunochemical assays and can immunoprecipitate the particular antigen from solution.

Generation of Antibodies

The surface-exposed antigens of the invention can be used to immunize a mammal, such as a mouse, rat, rabbit, guinea pig, monkey, or human, to produce polyclonal antibodies. If desired, an antigen can be conjugated to a carrier protein, such as bovine serum albumin, thyroglobulin, and keyhole limpet hemocyanin. Depending on the host species, various adjuvants can be used to increase the immunological response. Such adjuvants include those described above, as well as those not used in humans, for example, Freund's adjuvant.

Monoclonal antibodies which specifically bind to an antigen can be prepared using any technique which provides for the production of antibody molecules by continuous cell lines in culture. These techniques include, but are not limited to, the hybridoma technique, the human B-cell hybridoma technique, and the EBV-hybridoma technique [303-306].

In addition, techniques developed for the production of "chimeric antibodies," the splicing of mouse antibody genes to human antibody genes to obtain a molecule with appropriate antigen specificity and biological activity, can be used [307-309]. Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in reference 310.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries [311].

Single-chain antibodies also can be constructed using a DNA amplification method, such as PCR, using hybridoma cDNA as a template [312]. Single-chain antibodies can be mono- or bispecific, and can be bivalent or tetravalent. Construction of tetravalent, bispecific single-chain antibodies is taught, for example, in reference 313. Construction of bivalent, bispecific single-chain antibodies is taught in reference 314.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology [315, 316].

Antibodies which specifically bind to a particular antigen also can be produced by inducing in vivo production in the lymphocyte population or by screening immunoglobulin libraries or panels of highly specific binding reagents as disclosed in the literature [317, 293].

Chimeric antibodies can be constructed as disclosed in reference 318. Binding proteins which are derived from immunoglobulins and which are multivalent and multispecific, such as the "diabodies" described in reference 319, also can be prepared.

Antibodies can be purified by methods well known in the art. For example, antibodies can be affinity purified by passage over a column to which the relevant antigen is bound. The bound antibodies can then be eluted from the column using a buffer with a high salt concentration.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of *Current Protocols in Molecular Biology* (F. M. Ausubel et al., eds., 1987) Supplement 30. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) *Adv. Appl. Math.* 2: 482-489

The CT nomenclature was first described in reference 4, though further work on the identification of genes has been carried out using the methods described in reference 320. It is now the standard way of referring to proteins from *Chlamydia trachomatis*.

BRIEF DESCRIPTION OF THE DRAWINGS

FIG. 10 shows the PRED$^{BALB/c}$ system output for CT823, CT587 and CT043.

MODES FOR CARRYING OUT THE INVENTION

Identifying Surface-Exposed and/or Surface-Associated *Chlamydia* Antigens

Figure 1:
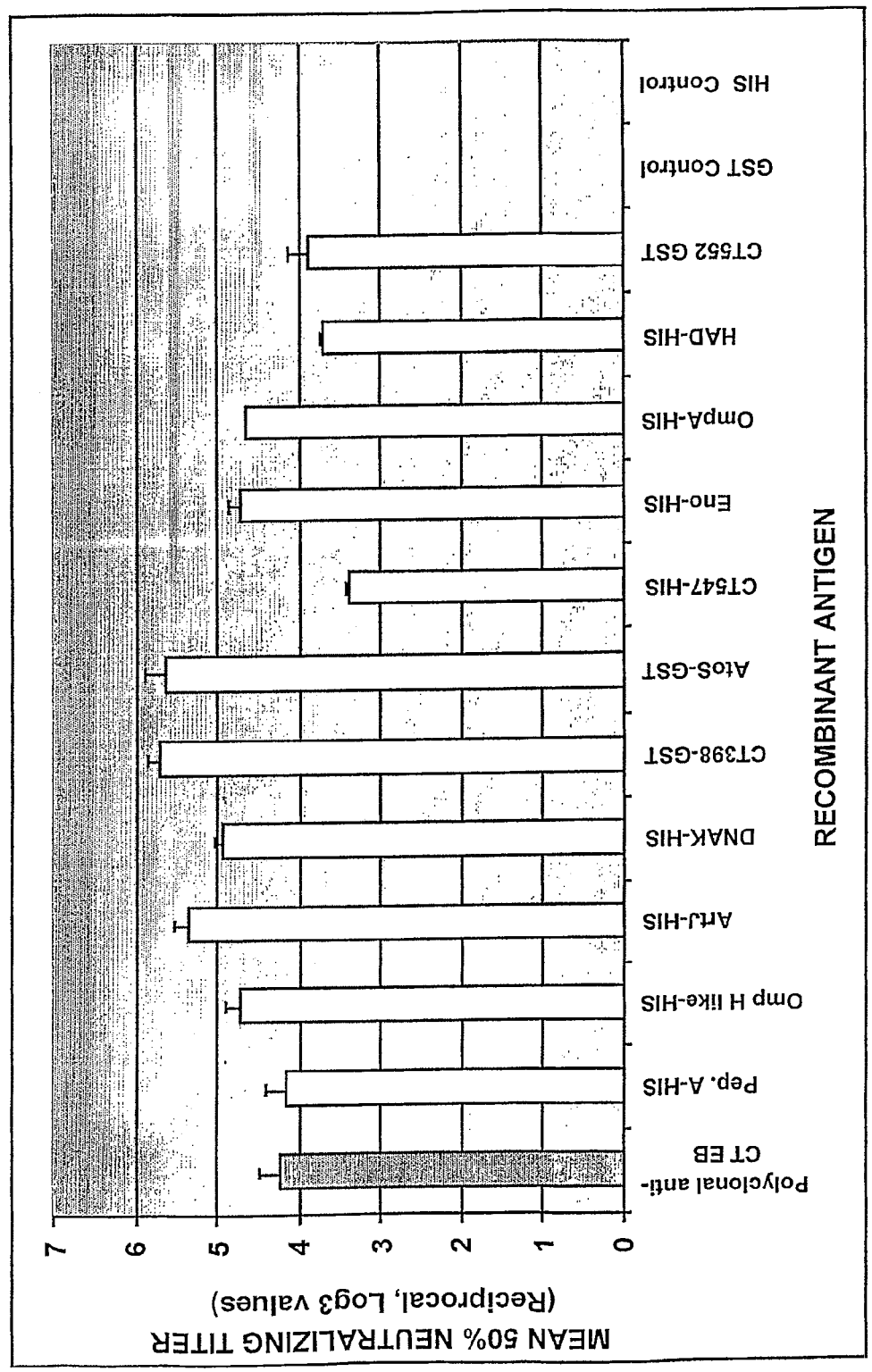
FIG. 1 shows the neutralizing titers of mouse sera against 11 CT recombinant antigens. To evaluate their neutralizing activity, sera of mice immunized with the recombinant proteins were pre-incubated with purified EBs before in vitro infection. Tit
Figure 2A:
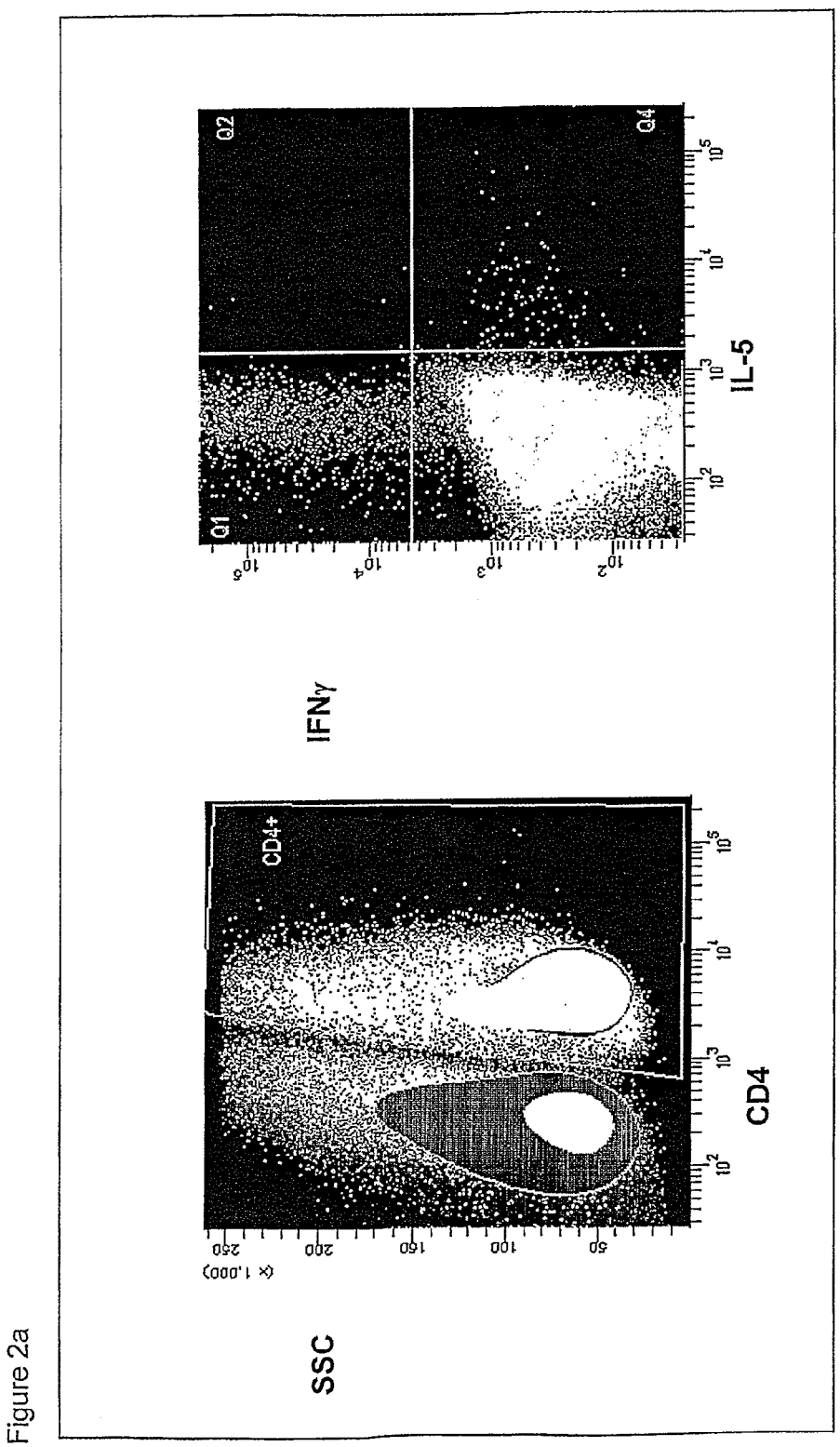
Figure 2B:
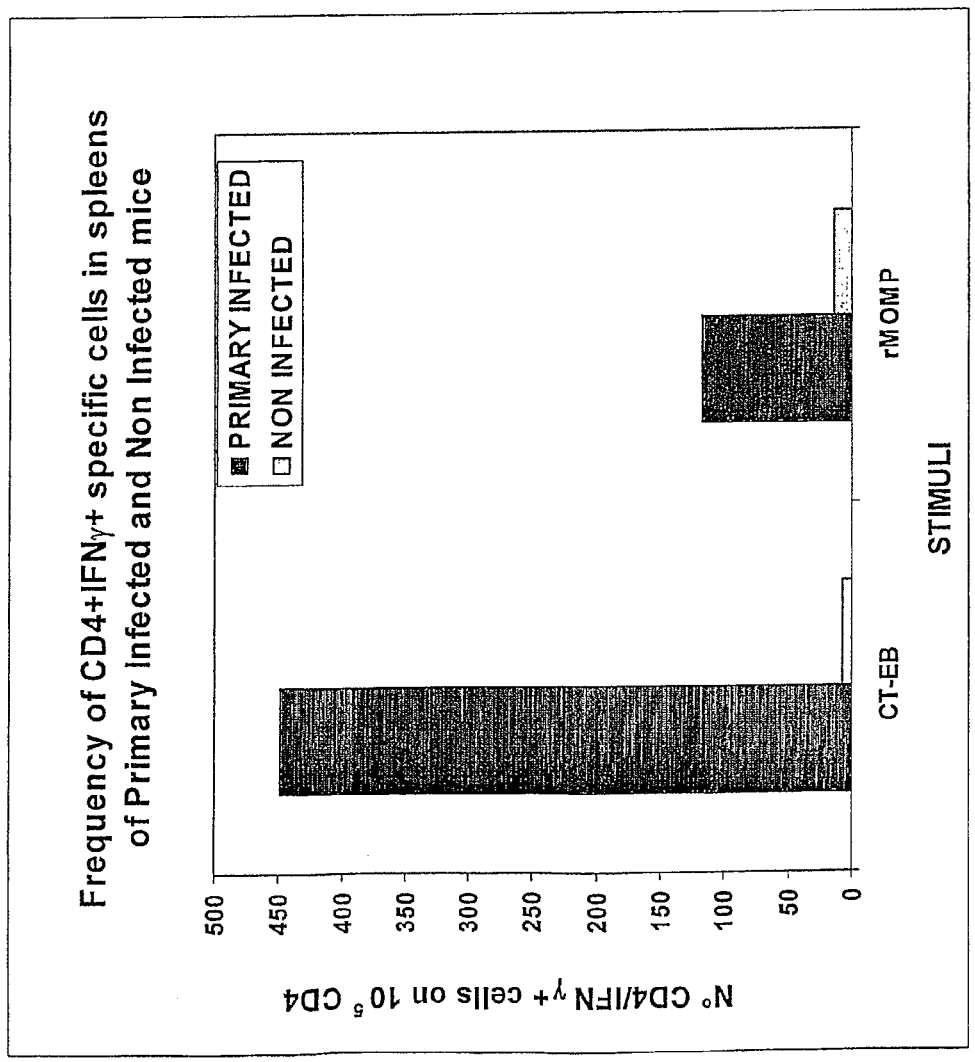
Figure 3:
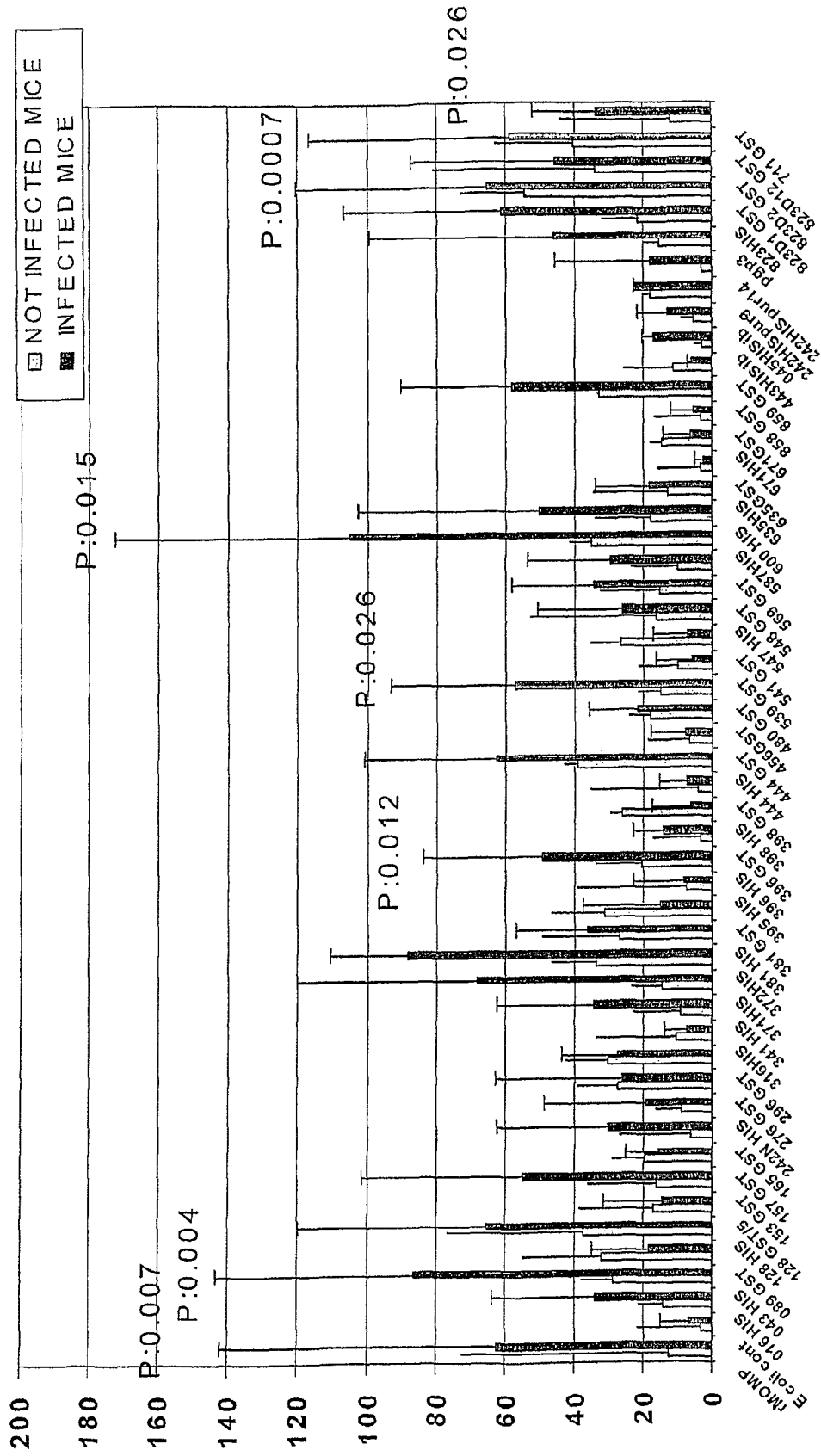

Surface-exposed and/or surface-associated *Chlamydia* antigens can be identified using any one or combination of several proteomics approaches as outlined below. These proteomics strategies have great potential for shortening the time needed for vaccine discovery when compared with other strategies, such as reverse vaccinology. Surface-exposed and/or surface-associated *Chlamydia* antigens identified by these methods can be used as active agents in compositions for preventing and for treating *Chlamydia* infections.

One method for identifying surface-exposed and/or surface-associated *Chlamydia* antigens is described as follows: the surface of *Chlamydia* Elementary bodies (EBs) is digested in vivo under physiological conditions using reagents which cleave proteins. Typically the reagents are proteases (e.g., trypsin, protease K, papain), although any protein cleavage reagent can be used. These reagents include, for example, formic acid, hydroxylamine, BNPS-skatole (3-bromo-3-methyl-2-(o-nitrophenylsulfenyl)-indolenine), which cleaves at Trp residues), cyanogen bromide (which cleaves polypeptides on the carboxyl side of methionine residues), metal chelate reagents such as Fe-EDTA, and the like. Proteases can be either free or anchored, this latter condition favoring the identification of surface extruding regions. Combinations of more than one protein cleavage regent can be used. The recovered peptides are then separated by liquid chromatography and identified by tandem mass spectrometry. The actual accessibility of identified proteins to the immune system can be assessed by fluorescence-activated cell sorting (FACS) analysis. This proteomic approach permits validation of software-based topology predictions and vice versa.

Another method for identifying surface-exposed and/or surface-associated *Chlamydia* antigens includes the production of cell wall and/or membrane fractions which are generated by chemical cell fractionation of bacterial cells using, for example, 6 M guanidinium, urea, or SDS. The cell wall is insoluble in these reagents. This property allows the isolation of the cell wall and identification of anchored cell wall proteins. *Chlamydia* proteins in these fractions can be separated and identified as described above.

A further method for identifying surface-exposed and/or surface-associated *Chlamydia* antigens involves labeling cell surface *Chlamydia* proteins (e.g., by biotinylation), lysing the cells, and isolating labeled proteins using affinity chromatography. The isolated proteins can be separated by electrophoresis and identified using mass spectrometry. Alternatively, the isolated proteins can be digested in solution, followed by isolation of labeled peptides by affinity chromatography, separation of the labeled peptides by liquid chromatography, and identification of the labeled peptides using tandem mass spectrometry. These methods selectively isolate the labeled peptides, therefore they allow identification of the truly exposed domains. In this case, the use of two affinity chromatography steps results in a reduction of complexity of the sample to be loaded on the chromatography column.

For all the above embodiments a mutant can be used which harbors a deleted gene for one of the more abundant known surface-exposed antigens. These mutants will increase the probability of spotting previously unidentified, less abundant surface proteins Proteolysis of the Chlamydial Surface and Analysis of Resultant Peptides.

Infectious forms (Elementary bodies, EBs) of *Chlamydia trachomatis* were grown in cell cultures and purified by gradient centrifugation as described in the literature. Approximately, $10^7$ IFU of purified EBs in SPG *Chlamydia* transport buffer were digested ("shaved") with trypsin. Limited digestion was carried out with 20 μg trypsin (Promega, Madison, Wis., USA) for 30 min at 37° C.

The digestion mixture was centrifuged in an Eppendorf centrifuge at 14,000 g for 30 min at 4° C., in order to separate the chlamydial cells from the peptides released by the surface proteolysis. The supernatant, containing the peptides released by trypsin digestion, was filtered from residual chlamydial cells either (a) by centrifugation at 4° C. in Centricon tubes or (b) by filtration using 10 kDa pore-size filters. The filtrate was treated with formic acid (0.1% formic acid final concentration) and submitted to proteomic analysis for the identification of the released peptides and consequent identification of the proteins which were exposed on the chlamydial surface.

In an alternative method, which has been found to recover around 20× more chlamydial elementary bodies, a Renografin density gradient is used.

Monolayers of rhesus monkey kidney (LLCMK2) cells were grown on glass coverslips in Eagle minimal essential medium (with Earle salts, 5% fetal bovine serum, gentamicin at 50 mg/ml, and cycloheximide at 1.5 mg/ml) and infected with the elementary bodies. 48 hours post-inoculation, cells were harvested with a cell scraper and disrupted by sonication (3×10 seconds, maximal power Sonicator IKA LAB-SYSTEM mod. U50 with probe MS 3 of 3 mm). Broken cells were centrifuged at 1,000×g for 10 min. at 4° C. The supernatant was recovered and centrifuged at 22,000×g for 30 min. at 4° C. Pellet was resuspended with 42 ml total of SP (0.01 M sodium phosphate (pH 7.2), 0.25 M sucrose), and sonicated as previously described. Two factions, each of 21 ml of this suspension were layered over 15 ml of 30% (v/v) Renografin-60 solution (diatrizoate meglumine and diatrizoate sodium, 60% for injection; Bracco Diogniostics, Irvine, Calif.). After centrifugation at 40,000×g for 30 min at 4° C., the two pellets were recovered, pooled and resuspended with 4 ml total of SP and sonicated 4×2 seconds with maximal power (see above). Finally, two fractions of 2 ml of suspension were layered over 2 discontinuous Renografin gradients, formed by adding successively in the centrifuge tubes 8 ml, 12 ml and 5 ml of Renografin solution at 54, 44 and 40% (v/v), respectively. The gradients were centrifuged at 40,000×g for 45 min at 4° C. The EB bands, located at the 44/54% Renografin interface, were collected, pooled, diluted with 3 volumes of SP, and then centrifuged at 30,000×g for 30 min. Purified EB were suspended in 1.2 ml total of SP. The titer was about $5 \times 10^6$ IFU/µl.

So far 88 proteins have been identified from the EB purified from the sucrose (64 proteins) and the renografin gradient (47 proteins). From both preparations, the membrane associated proteins (outer membrane, periplasmic and inner membrane proteins) as defined by PSORT software, represent about 50% of the identified proteins (53 and 49% from EB purified from sucrose and renografin gradient, respectively). Of 20 proteins identified from the sucrose gradient purified-EB that were also selected from the genomic approach, only 9 (45%) of them have been demonstrated to be FACS positive (reported in bold in the table 1), while from the 15 proteins identified from the renografin gradient purified-EB and previously selected from the genomic approach (reported in bold or highlighted in table 1), 12 (80%) have been shown to be FACS positive proteins. The results indicate that a protein identified from the surfome of the renografin gradient purified-EB is highly likely to be a surface exposed protein, independently of its prediction by PSORT software. In fact, from these 12 proteins demonstrated to be FACS positive, 8 are predicted to be inner membrane or cytoplasmic proteins. Moreover, the proteins include 5 out of the 11 in vitro neutralizing antigens identified (CT045 (Leucyl Aminopeptidase A), CT242 (OmpH-Like Outer Membrane Protein), CT587 (enolase), and CT681 (Major Outer Membrane Protein), and CT396 (HSP70)) and they include antigens stimulating IFN-γ producing CD4 cells (CT043 (hypothetical protein), CT587 (enolase) and CT823 (DO Serine Protease)).

Proteins, mainly those identified from the surfome of the renografin gradient purified-EB and not previously selected from the genomic approach, or already selected but lost during the screening are selected, cloned, expressed, and purified to be tested as potential vaccine (see below study on the identified proteins and on the saved peptides, and table 2).

TABLE 1

| TMD | ID | FACS_ctr | FACS_cpn | ctr_new_annotation | predicted localization | Surfome sucrose gradient purified -EB | Surfome rinographin gradient purified -EB |
|---|---|---|---|---|---|---|---|
| 0 | CT073 | | VEDI 6688 | predicted OMP [leader (19) peptide] | periplasmic space | x | |
| 0 | CT242 | | pos 6577 | (OmpH-Like Outer Membrane Protein) | periplasmic space | x | x |
| 0 | CT550 | | VEDI 7139 | hypothetical protein | periplasmic space | x | |
| 0 | CT600 | 10.46 | *NEG 7090* | Peptidoglycan-Associated Lipoprotein | periplasmic space | x | |
| 0 | CT681 | 34.66 | *pos 6998* | Major Outer Membrane Protein | periplasmic space | x | x |
| 0 | CT823 | 26.62 | *POS. 7306* | DO Serine Protease | periplasmic space | x | x |
| 0 | CT456 | pos | *VEDI 6866* | hypothetical protein | outer membrane | x | x |
| 0 | CT476 | | neg 6890 | hypothetical protein | outer membrane | x | |
| 0 | CT812 | 23.48 | *pos 7287* | Putative Outer Membrane Protein D | outer membrane | x | |
| 1 | CT011 | | | hypothetical protein | inner membrane | x | |
| 1 | CT045 | 16.81 | *pos 6664* | Leucyl Aminopeptidase A | inner membrane | x | x |
| 1 | CT055 | | | Dihydrolipoamide Succinyltransferase | inner membrane | | |
| 1 | CT067 | | neg | Solute Protein Binding Famity | inner membrane | x | |
| | CT072 | | VEDI 6618 | Metalloprotease | inner membrane | | x |
| 1 | CT102 | | | hypothetical protein | inner membrane | x | |
| 2 | CT223 | | | hypothetical protein | inner membrane | x | |
| 8 | CT230 | | | Neutral Amino Acid (Glutamate) Transporter | inner membrane | x | |
| 0 | CT253 | | | hypothetical protein | inner membrane | x | |
| 2 | CT270 | | VEDI 6700 | transglycolase/transpeptidase | inner membrane | x | |
| 1 | CT313 | | | Transaldolase | inner membrane | | x |
| 1 | CT316 | 9.68 | VEDI 6338 | L7/L12 Ribosomal Protein | inner membrane | | x |
| 1 | CT322 | | BEDI 6331 | Elongation Factor Tu | inner membrane | x | x |
| 1 | CT396 | 34.5 | pos 6790 | HSP-70 | inner membrane | x | x |
| 1 | CT413 | | pos 6830 | Putative outer membrane protein B | inner membrane | | x |
| 1 | CT437 | | | Elongation Factor G | inner membrane | x | x |
| 1 | CT443 | 21.28 | *pos 6849* | 60 kDa Cysteine-Rich OMP | inner membrane | | x |
| 10 | CT448 | | | Protein Export | inner membrane | x | |
| 2 | CT507 | | | RNA Polymerase Alpha | inner membrane | x | x |
| 11 | CT510 | | | Translocase | inner membrane | x | |

TABLE 1-continued

| TMD | ID | FACS_ctr | FACS_cpn | ctr_new_annotation | predicted localization | Surfome sucrose gradient purified -EB | Surfome rinographin gradient purified -EB |
|---|---|---|---|---|---|---|---|
| 0 | CT541 | 43.36 | *pos 6960* | FKBP-type pep-prol cis-trans isom. (MIP) | inner membrane | x | x |
| 1 | CT559 | 23.21 | *pos 7140* | Yop proteins translocation lipoprotein J | inner membrane |  | x |
| 1 | <u>CT578</u> |  |  | <u>hypothetical protein</u> | <u>inner membrane</u> | <u>x</u> | <u>x</u> |
| 2 | CT579 |  |  | hypothetical protein | inner membrane |  | x |
| 1 | CT592 |  |  | Succinate Dehydrogenase | inner membrane | x |  |
| 1 | CT608 |  |  | DNA Helicase | inner membrane | x |  |
| 11 | CT624 |  | no data | Integral Membrane Protein | inner membrane | x |  |
| 2 | CT664 |  | neg | (FHA domain; homology to adenylate cyclase) | inner membrane | x | x |
| 1 | CT680 |  |  | S2 Ribosomal Protein | inner membrane |  | x |
| 2 | CT686 |  |  | ABC Transporter Membrane Protein | inner membrane | x |  |
| 1 | CT714 |  |  | Glycerol-3-P Dehydrogenase | inner membrane | x |  |
| 1 | CT816 |  |  | Glucosamine-Fructose-6-P Aminotransferase | inner membrane | x |  |
| 2 | CT841 |  |  | ATP-dependent zinc protease | inner membrane |  | x |
| 2 | CT842 |  |  | Polyribonucleotide Nucleotidyltransferase | inner membrane |  | x |
| 11 | CT856 |  |  | Sulfate Transporter | inner membrane | x |  |
| 1 | CT041 |  |  | hypothetical protein | inner membrane | x |  |
|  | CT814 |  |  | hypothetical protein | inner membrane |  |  |
| 0 | CT003 |  |  | Glu tRNA Gln Amidotransferae (A subunit) | cytoplasm |  | x |
| 0 | CT043 | 25.29 | VEDI 6666 | hypothetical protein | cytoplasm |  | x |
| 0 | CT064 |  |  | GTPase | cytoplasm | x |  |
| 0 | CT098 |  |  | S1 Ribosomal Protein | cytoplasm | x |  |
| 0 | CT110 |  |  | HSP-60 | cytoplasm | x | x |
| 0 | CT111 |  |  | 10KDa Chaperonin | cytoplasm | x |  |
| 0 | CT113 |  |  | Clp Protease ATPase | cytoplasm | x |  |
| 0 | CT125 |  |  | L13 Ribosomal Protein | cytoplasm | x |  |
| 0 | CT126 |  |  | S9 Ribosomal Protein | cytoplasm | x | x |
| 0 | CT153 | 13.33 |  | hypothetical protein | cytoplasm |  | x |
| 0 | CT205 |  |  | Fructose-6-P Phosphotransferase | cytoplasm |  | x |
| 0 | CT215 |  |  | Predicted 1,6-Fructose biphosphate aldolase | cytoplasm | x |  |
| 0 | CT267 |  | VEDI 6697 | Integration Host Factor Alpha | cytoplasm | x |  |
| 0 | CT269 |  |  | UDP-N-acetylmuramoylalanylglutamyl DAP Ligas | cytoplasm | x |  |
| 0 | CT314 |  |  | RNA Polymerase Beta' | cytoplasm | x | x |
| 0 | CT315 |  |  | RNA Polymerase Beta | cytoplasm | x | x |
| 0 | CT318 |  |  | L1 Ribosomal Protein | cytoplasm | x |  |
| 0 | CT348 |  |  | ABC Transporter Protein ATPase | cytoplasm | x |  |
| 0 | CT436 |  |  | S10 Ribosomal Protein | cytoplasm | x |  |
| 0 | CT438 |  | VEDI 6842 | S7 Ribosomal Protein | cytoplasm | x |  |
| 0 | CT509 |  |  | S13 Ribosomal Protein | cytoplasm | x |  |
| 0 | CT511 |  |  | L15 Ribosomal Protein | cytoplasm | x | x |
| 0 | CT521 |  |  | L16 Ribosomal Protein | cytoplasm | x |  |
| 0 | CT527 |  |  | L4 Ribosomal Protein | cytoplasm |  | x |
| 0 | CT576 |  |  | Low Calcium Response Protein H | cytoplasm |  | x |
| 0 | CT577 |  |  | hypothetical protein | cytoplasm | x | x |
| 0 | CT587 | 20.85 | *pos7111* | enolase | cytoplasm |  | x |
| 0 | CT603 |  |  | Thio-specific Antioxidant (TSA) Peroxidase | cytoplasm |  | x |
| 0 | CT622 |  | *pos 7033* | CHLPN 76kDa Homolog | cytoplasm |  | x |
| 0 | CT636 |  |  | Transcription Elongation Factor G | cytoplasm | x | x |
| 0 | CT678 |  |  | UMP Kinase | cytoplasm |  | x |
| 0 | CT707 |  | VEDI 7163 | Trigger Factor-peptidyl prolyl isomerase | cytoplasm | x |  |
| 0 | CT743 |  |  | Histone-Like Developmental Protein | cytoplasm | x | x |
| 0 | CT748 |  |  | Transcription-Repair Coupling | cytoplasm | x |  |
| 0 | CT768 |  |  | hypothetical protein | cytoplasm | x | x |
| 0 | CT771 |  |  | hydrolase/phosphatase homolog | cytoplasm | x | x |
| 0 | CT834 |  |  | L35 Ribosomal Protein | cytoplasm | x |  |
| 0 | CT859 | 10.91 | VEDI 7348 | Metalloprotease | cytoplasm | x |  |
| 0 | CT875 |  |  | hypothetical protein | cytoplasm | x | x |
| 0 | CT236 |  |  | Acyl Carrier Protein | cytoplasm |  | x |
| 0 | CT523 |  |  | L22 Ribosomal Protein | cytoplasm |  | x |
| 0 | CT514 |  |  | L6 Ribosomal Protein | cytoplasm |  |  |

Highlighted = FACS NEG
Bold = FACS POS
*Italic* = CPn FACS POS
<u>Underlined</u> = NOT EXPRESSED
☐ = NOT SELECTED

TABLE 2

| Locus Name | TIGR Annotation | Experimental evidence | Cloning in the past | Cloning | Predicted Localization | Surfome sucrose gradient purified - EB | Surfome rinographin gradient purified - EB |
|---|---|---|---|---|---|---|---|
| CT110 | HSP-60 | surfoma (tripsina) and lecterature | Never done before | entire form | cytoplasm | x | x |

TABLE 2-continued

| Locus Name | TIGR Annotation | Experimental evidence | Cloning in the past | Cloning | Predicted Localization | Surfome sucrose gradient purified - EB | Surfome rinographin gradient purified - EB |
|---|---|---|---|---|---|---|---|
| CT113 | Clp Protease ATPase | surfoma (tripsina) and lecterature | Never done before | entire form | cytoplasm | x | |
| CT576 | Low Calcium Response Protein H | TTSS? | Never done before | entire form | cytoplasm | | x |
| CT577 . . . | hypothetical protein | TTSS? | Never done before | entire form | cytoplasm | | x |
| CT578 | hypothetical protein | surfoma (tripsina) and TTSS? | Done before, but not expression | entire form | inner membrane | | x |
| CT579 | hypothetical protein | surfoma (tripsina) and TTSS? | Never done before | entire form | inner membrane | | x |
| CT045 | Leucyl Aminopeptidase A | immunogenic (protein chip) and surfoma (tripsina) | Done | entire form | inner membrane | x | |
| CT622 | CHLPN 76 kDa Homolog | surfoma (tripsina) | Done | entire form | cytoplasm | | x |
| CT768 | hypothetical protein | surfoma (tripsina) | Never done before | entire form | cytoplasm | | x |
| CT814 | hypothetical protein | surfoma (tripsina) | Mever done before | entire form | cytoplasm | | x |
| CT841 | ATP-dependent zinc protease | surfoma (tripsina) | Never done before | entire form | inner membrane | | x |
| CT859 | Metalloprotease | immunogenic (protein chip) and surfoma (tripsina) | Never done before | entire form | cytoplasm | x | |
| CT875 | hypothetical protein | surfoma (tripsina) | Never done before | entire form | cytoplasm | x | x |
| CT664 | (FHA domain; homology to adenylate | surfoma (tripsina) | Never done before | entire form | inner membrane | x | x |
| CT242 | (OmpH-Like Outer Membrane Protein) | surfoma (tripsina) | Done | domain | periplasmic space | x | |
| CT812 | Putative Outer Membrane Protein D | immunogenic (protein chip) and surfoma (ProK) | Done | domain | outer membrane | x | |
| CT823 | DO Serine Protease | immunogenic (protein chip) and surfoma (tripsina) | Done | domain | periplasmic space | x | x |
| CT456 | hypothetical protein | immunogenic (protein chip) and surfoma (tripsina) | Done | domain | outer membrane | x | x |

Protein Identification by Nano-LC/MS/MS.

Two different experimental platforms were used for the chromatographic separation of peptides and further identification was performed by tandem mass spectrometry (MS/MS).

In the first platform, prior to analysis salts were removed by off-line HPLC, with a 7-min gradient of 2-80% acetonitrile (ACN) in 0.1% formic acid. Peptide fractions were concentrated with a Speed-vac centrifuge (Savant, Holbrook, N.Y.), and kept at −20° C. until further analysis. Peptides were separated by two-dimensional (2-D) nano-liquid chromatography (Dionex, Amsterdam, The Netherlands). In the first dimension, peptides were loaded on a strong cation exchange (SCX) column (10 cm×320 µm i. d.) and eluted by 5 salt concentrations (0.01, 0.05, 0.1, 0.5 and 1 M NaCl). In the second dimension, peptides were separated by a reversed phase C18 analytical column (15 cm×75 µm i. d., C18 PepMap100™, 3 µm, 100 Å) via a C18 trap column (PepMap™ C18 µ-precolumn, 300 µm i.d.×1 mm, Dionex). Peptides were eluted with a 45-min gradient from 5 to 50% of 80% ACN in 0.1% formic acid. The flow rate was 300 nl/min. Eluates were continuously spotted onto an Anchor-Chip® MALDI target (Bruker Daltoniks, Bremen, Germany), prepared with a thin layer of a saturated solution of α-cyano-4-hydroxycynnamic acid in acetone, every 60 s using a Proteineer FC robot (Bruker Daltoniks). After fraction collection, spots were recrystallized with 0.6 µl of ethanol/acetone/0.1% trifluoroacetic acid (6:3:1). Mass spectrometry analysis was performed automatically with an Ultraflex MALDI TOF-TOF instrument, under the control of the WARP LC software (Bruker Daltoniks).

In the second platform, peptides were separated by nano-LC on a CapLC HPLC system (Waters, Milford, Mass., USA) connected to a Q-ToF Micro ESI mass spectrometer equipped with a nanospray source (Waters). Samples were loaded onto an Atlantis C18 NanoEase column (100 µm i.d.×100 mm, Waters), via a C18 trap column (300 µm i.d.×5 mm, Dionex). Peptides were eluted with a 50-min gradient from 2% to 60% of 95% ACN, 0.1% formic acid at a flow of 400 nl/min. The eluted peptides were subjected to an automated data-dependent acquisition program, using the MassLynx software (Waters). For both platforms, searching and identification of peptides were performed in batch mode with a licensed version of MASCOT, in a local database.

Results

These experiments have demonstrated that (1) GroEL-1, (2) DnaK, (3) Ef-Tu, (4) Mip-like protein, (5) Major outer membrane protein (MOMP), (6) HctA, (7) CT577, (8) CT223, (9) GroeS, (10) Tarp, (11) Rs10, (12) OmpH-like protein, (13) Rs13, (14) R11, (15) CT875, (16) HtrA, (17) RpoA, (18) PepA, (19) Alanyl tRNA synthetase, (20) RpoC, (21) YaeL, (22) EF-G, (23) CT578, (24) CT579, (25) CT680 and (26) CT814 are surface exposed and/or surface-associated Chlamydial antigens which are useful in immunogenic/immunoprotective or vaccine compositions.

Immunisation Studies

Antigens are selected for combining to give a composition of the invention. BALB/c mice are divided into nine groups and immunized as follows:

| Group | Immunizing Composition | Route of Delivery |
|---|---|---|
| 1 | Mixture of antigens (10-20 µg protein/each) + CFA (Complete Freund's Adjuvant) | Intraperitoneal or intranasal or subcutaneous |
| 2 | Mixture of antigens (5 µg/each) + Al-hydroxide (200 µg) | Intraperitoneal or intranasal or subcutaneous |
| 3 | Mixture of antigens (10-20 µg protein/each) + CpG (10 µg) | Intraperitoneal or intranasal or subcutaneous |
| 4 | Mixture of antigens (10-20 µg protein/each) + Al-hydroxide (200 µg) + CpG (10 µg) | Intraperitoneal or intranasal or subcutaneous |
| 5 | CFA | Intraperitoneal or intranasal or subcutaneous |
| 6 | Mixture of antigens (10-20 µg protein/each) + LTK63 (5 µg) | Intraperitoneal or Intranasal or subcutaneous |
| 7 | Al-hydroxide (200 µg) + CpG (10 µg) | Intraperitoneal or intranasal or subcutaneous |
| 8 | CpG (10 µg) | Intraperitoneal or intranasal or subcutaneous |
| 9 | LTK63 (5 µg) | Intraperitoneal or intranasal or subcutaneous |

Mice are immunized at two-week intervals. Two to three weeks after the last immunization, all mice are challenged with the appropriate *Chlamydia* serovar strain. When mucosal immunization (e.g. intranasal) is used, the animal model is also challenged mucosally to test the protective effect of the mucosal immunogen. Immediately prior to challenge, mice are bled to determine antibody titre to the antigens that were administered.

For the mouse challenge, virulent bacteria will be grown in appropriate media. Bacteria are harvested by centrifugation, re-suspended, and serially diluted for the challenge inoculum. BALB/c mice are challenged and observed daily for 30 days post-exposure.

Total IgG and IgG1/IgG2A subtypes can be measured in mouse sera resulting from the different immunization regimens by using an ELISA assay on whole bacteria and on purified recombinant proteins. Furthermore, assessment of antigen-specific CD4$^+$ and CD8$^+$Th-cells in spleen cells and/or PBMC isolated from immunized mice can be carried out by multi-parametric FACS analysis, to evaluate the cytokine expression profiles of antigen-specific T-cells. In particular production of IFN-$\gamma$ and IL-5 can be measured after in vitro stimulation of T cells with purified antigens and/or whole *Chlamydia* Elementary bodies (EB). In addition, splenocytes and/or PBMC from mice immunized with each antigen/vaccine formulation may be collected 10-12 days after the last immunization dose and stimulated with whole *Chlamydia* bacteria. After 4 hours of stimulation, Brefeldin A is added to the cells for the following 12 hours, to block cytokines secretion. Afterwards cells are fixed and stained with antibodies to detect *Chlamydia*-specific T cells expressing IFN-$\gamma$ and IL-5.

T cells can be isolated from peripheral blood lymphocytes (PBLs) by a variety of procedures known to those skilled in the art. For example, T cell populations can be "enriched" from a population of PBLs through the removal of accessory and B cells. In particular, T cell enrichment can be accomplished by the elimination of non-T cells using anti-MHC class II monoclonal antibodies. Similarly, other antibodies can be used to deplete specific populations of non-T cells. For example, anti-Ig antibody molecules can be used to deplete B cells and anti-MacI antibody molecules can be used to deplete macrophages.

T cells can be further fractionated into a number of different subpopulations by techniques known to those skilled in the art. Two major subpopulations can be isolated based on their differential expression of the cell surface markers CD4 and CD8. For example, following the enrichment of T cells as described above, CD4$^+$ cells can be enriched using antibodies specific for CD4. The antibodies may be coupled to a solid support such as magnetic beads. Conversely, CD8+ cells can be enriched through the use of antibodies specific for CD4 (to remove CD4$^+$ cells), or can be-isolated by the use of CD8 antibodies coupled to a solid support. CD4 lymphocytes from *Chlamydia* infected patients can be expanded ex vivo, before or after transduction as described by reference 321.

Following purification of T cells, the purified T cells are pre-stimulated with various cytokines including but not limited to rIL-2, IL-10, IL-12, and IL-15, which promote growth and activation of lymphocytes.

*Chlamydia*-specific T cells, may be activated by the above-described immunogenic polypeptides. *Chlamydia*-specific T cells can be CD8$^+$ or CD4$^+$. *Chlamydia*-specific CD8$^+$ T cells can be cytotoxic T lymphocytes (CTL) which can kill *Chlamydia*-infected cells that display any of the above described polypeptides or fragments thereof complexed with an MHC class I molecule. *Chlamydia*-specific CD8$^+$ T cells can be detected by, for example, $^{51}$Cr release assays. $^{51}$Cr release assays measure the ability of *Chlamydia*-specific CD8$^+$ T cells to lyse target cells displaying one or more of these epitopes. *Chlamydia*-specific CD8$^+$ T cells which express antiviral agents, such as IFN-$\gamma$, are also contemplated herein and can also be detected by immunological methods, preferably by intracellular staining for IFN-$\gamma$ or like cytokine after in vitro stimulation with one or more of the above described *Chlamydia* polypeptides. *Chlamydia*-specific CD4$^+$ T cells can be detected by a lymphoproliferation assay. Lymphoproliferation assays measure the ability of *Chlamydia*-specific CD4$^+$ T cells to proliferate in response to one or more of the above described polypeptides.

Antigens Inducing an Ab-Mediated Reduction of Infection

Sera obtained by immunizing mice with 158 purified recombinant *C. trachomatis* (Ct) proteins have been tested in vitro for neutralization activity. In vitro neutralization assays were performed on LLC-MK2 (Rhesus monkey kidney) epithelial cell cultures. Serial four-fold dilutions of mouse immune and corresponding preimmune sera were prepared in sucrose-phosphate-glutamic acid buffer (SPG). Mouse polyclonal sera to whole EB were used as positive control of neutralization, whereas SPG buffer alone was used as negative control of neutralization (control of infection). Purified infectious EB from the serotype-D Ct strain GO/96 were diluted in SPG buffer to contain 3×10$^5$ IFU/ml, and 10 µl of EB suspension were added to each serum dilution in a final volume of 100 µl. Antibody-EB interaction was allowed to proceed for 30 min at 37° C. on a slowly rocking platform. The 100 µl of reaction mix from each sample was used to inoculate PBS-washed LLC-MK2 confluent monolayers (in triplicate for each serum dilution), in a 96-well tissue culture plate, and centrifuged at 805×g for 1 hour at 37° C. After centrifugation Eagle's minimal essential medium containing Earle's salts, 20% fetal bovine serum and 1 µg/ml cycloheximide was added. Infected cultures were incubated at 37° C. in 5% $CO_2$ for 72 hours. The monolayers were fixed with methanol and the chlamydial inclusions were detected by staining with a mouse anti-*Chlamydia* fluorescein-conjugated monoclonal antibody (Merifluor *Chlamydia*, Meridian Diagnostics, Inc.) and quantified by counting 5 fields per well at a magnification of 40×. The inhibition of infectivity due to EB interaction with the immune sera was calculated as percentage reduction in mean IFU number as compared to the SPG (buffer only)/EB control. In this calculation the IFU counts obtained with immune sera were corrected for background inhibition of infection observed with the corresponding pre-immune mouse serum. According to common practice, the sera were considered as "neutralizing" if they reduce infectivity by at least 50%. The corresponding neutralizing titer was defined as the serum dilution at which a 50% reduction of infectivity was observed. Experimental variability was evaluated by calculating the standard error of measurement (SEM) of three titration experiments for each recombinant antigen.

This analysis revealed 11 antigens showing neutralizing capability (CT681, CT467, CT398, CT587, CT823, CT396, CT381, CT242, CT552, CT547 and CT045) (see FIG. 1). In particular 5 antigens (CT242, OmpH-like; CT381, ArtJ; CT467, AtoS; CT547; and CT587, Enolase) have neutralizing titer which is superior to the titer observed with the polyclonal Abs against total EB. The remaining 6 antigens induce neutralizing Abs at a titer similar to EB. Interestingly, the homologs of 5 of the neutralizing antigens were also neutralizing in *C. pneumoniae*. In addition and most importantly, the neutralization capacity of all 11 antigens had never been described before.

Screening of Antigen-Specific Antisera for Their Capability to Induce Lysis of *C. trachomatis* Infected Cells in the Presence of Complement Confluent HeLa cells are infected with *C. trachomatis* EBs. 40 hours post infection, sera from mice is added in serial twofold dilutions. Following 2 h incubation, the cells are washed, overlaid with complement and then incubated at 37° C. for 3 h. The levels of cytotoxicity of both infected HeLa cell monolayers and matched, uninfected controls are assessed with a LDH cytotoxicity detection kit. This is a colorimetric assay for the quantification of cell death and cell lysis based on the measurement of lactate dehydrogenase (LDH) activity released from the cytosol of the damaged cells into the supernatant. The supernatants of both test and control samples are centrifuged at 250 g to remove cells and cell debris, and the cell-free supernatants are diluted and incubated with the kit reaction mixture. An increase in the amount of dead or plasma membrane damaged cells results in an increase in the LDH enzyme activity in the culture supernatant.

In Vitro Model for the Selection of Antigens Inducing a CD4 Th1 Response

Th1-type cytokines, such as IL-12 and IFN-γ, have been proposed to be important for resolution of chlamydial infection. Indeed, mice deficient in IFN-γ are unable to control chlamydial infection in the genital tract as *Chlamydia* disseminates to systemic sites [322, 323].

Two immunological screening approaches to identify *Chlamydia* antigens capable of inducing *Chlamydia*-specific IFNγ-producing $CD4^+$ T cells have been devised: 1) after experimental mouse infection with *Chlamydia trachomatis*, and 2) following mouse immunization with *Chlamydia* recombinant proteins. These antigens would be the most promising candidates to confer $CD4^+$-mediated protection.

In the first approach female BALB/c mice 6-7 weeks old were pretreated with 2.5 mg of medroxy-progesterone acetate (Depo-Provera) on day −5 and then infected intravaginally at day 0 by depositing 15 ml of SPG (250 mM Sucrose, 10 mM Sodium Phosphate, 5 mM L-Glutamic acid) containing $10^6$ IFU of *C. trachomatis* serovar D. Seven days post infection the course of infection was monitored by swabbing the vaginal vault and determining the number of recovered IFUs on LL-CMK2 cell monolayers using indirect immunofluorescence.

Splenocytes were prepared from spleens of mice infected with *Chlamydia trachomatis* (10 days post infection) and non-infected controls. Spleens of each group of mice were pooled and dispersed manually. Splenocytes were cultured in RPMI 1640 medium supplemented with 25 mM HEPES buffer, 100 UI/ml penicillin, 100 mg/ml streptomycin, 50 mM 2-mercaptoethanol, 0.15 mM L-glutamine, sodium pyruvate, vitamins, a cocktail of non-essential amino acids and 2.5% heat inactivated fetal calf serum.

Freshly prepared splenocytes from infected mice and non infected controls were stimulated for 4 hours in round-bottom 96 well plates with 20 mg/ml of various *Chlamydia trachomatis* recombinant antigens in the presence of 1 mg/ml anti-CD28. As positive controls of stimulation 1 mg/ml of anti-CD3 and 10 mg/ml of heat inactivated whole *C. trachomatis* Elementary Bodies were used. For the analysis of antigen induced intracellular cytokine expression, 2.5 mg/ml Brefeldin-A (Sigma) was added overnight. At the end of the stimulation period cells were fixed with 2% paraformaldeide and subsequently permeabilized with PBS-1% BSA-0.5% saponin. Fixed cells were stained for 30 min at room temperature with the following antibodies: antiCD4-FITC, antiCD8-PerCp, antiIFNg-APC and antiIL5-PE (all BD Pharmingen).

Stained cells were analyzed for cytokine production on a LSRII cytometer with a DIVA software.

In the second approach, mice were immunized intramuscularly on days 1, 14 and 28 with a panel of recombinant chlamydial proteins with proper adjuvants. A week after the last immunization, PBMC were isolated and assessed by spleen harvesting as described above, in the presence of syngeneic irradiated APC. Ex vivo stimulation was carried out for 24 hours using whole *Chlamydia trachomatis* EBs. Following stimulation the cells were analysed for cytokine production (IFN-γ and IL-5) as described above.

Both screening are carried out using multi-parametric FACS analysis to assess the cytokine expression profile of antigen-specific Th1-cells.

In the first assay, splenocytes from mice that had experienced and resolved a primary *C. trachomatis* infection were separately stimulated with EB and recombinant MOMP. Based on published data, a considerable proportion of spleen T lymphocytes from these mice should produce IFNγ upon EB stimulus. A similar cytokine production, although at a lower level, should be observed in lymphocytes stimulated with rMOMP, the only protective antigen in the mouse model so far described in peer reviewed journals. The data shown in FIGS. 2*a* and 2*b* confirmed the expected CD4-Th1 response. Splenocytes stimulated with EB show a poor frequency of $IL5^+$ cells and a high frequency of $IFN\gamma^+$ T cells. FIG. 3 shows that 7 of the 54 tested antigens were able to induce significant *C. trachomatis*-specific CD4-Th1 responses. These seven antigens were CT681 (Momp), CT043 (Hypo), CT711 (Hypo), CT587 (Enolase), CT823 (DO serine protease), CT396 (Hsp70) and CT480 (Oligopeptide Binding Lipoprotein).

Analysis of Antigens for MHCII Epitopes CT823, CT587, CT043 and CT153 were analysed using the PRED$^{BALB/c}$ system for predicting peptide binding to H2$^d$ molecules [324]. All of the peptides were predicted to contain MHC II epitopes. This indicates that these epitopes would be useful in raising a CD4-Th1 response. The epitopes predicted to be found in these antigens are recited in SEQ ID NOs: 261-275. The results of the analysis using the PRED$^{BALB/c}$ system is shown in FIG. 10.

Identification of Human Immunogens by Protein Array Analysis of Human Sera

A prototype protein array has been prepared containing 53 selected antigens, including all FACS positive antigens (see above). Spotting was performed on nitrocellulose FAST slides using a Chipwriter spotter. Proteins were spotted in four replicates at 0.3-0.5 mg/ml in PBS buffer. As positive control, human IgG was spotted at concentrations ranging from 0 to 0.5 mg/ml. Antigen recognition by human sera was obtained after 1 h incubation with human sera (1:1000 dilution), followed by incubation with Phycoerytrin-labelled goat anti-human IgG (1:500). Slide scanning was performed using a Scanarray 5000 instrument and spot quantification was done with Imagene 6.0 software. Data were processed using in-house developed software. For each protein, the mean fluorescence signal was determined after background subtraction and data were normalized to the mean fluorescence signals of human IgG spots. Proteins that, after background subtraction, showed mean fluorescence signal lower than 5000 were considered negative.

Figure 4:
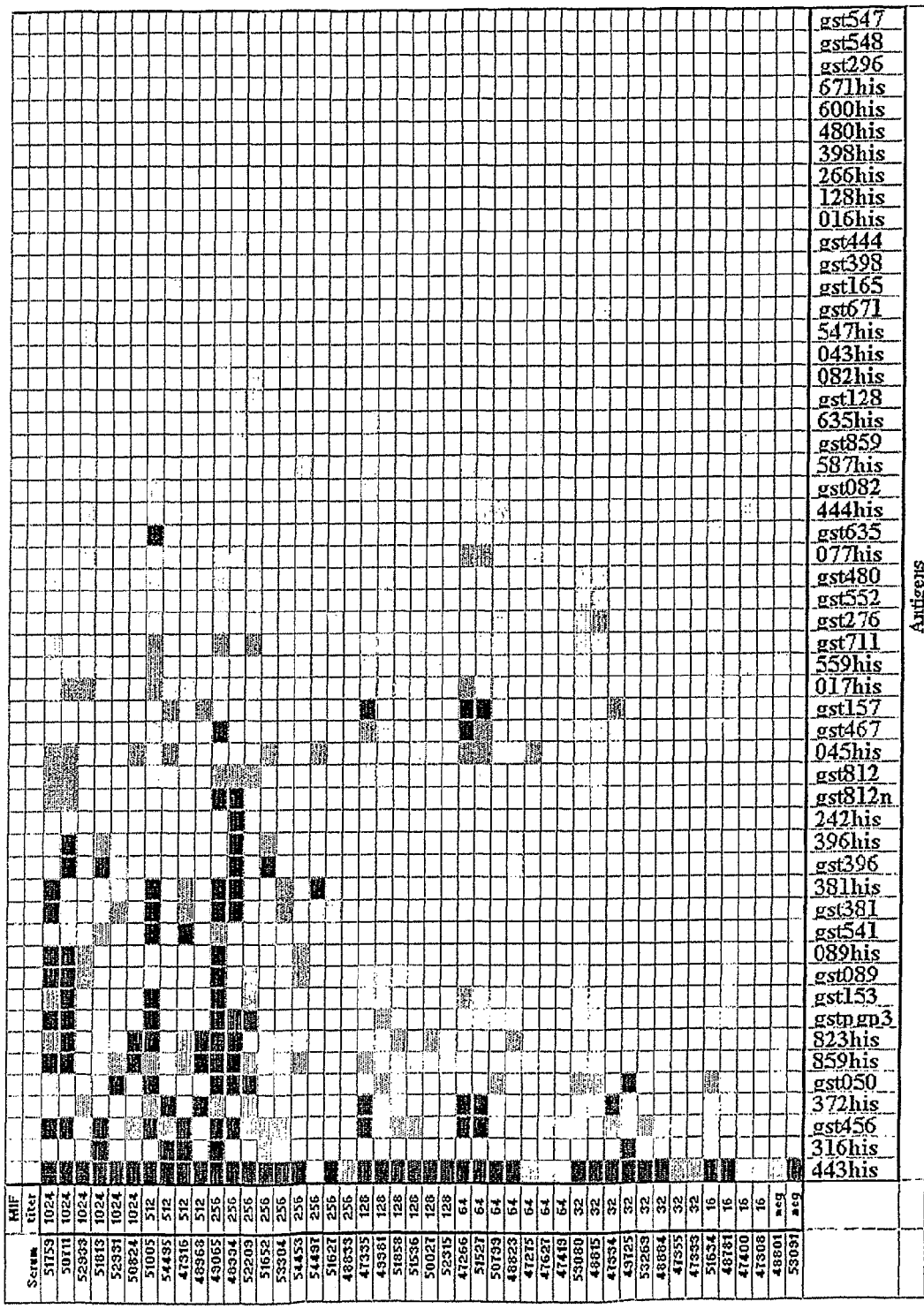

The array is being used for screening of a panel of 100 human sera from Chlamydia trachomatis positive patients. Results on a first batch of 53 sera out of the 100 (FIG. 4), indicate that 13 antigens appeared immunogenic (recognized by more than 30% of the tested sera) (Table 3). 5 proteins were recognized by more than 50% of the tested sera. 5 of the 13 were previously reported as immunogens (highlighted in yellow), while 8 proteins were never described before. 10 proteins were not detected by any of the tested sera.

TABLE 3

| Antigen ID | annotation | % of positive sera |
|---|---|---|
| 443 | 60 Kda Cys. Ric. Omp | 100 |
| 456 | Hypothetical Protein | 66 |
| 859 | Metalloprotease | 55 |
| 372 | Hypothetical Protein | 51 |
| 050 | Hypothetical Protein | 43 |
| 823 | DO Serine Protease | 42 |
| pgp3 | pgp3 | 36 |
| 153 | Hypothetical Protein | 32 |
| 089 | Low Ca Response E | 30 |
| 045 | Leucyl Aminopep. A | 32 |
| 467 | 2-comp regul sys | 30 |
| 017 | Hypothetical Protein | 38 |
| 559 | Yop transl lipop | 36 |

Setting-Up of the C. muridarum (Alias MoPn) and the C. trachomatis Serovar D Animal Models This model uses a murine strain of C. trachomatis which is more virulent in mice, and causes evident pathology of the urogenital tract (UGT) in a high percentage of infected mice. Owing to the only partial conservation of ortholog genes in the murine vs human genomes, immunizations in this model need to be carried out with the MoPn protein homologs to those being tested in parallel in the model with the human strain.

Figure 5:
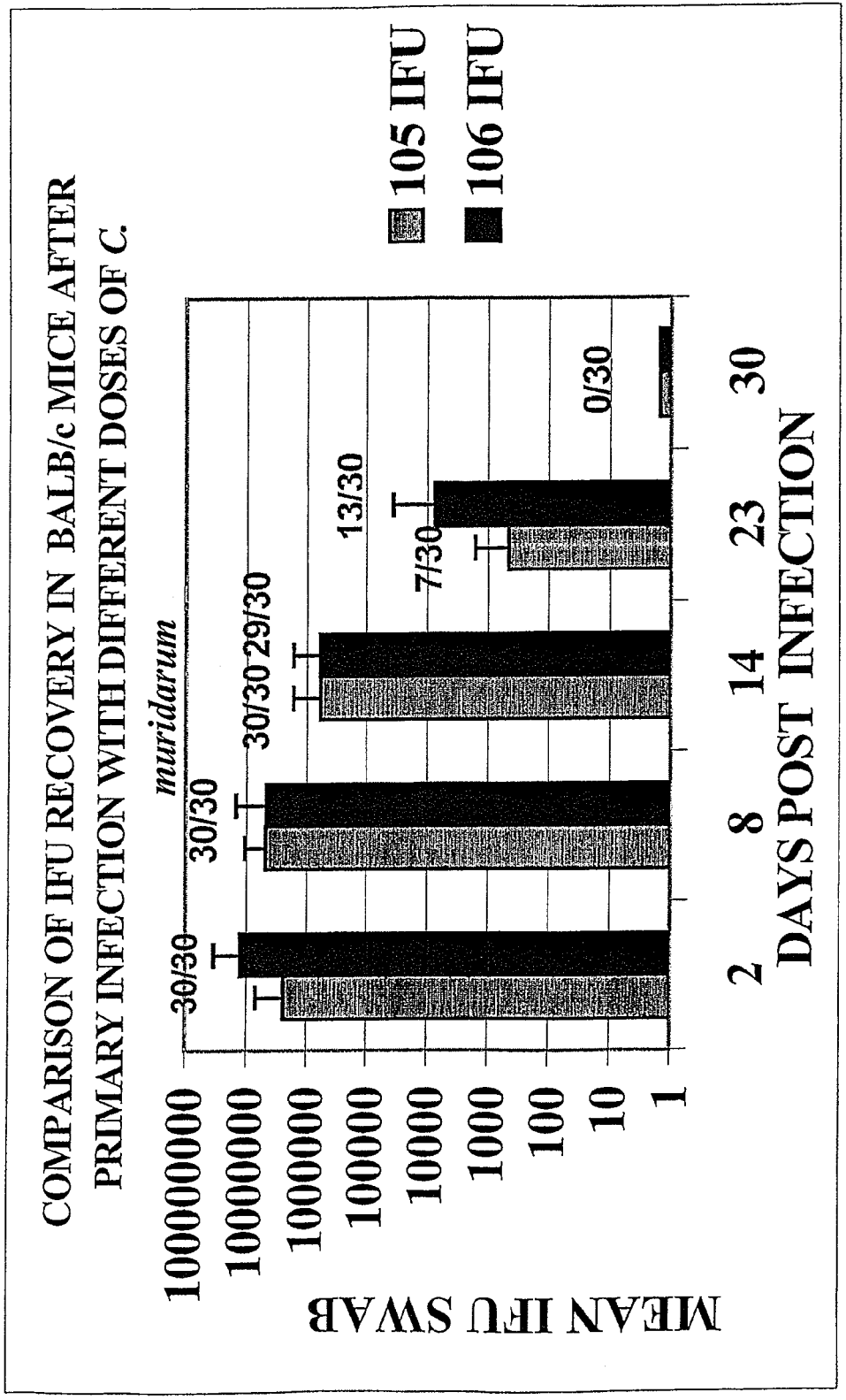

To set-up a mouse model of vaginal infection with C. muridarum, the optimal infectious dose was determined. C. muridarum was obtained from the ATCC and grown in LLCMK2 cells. The number of IFU (inclusion forming units=viable chlamydiae) recovered from vaginal swabs after infection of 3 different mouse strains (C57BL/6; BALB/c, C3H/Ne) with increasing infectious doses of MoPn EB ($10^4$, $10^5$, $10^6$ IFU) was compared. The experiment was performed twice using groups of 30 mice in each experiment, and showed that BALB/c mice can be infected in a high percentage both using $10^5$ or $10^6$ IFU as the infecting dose (see FIG. 5), whereas vaginal infection with $10^4$ IFU yielded a low percentage of infected mice (not shown). These experiments also showed that mice can be assessed for up to 21-23 days post infection (p.i.) while they completely recover by day 25 to 30 p.i.

Figure 6:
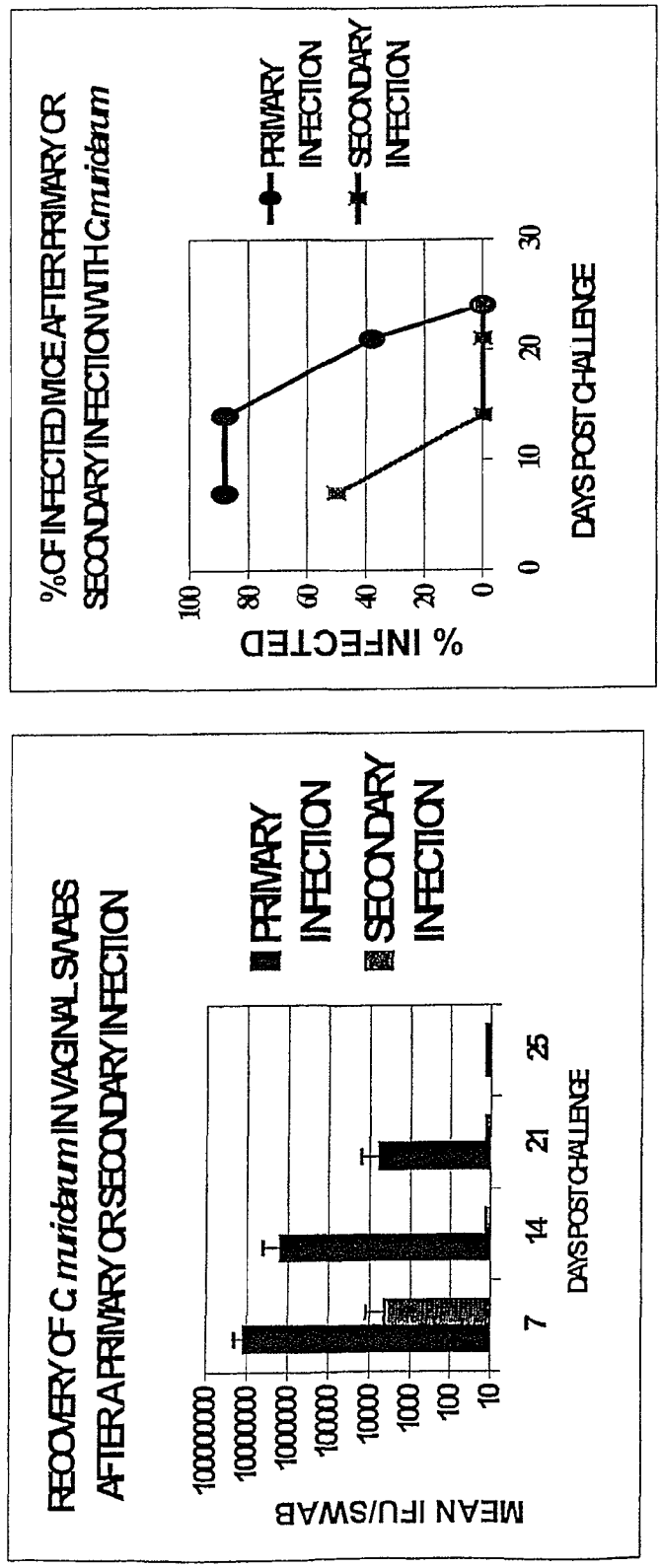
FIG. 6 shows the set up of positive control of protection with *C. muridarum*. Group of 30 BALB/c mice received a primary infection with $10^6$ *C. muridarum* IFU and vaginal swabs were collected at time intervals up to for 45 days p.i., to assure a complete bacterial clearance in the lower genital tract. Mice were then re-challenged with $10^5$ IFU of *C. muridarum*. Protection level was determined by measuring the mean IFU in vaginal swabs of mice that received only a primary infection and mice that were re-challenged at week intervals (left panel). Protection was also determined considering the percentage of mice with positive vaginal swabs at week intervals (right panel). Mice that received a secondary infection (red symbols) showed a complete clearance of infectious chlamydiae in the lower genital tract by day 14 p.i., as compared to mice that received only a primary infection (black symbols).

The positive control of protection (gold standard) was then set up, which is represented by the extent of natural immunity induced by a resolved primary infection. BALB/c mice received a primary infection with $10^6$ C. muridarum IFU and vaginal swabs were collected at time intervals up to for 45 days p.i., to assure a complete bacterial clearance in the lower genital tract. Mice were then challenged with $10^5$ IFU of C. muridarum and the protection level was determined by comparing IFU in vaginal swabs of mice that received only a primary infection with those of mice that received also a secondary infection (see FIG. 6). Mice that received a secondary infection showed a complete clearance of infectious chlamydiae in the lower genital tract by day 14 p.i., as shown by negative vaginal swab cultures.

Figure 7:
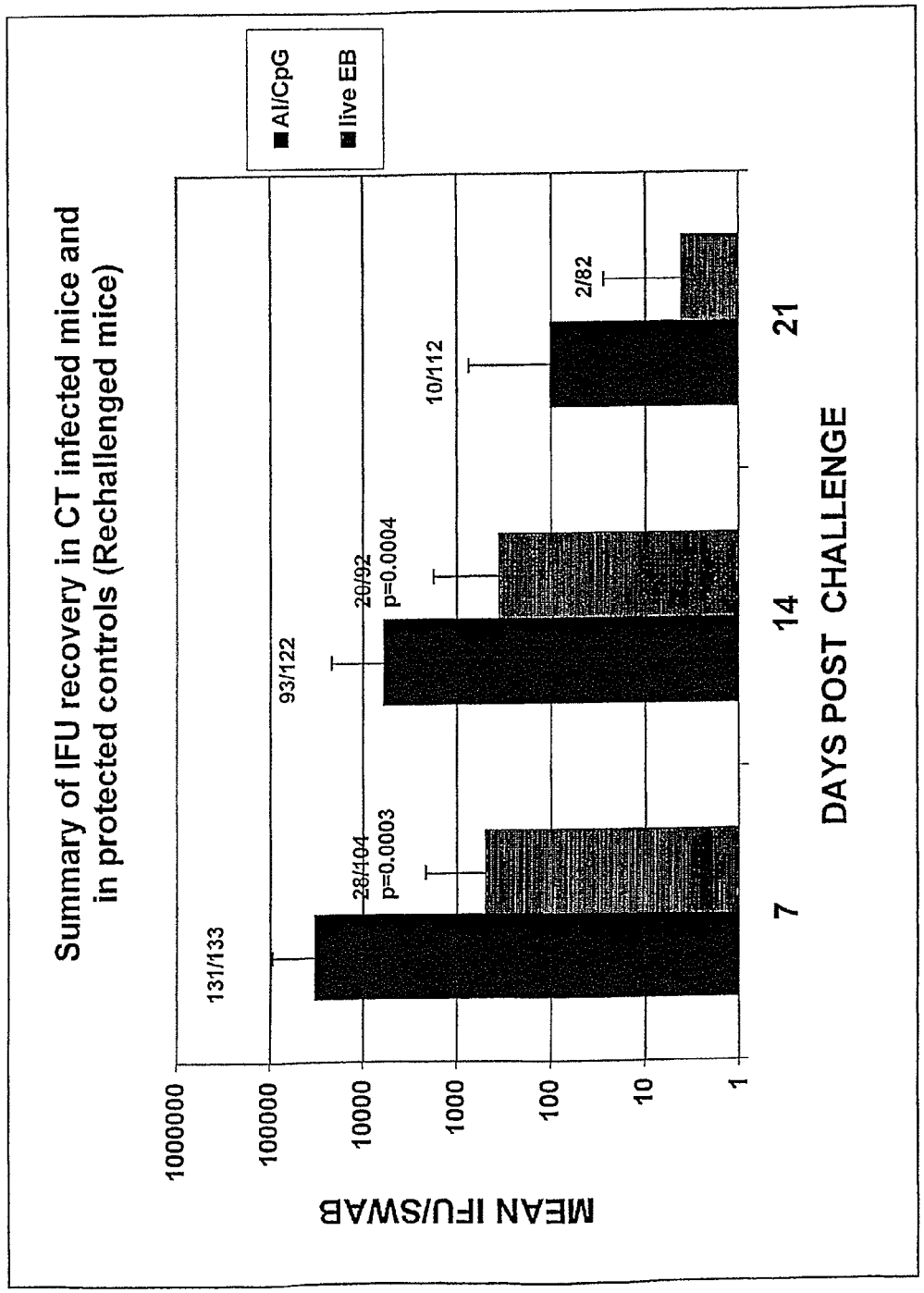
FIG. 7 shows the set up of the mouse model of vaginal infection with *C. trachomatis* serovar D. BALB/c mice received a primary infection with $10^6$ *C. trachomatis* serovar D IFU and vaginal swabs were collected at time intervals up to for 28 days p.i., to assure a complete bacterial clearance in the lower genital tract. Mice were then re-challenged with $10^5$ IFU of *C. trachomatis*. Protection level was determined by comparing, at week intervals, the mean IFU in the vaginal swabs of re-challenged mice (red bars) with those of mice that were immunized with PBS/alum CpG and subsequently infected with $10^5$ IFU of *C. trachomatis* (dark bars). Statistical significance of reduction of the mean IFU counts was done using Student t-test. Absolute numbers of infected mice are reported. Mice that received a secondary infection (light bars) showed a significant reduction in the number of IFU counts in the lower genital tract by day 7 p.i., as compared to mice that received only a primary infection.

A second model was set up by using the human serovar D. This model adopts the same technical approach with the difference that a 1-log higher infection dose is used to achieve 100% level of infection. Data is shown in FIG. 7.

Identification of Protective Antigens

The FACS positive and neutralizing antigens were tested for their capacity to induce protection against C. trachomatis serovar D challenge in vivo. Considering the complexity of the model, antigens were grouped in combination of 5 with the intention to deconvolute the mixture(s) which showed protective activity.

Figure 8:
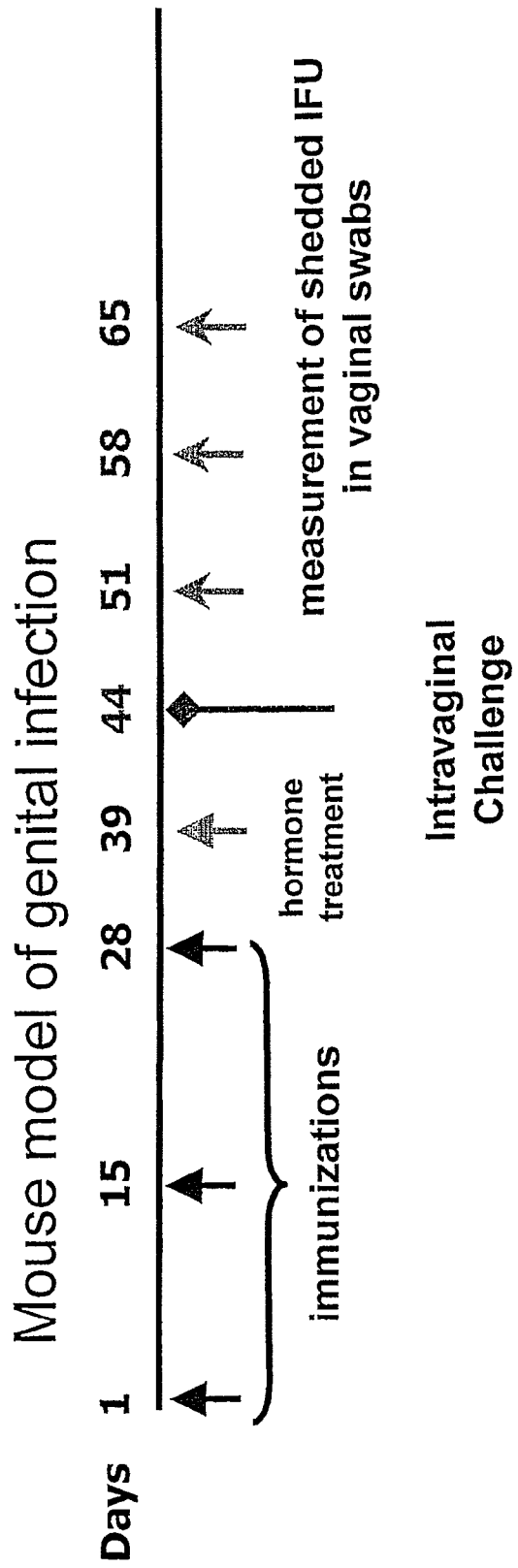
FIG. 8 shows the immunisation, challenge and read-out schedule for the protective antigen assay.

The antigen combinations included 15 µg of each selected proteins, 200 µg Alum and 10 µg of 1826-CpG (5' TCCAT-GACGTTCCTGACGTT 3'; SEQ ID NO: 260). Immunizations were carried out intra peritoneally by administering three doses every 14 days (see FIG. 8 for assay schedule). 10 days post last immunization mice were hormone-treated with 2.5 mg of Medroxyprogesterone acetate and 5 days later were challenged intra-vaginally with $10^5$ of C. trachomatis IFU. Vaginal swabs were collected at week-intervals, and chlamydiae were detached from the swabs under agitation in 200 µl SPG buffer. Serial dilutions of the Chlamydia suspension were used to infect a monolayer of LLC-MK2 cells and IFU counts were determined 48 hours later by fluorescence microscopy, after cell fixation and staining of inclusion with a fluorescently labelled anti-Chlamydia MAb.

A combination of 5 antigens, including CT089, CT045, CT381, CT398, CT396, showed a trend of reduction of infection in the immunized mice, as compared to control mice immunised with adjuvant alone.

Figure 9:
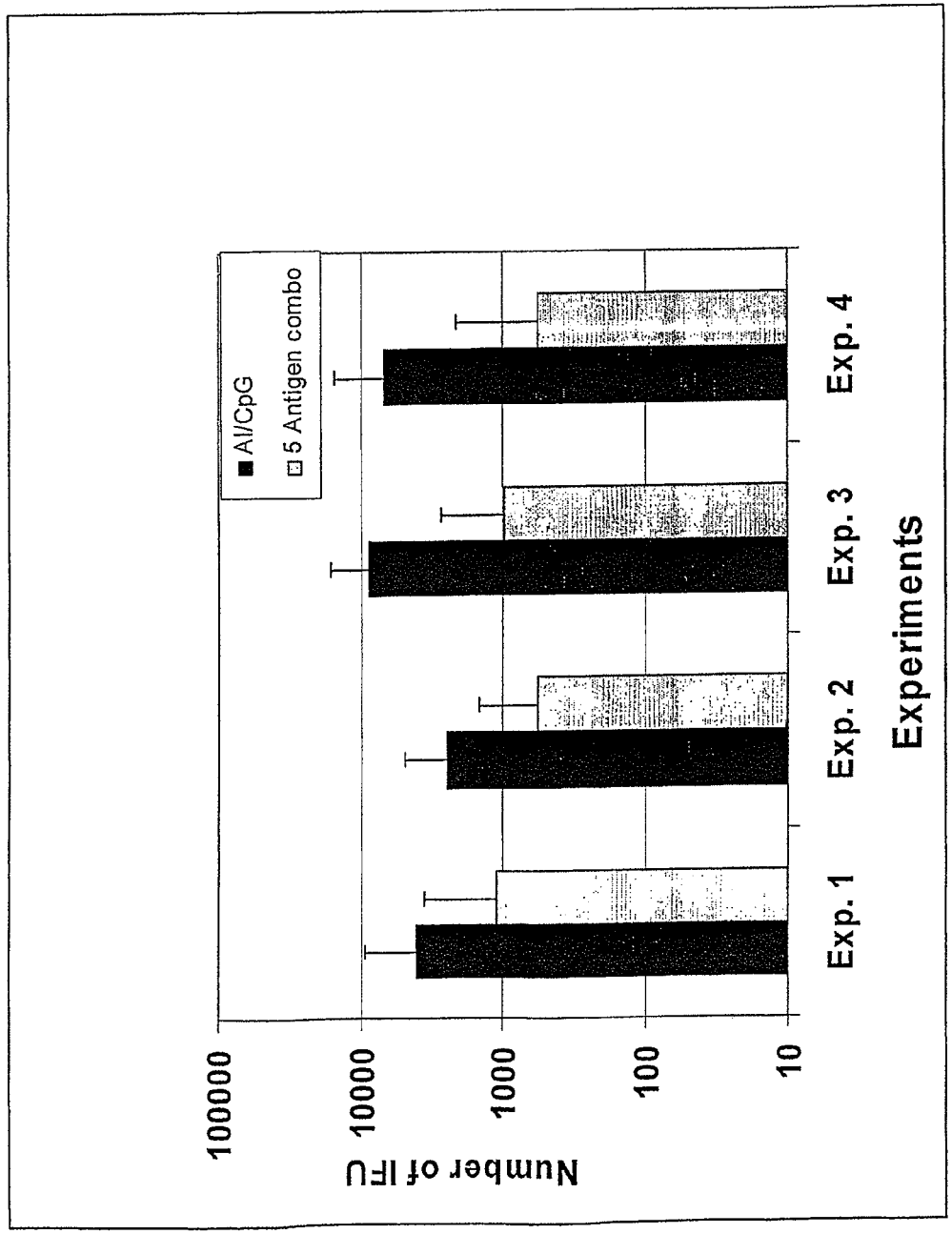
FIG. 9 shows the evaluation of the protective effect of the 5 antigen combo. A group of 10 BALB/c mice were immunized three times i.p. with a combination of 5 antigens, including CT089, CT045, CT381, CT398, CT396, with Alum+CpG as adjuvant. 10 days post last immunization the mice were hormone-treated with 2.5 mg of Medroxyprogesterone acetate and 5 days later were challenged intra-vaginally with $10^5$ IFU of *C. trachomatis*. Vaginal swabs were collected at week-intervals and number of viable chlamydiae (IFU) were measured. Data show the mean IFU counts at day 14 post challenge in the 5 antigen-combo immunized mice (light bars) and adjuvant immunized control (dark bars) in four independent experiments. The statistical significance of each experiment (p) was determined by Student t-test.
Figure 11A:
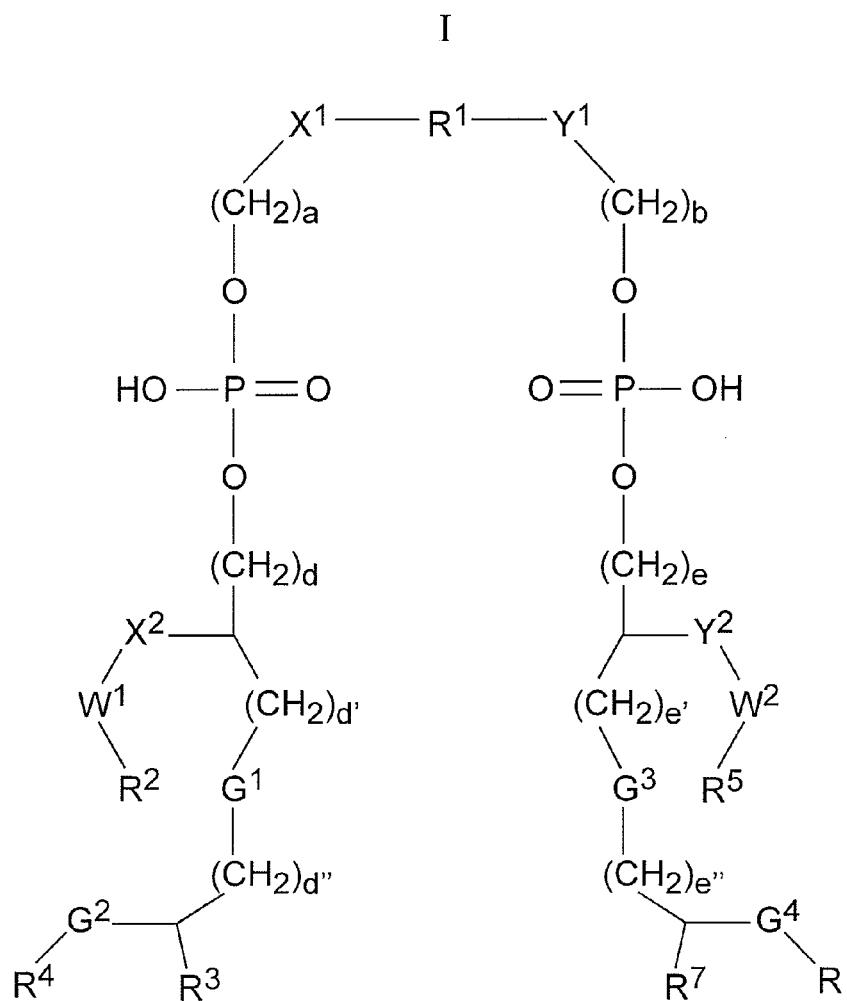
FIGS. 11A-11C show adjuvant compounds of formula I (FIG. 11A), formula II (FIG. 11B) and formula III (FIG. 11C) as described in the application.
Figure 11B:
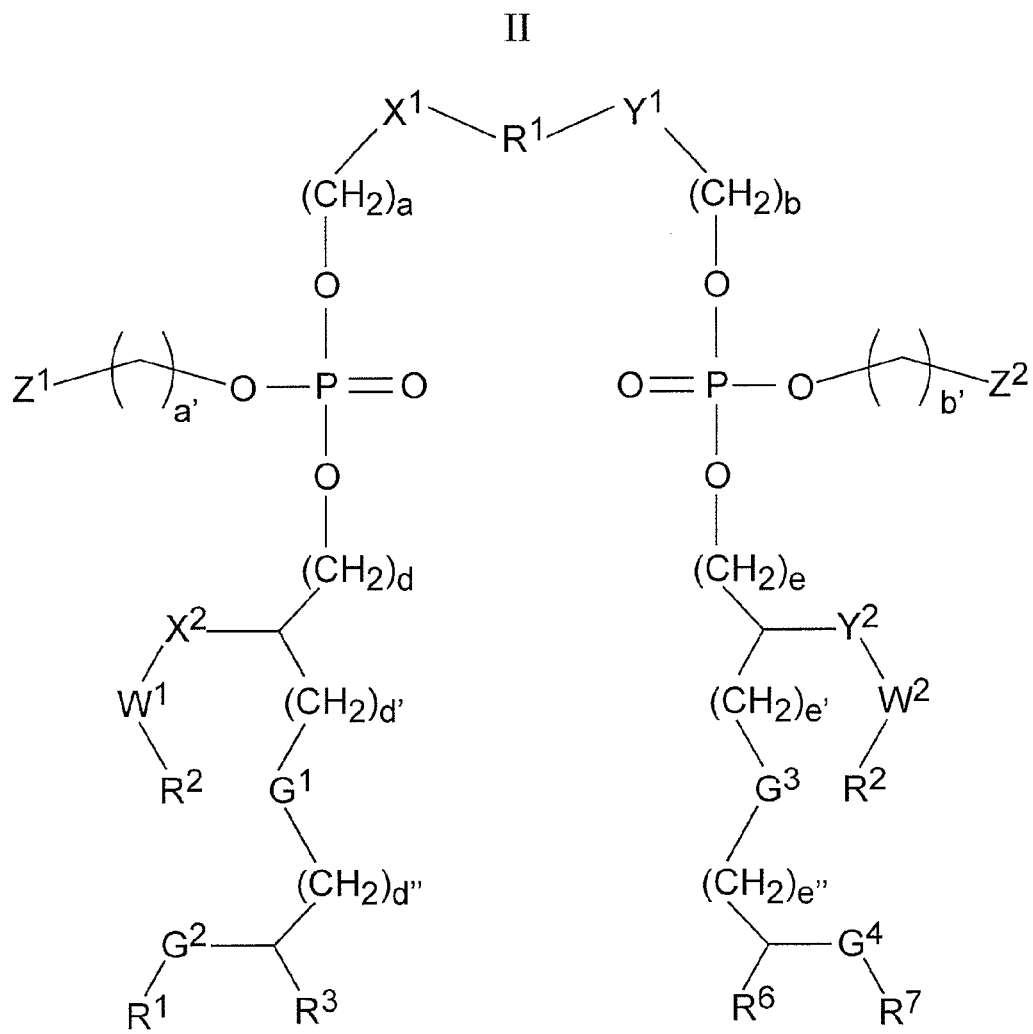
Figure 11C:
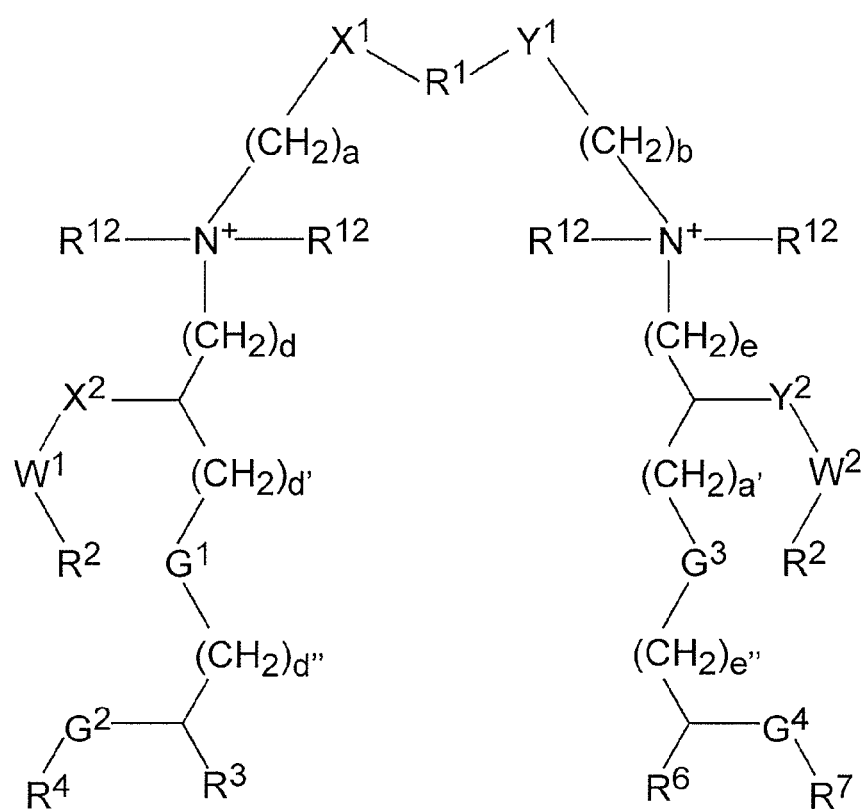

In particular, at day 14 post challenge an up to 1 log reduction in shed chlamydiae was observed in four independent experiments carried out in groups of 10 mice (FIG. 9). Furthermore, an average of 25% reduction in the number of infected mice was observed, suggesting the immunization with the combo not only reduced the number of shed chlamydiae but also accelerated the bacterial clearance.

It will be understood that the invention has been described by way of example only and modifications may be made whilst remaining within the scope and spirit of the invention.

REFERENCES

The Contents of Which are Hereby Incorporated in Full

[1] Kalman et al. (1999) *Nature Genetics* 21:385-389.
[2] Read et al. (2000) *Nucleic Acids Res* 28:1397-1406.
[3] Shirai et al. (2000) *Nucleic Acids Res* 28:2311-2314.
[4] Stephens et al. (1998) *Science* 282:754-759.
[5] WO 99/27105.
[6] WO 00/27994.
[7] WO 99/28475.
[8] Ward (1995) *Apmis.* 103:769-96.
[9] Moulder (1991) *Microbiol Rev* 55(1):143-190.
[10] Comanducci et al. (1994) *Infect Immun* 62(12):5491-5497.
[11] EP-A-0499681.
[12] WO 95/28487.
[13] Murdin et al. (1993) *Infect Immun* 61:4406-4414.
[14] Cerrone et al. (1991) *Infect Immun* 59(1):79-90.
[15] Raulston et al. (1993) *J. Biol. Chem.* 268:23139-23147.
[16] WO 03/049762.
[17] WO 2005/002619.
[18] Montigiani et al. (2002) *Infect Immun* 70(1):368-379.
[19] WO 00/37494.
[20] Birkelund et al. (1990) *Infect Immun* 58:2098-2104.
[21] Danilition et al. (1990) *Infect Immun* 58:189-196.
[22] Raulston et al. (1993) *J. Biol Chem* 268:23139-23147.
[23] Bavoil et al. (1984) Infection and Immunity 44:479-485.
[24] Hatch et al., (1986) *J. Bacteriol.* 165:379-385.
[25] Stephens et al., (1987) *J. Bacteriol.* 169:3879-3885.
[26] Yuan et al., (1989) *Infection and Immunity* 57: 1040-1049.
[27] Baehr et al., (1988) *PNAS USA* 85:4000-4004.
[28] Lucero et al., (1985) *Infection and Immunity* 50:595-597.
[29] Zhang et al., (1987) *J. Immunol.* 138:575-581.
[30] Peterson et al., (1988) *Infection and Immunity* 56:885-891.
[31] Zhang et al., (1989) *Infection and Immunity* 57:636-638.
[32] Allen et al., (1991) *J. Immunol.* 147:674-679.
[33] Su et al. (1990) *J. Exp. Med.* 172:203-212.
[34] Clifton et al. (2004) *PNAS* 101(27): 10166-71.
[35] Allen et al. (1990) *Mol. Microbiol.* 4:1543-1550.
[36] WO 03/049762.
[37] Ghaem-Maghami et al., (2003) *Clin. Exp. Immunol.* 132:436-442.
[38] Donati et al., (2003) *Vaccine* 21:1089-1093.
[39] Fling et al., (2001) *PNAS* 98(3): 1160-1165.
[40] Hessel, et al., (2001) *Infection and Immunity* 69(8): 4996-5000.
[41] Eckert, et al., (1997) *J. Infectious Disease* 175:1453-1458.
[42] Domeika et al., (1998) *J. Infectious Disease* 177:714-719.
[43] Deane et al., (1997) *Clin. Exp. Immunol.* 109(3): 439-445.
[44] Peeling et al., (1997) *J. Infect. Dis.* 175(5):1153-1158.
[45] Rank et al., (1995) *Invest Ophthalmol. Vis. Sci.* 36(7): 1344-1351.
[46] Yi et al., (1993) *Infection & Immunity* 61(3):1117-1120.
[47] Stephens et al., (2001) *Molecular Microbiology* 40(3): 691-699.
[48] Millman, et al., (2001) *J. of Bacteriology* 183(20):5997-6008.
[49] Mygind, et al., *Journal of Bacteriology* (1998) 180(21): 5784-5787.
[50] Bas, et al., (2001) *Journal of Clinical Microbiology* 39(11):4082-4085.
[51] Goodall, et al., (2001) *Clin. Exp. Immunol.* 126:488-493.
[52] Molloy (2006) *Nature Reviews Microbiology* 4:6-7.
[53] Philipovskiy et al. (2005) *Infect Immun.* 73(3):1532-42.
[54] WO 02/065129.
[55] *Vaccine Design* . . . (1995) eds. Powell & Newman. ISBN: 030644867X. Plenum.
[56] WO00/23105.
[57] WO90/14837.
[58] Podda & Del Giudice (2003) *Expert Rev Vaccines* 2:197-203.
[59] Podda (2001) *Vaccine* 19: 2673-2680.
[60] *Vaccine Adjuvants: Preparation Methods and Research Protocols* (Volume 42 of *Methods in Molecular Medicine* series). ISBN: 1-59259-083-7. Ed. O'Hagan.
[61] Allison & Byars (1992) *Res Immunol* 143:519-25.
[62] Hariharan et al. (1995) *Cancer Res* 55:3486-9.
[63] U.S. Pat. No. 5,057,540.
[64] WO96/33739.
[65] EP-A-0109942.
[66] WO96/11711.
[67] WO00/07621.
[68] Barr et al. (1998) *Advanced Drug Delivery Reviews* 32:247-271.
[69] Sjolander et al. (1998) *Advanced Drug Delivery Reviews* 32:321-338.
[70] Niikura et al. (2002) *Virology* 293:273-280.
[71] Lenz et al. (2001) *J Immunol* 166:5346-5355.
[72] Pinto et al. (2003) *J Infect Dis* 188:327-338.
[73] Gerber et al. (2001) *Virol* 75:4752-4760.
[74] WO03/024480
[75] WO03/024481
[76] Gluck et al. (2002) *Vaccine* 20:B10-B16.
[77] EP-A-0689454.
[78] Johnson et al. (1999) *Bioorg Med Chem Lett* 9:2273-2278.
[79] Evans et al. (2003) *Expert Rev Vaccines* 2:219-229.
[80] Meraldi et al. (2003) *Vaccine* 21:2485-2491.
[81] Pajak et al. (2003) *Vaccine* 21:836-842.
[82] Kandimalla et al. (2003) *Nucleic Acids Research* 31:2393-2400.
[83] WO02/26757.
[84] WO99/62923.
[85] Krieg (2003) *Nature Medicine* 9:831-835.
[86] McCluskie et al. (2002) *FEMS Immunology and Medical Microbiology* 32:179-185.
[87] WO98/40100.
[88] U.S. Pat. No. 6,207,646.
[89] U.S. Pat. No. 6,239,116.
[90] U.S. Pat. No. 6,429,199.
[91] Kandimalla et al. (2003) *Biochemical Society Transactions* 31 (part 3):654-658.
[92] Blackwell et al. (2003) *J Immunol* 170:4061-4068.
[93] Krieg (2002) *Trends Immunol* 23:64-65.
[94] WO01/95935.
[95] Kandimalla et al. (2003) *BBRC* 306:948-953.

[96] Bhagat et al. (2003) *BBRC* 300:853-861.
[97] WO03/035836.
[98] WO95/17211.
[99] WO98/42375.
[100] Beignon et al. (2002) *Infect Immun* 70:3012-3019.
[101] Pizza et al. (2001) *Vaccine* 19:2534-2541.
[102] Pizza et al. (2000) *Int J Med Microbiol* 290:455-461.
[103] Scharton-Kersten et al. (2000) *Infect Immun* 68:5306-5313.
[104] Ryan et al. (1999) *Infect Immun* 67:6270-6280.
[105] Partidos et al. (1999) *Immunol Lett* 67:209-216.
[106] Peppoloni et al. (2003) *Expert Rev Vaccines* 2:285-293.
[107] Pine et al. (2002) *J Control Release* 85:263-270.
[108] Domenighini et al. (1995) *Mol Microbiol* 15:1165-1167.
[109] WO03/011223.
[110] WO99/40936.
[111] Marshall et al. (2006) *Vaccine* 24:244-257.
[112] Matsui M. et al. (2004) *J. Virol* 78: 9093.
[113] WO99/44636.
[114] Lillard J W et al., (2003) *Blood* 101(3):807-14. Epub 2002 Sep. 12.
[115] Singh et al] (2001) *J Cont Release* 70:267-276.
[116] WO99/27960.
[117] U.S. Pat. No. 6,090,406
[118] U.S. Pat. No. 5,916,588
[119] EP-A-0626169.
[120] WO99/52549.
[121] WO01/21207.
[122] WO01/21152.
[123] Andrianov et al. (1998) *Biomaterials* 19:109-115.
[124] Payne et al. (1998) *Adv Drug Delivery Review* 31:185-196.
[125] U.S. Pat. No. 4,680,338.
[126] U.S. Pat. No. 4,988,815.
[127] WO92/15582.
[128] Stanley (2002) *Clin Exp Dermatol* 27:571-577.
[129] Wu et al. (2004) *Antiviral Res.* 64(2):79-83.
[130] Vasilakos et al. (2000) *Cell Immunol.* 204(1):64-74.
[131] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[132] Jones (2003) *Curr Opin Investig Drugs* 4:214-218.
[133] WO2004/060308.
[134] WO2004/064759.
[135] U.S. Pat. No. 6,924,271.
[136] US2005/0070556.
[137] U.S. Pat. No. 5,658,731.
[138] Wong et al. (2003) *J Clin Pharmacol* 43(7):735-42.
[139] US2005/0215517.
[140] WO02/072012.
[141] Signorelli & Hadden (2003) *Int Immunopharmacol* 3(8):1177-86.
[142] WO2004/064715.
[143] Cooper (1995) *Pharm Biotechnol* 6:559-80.
[144] PCT/US2005/022769.
[145] WO2004/87153.
[146] U.S. Pat. No. 6,605,617.
[147] WO02/18383.
[148] WO2004/018455.
[149] WO03/082272.
[150] U.S. Pat. No. 5,011,828.
[151] U.S. Pat. No. 6,586,409.
[152] WO99/11241.
[153] WO94/00153.
[154] WO98/57659.
[155] European patent applications 0835318, 0735898 and 0761231.
[156] Peterson et al. (1988) *Infect Immun.* 56(4):885-91.
[157] Rank et al. (1988) *Infect Immun.* 56(9):2243-9.
[158] Morrison et al. (1995) *Infect Immun.* 63(12):4661-8.
[159] WO 99/27961.
[160] WO 02/074244.
[161] WO 02/064162.
[162] WO 03/028760.
[163] Cooper et al. (1999) *Immunity* 10:439-449.
[164] Gennaro (2000) *Remington: The Science and Practice of Pharmacy.* 20th edition, ISBN: 0683306472.
[165] Bjune et al. (1991) *Lancet* 338(8775):1093-96.
[166] WO 01/52885.
[167] Fukasawa et al. (1999) *Vaccine* 17:2951-2958.
[168] Rosenqvist et al. (1998) *Dev. Biol. Stand* 92:323-333.
[169] Costantino et al. (1992) *Vaccine* 10:691-698.
[170] Costantino et al. (1999) *Vaccine* 17:1251-1263.
[171] WO 03/007985.
[172] WO 99/24578.
[173] WO 99/36544.
[174] WO 99/57280.
[175] WO 00/66791.
[176] WO 01/64922.
[177] WO 01/64920.
[178] WO 03/020756.
[179] WO 2004/032958.
[180] WO 2004/048404.
[181] Covacci & Rappuoli (2000) *J. Exp. Med* 19:587-592.
[182] WO 93/18150.
[183] Covacci et al. (1993) *Proc. Natl. Acad. Sci. USA* 90:5791-5795.
[184] Tummuru et al. (1994) *Infect. Immun.* 61:1799-1809.
[185] Marchetti et al. (1998) *Vaccine* 16:33-37.
[186] Telford et al. (1994) *J. Exp. Med.* 179:1653-1658.
[187] Evans et al. (1995) *Gene* 153:123-127.
[188] WO 96/01272 & WO96/01273, especially SEQ ID NO:6.
[189] WO 97/25429.
[190] WO 98/04702.
[191] Watson (2000) *Pediatr Infect Dis J* 19:331-332.
[192] Rubin (2000) *Pediatr Clin North Am* 47:269-285.
[193] Jedrzejas (2001) *Microbiol Mol Biol Rev* 65:187-207.
[194] Bell (2000) *Pediatr Infect Dis J* 19:1187-1188.
[195] Iwarson (1995) *APMIS* 103:321-326.
[196] Gerlich et al. (1990) *Vaccine* 8 Suppl:S63-68 & 79-80.
[197] Hsu et al. (1999) *Clin Liver Dis* 3:901-915.
[198] Stratov et al. (2004) *Curr Drug Tgts* 5(1):71-88.
[199] Vaccines (1988) eds. Plotkin & Mortimer. ISBN 0-7216-1946-0.
[200] Gustafsson et al. (1996) *N. Engl. J. Med.* 334:349-355.
[201] Rappuoli et al. (1991) *TIBTECH* 9:232-238.
[202] Sutter et al. (2000) *Pediatr Clin North Am* 47:287-308.
[203] Zimmerman & Spann (1999) *Am Fam Physician* 59:113-118, 125-126.
[204] WO 99/24578.
[205] WO 99/36544.
[206] WO 99/57280.
[207] WO 02/079243.
[208] WO 02/02606.
[209] Kalman et al. (1999) *Nature Genetics* 21:385-389.
[210] Read et al. (2000) *Nucleic Acids Res* 28:1397-406.

[211] Shirai et al. (2000) *J. Infect. Dis.* 181(Suppl 3):S524-S527.
[212] WO 99/27105.
[213] WO 00/27994.
[214] WO 00/37494.
[215] Ross et al. (2001) *Vaccine* 19:4135-4142.
[216] Dreesen (1997) *Vaccine* 15 Suppl:S2-6.
[217] *MMWR Morb Mortal Wkly Rep* 1998 Jan. 16; 47(1):12, 19.
[218] Anderson (2000) *Vaccine* 19 Suppl 1:S59-65.
[219] Kahn (2000) *Curr Opin Pediatr* 12:257-262.
[220] Crowe (1995) *Vaccine* 13:415-421.
[221] McMichael (2000) *Vaccine* 19 Suppl 1:S101-107.
[222] WO 02/34771.
[223] Dale (1999) *Infect Dis Clin North Am* 13:227-43, viii.
[224] Ferretti et al. (2001) *PNAS USA* 98:4658-4663.
[225] Kuroda et al. (2001) *Lancet* 357(9264):1225-1240; see also pages 1218-1219.
[226] Modlin et al. (2001) *J Toxicol Clin Toxicol* 39:85-100.
[227] Demicheli et al. (1998) *Vaccine* 16:880-884.
[228] Stepanov et al. (1996) *J Biotechnol* 44:155-160.
[229] Ingram (2001) *Trends Neurosci* 24:305-307.
[230] Rosenberg (2001) *Nature* 411:380-384.
[231] Moingeon (2001) *Vaccine* 19:1305-1326.
[232] Donnelly et al. (1997) *Annu Rev Immunol* 15:617-648.
[233] Strugnell et al. (1997) *Immunol Cell Biol* 75(4):364-369.
[234] Cui (2005) *Adv Genet* 54:257-89.
[235] Robinson & Tones (1997) *Seminars in Immunol* 9:271-283.
[236] Brunham et al. (2000) *J Infect Dis* 181 Suppl 3:S538-43.
[237] Svanholm et al. (2000) *Scand J Immunol* 51(4):345-53.
[238] *DNA Vaccination—Genetic Vaccination* (1998) eds. Koprowski et al. (ISBN 3540633928).
[239] *Gene Vaccination: Theory and Practice* (1998) ed. Raz (ISBN 3540644288).
[240] Wang et al. (2004) *Vaccine* 22:3348-57.
[241] Titball & Williamson (2004) *Expert Opin Biol Ther* 4:965-73.
[242] Garmory et al. (2004) *Vaccine* 22:947-57.
[243] Grosfeld et al. (2003) *Infect Immun* 71(1):374-83.
[244] Williamson et al. (2002) *Vaccine* 20:2933-41.
[245] Bennett et al. (1999) *Vaccine* 18(7-8):588-96.
[246] Findeis et al., *Trends Biotechnol.* (1993) 11:202.
[247] Chiou et al. (1994) *Gene Therapeutics: Methods And Applications Of Direct Gene Transfer*. ed. Wolff.
[248] Wu et al., *J. Biol. Chem.* (1988) 263:621.
[249] Wu et al., *J. Biol. Chem.* (1994) 269:542.
[250] Zenke et al., *Proc. Natl. Acad. Sci.* (USA) (1990) 87:3655.
[251] Wu et al., *J. Biol. Chem.* (1991) 266:338.
[252] Jolly, *Cancer Gene Therapy* (1994) 1:51.
[253] Kimura, *Human Gene Therapy* (1994) 5:845.
[254] Connelly, *Human Gene Therapy* (1995) 1:185.
[255] Kaplitt, *Nature Genetics* (1994) 6:148.
[256] WO 90/07936.
[257] WO 94/03622.
[258] WO 93/25698.
[259] WO 93/25234.
[260] U.S. Pat. No. 5,219,740.
[261] WO 93/11230.
[262] WO 93/10218.
[263] U.S. Pat. No. 4,777,127.
[264] GB 2,200,651.
[265] EP-A-0 345 242.
[266] WO 91/02805.
[267] WO 94/12649.
[268] WO 93/03769.
[269] WO 93/19191.
[270] WO 94/28938.
[271] WO 95/11984.
[272] WO 95/00655.
[273] Curiel, *Hum. Gene Ther.* (1992) 3:147.
[274] Wu, *J. Biol. Chem.* (1989) 264:16985.
[275] U.S. Pat. No. 5,814,482.
[276] WO 95/07994.
[277] WO 96/17072.
[278] WO 95/30763.
[279] WO 97/42338.
[280] WO 90/11092.
[281] U.S. Pat. No. 5,580,859.
[282] U.S. Pat. No. 5,422,120.
[283] WO 95/13796.
[284] WO 94/23697.
[285] WO 91/14445.
[286] EP 0524968.
[287] Philip, *Mol. Cell Biol.* (1994) 14:2411.
[288] Woffendin, *Proc. Natl. Acad. Sci.* (1994) 91:11581.
[289] U.S. Pat. No. 5,206,152.
[290] WO 92/11033.
[291] U.S. Pat. No. 5,149,655.
[292] WO 92/11033.
[293] Winter et al., (1991) *Nature* 349:293-99.
[294] U.S. Pat. No. 4,816,567.
[295] Inbar et al., (1972) *Proc. Natl. Acad. Sci. U.S.A.* 69:2659-62.
[296] Ehrlich et al., (1980) *Biochem* 19:4091-96.
[297] Huston et al., (1988) *Proc. Natl. Acad. Sci. U.S.A.* 85:5897-83.
[298] Pack et al., (1992) *Biochem* 31, 1579-84.
[299] Cumber et al., (1992) *J. Immunology* 149B, 120-26.
[300] Riechmann et al., (1988) *Nature* 332, 323-27.
[301] Verhoeyan et al., (1988) *Science* 239, 1534-36.
[302] GB 2,276,169.
[303] Kohler et al., (1985) *Nature* 256, 495-497.
[304] Kozbor et al., (1985) *J. Immunol. Methods* 81, 31-42.
[305] Cote et al., (1983) *Proc. Natl. Acad Sci.* 80, 2026-2030.
[306] Cole et al., (1984) *Mol. Cell Biol.* 62, 109-120.
[307] Morrison et al., (1984) *Proc. Natl. Acad. Sci.* 81, 6851-6855.
[308] Neuberger et al., (1984) *Nature* 312, 604-608.
[309] Takeda et al., (1985) *Nature* 314, 452-454.
[310] U.S. Pat. No. 5,565,332.
[311] Burton, (1991) *PNAS* 88:11120-23.
[312] Thirion et al., (1996) *Eur. J Cancer Prev.* 5, 507-11.
[313] Coloma & Morrison, (1997) *Nat. Biotechnol.* 15:159-63.
[314] Mallender & Voss, (1994) *J. Biol. Chem.* 269:199-206.
[315] Verhaar et al., (1995) *Int. J. Cancer* 61, 497-501.
[316] Nicholls et al., (1993) *J. Immunol. Meth.* 165, 81-91.
[317] Orlandi et al., (1989) *Proc. Natl. Acad. Sci.* 86, 3833-3837.
[318] WO 93/03151.
[319] WO 94/13804.
[320] Karp et al. (1999) *Trends Biotechnol* 17(7):275-81.
[321] Wilson et al. (1995) *J. Infect. Dis.* 172:88.
[322] Cotter et al. (1997) *Infect. Immun.* 65:2145-2152.
[323] Perry et al. (1997) *J. Immunol.* 158(7):3344-3352.
[324] Zhang et al. (2005) *Nucleic Acids Res.* 33:W180-183.

The invention claimed is:

1. An immunogenic composition comprising: (1) an antigen comprising the sequence of SEQ ID NO:43; and (2) an antigen comprising the sequence of SEQ ID NO:98.

2. The immunogenic composition of claim 1, wherein the composition comprises an antigen comprising the sequence of SEQ ID NO:42 and an antigen comprising the sequence of SEQ ID NO:98.

3. The immunogenic composition of claim 1, further comprising an immunoregulatory agent.

4. The immunogenic composition of claim 1, further comprising an adjuvant.

5. A method of raising an immune response in a mammal, the method comprising administering to the mammal the immunogenic composition of claim 1.

* * * * *

SEQUENCE LISTING

<160> NUMBER OF SEQ ID NOS: 275

<210> SEQ ID NO 1
<211> LENGTH: 544
<212> TYPE: PRT
<213> ORGANISM: Chlamydia trachomatis

<400> SEQUENCE: 1

```
Met Val Ala Lys Asn Ile Lys Tyr Asn Glu Ala Arg Lys Lys Ile
1               5                   10                  15

Gln Lys Gly Val Lys Thr Leu Ala Glu Ala Val Lys Val Thr Leu Gly
            20                  25                  30

Pro Lys Gly Arg His Val Val Ile Asp Lys Ser Phe Gly Ser Pro Gln
            35                  40                  45

Val Thr Lys Asp Gly Val Thr Val Ala Lys Glu Val Glu Leu Ala Asp
        50                  55                  60

Lys His Glu Asn Met Gly Ala Gln Met Val Lys Glu Val Ala Ser Lys
65                  70                  75                  80

Thr Ala Asp Lys Ala Gly Asp Gly Thr Thr Thr Ala Thr Val Leu Ala
                85                  90                  95

Glu Ala Ile Tyr Thr Glu Gly Leu Arg Asn Val Thr Ala Gly Ala Asn
            100                 105                 110

Pro Met Asp Leu Lys Arg Gly Ile Asp Lys Ala Val Lys Val Val Val
            115                 120                 125

Asp Gln Ile Arg Lys Ile Ser Lys Pro Val Gln His His Lys Glu Ile
130                 135                 140

Ala Gln Val Ala Thr Ile Ser Ala Asn Asn Asp Ala Glu Ile Gly Asn
145                 150                 155                 160

Leu Ile Ala Glu Ala Met Glu Lys Val Gly Lys Asn Gly Ser Ile Thr
                165                 170                 175

Val Glu Glu Ala Lys Gly Phe Glu Thr Val Leu Asp Ile Val Glu Gly
            180                 185                 190

Met Asn Phe Asn Arg Gly Tyr Leu Ser Ser Tyr Phe Ala Thr Asn Pro
            195                 200                 205

Glu Thr Gln Glu Cys Val Leu Glu Asp Ala Leu Val Leu Ile Tyr Asp
        210                 215                 220

Lys Lys Ile Ser Gly Ile Lys Asp Phe Leu Pro Val Leu Gln Gln Val
225                 230                 235                 240

Ala Glu Ser Gly Arg Pro Leu Leu Ile Ile Ala Glu Asp Ile Glu Gly
                245                 250                 255

Glu Ala Leu Ala Thr Leu Val Val Asn Arg Ile Arg Gly Gly Phe Arg
            260                 265                 270

Val Cys Ala Val Lys Ala Pro Gly Phe Gly Asp Arg Arg Lys Ala Met
            275                 280                 285

Leu Glu Asp Ile Ala Ile Leu Thr Gly Gly Gln Leu Ile Ser Glu Glu
        290                 295                 300

Leu Gly Met Lys Leu Glu Asn Ala Asn Leu Ala Met Leu Gly Lys Ala
305                 310                 315                 320

Lys Lys Val Ile Val Ser Lys Glu Asp Thr Thr Ile Val Glu Gly Met
                325                 330                 335

Gly Glu Lys Glu Ala Leu Glu Ala Arg Cys Glu Ser Ile Lys Lys Gln
            340                 345                 350

Ile Glu Asp Ser Ser Ser Asp Tyr Asp Lys Glu Lys Leu Gln Glu Arg
            355                 360                 365
```

-continued

```
Leu Ala Lys Leu Ser Gly Gly Val Ala Val Ile Arg Val Gly Ala Ala
            370                 375                 380

Thr Glu Ile Glu Met Lys Glu Lys Lys Asp Arg Val Asp Asp Ala Gln
385                 390                 395                 400

His Ala Thr Ile Ala Ala Val Glu Glu Gly Ile Leu Pro Gly Gly Gly
                405                 410                 415

Thr Ala Leu Ile Arg Cys Ile Pro Thr Leu Glu Ala Phe Leu Pro Met
            420                 425                 430

Leu Thr Asn Glu Asp Glu Gln Ile Gly Ala Arg Ile Val Leu Lys Ala
            435                 440                 445

Leu Ser Ala Pro Leu Lys Gln Ile Ala Ala Asn Ala Gly Lys Glu Gly
            450                 455                 460

Ala Ile Ile Phe Gln Gln Val Met Ser Arg Ser Ala Asn Glu Gly Tyr
465                 470                 475                 480

Asp Ala Leu Arg Asp Ala Tyr Thr Asp Met Leu Glu Ala Gly Ile Leu
                485                 490                 495

Asp Pro Ala Lys Val Thr Arg Ser Ala Leu Glu Ser Ala Ala Ser Val
            500                 505                 510

Ala Gly Leu Leu Leu Thr Thr Glu Ala Leu Ile Ala Glu Ile Pro Glu
            515                 520                 525

Glu Lys Pro Ala Ala Pro Ala Met Pro Gly Ala Gly Met Asp Tyr
530                 535                 540

<210> SEQ ID NO 2
<211> LENGTH: 21
<212> TYPE: PRT
<213> ORGANISM: Chlamydia trachomatis

<400> SEQUENCE: 2

Ala Gly Asp Gly Thr Thr Thr Ala Thr Val Leu Ala Glu Ala Ile Tyr
1               5                   10                  15

Thr Glu Gly Leu Arg
            20

<210> SEQ ID NO 3
<211> LENGTH: 16
<212> TYPE: PRT
<213> ORGANISM: Chlamydia trachomatis

<400> SEQUENCE: 3

Gly Phe Glu Thr Val Leu Asp Ile Val Glu Gly Met Asn Phe Asn Arg
1               5                   10                  15

<210> SEQ ID NO 4
<211> LENGTH: 22
<212> TYPE: PRT
<213> ORGANISM: Chlamydia trachomatis

<400> SEQUENCE: 4

Ala Met Leu Glu Asp Ile Ala Ile Leu Thr Gly Gly Gln Leu Ile Ser
1               5                   10                  15

Glu Glu Leu Gly Met Lys
            20

<210> SEQ ID NO 5
<211> LENGTH: 11
<212> TYPE: PRT
<213> ORGANISM: Chlamydia trachomatis
```

```
<400> SEQUENCE: 5

Leu Glu Asn Ala Asn Leu Ala Met Leu Gly Lys
1               5                   10

<210> SEQ ID NO 6
<211> LENGTH: 12
<212> TYPE: PRT
<213> ORGANISM: Chlamydia trachomatis

<400> SEQUENCE: 6

Glu Asp Thr Thr Ile Val Glu Gly Met Gly Glu Lys
1               5                   10

<210> SEQ ID NO 7
<211> LENGTH: 10
<212> TYPE: PRT
<213> ORGANISM: Chlamydia trachomatis

<400> SEQUENCE: 7

Val Gly Ala Ala Thr Glu Ile Glu Met Lys
1               5                   10

<210> SEQ ID NO 8
<211> LENGTH: 16
<212> TYPE: PRT
<213> ORGANISM: Chlamydia trachomatis

<400> SEQUENCE: 8

Asp Ala Tyr Thr Asp Met Leu Glu Ala Gly Ile Leu Asp Pro Ala Lys
1               5                   10                  15

<210> SEQ ID NO 9
<211> LENGTH: 660
<212> TYPE: PRT
<213> ORGANISM: Chlamydia trachomatis

<400> SEQUENCE: 9

Met Ser Glu Lys Arg Lys Ser Asn Lys Ile Ile Gly Ile Asp Leu Gly
1               5                   10                  15

Thr Thr Asn Ser Cys Val Ser Val Met Glu Gly Gly Gln Pro Lys Val
                20                  25                  30

Ile Ala Ser Ser Glu Gly Thr Arg Thr Thr Pro Ser Ile Val Ala Phe
            35                  40                  45

Lys Gly Gly Glu Thr Leu Val Gly Ile Pro Ala Lys Arg Gln Ala Val
        50                  55                  60

Thr Asn Pro Glu Lys Thr Leu Ala Ser Thr Lys Arg Phe Ile Gly Arg
65                  70                  75                  80

Lys Phe Ser Glu Val Glu Ser Glu Ile Lys Thr Val Pro Tyr Lys Val
                85                  90                  95

Ala Pro Asn Ser Lys Gly Asp Ala Val Phe Asp Val Glu Gln Lys Leu
            100                 105                 110

Tyr Thr Pro Glu Glu Ile Gly Ala Gln Ile Leu Met Lys Met Lys Glu
        115                 120                 125

Thr Ala Glu Ala Tyr Leu Gly Glu Thr Val Thr Glu Ala Val Ile Thr
130                 135                 140

Val Pro Ala Tyr Phe Asn Asp Ser Gln Arg Ala Ser Thr Lys Asp Ala
145                 150                 155                 160

Gly Arg Ile Ala Gly Leu Asp Val Lys Arg Ile Ile Pro Glu Pro Thr
                165                 170                 175

Ala Ala Ala Leu Ala Tyr Gly Ile Asp Lys Glu Gly Asp Lys Lys Ile
```

-continued

```
                    180                 185                 190
Ala Val Phe Asp Leu Gly Gly Thr Phe Asp Ile Ser Ile Leu Glu
                195                 200                 205
Ile Gly Asp Gly Val Phe Glu Val Leu Ser Thr Asn Gly Asp Thr His
            210                 215                 220
Leu Gly Asp Asp Phe Asp Gly Val Ile Ile Asn Trp Met Leu Asp
225                 230                 235                 240
Glu Phe Lys Lys Gln Glu Gly Ile Asp Leu Ser Lys Asn Met Ala
                245                 250                 255
Leu Gln Arg Leu Lys Asp Ala Ala Glu Lys Ala Lys Ile Glu Leu Ser
            260                 265                 270
Gly Val Ser Ser Thr Glu Ile Asn Gln Pro Phe Ile Thr Ile Asp Ala
            275                 280                 285
Asn Gly Pro Lys His Leu Ala Leu Thr Leu Thr Arg Ala Gln Phe Glu
        290                 295                 300
His Leu Ala Ser Ser Leu Ile Glu Arg Thr Lys Gln Pro Cys Ala Gln
305                 310                 315                 320
Ala Leu Lys Asp Ala Lys Leu Ser Ala Ser Asp Ile Asp Asp Val Leu
                325                 330                 335
Leu Val Gly Gly Met Ser Arg Met Pro Ala Val Gln Ala Val Val Lys
                340                 345                 350
Glu Ile Phe Gly Lys Glu Pro Asn Lys Gly Val Asn Pro Asp Glu Val
                355                 360                 365
Val Ala Ile Gly Ala Ala Ile Gln Gly Gly Val Leu Gly Gly Glu Val
            370                 375                 380
Lys Asp Val Leu Leu Leu Asp Val Ile Pro Leu Ser Leu Gly Ile Glu
385                 390                 395                 400
Thr Leu Gly Gly Val Met Thr Pro Leu Val Glu Arg Asn Thr Thr Ile
                        405                 410                 415
Pro Thr Gln Lys Lys Gln Ile Phe Ser Thr Ala Ala Asp Asn Gln Pro
            420                 425                 430
Ala Val Thr Ile Val Val Leu Gln Gly Glu Arg Pro Met Ala Lys Asp
            435                 440                 445
Asn Lys Glu Ile Gly Arg Phe Asp Leu Thr Asp Ile Pro Pro Ala Pro
450                 455                 460
Arg Gly His Pro Gln Ile Glu Val Thr Phe Asp Ile Asp Ala Asn Gly
465                 470                 475                 480
Ile Leu His Val Ser Ala Lys Asp Ala Ala Ser Gly Arg Glu Gln Lys
                485                 490                 495
Ile Arg Ile Glu Ala Ser Ser Gly Leu Lys Glu Asp Glu Ile Gln Gln
            500                 505                 510
Met Ile Arg Asp Ala Glu Leu His Lys Glu Glu Asp Lys Gln Arg Lys
            515                 520                 525
Glu Ala Ser Asp Val Lys Asn Glu Ala Asp Gly Met Ile Phe Arg Ala
        530                 535                 540
Glu Lys Ala Val Lys Asp Tyr His Asp Lys Ile Pro Ala Glu Leu Val
545                 550                 555                 560
Lys Glu Ile Glu Glu His Ile Glu Lys Val Arg Gln Ala Ile Lys Glu
                565                 570                 575
Asp Ala Ser Thr Thr Ala Ile Lys Ala Ala Ser Asp Glu Leu Ser Thr
            580                 585                 590
His Met Gln Lys Ile Gly Glu Ala Met Gln Ala Gln Ser Ala Ser Ala
                595                 600                 605
```

```
Ala Ala Ser Ser Ala Ala Asn Ala Gln Gly Gly Pro Asn Ile Asn Ser
        610                 615                 620

Glu Asp Leu Lys Lys His Ser Phe Ser Thr Arg Pro Pro Ala Gly Gly
625                 630                 635                 640

Ser Ala Ser Ser Thr Asp Asn Ile Glu Asp Ala Asp Val Glu Ile Val
                645                 650                 655

Asp Lys Pro Glu
            660

<210> SEQ ID NO 10
<211> LENGTH: 14
<212> TYPE: PRT
<213> ORGANISM: Chlamydia trachomatis

<400> SEQUENCE: 10

Leu Tyr Thr Pro Glu Glu Ile Gly Ala Gln Ile Leu Met Lys
1               5                   10

<210> SEQ ID NO 11
<211> LENGTH: 24
<212> TYPE: PRT
<213> ORGANISM: Chlamydia trachomatis

<400> SEQUENCE: 11

Ile Glu Leu Ser Gly Val Ser Ser Thr Glu Asn Gln Pro Phe Ile
1               5                   10                  15

Thr Ile Asp Ala Asn Gly Pro Lys
            20

<210> SEQ ID NO 12
<211> LENGTH: 17
<212> TYPE: PRT
<213> ORGANISM: Chlamydia trachomatis

<400> SEQUENCE: 12

Leu Ser Ala Ser Asp Ile Asp Asp Val Leu Leu Val Gly Gly Met Ser
1               5                   10                  15

Arg

<210> SEQ ID NO 13
<211> LENGTH: 24
<212> TYPE: PRT
<213> ORGANISM: Chlamydia trachomatis

<400> SEQUENCE: 13

Gly Val Asn Pro Asp Glu Val Val Ala Ile Gly Ala Ala Ile Gln Gly
1               5                   10                  15

Gly Val Leu Gly Gly Glu Val Lys
            20

<210> SEQ ID NO 14
<211> LENGTH: 394
<212> TYPE: PRT
<213> ORGANISM: Chlamydia trachomatis

<400> SEQUENCE: 14

Met Ser Lys Glu Thr Phe Gln Arg Asn Lys Pro His Ile Asn Ile Gly
1               5                   10                  15

Thr Ile Gly His Val Asp His Gly Lys Thr Thr Leu Thr Ala Ala Ile
            20                  25                  30

Thr Arg Ala Leu Ser Gly Asp Gly Leu Ala Asp Phe Arg Asp Tyr Ser
        35                  40                  45
```

```
Ser Ile Asp Asn Thr Pro Glu Glu Lys Ala Arg Gly Ile Thr Ile Asn
     50                  55                  60
Ala Ser His Val Glu Tyr Glu Thr Ala Asn Arg His Tyr Ala His Val
 65                  70                  75                  80
Asp Cys Pro Gly His Ala Asp Tyr Val Lys Asn Met Ile Thr Gly Ala
                 85                  90                  95
Ala Gln Met Asp Gly Ala Ile Leu Val Val Ser Ala Thr Asp Gly Ala
            100                 105                 110
Met Pro Gln Thr Lys Glu His Ile Leu Leu Ala Arg Gln Val Gly Val
        115                 120                 125
Pro Tyr Ile Val Val Phe Leu Asn Lys Ile Asp Met Ile Ser Glu Glu
    130                 135                 140
Asp Ala Glu Leu Val Asp Leu Val Glu Met Glu Leu Val Glu Leu Leu
145                 150                 155                 160
Glu Glu Lys Gly Tyr Lys Gly Cys Pro Ile Ile Arg Gly Ser Ala Leu
                165                 170                 175
Lys Ala Leu Glu Gly Asp Ala Ala Tyr Ile Glu Lys Val Arg Glu Leu
            180                 185                 190
Met Gln Ala Val Asp Asp Asn Ile Pro Thr Pro Glu Arg Glu Ile Asp
        195                 200                 205
Lys Pro Phe Leu Met Pro Ile Glu Asp Val Phe Ser Ile Ser Gly Arg
    210                 215                 220
Gly Thr Val Val Thr Gly Arg Ile Glu Arg Gly Ile Val Lys Val Ser
225                 230                 235                 240
Asp Lys Val Gln Leu Val Gly Leu Arg Asp Thr Lys Glu Thr Ile Val
                245                 250                 255
Thr Gly Val Glu Met Phe Arg Lys Glu Leu Pro Glu Gly Arg Ala Gly
            260                 265                 270
Glu Asn Val Gly Leu Leu Leu Arg Gly Ile Gly Lys Asn Asp Val Glu
        275                 280                 285
Arg Gly Met Val Val Cys Leu Pro Asn Ser Val Lys Pro His Thr Gln
    290                 295                 300
Phe Lys Cys Ala Val Tyr Val Leu Gln Lys Glu Glu Gly Gly Arg His
305                 310                 315                 320
Lys Pro Phe Phe Thr Gly Tyr Arg Pro Gln Phe Phe Phe Arg Thr Thr
                325                 330                 335
Asp Val Thr Gly Val Val Thr Leu Pro Glu Gly Ile Glu Met Val Met
            340                 345                 350
Pro Gly Asp Asn Val Glu Phe Glu Val Gln Leu Ile Ser Pro Val Ala
        355                 360                 365
Leu Glu Glu Gly Met Arg Phe Ala Ile Arg Glu Gly Gly Arg Thr Ile
    370                 375                 380
Gly Ala Gly Thr Ile Ser Lys Ile Ile Ala
385                 390

<210> SEQ ID NO 15
<211> LENGTH: 11
<212> TYPE: PRT
<213> ORGANISM: Chlamydia trachomatis

<400> SEQUENCE: 15

Ala Leu Glu Gly Asp Ala Ala Tyr Ile Glu Lys
1               5                   10

<210> SEQ ID NO 16
```

```
<211> LENGTH: 15
<212> TYPE: PRT
<213> ORGANISM: Chlamydia trachomatis

<400> SEQUENCE: 16

Glu Leu Met Gln Ala Val Asp Asp Asn Ile Pro Thr Pro Glu Arg
1               5                   10                  15

<210> SEQ ID NO 17
<211> LENGTH: 243
<212> TYPE: PRT
<213> ORGANISM: Chlamydia trachomatis

<400> SEQUENCE: 17

Met Lys Asn Ile Leu Ser Trp Met Leu Met Phe Ala Val Ala Leu Pro
1               5                   10                  15

Ile Val Gly Cys Asp Asn Gly Gly Ser Gln Thr Ser Ala Thr Glu
                20                  25                  30

Lys Ser Met Val Glu Asp Ser Ala Leu Thr Asp Asn Gln Lys Leu Ser
                35                  40                  45

Arg Thr Phe Gly His Leu Leu Ser Arg Gln Leu Ser Arg Thr Glu Asp
        50                  55                  60

Phe Ser Leu Asp Leu Val Glu Val Ile Lys Gly Met Gln Ser Glu Ile
65                  70                  75                  80

Asp Gly Gln Ser Ala Pro Leu Thr Asp Thr Glu Tyr Glu Lys Gln Met
                85                  90                  95

Ala Glu Val Gln Lys Ala Ser Phe Glu Ala Lys Cys Ser Glu Asn Leu
                100                 105                 110

Ala Ser Ala Glu Lys Phe Leu Lys Glu Asn Lys Glu Lys Ala Gly Val
                115                 120                 125

Ile Glu Leu Glu Pro Asn Lys Leu Gln Tyr Arg Val Val Lys Glu Gly
                130                 135                 140

Thr Gly Arg Val Leu Ser Gly Lys Pro Thr Ala Leu Leu His Tyr Thr
145                 150                 155                 160

Gly Ser Phe Ile Asp Gly Lys Val Phe Asp Ser Ser Glu Lys Asn Lys
                165                 170                 175

Glu Pro Ile Leu Leu Pro Leu Thr Lys Val Ile Pro Gly Phe Ser Gln
                180                 185                 190

Gly Met Gln Gly Met Lys Glu Glu Val Arg Val Leu Tyr Ile His
                195                 200                 205

Pro Asp Leu Ala Tyr Gly Thr Ala Gly Gln Leu Pro Pro Asn Ser Leu
        210                 215                 220

Leu Ile Phe Glu Val Lys Leu Ile Glu Ala Asn Asp Asn Val Ser
225                 230                 235                 240

Val Thr Glu

<210> SEQ ID NO 18
<211> LENGTH: 13
<212> TYPE: PRT
<213> ORGANISM: Chlamydia trachomatis

<400> SEQUENCE: 18

Ser Met Val Glu Asp Ser Ala Leu Thr Asp Asn Gln Lys
1               5                   10

<210> SEQ ID NO 19
<211> LENGTH: 13
<212> TYPE: PRT
<213> ORGANISM: Chlamydia trachomatis
```

<400> SEQUENCE: 19

Thr Glu Asp Phe Ser Leu Asp Leu Val Glu Val Ile Lys
1               5                   10

<210> SEQ ID NO 20
<211> LENGTH: 393
<212> TYPE: PRT
<213> ORGANISM: Chlamydia trachomatis

<400> SEQUENCE: 20

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
            35                  40                  45

Asp Pro Cys Ala Thr Trp Cys Asp Ala Ile Ser Met Arg Val Gly Tyr
        50                  55                  60

Tyr Gly Asp Phe Val Phe Asp Arg Val Leu Lys Thr Asp Val Asn Lys
65                  70                  75                  80

Glu Phe Gln Met Gly Ala Lys Pro Thr Thr Asp Thr Gly Asn Ser Ala
                85                  90                  95

Ala Pro Ser Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125

Ile Trp Asp Arg Phe Asp Val Phe Cys Thr Leu Gly Ala Thr Ser Gly
130                 135                 140

Tyr Leu Lys Gly Asn Ser Ala Ser Phe Asn Leu Val Gly Leu Phe Gly
145                 150                 155                 160

Asp Asn Glu Asn Gln Lys Thr Val Lys Ala Glu Ser Val Pro Asn Met
                165                 170                 175

Ser Phe Asp Gln Ser Val Val Glu Leu Tyr Thr Asp Thr Thr Phe Ala
            180                 185                 190

Trp Ser Val Gly Ala Arg Ala Ala Leu Trp Glu Cys Gly Cys Ala Thr
        195                 200                 205

Leu Gly Ala Ser Phe Gln Tyr Ala Gln Ser Lys Pro Lys Val Glu Glu
210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
290                 295                 300

Ala Gln Pro Lys Ser Ala Thr Ala Ile Phe Asp Thr Thr Thr Leu Asn
305                 310                 315                 320

Pro Thr Ile Ala Gly Ala Gly Asp Val Lys Thr Gly Ala Glu Gly Gln
                325                 330                 335

Leu Gly Asp Thr Met Gln Ile Val Ser Leu Gln Leu Asn Lys Met Lys
            340                 345                 350

```
Ser Arg Lys Ser Cys Gly Ile Ala Val Gly Thr Thr Ile Val Asp Ala
        355                 360                 365

Asp Lys Tyr Ala Val Thr Val Glu Thr Arg Leu Ile Asp Glu Arg Ala
        370                 375                 380

Ala His Val Asn Ala Gln Phe Arg Phe
385                 390

<210> SEQ ID NO 21
<211> LENGTH: 22
<212> TYPE: PRT
<213> ORGANISM: Chlamydia trachomatis

<400> SEQUENCE: 21

Ser Ala Thr Ala Ile Phe Asp Thr Thr Thr Leu Asn Pro Thr Ile Ala
1               5                   10                  15

Gly Ala Gly Asp Val Lys
            20

<210> SEQ ID NO 22
<211> LENGTH: 125
<212> TYPE: PRT
<213> ORGANISM: Chlamydia trachomatis

<400> SEQUENCE: 22

Met Ala Leu Lys Asp Thr Ala Lys Lys Met Thr Asp Leu Leu Glu Ser
1               5                   10                  15

Ile Gln Gln Asn Leu Leu Lys Ala Glu Lys Gly Asn Lys Ala Ala Ala
                20                  25                  30

Gln Arg Val Arg Thr Glu Ser Ile Lys Leu Glu Lys Ile Ala Lys Val
            35                  40                  45

Tyr Arg Lys Glu Ser Ile Lys Ala Glu Lys Met Gly Leu Met Lys Lys
        50                  55                  60

Ser Lys Ala Ala Ala Lys Lys Ala Lys Ala Ala Lys Lys Pro Val
65                  70                  75                  80

Arg Ala Ala Lys Thr Val Ala Lys Lys Ala Cys Thr Lys Arg Thr Cys
                85                  90                  95

Ala Thr Lys Ala Lys Val Lys Pro Thr Lys Ala Ala Pro Lys Thr
            100                 105                 110

Lys Val Lys Thr Ala Lys Lys Thr Arg Ser Thr Lys Lys
        115                 120                 125

<210> SEQ ID NO 23
<211> LENGTH: 14
<212> TYPE: PRT
<213> ORGANISM: Chlamydia trachomatis

<400> SEQUENCE: 23

Met Thr Asp Leu Leu Glu Ser Ile Gln Gln Asn Leu Leu Lys
1               5                   10

<210> SEQ ID NO 24
<211> LENGTH: 119
<212> TYPE: PRT
<213> ORGANISM: Chlamydia trachomatis

<400> SEQUENCE: 24

Met Ser Lys Lys His Lys His Lys Gln Ala His Thr Ser Ser Lys Pro
1               5                   10                  15

Lys Val Glu Pro Ala Tyr Val Ser Lys Lys Glu Ser Pro Ala Leu Gln
                20                  25                  30
```

```
Glu Leu Gln Asn Ala Met Ile Ser Phe Ser Gln Asp Leu Pro Leu Ala
            35                  40                  45

Gln Met Phe Ser Glu Ile Gln Asp Glu Lys Gln Leu Ala Lys Met Met
 50                  55                  60

Ala Ala Leu Ser Gly Met Leu Asp Ser Leu Pro Val Glu Thr Leu Thr
 65                  70                  75                  80

Lys Gly Val Phe Asp Asn Pro Lys Glu Ala Gln Leu Ser Gln Glu
                 85                  90                  95

Ile Ser Ser Ile Phe Leu Gly Leu Lys His Leu Thr Glu Thr Val Asn
                100                 105                 110

Lys His Ile Ala Asp Glu Lys
            115

<210> SEQ ID NO 25
<211> LENGTH: 19
<212> TYPE: PRT
<213> ORGANISM: Chlamydia trachomatis

<400> SEQUENCE: 25

Met Met Ala Ala Leu Ser Gly Met Leu Asp Ser Leu Pro Val Glu Thr
 1               5                  10                  15

Leu Thr Lys

<210> SEQ ID NO 26
<211> LENGTH: 270
<212> TYPE: PRT
<213> ORGANISM: Chlamydia trachomatis

<400> SEQUENCE: 26

Met Val Ser Leu Ala Leu Gly Thr Ser Asn Gly Val Glu Ala Asn Asn
 1               5                  10                  15

Gly Ile Asn Asp Leu Ser Pro Ala Pro Glu Ala Lys Lys Thr Gly Ser
                 20                  25                  30

Gly Leu Cys Tyr Lys Ile Ser Ala Val Ala Ala Leu Val Leu Gly Leu
             35                  40                  45

Leu Ala Ala Ala Gly Gly Ala Val Val Leu Ala Leu Phe Cys Thr Phe
 50                  55                  60

Ala Pro Pro Leu Phe Phe Tyr Ala Gly Val Ala Leu Val Ala Leu Gly
 65                  70                  75                  80

Ala Val Ile Leu Gly Val Gly Val Ser Asn Thr Cys Ser Cys Cys Leu
                 85                  90                  95

Arg Ser Arg Lys Ile Glu Ala His Lys Gln Leu Ile Leu Gln Gln Lys
                100                 105                 110

Glu Glu Ile Ser Gln Leu Glu Gln Leu Ala Lys Ala Leu Lys Glu
                115                 120                 125

Leu Asn Thr Lys Tyr Pro Ala Ser Leu Leu Glu Arg Arg Asp Leu Arg
130                 135                 140

Glu Asn Leu Lys Ala Trp Gln Ser Cys Cys Leu Asn Leu Lys Glu
145                 150                 155                 160

Val Arg Asp Leu Leu Thr Lys Leu Gly Gly Tyr Gln Glu Arg Leu Lys
                165                 170                 175

Val Leu Pro Ala Lys Glu Lys Gln Ile Glu Glu Leu Lys Ala Met Leu
                180                 185                 190

Glu His Tyr Ser Arg Ile Cys His Glu Arg Gly Glu Leu Ile Asn Leu
            195                 200                 205

Leu Lys Thr Ala Asn Lys Lys Leu Ser Lys Glu Ser Glu Lys Leu Leu
210                 215                 220
```

```
Phe Asn Tyr Lys Ala His Arg Asp Val Cys Leu Gly Glu Lys Val Leu
225                 230                 235                 240

Val Lys Ser Val Asn Leu Ile Asp Leu Asp Pro Lys Ser Asp Ser Ser
            245                 250                 255

Asp Gly Asp Asp Asp Gly Phe Asn Tyr Gly Ser Arg Val
        260                 265                 270

<210> SEQ ID NO 27
<211> LENGTH: 12
<212> TYPE: PRT
<213> ORGANISM: Chlamydia trachomatis

<400> SEQUENCE: 27

Glu Glu Ile Ser Gln Leu Glu Gln Gln Leu Ala Lys
1               5                   10

<210> SEQ ID NO 28
<211> LENGTH: 102
<212> TYPE: PRT
<213> ORGANISM: Chlamydia trachomatis

<400> SEQUENCE: 28

Met Ser Asp Gln Ala Thr Thr Leu Lys Ile Lys Pro Leu Gly Asp Arg
1               5                   10                  15

Ile Leu Val Lys Arg Glu Glu Ala Ser Thr Ala Arg Gly Gly Ile
            20                  25                  30

Ile Leu Pro Asp Thr Ala Lys Lys Gln Asp Arg Ala Glu Val Leu
        35                  40                  45

Ala Leu Gly Thr Gly Lys Lys Asp Asp Lys Gly Gln Gln Leu Pro Phe
    50                  55                  60

Glu Val Gln Val Gly Asn Ile Val Leu Ile Asp Lys Tyr Ser Gly Gln
65                  70                  75                  80

Glu Leu Thr Val Glu Gly Glu Tyr Val Ile Val Gln Met Ser Glu
                85                  90                  95

Val Ile Ala Val Leu Gln
            100

<210> SEQ ID NO 29
<211> LENGTH: 18
<212> TYPE: PRT
<213> ORGANISM: Chlamydia trachomatis

<400> SEQUENCE: 29

Gly Gln Gln Leu Pro Phe Glu Val Gln Val Gly Asn Ile Val Leu Ile
1               5                   10                  15

Asp Lys

<210> SEQ ID NO 30
<211> LENGTH: 1005
<212> TYPE: PRT
<213> ORGANISM: Chlamydia trachomatis

<400> SEQUENCE: 30

Met Thr Asn Ser Ile Ser Gly Tyr Gln Pro Thr Val Thr Thr Ser Thr
1               5                   10                  15

Ser Ser Thr Thr Ser Ala Ser Gly Ala Ser Gly Ser Leu Gly Ala Ser
            20                  25                  30

Ser Val Ser Thr Thr Ala Asn Ala Thr Val Gln Thr Ala Asn Ala
        35                  40                  45
```

-continued

```
Thr Asn Ser Ala Ala Thr Ser Ser Ile Gln Thr Thr Gly Glu Thr Val
 50                  55                  60

Val Asn Tyr Thr Asn Ser Ala Ser Ala Pro Asn Val Thr Val Ser Thr
 65                  70                  75                  80

Ser Ser Ser Ser Thr Gln Ala Thr Ala Thr Ser Asn Lys Thr Ser Gln
                 85                  90                  95

Ala Val Ala Gly Lys Ile Thr Ser Pro Asp Thr Ser Glu Ser Ser Glu
                100                 105                 110

Thr Ser Thr Ser Ser Ser Asp His Ile Pro Ser Asp Tyr Asp Asp
                115                 120                 125

Val Gly Ser Asn Ser Gly Asp Ile Ser Asn Asn Tyr Asp Asp Val Gly
    130                 135                 140

Ser Asn Asn Gly Asp Ile Ser Ser Asn Tyr Asp Asp Ala Ala Ala Asp
145                 150                 155                 160

Tyr Glu Pro Ile Arg Thr Thr Glu Asn Ile Tyr Glu Ser Ile Gly Gly
                165                 170                 175

Ser Arg Thr Ser Gly Pro Glu Asn Thr Ser Gly Gly Ala Ala Ala Ala
            180                 185                 190

Leu Asn Ser Leu Arg Gly Ser Ser Tyr Ser Asn Tyr Asp Asp Ala Ala
        195                 200                 205

Ala Asp Tyr Glu Pro Ile Arg Thr Thr Glu Asn Ile Tyr Glu Ser Ile
    210                 215                 220

Gly Gly Ser Arg Thr Ser Gly Pro Glu Asn Thr Ser Gly Gly Ala Ala
225                 230                 235                 240

Ala Ala Leu Asn Ser Leu Arg Gly Ser Ser Tyr Ser Asn Tyr Asp Asp
                245                 250                 255

Ala Ala Ala Asp Tyr Glu Pro Ile Arg Thr Thr Glu Asn Ile Tyr Glu
            260                 265                 270

Ser Ile Gly Gly Ser Arg Thr Ser Gly Pro Glu Asn Thr Ser Asp Gly
        275                 280                 285

Ala Ala Ala Ala Ala Leu Asn Ser Leu Arg Gly Ser Ser Tyr Thr Thr
    290                 295                 300

Gly Pro Arg Asn Glu Gly Val Phe Gly Pro Gly Pro Glu Gly Leu Pro
305                 310                 315                 320

Asp Met Ser Leu Pro Ser Tyr Asp Pro Thr Asn Lys Thr Ser Leu Leu
                325                 330                 335

Thr Phe Leu Ser Asn Pro His Val Lys Ser Lys Met Leu Glu Asn Ser
            340                 345                 350

Gly His Phe Val Phe Ile Asp Thr Asp Arg Ser Ser Phe Ile Leu Val
        355                 360                 365

Pro Asn Gly Asn Trp Asp Gln Val Cys Ser Ile Lys Val Gln Asn Gly
    370                 375                 380

Lys Thr Lys Glu Asp Leu Asp Ile Lys Asp Leu Glu Asn Met Cys Ala
385                 390                 395                 400

Lys Phe Cys Thr Gly Phe Ser Lys Phe Ser Gly Asp Trp Asp Ser Leu
                405                 410                 415

Val Glu Pro Met Val Ser Ala Lys Ala Gly Val Ala Ser Gly Gly Asn
            420                 425                 430

Leu Pro Asn Thr Val Ile Ile Asn Asn Lys Phe Lys Thr Cys Val Ala
        435                 440                 445

Tyr Gly Pro Trp Asn Ser Gln Glu Ala Ser Ser Gly Tyr Thr Pro Ser
    450                 455                 460

Ala Trp Arg Arg Gly His Arg Val Asp Phe Gly Gly Ile Phe Glu Lys
465                 470                 475                 480
```

```
Ala Asn Asp Phe Asn Lys Ile Asn Trp Gly Thr Gln Ala Gly Pro Ser
            485                 490                 495

Ser Glu Asp Asp Gly Ile Ser Phe Ser Asn Glu Thr Pro Gly Ala Gly
            500                 505                 510

Pro Ala Ala Ala Pro Ser Pro Thr Pro Ser Ser Ile Pro Ile Ile Asn
            515                 520                 525

Val Asn Val Asn Val Gly Gly Thr Asn Val Asn Ile Gly Asp Thr Asn
            530                 535                 540

Val Asn Thr Thr Asn Thr Thr Pro Thr Thr Gln Ser Thr Asp Ala Ser
545                 550                 555                 560

Thr Asp Thr Ser Asp Ile Asp Asp Ile Asn Thr Asn Asn Gln Thr Asp
            565                 570                 575

Asp Ile Asn Thr Thr Asp Lys Asp Ser Asp Gly Ala Gly Gly Val Asn
            580                 585                 590

Gly Asp Ile Ser Glu Thr Glu Ser Ser Gly Asp Asp Ser Gly Ser
            595                 600                 605

Val Ser Ser Ser Glu Ser Asp Lys Asn Ala Ser Val Gly Asn Asp Gly
            610                 615                 620

Pro Ala Met Lys Asp Ile Leu Ser Ala Val Arg Lys His Leu Asp Val
625                 630                 635                 640

Val Tyr Pro Gly Glu Asn Gly Gly Ser Thr Glu Gly Pro Leu Pro Ala
            645                 650                 655

Asn Gln Thr Leu Gly Asp Val Ile Ser Asp Val Glu Asn Lys Gly Ser
            660                 665                 670

Ala Gln Asp Thr Lys Leu Ser Gly Asn Thr Gly Ala Gly Asp Asp Asp
            675                 680                 685

Pro Thr Thr Thr Ala Ala Val Gly Asn Gly Ala Glu Glu Ile Thr Leu
            690                 695                 700

Ser Asp Thr Asp Ser Gly Ile Gly Asp Asp Val Ser Asp Thr Ala Ser
705                 710                 715                 720

Ser Ser Gly Asp Glu Ser Gly Gly Val Ser Ser Pro Ser Ser Glu Ser
            725                 730                 735

Asn Lys Asn Thr Ala Val Gly Asn Asp Gly Pro Ser Gly Leu Asp Ile
            740                 745                 750

Leu Ala Ala Val Arg Lys His Leu Asp Lys Val Tyr Pro Gly Asp Asn
            755                 760                 765

Gly Gly Ser Thr Glu Gly Pro Leu Gln Ala Asn Gln Thr Leu Gly Asp
            770                 775                 780

Ile Val Gln Asp Met Glu Thr Thr Gly Thr Ser Gln Glu Thr Val Val
785                 790                 795                 800

Ser Pro Trp Lys Gly Ser Thr Ser Thr Glu Ser Ala Gly Gly Ser
            805                 810                 815

Gly Ser Val Gln Thr Leu Leu Pro Ser Pro Pro Thr Pro Ser Thr
            820                 825                 830

Thr Thr Leu Arg Thr Gly Thr Gly Ala Thr Thr Ser Leu Met Met
            835                 840                 845

Gly Gly Pro Ile Lys Ala Asp Ile Ile Thr Gly Gly Gly Gly Arg
            850                 855                 860

Ile Pro Gly Gly Gly Thr Leu Glu Lys Leu Leu Pro Arg Ile Arg Ala
865                 870                 875                 880

His Leu Asp Ile Ser Phe Asp Ala Gln Gly Asp Leu Val Ser Thr Glu
            885                 890                 895

Glu Pro Gln Leu Gly Ser Ile Val Asn Lys Phe Arg Gln Glu Thr Gly
```

-continued

```
                900             905             910
Ser Arg Gly Ile Leu Ala Phe Val Glu Ser Ala Pro Gly Lys Pro Gly
            915                 920                 925

Ser Ala Gln Val Leu Thr Gly Thr Gly Asp Lys Gly Asn Leu Phe
        930                 935                 940

Gln Ala Ala Ala Val Thr Gln Ala Leu Gly Asn Val Ala Gly Lys
945                 950                 955                 960

Val Asn Leu Ala Ile Gln Gly Lys Leu Ser Leu Val Asn Asp
                965                 970                 975

Asp Gly Lys Gly Ser Val Gly Arg Asp Leu Phe Gln Ala Ala Ala Gln
            980                 985                 990

Thr Thr Gln Val Leu Ser Ala Leu Ile Asp Thr Val Gly
            995                 1000                1005
```

<210> SEQ ID NO 31
<211> LENGTH: 13
<212> TYPE: PRT
<213> ORGANISM: Chlamydia trachomatis

<400> SEQUENCE: 31

```
Thr Thr Glu Asn Ile Tyr Glu Ser Ile Gly Gly Ser Arg
1               5                   10
```

<210> SEQ ID NO 32
<211> LENGTH: 105
<212> TYPE: PRT
<213> ORGANISM: Chlamydia trachomatis

<400> SEQUENCE: 32

```
Met Lys Gln Gln Lys Gln Arg Ile Arg Ile Arg Leu Lys Gly Phe Asp
1               5                   10                  15

Gln Gly Gln Leu Asp Gln Ser Thr Ala Asn Ile Val Glu Thr Ala Lys
            20                  25                  30

Arg Thr Gly Ala Arg Val Val Gly Pro Ile Pro Leu Pro Thr Lys Arg
        35                  40                  45

Glu Val Tyr Thr Val Leu Arg Ser Pro His Val Asp Lys Lys Ser Arg
    50                  55                  60

Glu Gln Phe Glu Ile Arg Thr His Lys Arg Leu Ile Asp Ile Leu Asp
65                  70                  75                  80

Pro Thr Gly Lys Thr Ile Asp Ala Leu Lys Met Leu Ser Leu Pro Ala
                85                  90                  95

Gly Val Asp Ile Lys Ile Lys Ala Ala
            100                 105
```

<210> SEQ ID NO 33
<211> LENGTH: 19
<212> TYPE: PRT
<213> ORGANISM: Chlamydia trachomatis

<400> SEQUENCE: 33

```
Gly Phe Asp Gln Gly Gln Leu Asp Gln Ser Thr Ala Asn Ile Val Glu
1               5                   10                  15

Thr Ala Lys
```

<210> SEQ ID NO 34
<211> LENGTH: 173
<212> TYPE: PRT
<213> ORGANISM: Chlamydia trachomatis

<400> SEQUENCE: 34

```
Met Lys Lys Phe Leu Leu Leu Ser Leu Met Ser Leu Ser Ser Leu Pro
1               5                   10                  15

Thr Phe Ala Ala Asn Ser Thr Gly Thr Ile Gly Ile Val Asn Leu Arg
                20                  25                  30

Arg Cys Leu Glu Glu Ser Ala Leu Gly Lys Lys Glu Ser Ala Glu Phe
                35                  40                  45

Glu Lys Met Lys Asn Gln Phe Ser Asn Ser Met Gly Lys Met Glu Glu
            50                  55                  60

Glu Leu Ser Ser Ile Tyr Ser Lys Leu Gln Asp Asp Tyr Met Glu
65                  70                  75                  80

Gly Leu Ser Glu Thr Ala Ala Ala Glu Leu Arg Lys Lys Phe Glu Asp
                85                  90                  95

Leu Ser Ala Glu Tyr Asn Thr Ala Gln Gly Gln Tyr Tyr Gln Ile Leu
                100                 105                 110

Asn Gln Ser Asn Leu Lys Arg Met Gln Lys Ile Met Glu Glu Val Lys
            115                 120                 125

Lys Ala Ser Glu Thr Val Arg Ile Gln Glu Gly Leu Ser Val Leu Leu
            130                 135                 140

Asn Glu Asp Ile Val Leu Ser Ile Asp Ser Ser Ala Asp Lys Thr Asp
145                 150                 155                 160

Ala Val Ile Lys Val Leu Asp Asp Ser Phe Gln Asn Asn
                165                 170

<210> SEQ ID NO 35
<211> LENGTH: 11
<212> TYPE: PRT
<213> ORGANISM: Chlamydia trachomatis

<400> SEQUENCE: 35

Met Glu Glu Glu Leu Ser Ser Ile Tyr Ser Lys
1               5                   10

<210> SEQ ID NO 36
<211> LENGTH: 122
<212> TYPE: PRT
<213> ORGANISM: Chlamydia trachomatis

<400> SEQUENCE: 36

Met Pro Arg Ile Ile Gly Ile Asp Ile Pro Ala Lys Lys Lys Leu Lys
1               5                   10                  15

Ile Ser Leu Thr Tyr Ile Tyr Gly Ile Gly Pro Ala Leu Ser Lys Glu
                20                  25                  30

Ile Ile Ala Arg Leu Gln Leu Asn Pro Glu Ala Arg Ala Ala Glu Leu
                35                  40                  45

Thr Glu Glu Val Gly Arg Leu Asn Ala Leu Leu Gln Ser Asp Tyr
50                  55                  60

Val Val Glu Gly Asp Leu Arg Arg Val Gln Ser Asp Ile Lys Arg
65                  70                  75                  80

Leu Ile Thr Ile His Ala Tyr Arg Gly Gln Arg His Arg Leu Ser Leu
                85                  90                  95

Pro Val Arg Gly Gln Arg Thr Lys Thr Asn Ser Arg Thr Arg Lys Gly
                100                 105                 110

Lys Arg Lys Thr Val Ala Gly Lys Lys Lys
            115                 120

<210> SEQ ID NO 37
<211> LENGTH: 11
```

```
<212> TYPE: PRT
<213> ORGANISM: Chlamydia trachomatis

<400> SEQUENCE: 37

Ala Ala Glu Leu Thr Glu Glu Val Gly Arg
1               5                   10

<210> SEQ ID NO 38
<211> LENGTH: 232
<212> TYPE: PRT
<213> ORGANISM: Chlamydia trachomatis

<400> SEQUENCE: 38

Met Thr Lys His Gly Lys Arg Ile Arg Gly Ile Gln Glu Thr Tyr Asp
1               5                   10                  15

Leu Ala Lys Ser Tyr Ser Leu Gly Glu Ala Ile Asp Ile Leu Lys Gln
            20                  25                  30

Cys Pro Thr Val Arg Phe Asp Gln Thr Val Asp Val Ser Val Lys Leu
        35                  40                  45

Gly Ile Asp Pro Arg Lys Ser Asp Gln Gln Ile Arg Gly Ser Val Ser
    50                  55                  60

Leu Pro His Gly Thr Gly Lys Val Leu Arg Ile Leu Val Phe Ala Ala
65                  70                  75                  80

Gly Asp Lys Ala Ala Glu Ala Ile Glu Ala Gly Ala Asp Phe Val Gly
                85                  90                  95

Ser Asp Asp Leu Val Glu Lys Ile Lys Gly Gly Trp Val Asp Phe Asp
            100                 105                 110

Val Ala Val Ala Thr Pro Asp Met Met Arg Glu Val Gly Lys Leu Gly
        115                 120                 125

Lys Val Leu Gly Pro Arg Asn Leu Met Pro Thr Pro Lys Ala Gly Thr
    130                 135                 140

Val Thr Thr Asp Val Val Lys Thr Val Ala Glu Leu Arg Lys Gly Lys
145                 150                 155                 160

Ile Glu Phe Lys Ala Asp Arg Ala Gly Val Cys Asn Val Gly Val Ala
                165                 170                 175

Lys Leu Ser Phe Asp Ser Ala Gln Ile Lys Glu Asn Val Glu Ala Leu
            180                 185                 190

Cys Ala Ala Leu Val Lys Ala Lys Pro Ala Thr Ala Lys Gly Gln Tyr
        195                 200                 205

Leu Val Asn Phe Thr Ile Ser Ser Thr Met Gly Pro Gly Val Thr Val
    210                 215                 220

Asp Thr Arg Glu Leu Ile Ala Leu
225                 230

<210> SEQ ID NO 39
<211> LENGTH: 10
<212> TYPE: PRT
<213> ORGANISM: Chlamydia trachomatis

<400> SEQUENCE: 39

Phe Asp Gln Thr Val Asp Val Ser Val Lys
1               5                   10

<210> SEQ ID NO 40
<211> LENGTH: 591
<212> TYPE: PRT
<213> ORGANISM: Chlamydia trachomatis

<400> SEQUENCE: 40
```

```
Met Ser Ile Arg Gly Val Gly Asn Gly Asn Ser Arg Ile Pro Ser
1               5                   10                  15

His Asn Gly Asp Gly Ser Asn Arg Arg Ser Gln Asn Thr Lys Gly Asn
            20                  25                  30

Asn Lys Val Glu Asp Arg Val Cys Ser Leu Tyr Ser Ser Arg Ser Asn
                35                  40                  45

Glu Asn Arg Glu Ser Pro Tyr Ala Val Val Asp Val Ser Ser Met Ile
        50                  55                  60

Glu Ser Thr Pro Thr Ser Gly Glu Thr Thr Arg Ala Ser Arg Gly Val
65                      70                  75                  80

Phe Ser Arg Phe Gln Arg Gly Leu Val Arg Val Ala Asp Lys Val Arg
                85                  90                  95

Arg Ala Val Gln Cys Ala Trp Ser Ser Val Ser Thr Arg Arg Ser Ser
                100                 105                 110

Ala Thr Arg Ala Ala Glu Ser Gly Ser Ser Ser Arg Thr Ala Arg Gly
            115                 120                 125

Ala Ser Ser Gly Tyr Arg Glu Tyr Ser Pro Ser Ala Ala Arg Gly Leu
        130                 135                 140

Arg Leu Met Phe Thr Asp Phe Trp Arg Thr Arg Val Leu Arg Gln Thr
145                 150                 155                 160

Ser Pro Met Ala Gly Val Phe Gly Asn Leu Asp Val Asn Glu Ala Arg
                165                 170                 175

Leu Met Ala Ala Tyr Thr Ser Glu Cys Ala Asp His Leu Glu Ala Asn
                180                 185                 190

Lys Leu Ala Gly Pro Asp Gly Val Ala Ala Ala Arg Glu Ile Ala Lys
            195                 200                 205

Arg Trp Glu Gln Arg Val Arg Asp Leu Gln Asp Lys Gly Ala Ala Arg
        210                 215                 220

Lys Leu Leu Asn Asp Pro Leu Gly Arg Arg Thr Pro Asn Tyr Gln Ser
225                 230                 235                 240

Lys Asn Pro Gly Glu Tyr Thr Val Gly Asn Ser Met Phe Tyr Asp Gly
                245                 250                 255

Pro Gln Val Ala Asn Leu Gln Asn Val Asp Thr Gly Phe Trp Leu Asp
            260                 265                 270

Met Ser Asn Leu Ser Asp Val Val Leu Ser Arg Glu Ile Gln Thr Gly
        275                 280                 285

Leu Arg Ala Arg Ala Thr Leu Glu Glu Ser Met Pro Met Leu Glu Asn
        290                 295                 300

Leu Glu Glu Arg Phe Arg Leu Gln Glu Thr Cys Asp Ala Ala Arg
305                 310                 315                 320

Thr Glu Ile Glu Glu Ser Gly Trp Thr Arg Glu Ser Ala Ser Arg Met
                325                 330                 335

Glu Gly Asp Glu Ala Gln Gly Pro Ser Arg Ala Gln Ala Phe Gln
            340                 345                 350

Ser Phe Val Asn Glu Cys Asn Ser Ile Glu Phe Ser Phe Gly Ser Phe
        355                 360                 365

Gly Glu His Val Arg Val Leu Cys Ala Arg Val Ser Arg Gly Leu Ala
    370                 375                 380

Ala Ala Gly Glu Ala Ile Arg Arg Cys Phe Ser Cys Cys Lys Gly Ser
385                 390                 395                 400

Thr His Arg Tyr Ala Pro Arg Asp Leu Ser Pro Glu Gly Ala Ser
                405                 410                 415

Leu Ala Glu Thr Leu Ala Arg Phe Ala Asp Asp Met Gly Ile Glu Arg
            420                 425                 430
```

```
Gly Ala Asp Gly Thr Tyr Asp Ile Pro Leu Val Asp Asp Trp Arg Arg
            435                 440                 445

Gly Val Pro Ser Ile Glu Gly Glu Gly Ser Asp Ser Ile Tyr Glu Ile
            450                 455                 460

Met Met Pro Ile Tyr Glu Val Met Asp Met Asp Leu Glu Thr Arg Arg
465                 470                 475                 480

Ser Phe Ala Val Gln Gln Gly His Tyr Gln Asp Pro Arg Ala Ser Asp
            485                 490                 495

Tyr Asp Leu Pro Arg Ala Ser Asp Tyr Asp Leu Pro Arg Ser Pro Tyr
            500                 505                 510

Pro Thr Pro Pro Leu Pro Pro Arg Tyr Gln Leu Gln Asn Met Asp Val
            515                 520                 525

Glu Ala Gly Phe Arg Glu Ala Val Tyr Ala Ser Phe Val Ala Gly Met
            530                 535                 540

Tyr Asn Tyr Val Val Thr Gln Pro Gln Glu Arg Ile Pro Asn Ser Gln
545                 550                 555                 560

Gln Val Glu Gly Ile Leu Arg Asp Met Leu Thr Asn Gly Ser Gln Thr
            565                 570                 575

Phe Arg Asp Leu Met Arg Arg Trp Asn Arg Glu Val Asp Arg Glu
            580                 585                 590

<210> SEQ ID NO 41
<211> LENGTH: 24
<212> TYPE: PRT
<213> ORGANISM: Chlamydia trachomatis

<400> SEQUENCE: 41

Glu Ser Pro Tyr Ala Val Val Asp Val Ser Ser Met Ile Glu Ser Thr
1               5                   10                  15

Pro Thr Ser Gly Glu Thr Thr Arg
            20

<210> SEQ ID NO 42
<211> LENGTH: 497
<212> TYPE: PRT
<213> ORGANISM: Chlamydia trachomatis

<400> SEQUENCE: 42

Met Met Lys Arg Leu Leu Cys Val Leu Leu Ser Thr Ser Val Phe Ser
1               5                   10                  15

Ser Pro Met Leu Gly Tyr Ser Ala Ser Lys Lys Asp Ser Lys Ala Asp
            20                  25                  30

Ile Cys Leu Ala Val Ser Ser Gly Asp Gln Glu Val Ser Gln Glu Asp
        35                  40                  45

Leu Leu Lys Glu Val Ser Arg Gly Phe Ser Arg Val Ala Ala Lys Ala
    50                  55                  60

Thr Pro Gly Val Val Tyr Ile Glu Asn Phe Pro Lys Thr Gly Asn Gln
65                  70                  75                  80

Ala Ile Ala Ser Pro Gly Asn Lys Arg Gly Phe Gln Glu Asn Pro Phe
            85                  90                  95

Asp Tyr Phe Asn Asp Glu Phe Asn Arg Phe Phe Gly Leu Pro Ser
            100                 105                 110

His Arg Glu Gln Gln Arg Pro Gln Gln Arg Asp Ala Val Arg Gly Thr
        115                 120                 125

Gly Phe Ile Val Ser Glu Asp Gly Tyr Val Val Thr Asn His His Val
    130                 135                 140
```

```
Val Glu Asp Ala Gly Lys Ile His Val Thr Leu His Asp Gly Gln Lys
145                 150                 155                 160

Tyr Thr Ala Lys Ile Val Gly Leu Asp Pro Lys Thr Asp Leu Ala Val
                165                 170                 175

Ile Lys Ile Gln Ala Glu Lys Leu Pro Phe Leu Thr Phe Gly Asn Ser
            180                 185                 190

Asp Gln Leu Gln Ile Gly Asp Trp Ala Ile Ala Ile Gly Asn Pro Phe
        195                 200                 205

Gly Leu Gln Ala Thr Val Thr Val Gly Val Ile Ser Ala Lys Gly Arg
    210                 215                 220

Asn Gln Leu His Ile Val Asp Phe Glu Asp Phe Ile Gln Thr Asp Ala
225                 230                 235                 240

Ala Ile Asn Pro Gly Asn Ser Gly Pro Leu Leu Asn Ile Asn Gly
                245                 250                 255

Gln Val Ile Gly Val Asn Thr Ala Ile Val Ser Gly Ser Gly Gly Tyr
            260                 265                 270

Ile Gly Ile Gly Phe Ala Ile Pro Ser Leu Met Ala Lys Arg Val Ile
            275                 280                 285

Asp Gln Leu Ile Ser Asp Gly Gln Val Thr Arg Gly Phe Leu Gly Val
290                 295                 300

Thr Leu Gln Pro Ile Asp Ser Glu Leu Ala Thr Cys Tyr Lys Leu Glu
305                 310                 315                 320

Lys Val Tyr Gly Ala Leu Val Thr Asp Val Val Lys Gly Ser Pro Ala
                325                 330                 335

Glu Lys Ala Gly Leu Arg Gln Glu Asp Val Ile Ala Tyr Asn Gly
                340                 345                 350

Lys Glu Val Glu Ser Leu Ser Ala Leu Arg Asn Ala Ile Ser Leu Met
                355                 360                 365

Met Pro Gly Thr Arg Val Val Leu Lys Ile Val Arg Glu Gly Lys Thr
        370                 375                 380

Ile Glu Ile Pro Val Thr Val Thr Gln Ile Pro Thr Glu Asp Gly Val
385                 390                 395                 400

Ser Ala Leu Gln Lys Met Gly Val Arg Val Gln Asn Ile Thr Pro Glu
                405                 410                 415

Ile Cys Lys Lys Leu Gly Leu Ala Ala Asp Thr Arg Gly Ile Leu Val
            420                 425                 430

Val Ala Val Glu Ala Gly Ser Pro Ala Ala Ser Ala Gly Val Ala Pro
        435                 440                 445

Gly Gln Leu Ile Leu Ala Val Asn Arg Gln Arg Val Ala Ser Val Glu
    450                 455                 460

Glu Leu Asn Gln Val Leu Lys Asn Ser Lys Gly Glu Asn Val Leu Leu
465                 470                 475                 480

Met Val Ser Gln Gly Asp Val Val Arg Phe Ile Val Leu Lys Ser Asp
                485                 490                 495

Glu

<210> SEQ ID NO 43
<211> LENGTH: 15
<212> TYPE: PRT
<213> ORGANISM: Chlamydia trachomatis

<400> SEQUENCE: 43

Gly Glu Asn Val Leu Leu Met Val Ser Gln Gly Asp Val Val Arg
1               5                   10                  15
```

<210> SEQ ID NO 44
<211> LENGTH: 377
<212> TYPE: PRT
<213> ORGANISM: Chlamydia trachomatis

<400> SEQUENCE: 44

Met Ser Asp Ser Ser His Asn Leu Leu Tyr Asn Lys Phe Glu Leu Pro
1               5                   10                  15

Glu Ser Val Lys Met Ser Pro Val Gly Ala Val Gly Gly Ile Asp
            20                  25                  30

Lys Val Ala Arg Phe Val Ala Asp Pro Leu Glu Lys Gly Met Gly His
        35                  40                  45

Thr Leu Gly Ser Ala Leu Arg Arg Ala Leu Leu Ile Gly Leu Glu Ala
    50                  55                  60

Pro Ala Ile Val Ser Phe Ser Met Thr Gly Val Leu His Glu Tyr Met
65                  70                  75                  80

Ala Val Glu Gly Ile Ile Glu Asp Val Thr Asn Ile Val Leu Asn Leu
                85                  90                  95

Lys Gly Ser Leu Leu Lys Lys Tyr Pro Leu Gln Asp Cys Glu Gly Gly
            100                 105                 110

Arg Cys Ser Gln Lys Leu Arg Ala Thr Ile Ser Ile Asp Ala Ser Asp
        115                 120                 125

Leu Ala Ala Ala Gly Gly Gln Lys Glu Val Thr Leu Gly Asp Leu Leu
130                 135                 140

Gln Glu Gly Thr Phe Glu Ala Val Asn Pro Glu His Val Ile Phe Thr
145                 150                 155                 160

Val Thr Arg Pro Met Gln Leu Glu Val Met Leu Arg Val Ala Phe Gly
                165                 170                 175

Arg Gly Tyr Ser Pro Ser Glu Arg Ile Val Leu Glu Glu Arg Gly Met
            180                 185                 190

Asn Glu Ile Val Leu Asp Ala Ala Phe Ser Pro Val Val Leu Val Asn
        195                 200                 205

Tyr Phe Val Glu Asp Thr Arg Val Gly Gln Asp Thr Asp Phe Asp Arg
    210                 215                 220

Leu Val Leu Gln Val Glu Thr Asp Gly Arg Val Ala Pro Lys Glu Ala
225                 230                 235                 240

Val Ala Phe Ala Thr Gln Ile Leu Ser Lys His Phe Ser Val Phe Glu
                245                 250                 255

Lys Met Asp Glu Lys Arg Ile Val Phe Glu Glu Ala Ile Ser Val Glu
            260                 265                 270

Lys Glu Asn Lys Asp Asp Ile Leu His Lys Leu Val Leu Gly Ile Asn
        275                 280                 285

Glu Ile Glu Leu Ser Val Arg Ser Thr Asn Cys Leu Ser Asn Ala Asn
    290                 295                 300

Ile Glu Thr Ile Gly Glu Leu Val Ile Met Pro Glu Pro Arg Leu Leu
305                 310                 315                 320

Gln Phe Arg Asn Phe Gly Lys Lys Ser Leu Cys Glu Ile Lys Asn Lys
                325                 330                 335

Leu Lys Glu Met Lys Leu Glu Leu Gly Met Asp Leu Ser Gln Phe Gly
            340                 345                 350

Val Gly Leu Asp Asn Val Lys Glu Lys Met Lys Trp Tyr Ala Glu Lys
        355                 360                 365

Ile Arg Ser Ser Lys Asn Thr Lys Gly
    370                 375

```
<210> SEQ ID NO 45
<211> LENGTH: 13
<212> TYPE: PRT
<213> ORGANISM: Chlamydia trachomatis

<400> SEQUENCE: 45

Met Ser Pro Val Glu Gly Ala Val Gly Gly Ile Asp Lys
1               5                   10

<210> SEQ ID NO 46
<211> LENGTH: 499
<212> TYPE: PRT
<213> ORGANISM: Chlamydia trachomatis

<400> SEQUENCE: 46

Met Val Leu Leu Tyr Ser Gln Ala Ser Trp Asp Lys Arg Ser Lys Ala
1               5                   10                  15

Asp Ala Leu Val Leu Pro Phe Trp Met Lys Asn Ser Lys Ala Gln Glu
            20                  25                  30

Ala Ala Val Val Asp Glu Asp Tyr Lys Leu Val Tyr Gln Asn Ala Leu
        35                  40                  45

Ser Asn Phe Ser Gly Lys Lys Gly Glu Thr Ala Phe Leu Phe Gly Asn
    50                  55                  60

Asp His Thr Lys Glu Gln Lys Ile Val Leu Gly Leu Gly Lys Ser
65                  70                  75                  80

Glu Glu Val Ser Gly Thr Thr Val Leu Glu Ala Tyr Ala Gln Ala Thr
                85                  90                  95

Thr Val Leu Arg Lys Ala Lys Cys Lys Thr Val Asn Ile Leu Leu Pro
            100                 105                 110

Thr Ile Ser Gln Leu Arg Phe Ser Val Glu Glu Phe Leu Thr Asn Leu
        115                 120                 125

Ala Ala Gly Val Leu Ser Leu Asn Tyr Asn Tyr Pro Thr Tyr His Lys
    130                 135                 140

Val Asp Thr Ser Leu Pro Phe Leu Glu Lys Val Thr Val Met Gly Ile
145                 150                 155                 160

Val Ser Lys Val Gly Asp Lys Ile Phe Arg Lys Glu Ser Leu Phe
                165                 170                 175

Glu Gly Val Tyr Leu Thr Arg Asp Leu Val Asn Thr Asn Ala Asp Glu
            180                 185                 190

Val Thr Pro Glu Lys Leu Ala Ala Val Ala Lys Asp Leu Ala Gly Glu
        195                 200                 205

Phe Ala Ser Leu Asp Val Lys Ile Leu Asp Arg Lys Ala Ile Leu Lys
    210                 215                 220

Glu Lys Met Gly Leu Leu Ala Val Ala Lys Gly Ala Ala Val Glu
225                 230                 235                 240

Pro Arg Phe Ile Val Leu Asp Tyr Gln Gly Lys Pro Lys Ser Lys Asp
                245                 250                 255

Arg Thr Val Leu Ile Gly Lys Gly Val Thr Phe Asp Ser Gly Gly Leu
            260                 265                 270

Asp Leu Lys Pro Gly Lys Ala Met Ile Thr Met Lys Glu Asp Met Ala
        275                 280                 285

Gly Ala Ala Thr Val Leu Gly Ile Phe Ser Ala Leu Ala Ser Leu Glu
    290                 295                 300

Leu Pro Ile Asn Val Thr Gly Ile Ile Pro Ala Thr Glu Asn Ala Ile
305                 310                 315                 320

Gly Ser Ala Ala Tyr Lys Met Gly Asp Val Tyr Val Gly Met Thr Gly
                325                 330                 335
```

```
Leu Ser Val Glu Ile Gly Ser Thr Asp Ala Glu Gly Arg Leu Ile Leu
                340                 345                 350

Ala Asp Ala Ile Ser Tyr Ala Leu Lys Tyr Cys Asn Pro Thr Arg Ile
            355                 360                 365

Ile Asp Phe Ala Thr Leu Thr Gly Ala Met Val Val Ser Leu Gly Glu
        370                 375                 380

Ser Val Ala Gly Phe Phe Ala Asn Asn Asp Val Leu Ala Arg Asp Leu
385                 390                 395                 400

Ala Glu Ala Ser Ser Glu Thr Gly Glu Ala Leu Trp Arg Met Pro Leu
                405                 410                 415

Val Glu Lys Tyr Asp Gln Ala Leu His Ser Asp Ile Ala Asp Met Lys
            420                 425                 430

Asn Ile Gly Ser Asn Arg Ala Gly Ser Ile Thr Ala Ala Leu Phe Leu
        435                 440                 445

Gln Arg Phe Leu Glu Asp Asn Pro Val Ala Trp Ala His Leu Asp Ile
450                 455                 460

Ala Gly Thr Ala Tyr His Glu Lys Glu Glu Leu Pro Tyr Pro Lys Tyr
465                 470                 475                 480

Ala Thr Gly Phe Gly Val Arg Cys Leu Ile His Tyr Met Glu Lys Phe
                485                 490                 495

Leu Ser Lys

<210> SEQ ID NO 47
<211> LENGTH: 14
<212> TYPE: PRT
<213> ORGANISM: Chlamydia trachomatis

<400> SEQUENCE: 47

Asp Leu Val Asn Thr Asn Ala Asp Glu Val Thr Pro Glu Lys
1               5                   10

<210> SEQ ID NO 48
<211> LENGTH: 875
<212> TYPE: PRT
<213> ORGANISM: Chlamydia trachomatis

<400> SEQUENCE: 48

Met Leu Ser Asn Thr Leu Arg Ser Asn Phe Leu Lys Phe Tyr Ala Asn
1               5                   10                  15

Arg Asn His Thr Pro Val Ala Ser Ser Pro Val Phe Pro His Asn Asp
                20                  25                  30

Pro Ser Ile Leu Phe Thr Asn Ala Gly Met Asn Gln Phe Lys Asn Ile
            35                  40                  45

Phe Leu Gly Lys Glu Gln Thr Ser Tyr Thr Arg Ala Thr Thr Ser Gln
        50                  55                  60

Lys Cys Ile Arg Ala Gly Gly Lys His Asn Asp Leu Glu Asn Val Gly
65                  70                  75                  80

His Thr Ser Arg His Leu Thr Phe Phe Glu Met Leu Gly Asn Phe Ser
                85                  90                  95

Phe Gly Asp Tyr Phe Lys Gln Asp Ala Ile Ser Phe Ala Trp Glu Val
                100                 105                 110

Ser Leu Ser Ile Phe Asn Phe Asp Pro Asp Phe Ile Tyr Ala Thr Val
            115                 120                 125

His Glu Lys Asp Asp Glu Ala Phe Ala Leu Trp Glu Lys Tyr Leu Pro
        130                 135                 140

Thr Asp Arg Ile Phe Arg Leu Thr Asp Lys Asp Asn Phe Trp Ser Met
```

```
            145                 150                 155                 160
        Ala Asp Thr Gly Pro Cys Gly Phe Cys Ser Glu Leu Leu Phe Asp Arg
                        165                 170                 175

Gly Glu Lys Phe Gly Lys Ala Ala Ser Pro Leu Glu Asp Val Asp Gly
                        180                 185                 190

Glu Arg Phe Leu Glu Tyr Trp Asn Leu Val Phe Met Glu Phe Asn Arg
                        195                 200                 205

Thr Ser Asp Gly Thr Leu Leu Ala Leu Gln Lys Lys Cys Val Asp Thr
                        210                 215                 220

Gly Ala Gly Leu Glu Arg Leu Val Ser Leu Ala Glu Thr Glu Thr
        225                 230                 235                 240

Val Phe Glu Ala Asp Val Leu Arg His Leu Ile Ser Lys Ile Glu Asn
                        245                 250                 255

Leu Ser Gly Thr Thr Tyr Ser Pro Thr Glu Ala Lys Gly Ala Ala Phe
                        260                 265                 270

Arg Val Ile Ala Asp His Ile Arg Ser Leu Ser Phe Ala Ile Ala Asp
                        275                 280                 285

Gly Leu Leu Pro Gly Asn Thr Glu Arg Gly Tyr Val Leu Arg Lys Ile
                        290                 295                 300

Leu Arg Arg Ala Val Asn Tyr Gly Lys Arg Leu Gly Phe Asn Arg Pro
        305                 310                 315                 320

Phe Leu Ala Asp Val Val Pro Ser Leu Val Asp Val Met Gly Glu Ala
                        325                 330                 335

Tyr Pro Glu Leu Ser Ala Ser Val Thr Gln Ile Gln Glu Val Leu Thr
                        340                 345                 350

Thr Glu Glu Glu His Phe Phe Lys Thr Leu Gln Arg Gly Gly Asn Leu
                        355                 360                 365

Leu Gln Gln Val Leu Lys Ser Ser Ala Ser Ser Ala Lys Ile Ser Gly
                        370                 375                 380

Glu Asp Ala Phe Lys Leu Lys Asp Thr Tyr Gly Leu Pro Ile Asp Glu
        385                 390                 395                 400

Ile Ala Leu Leu Ala Lys Asp Tyr Asn Tyr Ala Ile Asp Met Asp Thr
                        405                 410                 415

Phe Glu Lys Leu Glu Val Glu Ala Lys Glu Arg Ser Arg Lys Asn Thr
                        420                 425                 430

Lys Lys Thr Lys Asn Asp Ser Asp Ser Val Phe Gln Asp Leu Asp Pro
                        435                 440                 445

Thr Asn Thr Ser Glu Phe Ile Gly Tyr Asp Thr Leu Ser Cys Asp Thr
        450                 455                 460

Phe Ile Glu Gly Ile Ile Lys Tyr Asn Glu Ile Ala Ser Ser Leu Glu
        465                 470                 475                 480

Glu Gly Asp Glu Gly Ala Ile Ile Leu Arg Thr Thr Pro Phe Tyr Ala
                        485                 490                 495

Gly Lys Gly Gly Gln Ile Gly Asp Ser Gly Ile Phe Cys Glu Ser
                        500                 505                 510

Gly Thr Phe Leu Val Ser His Thr Ile Ala Pro Lys Ala Gly Leu Ile
                        515                 520                 525

Val His Leu Gly Lys Leu Ser Gln Gly Ser Leu Thr Thr Thr Met Ala
                        530                 535                 540

Val Thr Ala Gln Val Asn Gln Asn Leu Arg Lys Lys Thr Ala Asn Asn
        545                 550                 555                 560

His Thr Gly Cys His Leu Leu Lys Ala Leu Glu Met Thr Leu Gly
                        565                 570                 575
```

```
Glu His Ile Arg Gln Ala Gly Ser Tyr Val Asp Ser Gln Lys Ile Arg
                580                 585                 590

Leu Asp Phe Thr His Asn Lys Ala Leu Ser Pro Glu Asp Leu Leu Ala
                595                 600                 605

Ile Glu Thr Leu Val Asn Glu Lys Ile Arg Glu Asn Asp Pro Val Thr
            610                 615                 620

Ile Arg Glu Val Leu Tyr Ser Asp Val Met Ser Ser Glu Ile Lys
625                 630                 635                 640

Gln Phe Phe Gly Asp Lys Tyr Gly Asp Ile Val Arg Val Val Ser Ala
                645                 650                 655

Gly Phe Ser His Glu Leu Cys Gly Gly Thr His Ala Gln Ala Thr Gly
            660                 665                 670

Asp Ile Gly Tyr Phe Arg Ile Thr Lys Glu His Ala Val Ala Thr Gly
        675                 680                 685

Ile Arg Arg Ile Glu Ala Thr Thr Gly Glu Asp Ala Glu Asn Ile Ala
            690                 695                 700

Arg Glu Gln Asp Val Asp Leu Asn Glu Ile Ala Thr Val Ile Gln Ser
705                 710                 715                 720

Pro Lys Asp Gln Ile Leu Val Lys Ile Arg Ser Val Met Glu Glu Lys
                725                 730                 735

Lys Asp Leu Ala Lys Gln Val Ala Asp Leu Glu Asn Gln Leu Val Gln
            740                 745                 750

Gln Gln Val Lys Thr Leu Leu Thr Ser Cys Glu Lys Ile Cys Asp Thr
        755                 760                 765

Ser Tyr Leu Val Tyr Tyr Leu Thr Glu Glu Glu Gly Arg Ile Gln
770                 775                 780

His Tyr Ala Asn Ala Ile His Lys Glu Ile Pro Thr Asn Phe Ile Ser
785                 790                 795                 800

Leu Trp Ile Thr Glu Lys Asn Gly Arg Tyr Ile Val Leu Ser Arg Val
                805                 810                 815

Ser Asp Asp Leu Thr Lys Arg Gly Val Gln Ala His Thr Leu Leu Ala
            820                 825                 830

Glu Leu Leu Ala Pro Tyr Gly Gly Arg Cys Gly Gly Lys Ala Ile Ser
        835                 840                 845

Ala Gln Gly Ser Ser Ala Glu Leu Pro Gln Ile Glu Phe Leu Asn Lys
850                 855                 860

Thr Leu Arg Gln Trp Ile Ser Thr Gln Leu Ala
865                 870                 875

<210> SEQ ID NO 49
<211> LENGTH: 17
<212> TYPE: PRT
<213> ORGANISM: Chlamydia trachomatis

<400> SEQUENCE: 49

Ala Leu Ser Pro Glu Asp Leu Leu Ala Ile Glu Thr Leu Val Asn Glu
1               5                   10                  15

Lys

<210> SEQ ID NO 50
<211> LENGTH: 1396
<212> TYPE: PRT
<213> ORGANISM: Chlamydia trachomatis

<400> SEQUENCE: 50

Met Phe Arg Glu Gly Ser Arg Asp Asp Ala Ala Leu Val Lys Glu Gly
1               5                   10                  15
```

Leu Phe Asp Lys Leu Glu Ile Gly Ile Ala Ser Asp Val Thr Ile Arg
             20                  25                  30

Asp Lys Trp Ser Cys Gly Glu Ile Lys Lys Pro Glu Thr Ile Asn Tyr
             35                  40                  45

Arg Thr Phe Lys Pro Glu Lys Gly Gly Leu Phe Cys Glu Lys Ile Phe
 50                  55                  60

Gly Pro Thr Lys Asp Trp Glu Cys Tyr Cys Gly Lys Tyr Lys Lys Ile
 65                  70                  75                  80

Lys His Lys Gly Ile Val Cys Asp Arg Cys Gly Val Glu Val Thr Leu
                 85                  90                  95

Ser Lys Val Arg Arg Glu Arg Met Ala His Ile Glu Leu Ala Val Pro
             100                 105                 110

Ile Val His Ile Trp Phe Phe Lys Thr Thr Pro Ser Arg Ile Gly Asn
             115                 120                 125

Val Leu Gly Met Thr Ala Ser Asp Leu Glu Arg Val Ile Tyr Tyr Glu
 130                 135                 140

Glu Tyr Val Val Ile Asp Pro Gly Asn Thr Asp Leu Val Lys Lys Gln
145                 150                 155                 160

Leu Leu Asn Asp Ala Lys Tyr Arg Glu Val Glu Lys Trp Gly Lys
             165                 170                 175

Asp Ala Phe Val Ala Lys Met Gly Gly Glu Ala Val Tyr Asp Leu Leu
             180                 185                 190

Lys Ser Glu Asp Leu Glu Ser Leu Leu Gly Glu Leu Lys Glu Arg Leu
             195                 200                 205

Arg Lys Thr Lys Ser Gln Gln Ala Arg Met Lys Leu Ala Lys Arg Leu
             210                 215                 220

Lys Ile Val Glu Gly Phe Val Ser Ser Ser Asn Arg Pro Glu Trp Met
225                 230                 235                 240

Val Leu Lys Asn Ile Pro Val Val Pro Pro Asp Leu Arg Pro Leu Val
             245                 250                 255

Pro Leu Asp Gly Gly Arg Phe Ala Thr Ser Asp Leu Asn Asp Leu Tyr
             260                 265                 270

Arg Arg Val Ile Asn Arg Asn Asn Arg Leu Lys Ala Ile Leu Arg Leu
             275                 280                 285

Lys Thr Pro Glu Val Ile Val Arg Asn Glu Lys Arg Met Leu Gln Glu
 290                 295                 300

Ala Val Asp Ala Leu Phe Asp Asn Gly Arg His Gly His Pro Val Met
305                 310                 315                 320

Gly Ala Gly Asn Arg Pro Leu Lys Ser Leu Ser Glu Met Leu Lys Gly
             325                 330                 335

Lys Asn Gly Arg Phe Arg Gln Asn Leu Leu Gly Lys Arg Val Asp Tyr
             340                 345                 350

Ser Gly Arg Ser Val Ile Ile Val Gly Pro Glu Leu Lys Phe Asn Gln
             355                 360                 365

Cys Gly Leu Pro Lys Glu Met Ala Leu Glu Leu Phe Glu Pro Phe Ile
 370                 375                 380

Ile Lys Arg Leu Lys Asp Gln Gly Ser Val Tyr Thr Ile Arg Ser Ala
385                 390                 395                 400

Lys Lys Met Ile Gln Arg Gly Ala Pro Glu Val Trp Asp Val Leu Glu
             405                 410                 415

Glu Ile Ile Lys Gly His Pro Val Leu Leu Asn Arg Ala Pro Thr Leu
             420                 425                 430

His Arg Leu Gly Ile Gln Ala Phe Glu Pro Val Leu Ile Glu Gly Lys

-continued

```
            435                 440                 445
Ala Ile Arg Val His Pro Leu Val Cys Ala Ala Phe Asn Ala Asp Phe
450                 455                 460

Asp Gly Asp Gln Met Ala Val His Val Pro Leu Ser Ile Glu Ala Gln
465                 470                 475                 480

Leu Glu Ala Lys Val Leu Met Met Ala Pro Asp Asn Ile Phe Leu Pro
                    485                 490                 495

Ser Ser Gly Lys Pro Val Ala Thr Pro Ser Lys Asp Met Thr Leu Gly
                500                 505                 510

Ile Tyr Tyr Leu Met Ala Asp Pro Thr Tyr Phe Pro Glu Glu His Gly
            515                 520                 525

Gly Lys Thr Lys Ala Phe Lys Asp Glu Val Glu Val Leu Arg Ala Leu
530                 535                 540

Asn Ala Gly Gly Phe Ile Leu Lys Asp Glu Ile Cys Gly Ser Arg Arg
545                 550                 555                 560

Asp Glu Thr Gly Arg Gly Ile His Ile His Glu Lys Ile Lys Val Arg
                    565                 570                 575

Ile Asp Gly Gln Ile Ile Glu Thr Thr Pro Gly Arg Val Phe Phe Asn
                580                 585                 590

Thr Ile Val Pro Lys Glu Leu Gly Phe Gln Asn Tyr Ser Met Pro Ser
            595                 600                 605

Lys Arg Ile Ser Glu Leu Ile Leu Gln Cys Tyr Lys Lys Val Gly Leu
610                 615                 620

Glu Ala Thr Val Arg Phe Leu Asp Asp Leu Lys Glu Leu Gly Phe Val
625                 630                 635                 640

Gln Ser Thr Lys Ala Ala Ile Ser Met Gly Leu Lys Asp Val Lys Ile
                    645                 650                 655

Pro Glu Ile Lys Lys Glu Ile Leu Lys Asp Ala Tyr Asp Lys Val Ala
                660                 665                 670

Val Val Lys Lys Gln Tyr Glu Asp Gly Ile Ile Thr Asp Gly Glu Arg
            675                 680                 685

His Ser Lys Thr Ile Ser Ile Trp Thr Glu Val Ser Asp Leu Leu Ser
690                 695                 700

Asn Ala Leu Tyr Ser Glu Ile Lys Lys Gln Thr Asn Ser Lys His Asn
705                 710                 715                 720

Pro Leu Phe Leu Met Ile Asp Ser Gly Ala Arg Gly Asn Lys Ser Gln
                    725                 730                 735

Leu Lys Gln Leu Gly Ala Leu Arg Gly Leu Met Ala Lys Pro Asn Gly
                740                 745                 750

Ala Ile Ile Glu Ser Pro Ile Thr Ser Asn Phe Arg Glu Gly Leu Thr
            755                 760                 765

Val Leu Glu Tyr Ser Ile Ser Ser His Gly Ala Arg Lys Gly Leu Ala
770                 775                 780

Asp Thr Ala Leu Lys Thr Ala Asp Ser Gly Tyr Leu Thr Arg Arg Leu
785                 790                 795                 800

Val Asp Val Ala Gln Asp Val Ile Ile Thr Glu Arg Asp Cys Gly Thr
                    805                 810                 815

Leu Asn His Ile Glu Val Ser Thr Ile Arg Gln Gly Ser Glu Glu Leu
                820                 825                 830

Leu Pro Leu Lys Asp Arg Val Tyr Gly Arg Thr Val Ser Glu Asn Ile
            835                 840                 845

Tyr Gln Pro Gly Asp Lys Ser Asn Val Leu Ala Tyr Ala Gly Asp Val
850                 855                 860
```

-continued

Leu Thr Ser Ala Gln Ala Glu Ala Ile Asp Asp Ala Gly Ile Glu Ser
865                 870                 875                 880

Val Lys Ile Arg Ser Thr Leu Thr Cys Glu Ser Arg Arg Gly Val Cys
                885                 890                 895

Ala Lys Cys Tyr Gly Leu Asn Leu Ala Asn Gly Arg Leu Ile Gly Leu
            900                 905                 910

Gly Glu Ala Val Gly Ile Ile Ala Ala Gln Ser Ile Gly Glu Pro Gly
        915                 920                 925

Thr Gln Leu Thr Met Arg Thr Phe His Leu Gly Gly Ile Ala Ala Thr
    930                 935                 940

Ser Ser Thr Pro Glu Ile Val Ala Glu Cys Asp Gly Ile Leu Val Tyr
945                 950                 955                 960

Leu Asp Leu Arg Val Val Asp Gln Glu Gly Asn Asn Leu Val Leu
                965                 970                 975

Asn Lys Met Gly Ala Leu His Leu Val Gln Asp Glu Gly Arg Ser Leu
            980                 985                 990

Ser Glu Tyr Lys Lys Leu Leu Ser Thr Lys Ser Ile Glu Ser Leu Ala
        995                 1000                1005

Thr Phe Pro Val Glu Leu Gly Ala Lys Ile Leu Val Asn Asp Gly Ala
    1010                1015                1020

Ala Val Ala Ala Gly Gln Arg Ile Ala Glu Val Glu Leu His Asn Ile
1025                1030                1035                1040

Pro Ile Ile Cys Asp Lys Pro Gly Phe Val His Tyr Glu Asp Leu Val
                1045                1050                1055

Glu Gly Val Ser Thr Glu Lys Val Thr Asn Lys Asn Thr Gly Leu Val
            1060                1065                1070

Glu Leu Ile Val Lys Gln His Arg Gly Glu Leu His Pro Gln Ile Ala
        1075                1080                1085

Ile Tyr Ala Asp Ala Asn Met Lys Glu Leu Val Gly Thr Tyr Ala Ile
    1090                1095                1100

Pro Ser Gly Ala Ile Ile Ser Val Glu Glu Gly Gln Arg Ile Ala Pro
1105                1110                1115                1120

Gly Met Leu Leu Ala Arg Leu Pro Arg Gly Ala Ile Lys Thr Lys Asp
                1125                1130                1135

Ile Thr Gly Gly Leu Pro Arg Val Ala Glu Leu Val Glu Ala Arg Lys
            1140                1145                1150

Pro Glu Asp Ala Ala Asp Ile Ala Lys Ile Asp Gly Val Val Asp Phe
        1155                1160                1165

Lys Gly Ile Gln Lys Asn Lys Arg Ile Leu Val Val Arg Asp Glu Ile
    1170                1175                1180

Thr Gly Met Glu Glu His Leu Ile Ser Leu Thr Lys His Leu Ile
1185                1190                1195                1200

Val Gln Arg Gly Asp Ser Val Ile Lys Gly Gln Gln Leu Thr Asp Gly
                1205                1210                1215

Leu Val Val Pro His Glu Ile Leu Glu Ile Cys Gly Val Arg Glu Leu
            1220                1225                1230

Gln Lys Tyr Leu Val Asn Glu Val Gln Glu Val Tyr Arg Leu Gln Gly
        1235                1240                1245

Val Asp Ile Asn Asp Lys His Val Glu Ile Ile Val Arg Gln Met Leu
    1250                1255                1260

Gln Lys Val Arg Ile Thr Asp Pro Gly Asp Thr Thr Leu Leu Phe Gly
1265                1270                1275                1280

Glu Asp Val Asp Lys Lys Glu Phe Tyr Glu Glu Asn Arg Arg Thr Glu
                1285                1290                1295

Glu Asp Gly Gly Lys Pro Ala Gln Ala Val Pro Val Leu Leu Gly Ile
            1300                1305                1310

Thr Lys Ala Ser Leu Gly Thr Glu Ser Phe Ile Ser Ala Ala Ser Phe
        1315                1320                1325

Gln Asp Thr Thr Arg Val Leu Thr Asp Ala Ala Cys Ser Ser Lys Thr
        1330                1335                1340

Asp Tyr Leu Leu Gly Phe Lys Glu Asn Val Ile Met Gly His Met Ile
1345                1350                1355                1360

Pro Gly Gly Thr Gly Phe Asp Thr His Lys Arg Ile Lys Gln His Leu
            1365                1370                1375

Glu Lys Glu Gln Glu Asp Leu Val Phe Asp Phe Asp Ser Glu Phe Glu
        1380                1385                1390

Ser Val Ala Gly
        1395

<210> SEQ ID NO 51
<211> LENGTH: 14
<212> TYPE: PRT
<213> ORGANISM: Chlamydia trachomatis

<400> SEQUENCE: 51

Gly Ala Pro Glu Val Trp Asp Val Leu Glu Glu Ile Ile Lys
1               5                   10

<210> SEQ ID NO 52
<211> LENGTH: 421
<212> TYPE: PRT
<213> ORGANISM: Chlamydia trachomatis

<400> SEQUENCE: 52

Met Thr Ala Ser Gly Gly Ala Gly Gly Leu Gly Ser Thr Gln Thr Val
1               5                   10                  15

Asp Val Ala Arg Ala Gln Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

-continued

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420

<210> SEQ ID NO 53
<211> LENGTH: 257
<212> TYPE: PRT
<213> ORGANISM: Chlamydia trachomatis

<400> SEQUENCE: 53

Met Cys Ile Lys Arg Lys Lys Thr Trp Ile Ala Phe Leu Ala Val Val
1               5                   10                  15

Cys Ser Phe Cys Leu Thr Gly Cys Lys Glu Gly Gly Asp Ser Asn
                20                  25                  30

Ser Glu Lys Phe Ile Val Gly Thr Asn Ala Thr Tyr Pro Pro Phe Glu
            35                  40                  45

Phe Val Asp Lys Arg Gly Glu Val Val Gly Phe Asp Ile Asp Leu Ala
        50                  55                  60

Arg Glu Ile Ser Asn Lys Leu Gly Lys Thr Leu Asp Val Arg Glu Phe
65                  70                  75                  80

Ser Phe Asp Ala Leu Ile Leu Asn Leu Lys Gln His Arg Ile Asp Ala
                85                  90                  95

Val Ile Thr Gly Met Ser Ile Thr Pro Ser Arg Leu Lys Glu Ile Leu
            100                 105                 110

Met Ile Pro Tyr Tyr Gly Glu Glu Ile Lys His Leu Val Leu Val Phe
        115                 120                 125

Lys Gly Glu Asn Lys His Pro Leu Pro Leu Thr Gln Tyr Arg Ser Val
    130                 135                 140

Ala Val Gln Thr Gly Thr Tyr Gln Glu Ala Tyr Leu Gln Ser Leu Ser
145                 150                 155                 160

```
Glu Val His Ile Arg Ser Phe Asp Ser Thr Leu Glu Val Leu Met Glu
                165                 170                 175

Val Met His Gly Lys Ser Pro Val Ala Val Leu Glu Pro Ser Ile Ala
            180                 185                 190

Gln Val Val Leu Lys Asp Phe Pro Ala Leu Ser Thr Ala Thr Ile Asp
        195                 200                 205

Leu Pro Glu Asp Gln Trp Val Leu Gly Tyr Gly Ile Gly Val Ala Ser
    210                 215                 220

Asp Arg Pro Ala Leu Ala Leu Lys Ile Glu Ala Ala Val Gln Glu Ile
225                 230                 235                 240

Arg Lys Glu Gly Val Leu Ala Glu Leu Gln Lys Trp Gly Leu Asn
                245                 250                 255

Asn

<210> SEQ ID NO 54
<211> LENGTH: 254
<212> TYPE: PRT
<213> ORGANISM: Chlamydia trachomatis

<400> SEQUENCE: 54

Met His Asp Ala Leu Gln Ser Ile Leu Ala Ile Gln Glu Leu Asp Ile
1               5                   10                  15

Lys Met Ile Arg Leu Met Arg Val Lys Lys Glu His Gln Asn Glu Leu
            20                  25                  30

Ala Lys Ile Gln Ala Leu Lys Thr Asp Ile Arg Arg Lys Val Glu Glu
        35                  40                  45

Lys Glu Gln Glu Met Glu Lys Leu Lys Asp Gln Ile Lys Gly Gly Glu
    50                  55                  60

Lys Arg Ile Gln Glu Ile Ser Asp Gln Ile Asn Lys Leu Glu Asn Gln
65                  70                  75                  80

Gln Ala Ala Val Lys Lys Met Asp Glu Phe Asn Ala Leu Thr Gln Glu
                85                  90                  95

Met Thr Ala Ala Asn Lys Glu Arg Arg Thr Leu Glu His Gln Leu Ser
            100                 105                 110

Asp Leu Met Asp Lys Gln Ala Gly Ser Glu Asp Leu Leu Ile Ser Leu
        115                 120                 125

Lys Glu Ser Leu Ser Ser Thr Glu Asn Ser Ser Ser Ala Ile Glu Glu
    130                 135                 140

Glu Ile Arg Glu Asn Ile Arg Lys Ile Asn Glu Glu Gly Arg Ser Leu
145                 150                 155                 160

Leu Ser Gln Arg Thr Gln Leu Lys Glu Thr Thr Asp Pro Glu Leu Phe
                165                 170                 175

Ser Ile Tyr Glu Arg Leu Leu Asn Asn Lys Lys Asp Arg Val Val Val
            180                 185                 190

Pro Ile Glu Asn Arg Val Cys Ser Gly Cys His Ile Ala Leu Thr Pro
        195                 200                 205

Gln His Glu Asn Leu Val Arg Lys Gln Asp His Leu Val Phe Cys Glu
    210                 215                 220

His Cys Ser Arg Ile Leu Tyr Trp Gln Glu Leu Gln Ser Pro Ser Ala
225                 230                 235                 240

Glu Gly Ala Thr Thr Lys Arg Arg Arg Arg Thr Ala Val
                245                 250

<210> SEQ ID NO 55
<211> LENGTH: 130
<212> TYPE: PRT
```

<213> ORGANISM: Chlamydia trachomatis

<400> SEQUENCE: 55

Met Thr Thr Glu Ser Leu Glu Thr Leu Val Glu Gln Leu Ser Gly Leu
1 5 10 15

Thr Val Leu Glu Leu Ser Gln Leu Lys Lys Leu Leu Glu Glu Lys Trp
20 25 30

Asp Val Thr Ala Ala Ala Pro Val Val Ala Val Ala Gly Ala Ala Ala
35 40 45

Ala Gly Asp Ala Pro Ala Ser Ala Glu Pro Thr Glu Phe Ala Val Ile
50 55 60

Leu Glu Asp Val Pro Ser Asp Lys Lys Ile Gly Val Leu Lys Val Val
65 70 75 80

Arg Glu Val Thr Gly Leu Ala Leu Lys Glu Ala Lys Glu Met Thr Glu
85 90 95

Gly Leu Pro Lys Thr Val Lys Glu Lys Thr Ser Lys Ser Asp Ala Glu
100 105 110

Asp Thr Val Lys Lys Leu Gln Glu Ala Gly Ala Lys Ala Val Ala Lys
115 120 125

Gly Leu
130

<210> SEQ ID NO 56
<211> LENGTH: 88
<212> TYPE: PRT
<213> ORGANISM: Chlamydia trachomatis

<400> SEQUENCE: 56

Met Lys Lys Thr Ala Leu Leu Ala Ala Leu Cys Ser Val Val Ser Leu
1 5 10 15

Ser Ser Cys Cys Arg Ile Val Asp Cys Cys Phe Glu Asp Pro Cys Ala
20 25 30

Pro Ile Gln Cys Ser Pro Cys Glu Ser Lys Lys Lys Asp Val Asp Gly
35 40 45

Gly Cys Asn Ser Cys Asn Gly Tyr Val Pro Ala Cys Lys Pro Cys Gly
50 55 60

Gly Asp Thr His Gln Asp Ala Lys His Gly Pro Gln Ala Arg Gly Ile
65 70 75 80

Pro Val Asp Gly Lys Cys Arg Gln
85

<210> SEQ ID NO 57
<211> LENGTH: 352
<212> TYPE: PRT
<213> ORGANISM: Chlamydia trachomatis

<400> SEQUENCE: 57

Met Pro Lys Ile Asp Thr Cys Asp Ser Cys Val Ser Asn Thr Glu Leu
1 5 10 15

Leu Ala Ile Arg Thr Arg Val Thr Gln Ser Tyr Asn Glu Ala Gln Thr
20 25 30

Ile Leu Ser Ser Ile Pro Asp Gly Ile Phe Leu Leu Ser Glu Ser Gly
35 40 45

Glu Ile Leu Ile Cys Asn Pro Gln Ala Arg Ala Ile Leu Gly Ile Pro
50 55 60

Glu Asp Ile Gln Leu Val Thr Arg Met Phe His Asp Phe Phe Pro Asp
65 70 75 80

```
Thr Phe Phe Gly Phe Ser Val Gln Glu Ala Leu Glu Lys Glu Val Pro
                85                  90                  95

Pro Lys Thr Ile Arg Leu Thr Leu Ser Gln Glu Leu Ser Gln Lys Glu
            100                 105                 110

Val Glu Val Phe Val Arg Lys Asn Ile Ser His Asp Phe Leu Phe Leu
        115                 120                 125

Leu Ile Arg Asp Arg Ser Asp Tyr Arg Gln Leu Glu Gln Ala Ile Glu
    130                 135                 140

Lys Tyr Arg Ser Ile Ser Glu Leu Gly Lys Ile Ala Ala Thr Leu Ala
145                 150                 155                 160

His Glu Ile Arg Asn Pro Leu Thr Ser Ile Ser Gly Phe Ala Thr Leu
                165                 170                 175

Leu Lys Glu Glu Leu Ser Ser Glu Arg His Gln Arg Met Leu Asn Val
            180                 185                 190

Ile Ile Glu Gly Thr Arg Ser Leu Asn Ser Leu Val Ser Ser Met Leu
        195                 200                 205

Glu Tyr Thr Lys Ile Gln Pro Leu Asn Leu Arg Ser Ile Asp Leu Gln
    210                 215                 220

Asp Phe Ser Ser Leu Ile Pro Glu Leu Ser Leu Thr Phe Pro Ser
225                 230                 235                 240

Cys Thr Phe Arg Arg Thr Ile Leu Ser Pro Ile Gln Arg Ser Ile Asp
                245                 250                 255

Pro Asp Arg Leu Arg Cys Val Ile Trp Asn Leu Val Lys Asn Ala Val
            260                 265                 270

Glu Ala Ser Asp Glu Glu Ile Phe Leu Glu Leu His Glu Lys Gly Phe
        275                 280                 285

Ser Val Ile Asn Thr Gly Thr Leu Pro Pro Asn Ile Gln Glu Lys Leu
    290                 295                 300

Phe Ile Pro Phe Phe Thr Thr Lys Pro Gln Gly Asn Gly Leu Gly Leu
305                 310                 315                 320

Ala Glu Ala His Lys Ile Met Arg Leu His Gly Gly Asp Leu Val Val
                325                 330                 335

Ser Thr Gln Asp Asn Arg Thr Thr Phe Thr Ile Leu Trp Thr Pro Ala
            340                 345                 350

<210> SEQ ID NO 58
<211> LENGTH: 318
<212> TYPE: PRT
<213> ORGANISM: Chlamydia trachomatis

<400> SEQUENCE: 58

Met Lys Val Ile Leu Arg Ala Leu Cys Leu Phe Leu Val Leu Pro Cys
1               5                   10                  15

Gly Cys Tyr Ala Arg Val Pro Ser Phe Glu Pro Phe Arg Gly Ala Ile
                20                  25                  30

Ala Pro Asn Arg Tyr Thr Pro Lys His Ser Pro Glu Leu Tyr Phe Glu
            35                  40                  45

Met Gly Asp Lys Tyr Phe Gln Ala Lys Lys Phe Lys Gln Ala Leu Leu
    50                  55                  60

Cys Phe Gly Met Ile Thr His His Phe Pro Glu His Ala Leu His Pro
65                  70                  75                  80

Lys Ala Gln Phe Leu Val Gly Leu Cys Tyr Leu Glu Met Gly His Pro
                85                  90                  95

Asp Leu Ala Asp Lys Ala Leu Thr Gln Tyr Gln Glu Leu Ala Asp Thr
            100                 105                 110
```

```
Glu Tyr Ser Glu Gln Leu Phe Ala Ile Lys Tyr Ser Ile Ala Gln Ser
            115                 120                 125

Phe Ala Asn Gly Lys Arg Lys Asn Ile Val Pro Leu Glu Gly Phe Pro
        130                 135                 140

Lys Leu Leu Lys Ala Asp Thr Asp Ala Leu Arg Ile Phe Glu Glu Ile
145                 150                 155                 160

Val Thr Ala Ser Ser Asp Ala Asp Leu Lys Ala Ser Ala Leu Tyr Ala
                165                 170                 175

Lys Gly Ala Leu Leu Phe Asp Arg Lys Glu Tyr Ser Glu Ala Ile Lys
            180                 185                 190

Thr Leu Lys Lys Val Ser Leu Gln Phe Pro Ser His Ser Leu Ser Pro
        195                 200                 205

Glu Ser Phe Thr Leu Ile Ala Lys Ile His Cys Leu Gln Ala Leu Gln
210                 215                 220

Glu Pro Tyr Asn Glu Gln Tyr Leu Gln Asp Ala Arg Met Asn Ala Ala
225                 230                 235                 240

Ala Leu Arg Lys Gln His Pro Asn His Pro Ser Asn Thr Glu Val Glu
                245                 250                 255

Asn Tyr Ile His His Met Cys Glu Ala Tyr Ala Ser Cys Leu Tyr Ser
            260                 265                 270

Thr Gly Arg Phe Tyr Glu Lys Lys Arg Lys Ala Ser Ser Ala Lys Ile
        275                 280                 285

Tyr Tyr Ser Ile Ala Leu Glu Asn Phe Pro Asp Thr Ser Tyr Val Ala
290                 295                 300

Lys Cys Asn Lys Arg Leu Glu Arg Leu Ser Lys Gln Met Ser
305                 310                 315

<210> SEQ ID NO 59
<211> LENGTH: 424
<212> TYPE: PRT
<213> ORGANISM: Chlamydia trachomatis

<400> SEQUENCE: 59

Met Phe Asp Val Val Ile Ser Asp Ile Glu Ala Arg Glu Ile Leu Asp
1               5                   10                  15

Ser Arg Gly Tyr Pro Thr Leu Cys Val Lys Val Ile Thr Asn Thr Gly
            20                  25                  30

Thr Phe Gly Glu Ala Cys Val Pro Ser Gly Ala Ser Thr Gly Ile Lys
        35                  40                  45

Glu Ala Leu Glu Leu Arg Asp Lys Asp Pro Lys Arg Tyr Gln Gly Lys
    50                  55                  60

Gly Val Leu Gln Ala Ile Ser Asn Val Glu Lys Val Leu Met Pro Ala
65                  70                  75                  80

Leu Gln Gly Phe Ser Val Phe Asp Gln Ile Thr Ala Asp Ala Ile Met
            85                  90                  95

Ile Asp Ala Asp Gly Thr Pro Asn Lys Glu Lys Leu Gly Ala Asn Ala
            100                 105                 110

Ile Leu Gly Val Ser Leu Ala Leu Ala Lys Ala Ala Asn Thr Leu
            115                 120                 125

Gln Arg Pro Leu Tyr Arg Tyr Leu Gly Gly Ser Phe Ser His Val Leu
        130                 135                 140

Pro Cys Pro Met Met Asn Leu Ile Asn Gly Gly Met His Ala Thr Asn
145                 150                 155                 160

Gly Leu Gln Phe Gln Glu Phe Met Ile Arg Pro Ile Ser Ala Pro Ser
                165                 170                 175
```

```
Leu Thr Glu Ala Val Arg Met Gly Ala Glu Val Phe Asn Ala Leu Lys
            180                 185                 190

Lys Ile Leu Gln Asn Arg Gln Leu Ala Thr Gly Val Gly Asp Glu Gly
        195                 200                 205

Gly Phe Ala Pro Asn Leu Ala Ser Asn Ala Glu Ala Leu Asp Leu Leu
        210                 215                 220

Leu Thr Ala Ile Glu Thr Ala Gly Phe Thr Pro Arg Glu Asp Ile Ser
225                 230                 235                 240

Leu Ala Leu Asp Cys Ala Ala Ser Ser Phe Tyr Asn Thr Gln Asp Lys
                245                 250                 255

Thr Tyr Asp Gly Lys Ser Tyr Ala Asp Gln Val Gly Ile Leu Ala Glu
            260                 265                 270

Leu Cys Glu His Tyr Pro Ile Asp Ser Ile Glu Asp Gly Leu Ala Glu
        275                 280                 285

Glu Asp Phe Glu Gly Trp Lys Leu Leu Ser Glu Thr Leu Gly Asp Arg
        290                 295                 300

Val Gln Leu Val Gly Asp Asp Leu Phe Val Thr Asn Ser Ala Leu Ile
305                 310                 315                 320

Ala Glu Gly Ile Ala Gln Gly Leu Ala Asn Ala Val Leu Ile Lys Pro
                325                 330                 335

Asn Gln Ile Gly Thr Leu Thr Glu Thr Ala Glu Ala Ile Arg Leu Ala
            340                 345                 350

Thr Ile Gln Gly Tyr Ala Thr Ile Leu Ser His Arg Ser Gly Glu Thr
        355                 360                 365

Glu Asp Thr Thr Ile Ala Asp Leu Ala Val Ala Phe Asn Thr Gly Gln
        370                 375                 380

Ile Lys Thr Gly Ser Leu Ser Arg Ser Glu Arg Ile Ala Lys Tyr Asn
385                 390                 395                 400

Arg Leu Met Ala Ile Glu Glu Glu Met Gly Pro Glu Ala Leu Phe Gln
                405                 410                 415

Asp Ser Asn Pro Phe Ser Lys Ala
            420

<210> SEQ ID NO 60
<211> LENGTH: 352
<212> TYPE: PRT
<213> ORGANISM: Chlamydia trachomatis

<400> SEQUENCE: 60

Met Lys Lys Ile Asn Lys Ile Val Leu Ala Val Gly Gly Thr Gly Gly
1               5                   10                  15

His Ile Ile Pro Ala Leu Ala Ala Arg Glu Thr Phe Ile His Glu Asp
            20                  25                  30

Ile Glu Val Leu Leu Leu Gly Lys Gly Leu Ala His Phe Leu Gly Asp
        35                  40                  45

Asp Ser Glu Val Ala Tyr Cys Asp Ile Pro Ser Gly Ser Pro Phe Ser
    50                  55                  60

Leu Arg Val Asn Arg Met Phe Ser Gly Ala Lys Gln Leu Tyr Lys Gly
65                  70                  75                  80

Tyr Val Ala Ala Leu Gln Lys Ile Arg Asp Phe Thr Pro Asp Leu Ala
                85                  90                  95

Ile Gly Phe Gly Ser Tyr His Ser Leu Pro Ala Met Leu Ala Ser Ile
            100                 105                 110

Arg Ser Arg Ile Pro Leu Phe Leu His Glu Gln Asn Ile Val Pro Gly
        115                 120                 125
```

-continued

```
Lys Val Asn Lys Leu Phe Ser Arg Phe Ala Lys Gly Val Gly Met Ser
            130                 135                 140

Phe Ala Ala Ala Gly Glu His Phe His Cys Arg Ala Glu Glu Val Phe
145                 150                 155                 160

Leu Pro Ile Arg Lys Leu Ser Glu Gln Ile Val Phe Pro Gly Ala Ser
                165                 170                 175

Pro Val Ile Cys Val Val Gly Ser Gln Gly Ala Lys Ile Leu Asn
                180                 185                 190

Asp Val Val Pro Lys Ala Leu Ala Arg Ile Arg Glu Ser Tyr Ser Asn
                195                 200                 205

Leu Tyr Val His His Ile Val Gly Pro Lys Gly Asp Leu Gln Ala Val
            210                 215                 220

Ser Gln Val Tyr Gln Asp Ala Gly Ile Asn His Thr Val Thr Ala Phe
225                 230                 235                 240

Asp His Asn Met Leu Gly Val Leu Gln Ala Ser Asp Leu Val Ile Ser
                245                 250                 255

Arg Ser Gly Ala Thr Met Leu Asn Glu Leu Leu Trp Val Gln Val Pro
                260                 265                 270

Ala Ile Leu Ile Pro Tyr Pro Gly Ala Tyr Gly His Gln Glu Val Asn
            275                 280                 285

Ala Lys Phe Phe Thr His Thr Val Gly Gly Gly Thr Met Ile Leu Gln
        290                 295                 300

Lys Tyr Leu Thr Glu Glu Ser Leu Ser Lys Gln Val Leu Leu Ala Leu
305                 310                 315                 320

Asp Pro Ala Thr Ser Glu Asn Arg Arg Lys Ala Met Leu Ser Ala Gln
                325                 330                 335

Gln Lys Lys Ser Phe Lys Ser Leu Tyr Gln Phe Ile Cys Glu Ser Leu
                340                 345                 350

<210> SEQ ID NO 61
<211> LENGTH: 264
<212> TYPE: PRT
<213> ORGANISM: Chlamydia trachomatis

<400> SEQUENCE: 61

Met Gly Asn Ser Gly Phe Tyr Leu Tyr Asn Thr Gln Asn Cys Val Phe
1               5                   10                  15

Ala Asp Asn Ile Lys Val Gly Gln Met Thr Glu Pro Leu Lys Asp Gln
                20                  25                  30

Gln Ile Ile Leu Gly Thr Thr Ser Thr Pro Val Ala Ala Lys Met Thr
            35                  40                  45

Ala Ser Asp Gly Ile Ser Leu Thr Val Ser Asn Asn Pro Ser Thr Asn
50                  55                  60

Ala Ser Ile Thr Ile Gly Leu Asp Ala Glu Lys Ala Tyr Gln Leu Ile
65                  70                  75                  80

Leu Glu Lys Leu Gly Asp Gln Ile Leu Gly Ile Ala Asp Thr Ile
                85                  90                  95

Val Asp Ser Thr Val Gln Asp Ile Leu Asp Lys Ile Thr Thr Asp Pro
            100                 105                 110

Ser Leu Gly Leu Leu Lys Ala Phe Asn Asn Phe Pro Ile Thr Asn Lys
        115                 120                 125

Ile Gln Cys Asn Gly Leu Phe Thr Pro Arg Asn Ile Glu Thr Leu Leu
    130                 135                 140

Gly Gly Thr Glu Ile Gly Lys Phe Thr Val Thr Pro Lys Ser Ser Gly
145                 150                 155                 160
```

```
Ser Met Phe Leu Val Ser Ala Asp Ile Ile Ala Ser Arg Met Glu Gly
                165                 170                 175

Gly Val Val Leu Ala Leu Val Arg Glu Gly Asp Ser Lys Pro Tyr Ala
            180                 185                 190

Ile Ser Tyr Gly Tyr Ser Ser Gly Val Pro Asn Leu Cys Ser Leu Arg
        195                 200                 205

Thr Arg Ile Ile Asn Thr Gly Leu Thr Pro Thr Tyr Ser Leu Arg
    210                 215                 220

Val Gly Gly Leu Glu Ser Gly Val Val Trp Val Asn Ala Leu Ser Asn
225                 230                 235                 240

Gly Asn Asp Ile Leu Gly Ile Thr Asn Thr Ser Asn Val Ser Phe Leu
                245                 250                 255

Glu Val Ile Pro Gln Thr Asn Ala
                260

<210> SEQ ID NO 62
<211> LENGTH: 975
<212> TYPE: PRT
<213> ORGANISM: Chlamydia trachomatis

<400> SEQUENCE: 62

Met Asn Arg Val Ile Glu Ile His Ala His Tyr Asp Gln Arg Gln Leu
1               5                   10                  15

Ser Gln Ser Pro Asn Thr Asn Phe Leu Val His Pro Tyr Leu Thr
            20                  25                  30

Leu Ile Pro Lys Phe Leu Leu Gly Ala Leu Ile Val Tyr Ala Pro Tyr
        35                  40                  45

Ser Phe Ala Glu Met Glu Leu Ala Ile Ser Gly His Lys Gln Gly Lys
    50                  55                  60

Asp Arg Asp Thr Phe Thr Met Ile Ser Ser Cys Pro Glu Gly Thr Asn
65                  70                  75                  80

Tyr Ile Ile Asn Arg Lys Leu Ile Leu Ser Asp Phe Ser Leu Leu Asn
                85                  90                  95

Lys Val Ser Ser Gly Gly Ala Phe Arg Asn Leu Ala Gly Lys Ile Ser
            100                 105                 110

Phe Leu Gly Lys Asn Ser Ser Ala Ser Ile His Phe Lys His Ile Asn
        115                 120                 125

Ile Asn Gly Phe Gly Ala Gly Val Phe Ser Glu Ser Ser Ile Glu Phe
    130                 135                 140

Thr Asp Leu Arg Lys Leu Val Ala Phe Gly Ser Glu Ser Thr Gly Gly
145                 150                 155                 160

Ile Phe Thr Ala Lys Glu Asp Ile Ser Phe Lys Asn Asn His His Ile
                165                 170                 175

Ala Phe Arg Asn Asn Ile Thr Lys Gly Asn Gly Val Ile Gln Leu
            180                 185                 190

Gln Gly Asp Met Lys Gly Ser Val Ser Phe Val Asp Gln Arg Gly Ala
        195                 200                 205

Ile Ile Phe Thr Asn Asn Gln Ala Val Thr Ser Ser Ser Met Lys His
    210                 215                 220

Ser Gly Arg Gly Gly Ala Ile Ser Gly Asp Phe Ala Gly Ser Arg Ile
225                 230                 235                 240

Leu Phe Leu Asn Asn Gln Gln Ile Thr Phe Glu Gly Asn Ser Ala Val
                245                 250                 255

His Gly Gly Ala Ile Tyr Asn Lys Asn Gly Leu Val Glu Phe Leu Gly
            260                 265                 270
```

-continued

```
Asn Ala Gly Pro Leu Ala Phe Lys Glu Asn Thr Thr Ile Ala Asn Gly
        275                 280                 285

Gly Ala Ile Tyr Thr Ser Asn Phe Lys Ala Asn Gln Gln Thr Ser Pro
    290                 295                 300

Ile Leu Phe Ser Gln Asn His Ala Asn Lys Lys Gly Ala Ile Tyr
305                 310                 315                 320

Ala Gln Tyr Val Asn Leu Glu Gln Asn Gln Asp Thr Ile Arg Phe Glu
                325                 330                 335

Lys Asn Thr Ala Lys Glu Gly Gly Ala Ile Thr Ser Ser Gln Cys
                340                 345                 350

Ser Ile Thr Ala His Asn Thr Ile Ile Phe Ser Asp Asn Ala Ala Gly
            355                 360                 365

Asp Leu Gly Gly Gly Ala Ile Leu Leu Glu Gly Lys Lys Pro Ser Leu
    370                 375                 380

Thr Leu Ile Ala His Ser Gly Asn Ile Ala Phe Ser Gly Asn Thr Met
385                 390                 395                 400

Leu His Ile Thr Lys Lys Ala Ser Leu Asp Arg His Asn Ser Ile Leu
                405                 410                 415

Ile Lys Glu Ala Pro Tyr Lys Ile Gln Leu Ala Ala Asn Lys Asn His
                420                 425                 430

Ser Ile His Phe Phe Asp Pro Val Met Ala Leu Ser Ala Ser Ser Ser
            435                 440                 445

Pro Ile Gln Ile Asn Ala Pro Glu Tyr Glu Thr Pro Phe Phe Ser Pro
450                 455                 460

Lys Gly Met Ile Val Phe Ser Gly Ala Asn Leu Leu Asp Asp Ala Arg
465                 470                 475                 480

Glu Asp Val Ala Asn Arg Thr Ser Ile Phe Asn Gln Pro Val His Leu
                485                 490                 495

Tyr Asn Gly Thr Leu Ser Ile Glu Asn Gly Ala His Leu Ile Val Gln
                500                 505                 510

Ser Phe Lys Gln Thr Gly Gly Arg Ile Ser Leu Ser Pro Gly Ser Ser
        515                 520                 525

Leu Ala Leu Tyr Thr Met Asn Ser Phe His Gly Asn Ile Ser Ser
    530                 535                 540

Lys Glu Pro Leu Glu Ile Asn Gly Leu Ser Phe Gly Val Asp Ile Ser
545                 550                 555                 560

Pro Ser Asn Leu Gln Ala Glu Ile Arg Ala Gly Asn Ala Pro Leu Arg
                565                 570                 575

Leu Ser Gly Ser Pro Ser Ile His Asp Pro Glu Gly Leu Phe Tyr Glu
            580                 585                 590

Asn Arg Asp Thr Ala Ala Ser Pro Tyr Gln Met Glu Ile Leu Leu Thr
        595                 600                 605

Ser Asp Lys Ile Val Asp Ile Ser Lys Phe Thr Thr Asp Ser Leu Val
    610                 615                 620

Thr Asn Lys Gln Ser Gly Phe Gln Gly Ala Trp His Phe Ser Trp Gln
625                 630                 635                 640

Pro Asn Thr Ile Asn Asn Thr Lys Gln Lys Ile Leu Arg Ala Ser Trp
                645                 650                 655

Leu Pro Thr Gly Glu Tyr Val Leu Glu Ser Asn Arg Val Gly Arg Ala
            660                 665                 670

Val Pro Asn Ser Leu Trp Ser Thr Phe Leu Leu Gln Thr Ala Ser
        675                 680                 685

His Asn Leu Gly Asp His Leu Cys Asn Asn Arg Ser Leu Ile Pro Thr
    690                 695                 700
```

```
Ser Tyr Phe Gly Val Leu Ile Gly Gly Thr Gly Ala Glu Met Ser Thr
705                 710                 715                 720

His Ser Ser Glu Glu Glu Ser Phe Ile Ser Arg Leu Gly Ala Thr Gly
                725                 730                 735

Thr Ser Ile Ile Arg Leu Thr Pro Ser Leu Thr Leu Ser Gly Gly Gly
            740                 745                 750

Ser His Met Phe Gly Asp Ser Phe Val Ala Asp Leu Pro Glu His Ile
        755                 760                 765

Thr Ser Glu Gly Ile Val Gln Asn Val Gly Leu Thr His Val Trp Gly
    770                 775                 780

Pro Leu Thr Val Asn Ser Thr Leu Cys Ala Ala Leu Asp His Asn Ala
785                 790                 795                 800

Met Val Arg Ile Cys Ser Lys Lys Asp His Thr Tyr Gly Lys Trp Asp
                805                 810                 815

Thr Phe Gly Met Arg Gly Thr Leu Gly Ala Ser Tyr Thr Phe Leu Glu
            820                 825                 830

Tyr Asp Gln Thr Met Arg Val Phe Ser Phe Ala Asn Ile Glu Ala Thr
        835                 840                 845

Asn Ile Leu Gln Arg Ala Phe Thr Glu Thr Gly Tyr Asn Pro Arg Ser
    850                 855                 860

Phe Ser Lys Thr Lys Leu Leu Asn Ile Ala Ile Pro Ile Gly Ile Gly
865                 870                 875                 880

Tyr Glu Phe Cys Leu Gly Asn Ser Ser Phe Ala Leu Leu Gly Lys Gly
                885                 890                 895

Ser Ile Gly Tyr Ser Arg Asp Ile Lys Arg Glu Asn Pro Ser Thr Leu
            900                 905                 910

Ala His Leu Ala Met Asn Asp Phe Ala Trp Thr Thr Asn Gly Cys Ser
        915                 920                 925

Val Pro Thr Ser Ala His Thr Leu Ala Asn Gln Leu Ile Leu Arg Tyr
    930                 935                 940

Lys Ala Cys Ser Leu Tyr Ile Thr Ala Tyr Thr Ile Asn Arg Glu Gly
945                 950                 955                 960

Lys Asn Leu Ser Asn Ser Leu Ser Cys Gly Gly Tyr Val Gly Phe
                965                 970                 975

<210> SEQ ID NO 63
<211> LENGTH: 1751
<212> TYPE: PRT
<213> ORGANISM: Chlamydia trachomatis

<400> SEQUENCE: 63

Met Lys Trp Leu Ser Ala Thr Ala Val Phe Ala Val Leu Pro Ser
1               5                   10                  15

Val Ser Gly Phe Cys Phe Pro Glu Pro Lys Glu Leu Asn Phe Ser Arg
                20                  25                  30

Val Gly Thr Ser Ser Thr Thr Phe Thr Glu Thr Val Gly Glu Ala
            35                  40                  45

Gly Ala Glu Tyr Ile Val Ser Gly Asn Ala Ser Phe Thr Lys Phe Thr
        50                  55                  60

Asn Ile Pro Thr Thr Asp Thr Thr Thr Pro Thr Asn Ser Asn Ser Ser
65                  70                  75                  80

Ser Ser Asn Gly Glu Thr Ala Ser Val Ser Glu Asp Ser Asp Ser Thr
                85                  90                  95

Thr Thr Thr Pro Asp Pro Lys Gly Gly Gly Ala Phe Tyr Asn Ala His
            100                 105                 110
```

Ser Gly Val Leu Ser Phe Met Thr Arg Ser Gly Thr Glu Gly Ser Leu
        115                 120                 125

Thr Leu Ser Glu Ile Lys Ile Thr Gly Glu Gly Ala Ile Phe Ser
130                 135                 140

Gln Gly Glu Leu Leu Phe Thr Asp Leu Thr Gly Leu Thr Ile Gln Asn
145                 150                 155                 160

Asn Leu Ser Gln Leu Ser Gly Gly Ala Ile Phe Gly Glu Ser Thr Ile
                165                 170                 175

Ser Leu Ser Gly Ile Thr Lys Ala Thr Phe Ser Ser Asn Ser Ala Glu
                180                 185                 190

Val Pro Ala Pro Val Lys Lys Pro Thr Glu Pro Lys Ala Gln Thr Ala
            195                 200                 205

Ser Glu Thr Ser Gly Ser Ser Ser Ser Gly Asn Asp Ser Val Ser
        210                 215                 220

Ser Pro Ser Ser Ser Arg Ala Glu Pro Ala Ala Ala Asn Leu Gln Ser
225                 230                 235                 240

His Phe Ile Cys Ala Thr Ala Thr Pro Ala Ala Gln Thr Asp Thr Glu
                245                 250                 255

Thr Ser Thr Pro Ser His Lys Pro Gly Ser Gly Ala Ile Tyr Ala
            260                 265                 270

Lys Gly Asp Leu Thr Ile Ala Asp Ser Gln Glu Val Leu Phe Ser Ile
            275                 280                 285

Asn Lys Ala Thr Lys Asp Gly Gly Ala Ile Phe Ala Glu Lys Asp Val
290                 295                 300

Ser Phe Glu Asn Ile Thr Ser Leu Lys Val Gln Thr Asn Gly Ala Glu
305                 310                 315                 320

Glu Lys Gly Gly Ala Ile Tyr Ala Lys Gly Asp Leu Ser Ile Gln Ser
                325                 330                 335

Ser Lys Gln Ser Leu Phe Asn Ser Asn Tyr Ser Lys Gln Gly Gly Gly
                340                 345                 350

Ala Leu Tyr Val Glu Gly Asp Ile Asn Phe Gln Asp Leu Glu Glu Ile
            355                 360                 365

Arg Ile Lys Tyr Asn Lys Ala Gly Thr Phe Glu Thr Lys Lys Ile Thr
            370                 375                 380

Leu Pro Lys Ala Gln Ala Ser Ala Gly Asn Ala Asp Ala Trp Ala Ser
385                 390                 395                 400

Ser Ser Pro Gln Ser Gly Ser Gly Ala Thr Thr Val Ser Asn Ser Gly
                405                 410                 415

Asp Ser Ser Ser Gly Ser Asp Ser Asp Thr Ser Glu Thr Val Pro Ala
            420                 425                 430

Thr Ala Lys Gly Gly Gly Leu Tyr Thr Asp Lys Asn Leu Ser Ile Thr
            435                 440                 445

Asn Ile Thr Gly Ile Ile Glu Ile Ala Asn Asn Lys Ala Thr Asp Val
450                 455                 460

Gly Gly Gly Ala Tyr Val Lys Gly Thr Leu Thr Cys Glu Asn Ser His
465                 470                 475                 480

Arg Leu Gln Phe Leu Lys Asn Ser Ser Asp Lys Gln Gly Gly Gly Ile
                485                 490                 495

Tyr Gly Glu Asp Asn Ile Thr Leu Ser Asn Leu Thr Lys Thr Leu
            500                 505                 510

Phe Gln Glu Asn Thr Ala Lys Glu Glu Gly Gly Gly Leu Phe Ile Lys
            515                 520                 525

Gly Thr Asp Lys Ala Leu Thr Met Thr Gly Leu Asp Ser Phe Cys Leu

-continued

```
               530                 535                 540
Ile Asn Asn Thr Ser Glu Lys His Gly Gly Gly Ala Phe Val Thr Lys
545                 550                 555                 560

Glu Ile Ser Gln Thr Tyr Thr Ser Asp Val Glu Thr Ile Pro Gly Ile
                565                 570                 575

Thr Pro Val His Gly Glu Thr Val Ile Thr Gly Asn Lys Ser Thr Gly
                580                 585                 590

Gly Asn Gly Gly Gly Val Cys Thr Lys Arg Leu Ala Leu Ser Asn Leu
                595                 600                 605

Gln Ser Ile Ser Ile Ser Gly Asn Ser Ala Ala Glu Asn Gly Gly Gly
610                 615                 620

Ala His Thr Cys Pro Asp Ser Phe Pro Thr Ala Asp Thr Ala Glu Gln
625                 630                 635                 640

Pro Ala Ala Ala Ser Ala Ala Thr Ser Thr Pro Glu Ser Ala Pro Val
                645                 650                 655

Val Ser Thr Ala Leu Ser Thr Pro Ser Ser Ser Thr Val Ser Ser Leu
                660                 665                 670

Thr Leu Leu Ala Ala Ser Ser Gln Ala Ser Pro Ala Thr Ser Asn Lys
                675                 680                 685

Glu Thr Gln Asp Pro Asn Ala Asp Thr Asp Leu Leu Ile Asp Tyr Val
690                 695                 700

Val Asp Thr Thr Ile Ser Lys Asn Thr Ala Lys Gly Gly Gly Ile
705                 710                 715                 720

Tyr Ala Lys Lys Ala Lys Met Ser Arg Ile Asp Gln Leu Asn Ile Ser
                725                 730                 735

Glu Asn Ser Ala Thr Glu Ile Gly Gly Gly Ile Cys Cys Lys Glu Ser
                740                 745                 750

Leu Glu Leu Asp Ala Leu Val Ser Leu Ser Val Thr Glu Asn Leu Val
                755                 760                 765

Gly Lys Glu Gly Gly Gly Leu His Ala Lys Thr Val Asn Ile Ser Asn
                770                 775                 780

Leu Lys Ser Gly Phe Ser Phe Ser Asn Asn Lys Ala Asn Ser Ser Ser
785                 790                 795                 800

Thr Gly Val Ala Thr Thr Ala Ser Ala Pro Ala Ala Ala Ala Ser
                805                 810                 815

Leu Gln Ala Ala Ala Ala Val Pro Ser Ser Pro Ala Thr Pro Thr
                820                 825                 830

Tyr Ser Gly Val Val Gly Gly Ala Ile Tyr Gly Glu Lys Val Thr Phe
                835                 840                 845

Ser Gln Cys Ser Gly Thr Cys Gln Phe Ser Gly Asn Gln Ala Ile Asp
850                 855                 860

Asn Asn Pro Ser Gln Ser Ser Leu Asn Val Gln Gly Gly Ala Ile Tyr
865                 870                 875                 880

Ala Lys Thr Ser Leu Ser Ile Gly Ser Ser Asp Ala Gly Thr Ser Tyr
                885                 890                 895

Ile Phe Ser Gly Asn Ser Val Ser Thr Gly Lys Ser Gln Thr Thr Gly
                900                 905                 910

Gln Ile Ala Gly Gly Ala Ile Tyr Ser Pro Thr Val Thr Leu Asn Cys
                915                 920                 925

Pro Ala Thr Phe Ser Asn Asn Thr Ala Ser Met Ala Thr Pro Lys Thr
                930                 935                 940

Ser Ser Glu Asp Gly Ser Ser Gly Asn Ser Ile Lys Asp Thr Ile Gly
945                 950                 955                 960
```

```
Gly Ala Ile Ala Gly Thr Ala Ile Thr Leu Ser Gly Val Ser Arg Phe
                965                 970                 975

Ser Gly Asn Thr Ala Asp Leu Gly Ala Ala Ile Gly Thr Leu Ala Asn
            980                 985                 990

Ala Asn Thr Pro Ser Ala Thr Ser Gly Ser Gln Asn Ser Ile Thr Glu
        995                 1000                1005

Lys Ile Thr Leu Glu Asn Gly Ser Phe Ile Phe Glu Arg Asn Gln Ala
    1010                1015                1020

Asn Lys Arg Gly Ala Ile Tyr Ser Pro Ser Val Ser Ile Lys Gly Asn
1025                1030                1035                1040

Asn Ile Thr Phe Asn Gln Asn Thr Ser Thr His Asp Gly Ser Ala Ile
                1045                1050                1055

Tyr Phe Thr Lys Asp Ala Thr Ile Glu Ser Leu Gly Ser Val Leu Phe
            1060                1065                1070

Thr Gly Asn Asn Val Thr Ala Thr Gln Ala Ser Ser Ala Thr Ser Gly
        1075                1080                1085

Gln Asn Thr Asn Thr Ala Asn Tyr Gly Ala Ala Ile Phe Gly Asp Pro
    1090                1095                1100

Gly Thr Thr Gln Ser Ser Gln Thr Asp Ala Ile Leu Thr Leu Leu Ala
1105                1110                1115                1120

Ser Ser Gly Asn Ile Thr Phe Ser Asn Asn Ser Leu Gln Asn Asn Gln
                1125                1130                1135

Gly Asp Thr Pro Ala Ser Lys Phe Cys Ser Ile Ala Gly Tyr Val Lys
            1140                1145                1150

Leu Ser Leu Gln Ala Ala Lys Gly Lys Thr Ile Ser Phe Phe Asp Cys
        1155                1160                1165

Val His Thr Ser Thr Lys Lys Ile Gly Ser Thr Gln Asn Val Tyr Glu
    1170                1175                1180

Thr Leu Asp Ile Asn Lys Glu Glu Asn Ser Asn Pro Tyr Thr Gly Thr
1185                1190                1195                1200

Ile Val Phe Ser Ser Glu Leu His Glu Asn Lys Ser Tyr Ile Pro Gln
                1205                1210                1215

Asn Ala Ile Leu His Asn Gly Thr Leu Val Leu Lys Glu Lys Thr Glu
            1220                1225                1230

Leu His Val Val Ser Phe Glu Gln Lys Glu Gly Ser Lys Leu Ile Met
        1235                1240                1245

Lys Pro Gly Ala Val Leu Ser Asn Gln Asn Ile Ala Asn Gly Ala Leu
    1250                1255                1260

Val Ile Asn Gly Leu Thr Ile Asp Leu Ser Ser Met Gly Thr Pro Gln
1265                1270                1275                1280

Ala Gly Glu Ile Phe Ser Pro Pro Glu Leu Arg Ile Val Ala Thr Thr
                1285                1290                1295

Ser Ser Ala Ser Gly Gly Ser Gly Val Ser Ser Ile Pro Thr Asn
            1300                1305                1310

Pro Lys Arg Ile Ser Ala Ala Ala Pro Ser Gly Ser Ala Ala Thr Thr
        1315                1320                1325

Pro Thr Met Ser Glu Asn Lys Val Phe Leu Thr Gly Asp Leu Thr Leu
    1330                1335                1340

Ile Asp Pro Asn Gly Asn Phe Tyr Gln Asn Pro Met Leu Gly Ser Asp
1345                1350                1355                1360

Leu Asp Val Pro Leu Ile Lys Leu Pro Thr Asn Thr Ser Asp Val Gln
                1365                1370                1375

Val Tyr Asp Leu Thr Leu Ser Gly Asp Leu Phe Pro Gln Lys Gly Tyr
            1380                1385                1390
```

```
Met Gly Thr Trp Thr Leu Asp Ser Asn Pro Gln Thr Gly Lys Leu Gln
        1395                1400                1405
Ala Arg Trp Thr Phe Asp Thr Tyr Arg Arg Trp Val Tyr Ile Pro Arg
    1410                1415                1420
Asp Asn His Phe Tyr Ala Asn Ser Ile Leu Gly Ser Gln Asn Ser Met
1425                1430                1435                1440
Ile Val Val Lys Gln Gly Leu Ile Asn Asn Met Leu Asn Asn Ala Arg
            1445                1450                1455
Phe Asp Asp Ile Ala Tyr Asn Asn Phe Trp Val Ser Gly Val Gly Thr
        1460                1465                1470
Phe Leu Ala Gln Gln Gly Thr Pro Leu Ser Glu Glu Phe Ser Tyr Tyr
    1475                1480                1485
Ser Arg Gly Thr Ser Val Ala Ile Asp Ala Lys Pro Arg Gln Asp Phe
        1490                1495                1500
Ile Leu Gly Ala Ala Phe Ser Lys Met Val Gly Lys Thr Lys Ala Ile
1505                1510                1515                1520
Lys Lys Met His Asn Tyr Phe His Lys Gly Ser Glu Tyr Ser Tyr Gln
            1525                1530                1535
Ala Ser Val Tyr Gly Gly Lys Phe Leu Tyr Phe Leu Leu Asn Lys Gln
        1540                1545                1550
His Gly Trp Ala Leu Pro Phe Leu Ile Gln Gly Val Val Ser Tyr Gly
    1555                1560                1565
His Ile Lys His Asp Thr Thr Thr Leu Tyr Pro Ser Ile His Glu Arg
        1570                1575                1580
Asn Lys Gly Asp Trp Glu Asp Leu Gly Trp Leu Ala Asp Leu Arg Ile
1585                1590                1595                1600
Ser Met Asp Leu Lys Glu Pro Ser Lys Asp Ser Ser Lys Arg Ile Thr
            1605                1610                1615
Val Tyr Gly Glu Leu Glu Tyr Ser Ser Ile Arg Gln Lys Gln Phe Thr
        1620                1625                1630
Glu Ile Asp Tyr Asp Pro Arg His Phe Asp Asp Cys Ala Tyr Arg Asn
    1635                1640                1645
Leu Ser Leu Pro Val Gly Cys Ala Val Glu Gly Ala Ile Met Asn Cys
        1650                1655                1660
Asn Ile Leu Met Tyr Asn Lys Leu Ala Leu Ala Tyr Met Pro Ser Ile
1665                1670                1675                1680
Tyr Arg Asn Asn Pro Val Cys Lys Tyr Arg Val Leu Ser Ser Asn Glu
            1685                1690                1695
Ala Gly Gln Val Ile Cys Gly Val Pro Thr Arg Thr Ser Ala Arg Ala
        1700                1705                1710
Glu Tyr Ser Thr Gln Leu Tyr Leu Gly Pro Phe Trp Thr Leu Tyr Gly
    1715                1720                1725
Asn Tyr Thr Ile Asp Val Gly Met Tyr Thr Leu Ser Gln Met Thr Ser
        1730                1735                1740
Cys Gly Ala Arg Met Ile Phe
1745                1750

<210> SEQ ID NO 64
<211> LENGTH: 1770
<212> TYPE: PRT
<213> ORGANISM: Chlamydia trachomatis

<400> SEQUENCE: 64

Met Lys Phe Met Ser Ala Thr Ala Val Phe Ala Ala Ala Leu Ser Ser
1               5                   10                  15
```

Val Thr Glu Ala Ser Ser Ile Gln Asp Gln Ile Lys Asn Thr Asp Cys
            20                  25                  30

Asn Val Ser Lys Leu Gly Tyr Ser Thr Ser Gln Ala Phe Thr Asp Met
            35                  40                  45

Met Leu Ala Asp Asn Thr Glu Tyr Arg Ala Ala Asp Ser Val Ser Phe
    50                  55                  60

Tyr Asp Phe Ser Thr Ser Ser Arg Leu Pro Arg Lys His Leu Ser Ser
65                  70                  75                  80

Ser Ser Glu Ala Ser Pro Thr Thr Glu Gly Val Ser Ser Ser Ser Ser
                85                  90                  95

Gly Glu Thr Asp Glu Lys Thr Glu Glu Leu Asp Asn Gly Gly Ile
            100                 105                 110

Ile Tyr Ala Arg Glu Lys Leu Thr Ile Ser Glu Ser Gln Asp Ser Leu
            115                 120                 125

Ser Asn Gln Ser Ile Glu Leu His Asp Asn Ser Ile Phe Phe Gly Glu
    130                 135                 140

Gly Glu Val Ile Phe Asp His Arg Val Ala Leu Lys Asn Gly Gly Ala
145                 150                 155                 160

Ile Tyr Gly Glu Lys Glu Val Val Phe Glu Asn Ile Lys Ser Leu Leu
            165                 170                 175

Val Glu Val Asn Ile Ala Val Glu Lys Gly Gly Ser Val Tyr Ala Lys
            180                 185                 190

Glu Arg Val Ser Leu Glu Asn Val Thr Glu Ala Thr Phe Ser Ser Asn
            195                 200                 205

Gly Gly Glu Gln Gly Gly Gly Ile Tyr Ser Glu Gln Asp Met Leu
            210                 215                 220

Ile Ser Asp Cys Asn Asn Val His Phe Gln Gly Asn Ala Ala Gly Ala
225                 230                 235                 240

Thr Ala Val Lys Gln Cys Leu Asp Glu Glu Met Ile Val Leu Leu Ala
            245                 250                 255

Glu Cys Val Asp Ser Leu Ser Glu Asp Thr Leu Asp Ser Thr Pro Glu
            260                 265                 270

Thr Glu Gln Thr Glu Ser Asn Gly Asn Gln Asp Gly Ser Ser Glu Thr
            275                 280                 285

Glu Asp Thr Gln Val Ser Glu Ser Pro Glu Ser Thr Pro Ser Pro Asp
290                 295                 300

Asp Val Leu Gly Lys Gly Gly Ile Tyr Thr Glu Lys Ser Leu Thr
305                 310                 315                 320

Ile Thr Gly Ile Thr Gly Thr Ile Asp Phe Val Ser Asn Ile Ala Thr
            325                 330                 335

Asp Ser Gly Ala Gly Val Phe Thr Lys Glu Asn Leu Ser Cys Thr Asn
            340                 345                 350

Thr Asn Ser Leu Gln Phe Leu Lys Asn Ser Ala Gly Gln His Gly Gly
            355                 360                 365

Gly Ala Tyr Val Thr Gln Thr Met Ser Val Thr Asn Thr Thr Ser Glu
    370                 375                 380

Ser Ile Thr Thr Pro Pro Leu Ile Gly Glu Val Ile Phe Ser Glu Asn
385                 390                 395                 400

Thr Ala Lys Gly His Gly Gly Ile Cys Thr Asn Lys Leu Ser Leu
            405                 410                 415

Ser Asn Leu Lys Thr Val Thr Leu Thr Lys Asn Ser Ala Lys Glu Ser
            420                 425                 430

Gly Gly Ala Ile Phe Thr Asp Leu Ala Ser Ile Pro Ile Thr Asp Thr

```
                435                 440                 445
Pro Glu Ser Ser Thr Pro Ser Ser Ser Pro Ala Ser Thr Pro Glu
            450                 455                 460

Val Val Ala Ser Ala Lys Ile Asn Arg Phe Phe Ala Ser Thr Ala Lys
465                 470                 475                 480

Pro Ala Ala Pro Ser Leu Thr Glu Ala Glu Ser Asp Gln Thr Asp Gln
                485                 490                 495

Thr Glu Thr Ser Asp Thr Asn Ser Asp Ile Asp Val Ser Ile Glu Asn
            500                 505                 510

Ile Leu Asn Val Ala Ile Asn Gln Asn Thr Ser Ala Lys Lys Gly Gly
            515                 520                 525

Ala Ile Tyr Gly Lys Lys Ala Lys Leu Ser Arg Ile Asn Asn Leu Glu
            530                 535                 540

Leu Ser Gly Asn Ser Ser Gln Asp Val Gly Gly Leu Cys Leu Thr
545                 550                 555                 560

Glu Ser Val Glu Phe Asp Ala Ile Gly Ser Leu Leu Ser His Tyr Asn
                565                 570                 575

Ser Ala Ala Lys Glu Gly Gly Ala Ile His Ser Lys Thr Val Thr Leu
            580                 585                 590

Ser Asn Leu Lys Ser Thr Phe Thr Phe Ala Asp Asn Thr Val Lys Ala
            595                 600                 605

Ile Val Glu Ser Thr Pro Glu Ala Pro Glu Glu Ile Pro Pro Val Glu
            610                 615                 620

Gly Glu Glu Ser Thr Ala Thr Glu Asp Pro Asn Ser Asn Thr Glu Gly
625                 630                 635                 640

Ser Ser Ala Asn Thr Asn Leu Glu Gly Ser Gln Gly Asp Thr Ala Asp
                645                 650                 655

Thr Gly Thr Gly Asp Val Asn Asn Glu Ser Gln Asp Thr Ser Asp Thr
            660                 665                 670

Gly Asn Ala Glu Ser Glu Glu Gln Leu Gln Asp Ser Thr Gln Ser Asn
            675                 680                 685

Glu Glu Asn Thr Leu Pro Asn Ser Asn Ile Asp Gln Ser Asn Glu Asn
            690                 695                 700

Thr Asp Glu Ser Ser Asp Ser His Thr Glu Glu Ile Thr Asp Glu Ser
705                 710                 715                 720

Val Ser Ser Ser Ser Glu Ser Gly Ser Ser Thr Pro Gln Asp Gly Gly
                725                 730                 735

Ala Ala Ser Ser Gly Ala Pro Ser Gly Asp Gln Ser Ile Ser Ala Asn
            740                 745                 750

Ala Cys Leu Ala Lys Ser Tyr Ala Ala Ser Thr Asp Ser Ser Pro Val
            755                 760                 765

Ser Asn Ser Ser Gly Ser Glu Glu Pro Val Thr Ser Ser Ser Asp Ser
            770                 775                 780

Asp Val Thr Ala Ser Ser Asp Asn Pro Asp Ser Ser Ser Gly Asp
785                 790                 795                 800

Ser Ala Gly Asp Ser Glu Glu Pro Thr Glu Pro Glu Ala Gly Ser Thr
                805                 810                 815

Thr Glu Thr Leu Thr Leu Ile Gly Gly Gly Ala Ile Tyr Gly Glu Thr
            820                 825                 830

Val Lys Ile Glu Asn Phe Ser Gly Gln Gly Ile Phe Ser Gly Asn Lys
            835                 840                 845

Ala Ile Asp Asn Thr Thr Glu Gly Ser Ser Ser Lys Ser Asp Val Leu
            850                 855                 860
```

```
                                         -continued
Gly Gly Ala Val Tyr Ala Lys Thr Leu Phe Asn Leu Asp Ser Gly Ser
865                 870                 875                 880

Ser Arg Arg Thr Val Thr Phe Ser Gly Asn Thr Val Ser Ser Gln Ser
            885                 890                 895

Thr Thr Gly Gln Val Ala Gly Gly Ala Ile Tyr Ser Pro Thr Val Thr
        900                 905                 910

Ile Ala Thr Pro Val Val Phe Ser Lys Asn Ser Ala Thr Asn Asn Ala
    915                 920                 925

Asn Asn Thr Thr Asp Thr Gln Arg Lys Asp Thr Phe Gly Gly Ala Ile
930                 935                 940

Gly Ala Thr Ser Ala Val Ser Leu Ser Gly Gly Ala His Phe Leu Glu
945                 950                 955                 960

Asn Val Ala Asp Leu Gly Ser Ala Ile Gly Leu Val Pro Gly Thr Gln
            965                 970                 975

Asn Thr Glu Thr Val Lys Leu Glu Ser Gly Ser Tyr Tyr Phe Glu Lys
        980                 985                 990

Asn Lys Ala Leu Lys Arg Ala Thr Ile Tyr Ala Pro Val Val Ser Ile
    995                 1000                1005

Lys Ala Tyr Thr Ala Thr Phe Asn Gln Asn Arg Ser Leu Glu Glu Gly
1010                1015                1020

Ser Ala Ile Tyr Phe Thr Lys Glu Ala Ser Ile Glu Ser Leu Gly Ser
1025                1030                1035                1040

Val Leu Phe Thr Gly Asn Leu Val Thr Leu Thr Leu Ser Thr Thr Thr
            1045                1050                1055

Glu Gly Thr Pro Ala Thr Thr Ser Gly Asp Val Thr Lys Tyr Gly Ala
        1060                1065                1070

Ala Ile Phe Gly Gln Ile Ala Ser Ser Asn Gly Ser Gln Thr Asp Asn
    1075                1080                1085

Leu Pro Leu Lys Leu Ile Ala Ser Gly Gly Asn Ile Cys Phe Arg Asn
1090                1095                1100

Asn Glu Tyr Arg Pro Thr Ser Ser Asp Thr Gly Thr Ser Thr Phe Cys
1105                1110                1115                1120

Ser Ile Ala Gly Asp Val Lys Leu Thr Met Gln Ala Ala Lys Gly Lys
            1125                1130                1135

Thr Ile Ser Phe Phe Asp Ala Ile Arg Thr Ser Thr Lys Lys Thr Gly
        1140                1145                1150

Thr Gln Ala Thr Ala Tyr Asp Thr Leu Asp Ile Asn Lys Ser Glu Asp
    1155                1160                1165

Ser Glu Thr Val Asn Ser Ala Phe Thr Gly Thr Ile Leu Phe Ser Ser
    1170                1175                1180

Glu Leu His Glu Asn Lys Ser Tyr Ile Pro Gln Asn Val Val Leu His
1185                1190                1195                1200

Ser Gly Ser Leu Val Leu Lys Pro Asn Thr Glu Leu His Val Ile Ser
            1205                1210                1215

Phe Glu Gln Lys Glu Gly Ser Ser Leu Val Met Thr Pro Gly Ser Val
        1220                1225                1230

Leu Ser Asn Gln Thr Val Ala Asp Gly Ala Leu Val Ile Asn Asn Met
    1235                1240                1245

Thr Ile Asp Leu Ser Ser Val Glu Lys Asn Gly Ile Ala Glu Gly Asn
    1250                1255                1260

Ile Phe Thr Pro Pro Glu Leu Arg Ile Ile Asp Thr Thr Gly Gly
1265                1270                1275                1280

Ser Gly Gly Thr Pro Ser Thr Asp Ser Glu Ser Asn Gln Asn Ser Asp
            1285                1290                1295
```

```
Asp Thr Glu Glu Gln Asn Asn Asn Asp Ala Ser Asn Gln Gly Glu Ser
            1300                1305                1310

Ala Asn Gly Ser Ser Ser Pro Ala Val Ala Ala Ala His Thr Ser Arg
            1315                1320                1325

Thr Arg Asn Phe Ala Ala Ala Ala Thr Ala Thr Pro Thr Thr Thr Pro
            1330                1335                1340

Thr Ala Thr Thr Thr Thr Ser Asn Gln Val Ile Leu Gly Gly Glu Ile
1345                1350                1355                1360

Lys Leu Ile Asp Pro Asn Gly Thr Phe Phe Gln Asn Pro Ala Leu Arg
            1365                1370                1375

Ser Asp Gln Gln Ile Ser Leu Leu Val Leu Pro Thr Asp Ser Ser Lys
            1380                1385                1390

Met Gln Ala Gln Lys Ile Val Leu Thr Gly Asp Ile Ala Pro Gln Lys
            1395                1400                1405

Gly Tyr Thr Gly Thr Leu Thr Leu Asp Pro Asp Gln Leu Gln Asn Gly
            1410                1415                1420

Thr Ile Ser Val Leu Trp Lys Phe Asp Ser Tyr Arg Gln Trp Ala Tyr
1425                1430                1435                1440

Val Pro Arg Asp Asn His Phe Tyr Ala Asn Ser Ile Leu Gly Ser Gln
            1445                1450                1455

Met Leu Met Val Thr Val Lys Gln Gly Leu Leu Asn Asp Lys Met Asn
            1460                1465                1470

Leu Ala Arg Phe Glu Glu Val Ser Tyr Asn Asn Leu Trp Ile Ser Gly
            1475                1480                1485

Leu Gly Thr Met Leu Ser Gln Val Gly Thr Pro Thr Ser Glu Glu Phe
            1490                1495                1500

Thr Tyr Tyr Ser Arg Gly Ala Ser Val Ala Leu Asp Ala Lys Pro Ala
1505                1510                1515                1520

His Asp Val Ile Val Gly Ala Ala Phe Ser Lys Met Ile Gly Lys Thr
            1525                1530                1535

Lys Ser Leu Lys Arg Glu Asn Asn Tyr Thr His Lys Gly Ser Glu Tyr
            1540                1545                1550

Ser Tyr Gln Ala Ser Val Tyr Gly Gly Lys Pro Phe His Phe Val Ile
            1555                1560                1565

Asn Lys Lys Thr Glu Lys Ser Leu Pro Leu Leu Leu Gln Gly Val Ile
            1570                1575                1580

Ser Tyr Gly Tyr Ile Lys His Asp Thr Val Thr His Tyr Pro Thr Ile
1585                1590                1595                1600

Arg Glu Arg Asn Lys Gly Glu Trp Glu Asp Leu Gly Trp Leu Thr Ala
            1605                1610                1615

Leu Arg Val Ser Ser Val Leu Arg Thr Pro Ala Gln Gly Asp Thr Lys
            1620                1625                1630

Arg Ile Thr Val Tyr Gly Glu Leu Glu Tyr Ser Ser Ile Arg Gln Lys
            1635                1640                1645

Gln Phe Thr Glu Thr Glu Tyr Asp Pro Arg Tyr Phe Asp Asn Cys Thr
            1650                1655                1660

Tyr Arg Asn Leu Ala Ile Pro Met Gly Leu Ala Phe Glu Gly Glu Leu
1665                1670                1675                1680

Ser Gly Asn Asp Ile Leu Met Tyr Asn Arg Phe Ser Val Ala Tyr Met
            1685                1690                1695

Leu Ser Ile Tyr Arg Asn Ser Pro Thr Cys Lys Tyr Gln Val Leu Ser
            1700                1705                1710

Ser Gly Glu Gly Gly Glu Ile Ile Cys Gly Val Pro Thr Arg Asn Ser
```

1715                1720                    1725
Ala Arg Gly Glu Tyr Ser Thr Gln Leu Tyr Leu Gly Pro Leu Trp Thr
            1730                1735                1740

Leu Tyr Gly Ser Tyr Thr Ile Glu Ala Asp Ala His Thr Leu Ala His
1745                1750                1755                1760

Met Met Asn Cys Gly Ala Arg Met Thr Phe
                1765                1770

<210> SEQ ID NO 65
<211> LENGTH: 1531
<212> TYPE: PRT
<213> ORGANISM: Chlamydia trachomatis

<400> SEQUENCE: 65

Met Ser Ser Glu Lys Asp Ile Lys Ser Thr Cys Ser Lys Phe Ser Leu
1               5                   10                  15

Ser Val Ala Ala Ile Leu Ala Ser Val Ser Gly Leu Ala Ser Cys
            20                  25                  30

Val Asp Leu His Ala Gly Gly Gln Ser Val Asn Glu Leu Val Tyr Val
            35                  40                  45

Gly Pro Gln Ala Val Leu Leu Leu Asp Gln Ile Arg Asp Leu Phe Val
        50                  55                  60

Gly Ser Lys Asp Ser Gln Ala Glu Gly Gln Tyr Arg Leu Ile Val Gly
65                  70                  75                  80

Asp Pro Ser Ser Phe Gln Glu Lys Asp Ala Asp Thr Leu Pro Gly Lys
                85                  90                  95

Val Glu Gln Ser Thr Leu Phe Ser Val Thr Asn Pro Val Val Phe Gln
            100                 105                 110

Gly Val Asp Gln Gln Asp Gln Val Ser Ser Gln Gly Leu Ile Cys Ser
        115                 120                 125

Phe Thr Ser Ser Asn Leu Asp Ser Pro Arg Asp Gly Glu Ser Phe Leu
130                 135                 140

Gly Ile Ala Phe Val Gly Asp Ser Ser Lys Ala Gly Ile Thr Leu Thr
145                 150                 155                 160

Asp Val Lys Ala Ser Leu Ser Gly Ala Ala Leu Tyr Ser Thr Glu Asp
                165                 170                 175

Leu Ile Phe Glu Lys Ile Lys Gly Gly Leu Glu Phe Ala Ser Cys Ser
            180                 185                 190

Ser Leu Glu Gln Gly Gly Ala Cys Ala Ala Gln Ser Ile Leu Ile His
        195                 200                 205

Asp Cys Gln Gly Leu Gln Val Lys His Cys Thr Thr Ala Val Asn Ala
210                 215                 220

Glu Gly Ser Ser Ala Asn Asp His Leu Gly Phe Gly Gly Gly Ala Phe
225                 230                 235                 240

Phe Val Thr Gly Ser Leu Ser Gly Glu Lys Ser Leu Tyr Met Pro Ala
                245                 250                 255

Gly Asp Met Val Val Ala Asn Cys Asp Gly Ala Ile Ser Phe Glu Gly
            260                 265                 270

Asn Ser Ala Asn Phe Ala Asn Gly Gly Ala Ile Ala Ala Ser Gly Lys
        275                 280                 285

Val Leu Phe Val Ala Asn Asp Lys Lys Thr Ser Phe Ile Glu Asn Arg
        290                 295                 300

Ala Leu Ser Gly Gly Ala Ile Ala Ala Ser Ser Asp Ile Ala Phe Gln
305                 310                 315                 320

Asn Cys Ala Glu Leu Val Phe Lys Gly Asn Cys Ala Ile Gly Thr Glu

```
                        325                 330                 335
Asp Lys Gly Ser Leu Gly Gly Gly Ala Ile Ser Ser Leu Gly Thr Val
            340                 345                 350
Leu Leu Gln Gly Asn His Gly Ile Thr Cys Asp Lys Asn Glu Ser Ala
            355                 360                 365
Ser Gln Gly Gly Ala Ile Phe Gly Lys Asn Cys Gln Ile Ser Asp Asn
            370                 375                 380
Glu Gly Pro Val Val Phe Arg Asp Ser Thr Ala Cys Leu Gly Gly Gly
385                 390                 395                 400
Ala Ile Ala Ala Gln Glu Ile Val Ser Ile Gln Asn Asn Gln Ala Gly
            405                 410                 415
Ile Ser Phe Glu Gly Gly Lys Ala Ser Phe Gly Gly Gly Ile Ala Cys
            420                 425                 430
Gly Ser Phe Ser Ser Ala Gly Ala Ser Val Leu Gly Thr Ile Asp
            435                 440                 445
Ile Ser Lys Asn Leu Gly Ala Ile Ser Phe Ser Arg Thr Leu Cys Thr
            450                 455                 460
Thr Ser Asp Leu Gly Gln Met Glu Tyr Gln Gly Gly Ala Leu Phe
465                 470                 475                 480
Gly Glu Asn Ile Ser Leu Ser Glu Asn Ala Gly Val Leu Thr Phe Lys
            485                 490                 495
Asp Asn Ile Val Lys Thr Phe Ala Ser Asn Gly Lys Ile Leu Gly Gly
            500                 505                 510
Gly Ala Ile Leu Ala Thr Gly Lys Val Glu Ile Thr Asn Asn Ser Glu
            515                 520                 525
Gly Ile Ser Phe Thr Gly Asn Ala Arg Ala Pro Gln Ala Leu Pro Thr
            530                 535                 540
Gln Glu Glu Phe Pro Leu Phe Ser Lys Lys Glu Gly Arg Pro Leu Ser
545                 550                 555                 560
Ser Gly Tyr Ser Gly Gly Ala Ile Leu Gly Arg Glu Val Ala Ile
            565                 570                 575
Leu His Asn Ala Ala Val Val Phe Glu Gln Asn Arg Leu Gln Cys Ser
            580                 585                 590
Glu Glu Glu Ala Thr Leu Leu Gly Cys Cys Gly Gly Ala Val His
            595                 600                 605
Gly Met Asp Ser Thr Ser Ile Val Gly Asn Ser Ser Val Arg Phe Gly
            610                 615                 620
Asn Asn Tyr Ala Met Gly Gln Gly Val Ser Gly Ala Leu Leu Ser
625                 630                 635                 640
Lys Thr Val Gln Leu Ala Gly Asn Gly Ser Val Asp Phe Ser Arg Asn
            645                 650                 655
Ile Ala Ser Leu Gly Gly Gly Ala Leu Gln Ala Ser Glu Gly Asn Cys
            660                 665                 670
Glu Leu Val Asp Asn Gly Tyr Val Leu Phe Arg Asp Asn Arg Gly Arg
            675                 680                 685
Val Tyr Gly Gly Ala Ile Ser Cys Leu Arg Gly Asp Val Val Ile Ser
            690                 695                 700
Gly Asn Lys Gly Arg Val Glu Phe Lys Asp Asn Ile Ala Thr Arg Leu
705                 710                 715                 720
Tyr Val Glu Glu Thr Val Glu Lys Val Glu Val Glu Pro Ala Pro
            725                 730                 735
Glu Gln Lys Asp Asn Asn Glu Leu Ser Phe Leu Gly Arg Ala Glu Gln
            740                 745                 750
```

-continued

```
Ser Phe Ile Thr Ala Ala Asn Gln Ala Leu Phe Ala Ser Glu Asp Gly
        755                 760                 765

Asp Leu Ser Pro Glu Ser Ser Ile Ser Ser Glu Glu Leu Ala Lys Arg
    770                 775                 780

Arg Glu Cys Ala Gly Gly Ala Ile Phe Ala Lys Arg Val Arg Ile Val
785                 790                 795                 800

Asp Asn Gln Glu Ala Val Val Phe Ser Asn Asn Phe Ser Asp Ile Tyr
                805                 810                 815

Gly Gly Ala Ile Phe Thr Gly Ser Leu Arg Glu Glu Asp Lys Leu Asp
                820                 825                 830

Gly Gln Ile Pro Glu Val Leu Ile Ser Gly Asn Ala Gly Asp Val Val
                835                 840                 845

Phe Ser Gly Asn Ser Ser Lys Arg Asp Glu His Leu Pro His Thr Gly
    850                 855                 860

Gly Gly Ala Ile Cys Thr Gln Asn Leu Thr Ile Ser Gln Asn Thr Gly
865                 870                 875                 880

Asn Val Leu Phe Tyr Asn Asn Val Ala Cys Ser Gly Ala Val Arg
                885                 890                 895

Ile Glu Asp His Gly Asn Val Leu Leu Glu Ala Phe Gly Gly Asp Ile
                900                 905                 910

Val Phe Lys Gly Asn Ser Ser Phe Arg Ala Gln Gly Ser Asp Ala Ile
    915                 920                 925

Tyr Phe Ala Gly Lys Glu Ser His Ile Thr Ala Leu Asn Ala Thr Glu
    930                 935                 940

Gly His Ala Ile Val Phe His Asp Ala Leu Val Phe Glu Asn Leu Glu
945                 950                 955                 960

Glu Arg Lys Ser Ala Glu Val Leu Leu Ile Asn Ser Arg Glu Asn Pro
                965                 970                 975

Gly Tyr Thr Gly Ser Ile Arg Phe Leu Glu Ala Glu Ser Lys Val Pro
                980                 985                 990

Gln Cys Ile His Val Gln Gln Gly Ser Leu Glu Leu Leu Asn Gly Ala
            995                 1000                1005

Thr Leu Cys Ser Tyr Gly Phe Lys Gln Asp Ala Gly Ala Lys Leu Val
    1010                1015                1020

Leu Ala Ala Gly Ala Lys Leu Lys Ile Leu Asp Ser Gly Thr Pro Val
1025                1030                1035                1040

Gln Gln Gly His Ala Ile Ser Lys Pro Glu Ala Glu Ile Glu Ser Ser
                1045                1050                1055

Ser Glu Pro Glu Gly Ala His Ser Leu Trp Ile Ala Lys Asn Ala Gln
                1060                1065                1070

Thr Thr Val Pro Met Val Asp Ile His Thr Ile Ser Val Asp Leu Ala
            1075                1080                1085

Ser Phe Ser Ser Ser Gln Gln Glu Gly Thr Val Glu Ala Pro Gln Val
    1090                1095                1100

Ile Val Pro Gly Gly Ser Tyr Val Arg Ser Gly Glu Leu Asn Leu Glu
1105                1110                1115                1120

Leu Val Asn Thr Thr Gly Thr Gly Tyr Glu Asn His Ala Leu Leu Lys
                1125                1130                1135

Asn Glu Ala Lys Val Pro Leu Met Ser Phe Val Ala Ser Gly Asp Glu
                1140                1145                1150

Ala Ser Ala Glu Ile Ser Asn Leu Ser Val Ser Asp Leu Gln Ile His
            1155                1160                1165

Val Val Thr Pro Glu Ile Glu Glu Asp Thr Tyr Gly His Met Gly Asp
        1170                1175                1180
```

```
Trp Ser Glu Ala Lys Ile Gln Asp Gly Thr Leu Val Ile Ser Trp Asn
1185                1190                1195                1200

Pro Thr Gly Tyr Arg Leu Asp Pro Gln Lys Ala Gly Ala Leu Val Phe
            1205                1210                1215

Asn Ala Leu Trp Glu Glu Gly Ala Val Leu Ser Ala Leu Lys Asn Ala
        1220                1225                1230

Arg Phe Ala His Asn Leu Thr Ala Gln Arg Met Glu Phe Asp Tyr Ser
    1235                1240                1245

Thr Asn Val Trp Gly Phe Ala Phe Gly Gly Phe Arg Thr Leu Ser Ala
1250                1255                1260

Glu Asn Leu Val Ala Ile Asp Gly Tyr Lys Gly Ala Tyr Gly Gly Ala
1265                1270                1275                1280

Ser Ala Gly Val Asp Ile Gln Leu Met Glu Asp Phe Val Leu Gly Val
            1285                1290                1295

Ser Gly Ala Ala Phe Leu Gly Lys Met Asp Ser Gln Lys Phe Asp Ala
        1300                1305                1310

Glu Val Ser Arg Lys Gly Val Val Gly Ser Val Tyr Thr Gly Phe Leu
    1315                1320                1325

Ala Gly Ser Trp Phe Phe Lys Gly Gln Tyr Ser Leu Gly Glu Thr Gln
1330                1335                1340

Asn Asp Met Lys Thr Arg Tyr Gly Val Leu Gly Glu Ser Ser Ala Ser
1345                1350                1355                1360

Trp Thr Ser Arg Gly Val Leu Ala Asp Ala Leu Val Glu Tyr Arg Ser
            1365                1370                1375

Leu Val Gly Pro Val Arg Pro Thr Phe Tyr Ala Leu His Phe Asn Pro
        1380                1385                1390

Tyr Val Glu Val Ser Tyr Ala Ser Met Lys Phe Pro Gly Phe Thr Glu
    1395                1400                1405

Gln Gly Arg Glu Ala Arg Ser Phe Glu Asp Ala Ser Leu Thr Asn Ile
1410                1415                1420

Thr Ile Pro Leu Gly Met Lys Phe Glu Leu Ala Phe Ile Lys Gly Gln
1425                1430                1435                1440

Phe Ser Glu Val Asn Ser Leu Gly Ile Ser Tyr Ala Trp Glu Ala Tyr
            1445                1450                1455

Arg Lys Val Glu Gly Gly Ala Val Gln Leu Leu Glu Ala Gly Phe Asp
        1460                1465                1470

Trp Glu Gly Ala Pro Met Asp Leu Pro Arg Gln Glu Leu Arg Val Ala
    1475                1480                1485

Leu Glu Asn Asn Thr Glu Trp Ser Ser Tyr Phe Ser Thr Val Leu Gly
1490                1495                1500

Leu Thr Ala Phe Cys Gly Gly Phe Thr Ser Thr Asp Ser Lys Leu Gly
1505                1510                1515                1520

Tyr Glu Ala Asn Thr Gly Leu Arg Leu Ile Phe
            1525                1530

<210> SEQ ID NO 66
<211> LENGTH: 964
<212> TYPE: PRT
<213> ORGANISM: Chlamydia trachomatis

<400> SEQUENCE: 66

Met Lys Lys Ala Phe Phe Phe Leu Ile Gly Asn Ser Leu Ser Gly
1               5                   10                  15

Leu Ala Arg Glu Val Pro Ser Arg Ile Phe Leu Met Pro Asn Ser Val
                20                  25                  30
```

```
Pro Asp Pro Thr Lys Glu Ser Leu Ser Asn Lys Ile Ser Leu Thr Gly
         35                  40                  45
Asp Thr His Asn Leu Thr Asn Cys Tyr Leu Asp Asn Leu Arg Tyr Ile
 50                  55                  60
Leu Ala Ile Leu Gln Lys Thr Pro Asn Glu Gly Ala Ala Val Thr Ile
 65                  70                  75                  80
Thr Asp Tyr Leu Ser Phe Phe Asp Thr Gln Lys Glu Gly Ile Tyr Phe
                 85                  90                  95
Ala Lys Asn Leu Thr Pro Glu Ser Gly Gly Ala Ile Gly Tyr Ala Ser
                100                 105                 110
Pro Asn Ser Pro Thr Val Glu Ile Arg Asp Thr Ile Gly Pro Val Ile
                115                 120                 125
Phe Glu Asn Asn Thr Cys Cys Arg Leu Phe Thr Trp Arg Asn Pro Tyr
                130                 135                 140
Ala Ala Asp Lys Ile Arg Glu Gly Gly Ala Ile His Ala Gln Asn Leu
145                 150                 155                 160
Tyr Ile Asn His Asn His Asp Val Val Gly Phe Met Lys Asn Phe Ser
                165                 170                 175
Tyr Val Gln Gly Gly Ala Ile Ser Thr Ala Asn Thr Phe Val Val Ser
                180                 185                 190
Glu Asn Gln Ser Cys Phe Leu Phe Met Asp Asn Ile Cys Ile Gln Thr
                195                 200                 205
Asn Thr Ala Gly Lys Gly Gly Ala Ile Tyr Ala Gly Thr Ser Asn Ser
210                 215                 220
Phe Glu Ser Asn Asn Cys Asp Leu Phe Phe Ile Asn Asn Ala Cys Cys
225                 230                 235                 240
Ala Gly Gly Ala Ile Phe Ser Pro Ile Cys Ser Leu Thr Gly Asn Arg
                245                 250                 255
Gly Asn Ile Val Phe Tyr Asn Asn Arg Cys Phe Lys Asn Val Glu Thr
                260                 265                 270
Ala Ser Ser Glu Ala Ser Asp Gly Gly Ala Ile Lys Val Thr Thr Arg
                275                 280                 285
Leu Asp Val Thr Gly Asn Arg Gly Arg Ile Phe Phe Ser Asp Asn Ile
                290                 295                 300
Thr Lys Asn Tyr Gly Gly Ala Ile Tyr Ala Pro Val Val Thr Leu Val
305                 310                 315                 320
Asp Asn Gly Pro Thr Tyr Phe Ile Asn Asn Ile Ala Asn Asn Lys Gly
                325                 330                 335
Gly Ala Ile Tyr Ile Asp Gly Thr Ser Asn Ser Lys Ile Ser Ala Asp
                340                 345                 350
Arg His Ala Ile Ile Phe Asn Glu Asn Ile Val Thr Asn Val Thr Asn
                355                 360                 365
Ala Asn Gly Thr Ser Thr Ser Ala Asn Pro Pro Arg Arg Asn Ala Ile
                370                 375                 380
Thr Val Ala Ser Ser Ser Gly Glu Ile Leu Leu Gly Ala Gly Ser Ser
385                 390                 395                 400
Gln Asn Leu Ile Phe Tyr Asp Pro Ile Glu Val Ser Asn Ala Gly Val
                405                 410                 415
Ser Val Ser Phe Asn Lys Glu Ala Asp Gln Thr Gly Ser Val Val Phe
                420                 425                 430
Ser Gly Ala Thr Val Asn Ser Ala Asp Phe His Gln Arg Asn Leu Gln
                435                 440                 445
Thr Lys Thr Pro Ala Pro Leu Thr Leu Ser Asn Gly Phe Leu Cys Ile
```

```
                450                   455                   460
Glu Asp His Ala Gln Leu Thr Val Asn Arg Phe Thr Gln Thr Gly Gly
465                 470                 475                 480
Val Val Ser Leu Gly Asn Gly Ala Val Leu Ser Cys Tyr Lys Asn Gly
                485                 490                 495
Thr Gly Asp Ser Ala Ser Asn Ala Ser Ile Thr Leu Lys His Ile Gly
                500                 505                 510
Leu Asn Leu Ser Ser Ile Leu Lys Ser Gly Ala Glu Ile Pro Leu Leu
                515                 520                 525
Trp Val Glu Pro Thr Asn Asn Ser Asn Asn Tyr Thr Ala Asp Thr Ala
530                 535                 540
Ala Thr Phe Ser Leu Ser Asp Val Lys Leu Ser Leu Ile Asp Asp Tyr
545                 550                 555                 560
Gly Asn Ser Pro Tyr Glu Ser Thr Asp Leu Thr His Ala Leu Ser Ser
                565                 570                 575
Gln Pro Met Leu Ser Ile Ser Glu Ala Ser Asp Asn Gln Leu Gln Ser
                580                 585                 590
Glu Asn Ile Asp Phe Ser Gly Leu Asn Val Pro His Tyr Gly Trp Gln
                595                 600                 605
Gly Leu Trp Thr Trp Gly Trp Ala Lys Thr Gln Asp Pro Glu Pro Ala
                610                 615                 620
Ser Ser Ala Thr Ile Thr Asp Pro Gln Lys Ala Asn Arg Phe His Arg
625                 630                 635                 640
Thr Leu Leu Leu Thr Trp Leu Pro Ala Gly Tyr Val Pro Ser Pro Lys
                645                 650                 655
His Arg Ser Pro Leu Ile Ala Asn Thr Leu Trp Gly Asn Met Leu Leu
                660                 665                 670
Ala Thr Glu Ser Leu Lys Asn Ser Ala Glu Leu Thr Pro Ser Gly His
                675                 680                 685
Pro Phe Trp Gly Ile Thr Gly Gly Leu Gly Met Met Val Tyr Gln
                690                 695                 700
Asp Pro Arg Glu Asn His Pro Gly Phe His Met Arg Ser Ser Gly Tyr
705                 710                 715                 720
Ser Ala Gly Met Ile Ala Gly Gln Thr His Thr Phe Ser Leu Lys Phe
                725                 730                 735
Ser Gln Thr Tyr Thr Lys Leu Asn Glu Arg Tyr Ala Lys Asn Asn Val
                740                 745                 750
Ser Ser Lys Asn Tyr Ser Cys Gln Gly Glu Met Leu Phe Ser Leu Gln
                755                 760                 765
Glu Gly Phe Leu Leu Thr Lys Leu Val Gly Leu Tyr Ser Tyr Gly Asp
                770                 775                 780
His Asn Cys His His Phe Tyr Thr Gln Gly Glu Asn Leu Thr Ser Gln
785                 790                 795                 800
Gly Thr Phe Arg Ser Gln Thr Met Gly Gly Ala Val Phe Phe Asp Leu
                805                 810                 815
Pro Met Lys Pro Phe Gly Ser Thr His Ile Leu Thr Ala Pro Phe Leu
                820                 825                 830
Gly Ala Leu Gly Ile Tyr Ser Ser Leu Ser His Phe Thr Glu Val Gly
                835                 840                 845
Ala Tyr Pro Arg Ser Phe Ser Thr Lys Thr Pro Leu Ile Asn Val Leu
                850                 855                 860
Val Pro Ile Gly Val Lys Gly Ser Phe Met Asn Ala Thr His Arg Pro
865                 870                 875                 880
```

```
Gln Ala Trp Thr Val Glu Leu Ala Tyr Gln Pro Val Leu Tyr Arg Gln
                885                 890                 895

Glu Pro Gly Ile Ala Ala Gln Leu Leu Ala Ser Lys Gly Ile Trp Phe
            900                 905                 910

Gly Ser Gly Ser Pro Ser Ser Arg His Ala Met Ser Tyr Lys Ile Ser
        915                 920                 925

Gln Gln Thr Gln Pro Leu Ser Trp Leu Thr Leu His Phe Gln Tyr His
    930                 935                 940

Gly Phe Tyr Ser Ser Ser Thr Phe Cys Asn Tyr Leu Asn Gly Glu Ile
945                 950                 955                 960

Ala Leu Arg Phe

<210> SEQ ID NO 67
<211> LENGTH: 1034
<212> TYPE: PRT
<213> ORGANISM: Chlamydia trachomatis

<400> SEQUENCE: 67

Met Ile Lys Arg Thr Ser Leu Ser Phe Ala Cys Leu Ser Phe Phe Tyr
1               5                   10                  15

Leu Ser Thr Ile Ser Ile Leu Gln Ala Asn Glu Thr Asp Thr Leu Gln
            20                  25                  30

Phe Arg Arg Phe Thr Phe Ser Asp Arg Glu Ile Gln Phe Val Leu Asp
        35                  40                  45

Pro Ala Ser Leu Ile Thr Ala Gln Asn Ile Val Leu Ser Asn Leu Gln
    50                  55                  60

Ser Asn Gly Thr Gly Ala Cys Thr Ile Ser Gly Asn Thr Gln Thr Gln
65                  70                  75                  80

Ile Phe Ser Asn Ser Val Asn Thr Thr Ala Asp Ser Gly Gly Ala Phe
                85                  90                  95

Asp Met Val Thr Thr Ser Phe Thr Ala Ser Asp Asn Ala Asn Leu Leu
            100                 105                 110

Phe Cys Asn Asn Tyr Cys Thr His Asn Lys Gly Gly Gly Ala Ile Arg
        115                 120                 125

Ser Gly Gly Pro Ile Arg Phe Leu Asn Asn Gln Asp Val Leu Phe Tyr
    130                 135                 140

Asn Asn Ile Ser Ala Gly Ala Lys Tyr Val Gly Thr Gly Asp His Asn
145                 150                 155                 160

Glu Lys Asn Arg Gly Gly Ala Leu Tyr Ala Thr Thr Ile Thr Leu Thr
                165                 170                 175

Gly Asn Arg Thr Leu Ala Phe Ile Asn Asn Met Ser Gly Asp Cys Gly
            180                 185                 190

Gly Ala Ile Ser Ala Asp Thr Gln Ile Ser Ile Thr Asp Thr Val Lys
        195                 200                 205

Gly Ile Leu Phe Glu Asn Asn His Thr Leu Asn His Ile Pro Tyr Thr
    210                 215                 220

Gln Ala Glu Asn Met Ala Arg Gly Gly Ala Ile Cys Ser Arg Arg Asp
225                 230                 235                 240

Leu Cys Ser Ile Ser Asn Asn Ser Gly Pro Ile Val Phe Asn Tyr Asn
                245                 250                 255

Gln Gly Gly Lys Gly Gly Ala Ile Ser Ala Thr Arg Cys Val Ile Asp
            260                 265                 270

Asn Asn Lys Glu Arg Ile Ile Phe Ser Asn Asn Ser Ser Leu Gly Trp
        275                 280                 285

Ser Gln Ser Ser Ser Ala Ser Asn Gly Gly Ala Ile Gln Thr Thr Gln
```

```
            290                 295                 300
Gly Phe Thr Leu Arg Asn Asn Lys Gly Ser Ile Tyr Phe Asp Ser Asn
305                 310                 315                 320

Thr Ala Thr His Ala Gly Gly Ala Ile Asn Cys Gly Tyr Ile Asp Ile
                325                 330                 335

Arg Asp Asn Gly Pro Val Tyr Phe Leu Asn Asn Ser Ala Ala Trp Gly
                340                 345                 350

Ala Ala Phe Asn Leu Ser Lys Pro Arg Ser Ala Thr Asn Tyr Ile His
                355                 360                 365

Thr Gly Thr Gly Asp Ile Val Phe Asn Asn Asn Val Val Phe Thr Leu
370                 375                 380

Asp Gly Asn Leu Leu Gly Lys Arg Lys Leu Phe His Ile Asn Asn Asn
385                 390                 395                 400

Glu Ile Thr Pro Tyr Thr Leu Ser Leu Gly Ala Lys Lys Asp Thr Arg
                405                 410                 415

Ile Tyr Phe Tyr Asp Leu Phe Gln Trp Glu Arg Val Lys Glu Asn Thr
                420                 425                 430

Ser Asn Asn Pro Pro Ser Pro Thr Ser Arg Asn Thr Ile Thr Val Asn
                435                 440                 445

Pro Glu Thr Glu Phe Ser Gly Ala Val Val Phe Ser Tyr Asn Gln Met
450                 455                 460

Ser Ser Asp Ile Arg Thr Leu Met Gly Lys Glu His Asn Tyr Ile Lys
465                 470                 475                 480

Glu Ala Pro Thr Thr Leu Lys Phe Gly Thr Leu Ala Ile Glu Asp Asp
                485                 490                 495

Ala Glu Leu Glu Ile Phe Asn Ile Pro Phe Thr Gln Asn Pro Thr Ser
                500                 505                 510

Leu Leu Ala Leu Gly Ser Gly Ala Thr Leu Thr Val Gly Lys His Gly
                515                 520                 525

Lys Leu Asn Ile Thr Asn Leu Gly Val Ile Leu Pro Ile Ile Leu Lys
                530                 535                 540

Glu Gly Lys Ser Pro Pro Cys Ile Arg Val Asn Pro Gln Asp Met Thr
545                 550                 555                 560

Gln Asn Thr Gly Thr Gly Gln Thr Pro Ser Ser Thr Ser Ser Ile Ser
                565                 570                 575

Thr Pro Met Ile Ile Phe Asn Gly Arg Leu Ser Ile Val Asp Glu Asn
                580                 585                 590

Tyr Glu Ser Val Tyr Asp Ser Met Asp Leu Ser Arg Gly Lys Ala Glu
                595                 600                 605

Gln Leu Ile Leu Ser Ile Glu Thr Thr Asn Asp Gly Gln Leu Asp Ser
610                 615                 620

Asn Trp Gln Ser Ser Leu Asn Thr Ser Leu Leu Ser Pro Pro His Tyr
625                 630                 635                 640

Gly Tyr Gln Gly Leu Trp Thr Pro Asn Trp Ile Thr Thr Thr Tyr Thr
                645                 650                 655

Ile Thr Leu Asn Asn Asn Ser Ser Ala Pro Thr Ser Ala Thr Ser Ile
                660                 665                 670

Ala Glu Gln Lys Lys Thr Ser Glu Thr Phe Thr Pro Ser Asn Thr Thr
                675                 680                 685

Thr Ala Ser Ile Pro Asn Ile Lys Ala Ser Ala Gly Ser Gly Ser Gly
                690                 695                 700

Ser Ala Ser Asn Ser Gly Glu Val Thr Ile Thr Lys His Thr Leu Val
705                 710                 715                 720
```

```
Val Asn Trp Ala Pro Val Gly Tyr Ile Val Asp Pro Ile Arg Arg Gly
                725                 730                 735

Asp Leu Ile Ala Asn Ser Leu Val His Ser Gly Arg Asn Met Thr Met
            740                 745                 750

Gly Leu Arg Ser Leu Leu Pro Asp Asn Ser Trp Phe Ala Leu Gln Gly
        755                 760                 765

Ala Ala Thr Thr Leu Phe Thr Lys Gln Gln Lys Arg Leu Ser Tyr His
    770                 775                 780

Gly Tyr Ser Ser Ala Ser Lys Gly Tyr Thr Val Ser Ser Gln Ala Ser
785                 790                 795                 800

Gly Ala His Gly His Lys Phe Leu Leu Ser Phe Ser Gln Ser Ser Asp
                805                 810                 815

Lys Met Lys Glu Lys Glu Thr Asn Asn Arg Leu Ser Ser Arg Tyr Tyr
            820                 825                 830

Leu Ser Ala Leu Cys Phe Glu His Pro Met Phe Asp Arg Ile Ala Leu
        835                 840                 845

Ile Gly Ala Ala Ala Cys Asn Tyr Gly Thr His Asn Met Arg Ser Phe
    850                 855                 860

Tyr Gly Thr Lys Lys Ser Ser Lys Gly Lys Phe His Ser Thr Thr Leu
865                 870                 875                 880

Gly Ala Ser Leu Arg Cys Glu Leu Arg Asp Ser Met Pro Leu Arg Ser
                885                 890                 895

Ile Met Leu Thr Pro Phe Ala Gln Ala Leu Phe Ser Arg Thr Glu Pro
            900                 905                 910

Ala Ser Ile Arg Glu Ser Gly Asp Leu Ala Arg Leu Phe Thr Leu Glu
        915                 920                 925

Gln Ala His Thr Ala Val Val Ser Pro Ile Gly Ile Lys Gly Ala Tyr
    930                 935                 940

Ser Ser Asp Thr Trp Pro Thr Leu Ser Trp Glu Met Glu Leu Ala Tyr
945                 950                 955                 960

Gln Pro Thr Leu Tyr Trp Lys Arg Pro Leu Leu Asn Thr Leu Leu Ile
                965                 970                 975

Gln Asn Asn Gly Ser Trp Val Thr Thr Asn Thr Pro Leu Ala Lys His
            980                 985                 990

Ser Phe Tyr Gly Arg Gly Ser His Ser Leu Lys Phe Ser His Leu Lys
        995                 1000                1005

Leu Phe Ala Asn Tyr Gln Ala Glu Val Ala Thr Ser Thr Val Ser His
    1010                1015                1020

Tyr Ile Asn Ala Gly Gly Ala Leu Val Phe
1025                1030

<210> SEQ ID NO 68
<211> LENGTH: 1013
<212> TYPE: PRT
<213> ORGANISM: Chlamydia trachomatis

<400> SEQUENCE: 68

Met Gln Thr Ser Phe His Lys Phe Phe Leu Ser Met Ile Leu Ala Tyr
1               5                   10                  15

Ser Cys Cys Ser Leu Ser Gly Gly Gly Tyr Ala Ala Glu Ile Met Ile
                20                  25                  30

Pro Gln Gly Ile Tyr Asp Gly Glu Thr Leu Thr Val Ser Phe Pro Tyr
            35                  40                  45

Thr Val Ile Gly Asp Pro Ser Gly Thr Thr Val Phe Ser Ala Gly Glu
        50                  55                  60
```

-continued

```
Leu Thr Leu Lys Asn Leu Asp Asn Ser Ile Ala Ala Leu Pro Leu Ser
 65                  70                  75                  80

Cys Phe Gly Asn Leu Leu Gly Ser Phe Thr Val Leu Gly Arg Gly His
                 85                  90                  95

Ser Leu Thr Phe Glu Asn Ile Arg Thr Ser Thr Asn Gly Ala Ala Leu
            100                 105                 110

Ser Asp Ser Ala Asn Ser Gly Leu Phe Thr Ile Glu Gly Phe Lys Glu
        115                 120                 125

Leu Ser Phe Ser Asn Cys Asn Ser Leu Leu Ala Val Leu Pro Ala Ala
    130                 135                 140

Thr Thr Asn Asn Gly Ser Gln Thr Pro Thr Thr Thr Ser Thr Pro Ser
145                 150                 155                 160

Asn Gly Thr Ile Tyr Ser Lys Thr Asp Leu Leu Leu Asn Asn Glu
                165                 170                 175

Lys Phe Ser Phe Tyr Ser Asn Leu Val Ser Gly Asp Gly Ala Ile
                180                 185                 190

Asp Ala Lys Ser Leu Thr Val Gln Gly Ile Ser Lys Leu Cys Val Phe
        195                 200                 205

Gln Glu Asn Thr Ala Gln Ala Asp Gly Ala Cys Gln Val Val Thr
    210                 215                 220

Ser Phe Ser Ala Met Ala Asn Glu Ala Pro Ile Ala Phe Ile Ala Asn
225                 230                 235                 240

Val Ala Gly Val Arg Gly Gly Ile Ala Ala Val Gln Asp Gly Gln
                245                 250                 255

Gln Gly Val Ser Ser Ser Thr Ser Thr Glu Asp Pro Val Val Ser Phe
            260                 265                 270

Ser Arg Asn Thr Ala Val Glu Phe Asp Gly Asn Val Ala Arg Val Gly
        275                 280                 285

Gly Gly Ile Tyr Ser Tyr Gly Asn Val Ala Phe Leu Asn Asn Gly Lys
    290                 295                 300

Thr Leu Phe Leu Asn Asn Val Ala Ser Pro Val Tyr Ile Ala Ala Glu
305                 310                 315                 320

Gln Pro Thr Asn Gly Gln Ala Ser Asn Thr Ser Asp Asn Tyr Gly Asp
                325                 330                 335

Gly Gly Ala Ile Phe Cys Lys Asn Gly Ala Gln Ala Ala Gly Ser Asn
            340                 345                 350

Asn Ser Gly Ser Val Ser Phe Asp Gly Glu Gly Val Val Phe Phe Ser
        355                 360                 365

Ser Asn Val Ala Ala Gly Lys Gly Gly Ala Ile Tyr Ala Lys Lys Leu
    370                 375                 380

Ser Val Ala Asn Cys Gly Pro Val Gln Phe Leu Gly Asn Ile Ala Asn
385                 390                 395                 400

Asp Gly Gly Ala Ile Tyr Leu Gly Glu Ser Gly Glu Leu Ser Leu Ser
                405                 410                 415

Ala Asp Tyr Gly Asp Ile Ile Phe Asp Gly Asn Leu Lys Arg Thr Ala
            420                 425                 430

Lys Glu Asn Ala Ala Asp Val Asn Gly Val Thr Val Ser Ser Gln Ala
        435                 440                 445

Ile Ser Met Gly Ser Gly Gly Lys Ile Thr Thr Leu Arg Ala Lys Ala
    450                 455                 460

Gly His Gln Ile Leu Phe Asn Asp Pro Ile Glu Met Ala Asn Gly Asn
465                 470                 475                 480

Asn Gln Pro Ala Gln Ser Ser Glu Pro Leu Lys Ile Asn Asp Gly Glu
                485                 490                 495
```

```
Gly Tyr Thr Gly Asp Ile Val Phe Ala Asn Gly Asn Ser Thr Leu Tyr
            500                 505                 510

Gln Asn Val Thr Ile Glu Gln Gly Arg Ile Val Leu Arg Glu Lys Ala
            515                 520                 525

Lys Leu Ser Val Asn Ser Ser Gln Thr Gly Gly Ser Leu Tyr Met
530                 535                 540

Glu Ala Gly Ser Thr Leu Asp Phe Val Thr Pro Gln Pro Gln Gln
545                 550                 555                 560

Pro Pro Ala Ala Asn Gln Leu Ile Thr Leu Ser Asn Leu His Leu Ser
            565                 570                 575

Leu Ser Ser Leu Leu Ala Asn Asn Ala Val Thr Asn Pro Pro Thr Asn
            580                 585                 590

Pro Pro Ala Gln Asp Ser His Pro Ala Ile Ile Gly Ser Thr Thr Ala
            595                 600                 605

Gly Ser Val Thr Ile Ser Gly Pro Ile Phe Phe Glu Asp Leu Asp Asp
            610                 615                 620

Thr Ala Tyr Asp Arg Tyr Asp Trp Leu Gly Ser Asn Gln Lys Ile Asp
625                 630                 635                 640

Val Leu Lys Leu Gln Leu Gly Thr Gln Pro Ser Ala Asn Ala Pro Ser
            645                 650                 655

Asp Leu Thr Leu Gly Asn Glu Met Pro Lys Tyr Gly Tyr Gln Gly Ser
            660                 665                 670

Trp Lys Leu Ala Trp Asp Pro Asn Thr Ala Asn Asn Gly Pro Tyr Thr
            675                 680                 685

Leu Lys Ala Thr Trp Thr Lys Thr Gly Tyr Asn Pro Gly Pro Glu Arg
            690                 695                 700

Val Ala Ser Leu Val Pro Asn Ser Leu Trp Gly Ser Ile Leu Asp Ile
705                 710                 715                 720

Arg Ser Ala His Ser Ala Ile Gln Ala Ser Val Asp Gly Arg Ser Tyr
            725                 730                 735

Cys Arg Gly Leu Trp Val Ser Gly Val Ser Asn Phe Phe Tyr His Asp
            740                 745                 750

Arg Asp Ala Leu Gly Gln Gly Tyr Arg Tyr Ile Ser Gly Gly Tyr Ser
            755                 760                 765

Leu Gly Ala Asn Ser Tyr Phe Gly Ser Ser Met Phe Gly Leu Ala Phe
            770                 775                 780

Thr Glu Val Phe Gly Arg Ser Lys Asp Tyr Val Val Cys Arg Ser Asn
785                 790                 795                 800

His His Ala Cys Ile Gly Ser Val Tyr Leu Ser Thr Lys Gln Ala Leu
            805                 810                 815

Cys Gly Ser Tyr Leu Phe Gly Asp Ala Phe Ile Arg Ala Ser Tyr Gly
            820                 825                 830

Phe Gly Asn Gln His Met Lys Thr Ser Tyr Thr Phe Ala Glu Glu Ser
            835                 840                 845

Asp Val Arg Trp Asp Asn Asn Cys Leu Val Gly Glu Ile Gly Val Gly
850                 855                 860

Leu Pro Ile Val Ile Thr Pro Ser Lys Leu Tyr Leu Asn Glu Leu Arg
865                 870                 875                 880

Pro Phe Val Gln Ala Glu Phe Ser Tyr Ala Asp His Glu Ser Phe Thr
            885                 890                 895

Glu Glu Gly Asp Gln Ala Arg Ala Phe Arg Ser Gly His Leu Met Asn
            900                 905                 910

Leu Ser Val Pro Val Gly Val Lys Phe Asp Arg Cys Ser Ser Thr His
```

```
                    915                 920                 925

Pro Asn Lys Tyr Ser Phe Met Gly Ala Tyr Ile Cys Asp Ala Tyr Arg
    930                 935                 940

Thr Ile Ser Gly Thr Gln Thr Thr Leu Leu Ser His Gln Glu Thr Trp
945                 950                 955                 960

Thr Thr Asp Ala Phe His Leu Ala Arg His Gly Val Ile Val Arg Gly
                965                 970                 975

Ser Met Tyr Ala Ser Leu Thr Ser Asn Ile Glu Val Tyr Gly His Gly
            980                 985                 990

Arg Tyr Glu Tyr Arg Asp Thr Ser Arg Gly Tyr Gly Leu Ser Ala Gly
        995                 1000                1005

Ser Lys Val Arg Phe
    1010

<210> SEQ ID NO 69
<211> LENGTH: 1016
<212> TYPE: PRT
<213> ORGANISM: Chlamydia trachomatis

<400> SEQUENCE: 69

Met Pro Phe Ser Leu Arg Ser Thr Ser Phe Cys Phe Leu Ala Cys Leu
1               5                   10                  15

Cys Ser Tyr Ser Tyr Gly Phe Ala Ser Ser Pro Gln Val Leu Thr Pro
            20                  25                  30

Asn Val Thr Thr Pro Phe Lys Gly Asp Asp Val Tyr Leu Asn Gly Asp
        35                  40                  45

Cys Ala Phe Val Asn Val Tyr Ala Gly Ala Glu Asn Gly Ser Ile Ile
50                  55                  60

Ser Ala Asn Gly Asp Asn Leu Thr Ile Thr Gly Gln Asn His Thr Leu
65                  70                  75                  80

Ser Phe Thr Asp Ser Gln Gly Pro Val Leu Gln Asn Tyr Ala Phe Ile
                85                  90                  95

Ser Ala Gly Glu Thr Leu Thr Leu Lys Asp Phe Ser Ser Leu Met Phe
            100                 105                 110

Ser Lys Asn Val Ser Cys Gly Glu Lys Gly Met Ile Ser Gly Lys Thr
        115                 120                 125

Val Ser Ile Ser Gly Ala Gly Glu Val Ile Phe Trp Asp Asn Ser Val
    130                 135                 140

Gly Tyr Ser Pro Leu Ser Ile Val Pro Ala Ser Thr Pro Thr Pro Pro
145                 150                 155                 160

Ala Pro Ala Pro Ala Pro Ala Ala Ser Ser Ser Leu Ser Pro Thr Val
                165                 170                 175

Ser Asp Ala Arg Lys Gly Ser Ile Phe Ser Val Glu Thr Ser Leu Glu
            180                 185                 190

Ile Ser Gly Val Lys Lys Gly Val Met Phe Asp Asn Asn Ala Gly Asn
        195                 200                 205

Phe Gly Thr Val Phe Arg Gly Asn Ser Asn Asn Ala Gly Ser Gly
    210                 215                 220

Gly Ser Gly Ser Ala Thr Thr Pro Ser Phe Thr Val Lys Asn Cys Lys
225                 230                 235                 240

Gly Lys Val Ser Phe Thr Asp Asn Val Ala Ser Cys Gly Gly Gly Val
                245                 250                 255

Val Tyr Lys Gly Thr Val Leu Phe Lys Asp Asn Glu Gly Gly Ile Phe
            260                 265                 270

Phe Arg Gly Asn Thr Ala Tyr Asp Asp Leu Gly Ile Leu Ala Ala Thr
```

```
                    275                 280                 285
Ser Arg Asp Gln Asn Thr Glu Thr Gly Gly Gly Gly Val Ile Cys
290                 295                 300
Ser Pro Asp Ser Val Lys Phe Glu Gly Asn Lys Gly Ser Ile Val
305                 310                 315                 320
Phe Asp Tyr Asn Phe Ala Lys Gly Arg Gly Gly Ser Ile Leu Thr Lys
                325                 330                 335
Glu Phe Ser Leu Val Ala Asp Asp Ser Val Val Phe Ser Asn Asn Thr
                340                 345                 350
Ala Glu Lys Gly Gly Gly Ala Ile Tyr Ala Pro Thr Ile Asp Ile Ser
                355                 360                 365
Thr Asn Gly Gly Ser Ile Leu Phe Glu Arg Asn Arg Ala Ala Glu Gly
            370                 375                 380
Gly Ala Ile Cys Val Ser Glu Ala Ser Ser Gly Ser Thr Gly Asn Leu
385                 390                 395                 400
Thr Leu Ser Ala Ser Asp Gly Asp Ile Val Phe Ser Gly Asn Met Thr
                405                 410                 415
Ser Asp Arg Pro Gly Glu Arg Ser Ala Ala Arg Ile Leu Ser Asp Gly
                420                 425                 430
Thr Thr Val Ser Leu Asn Ala Ser Gly Leu Ser Lys Leu Ile Phe Tyr
            435                 440                 445
Asp Pro Val Val Gln Asn Asn Ser Ala Ala Gly Ala Ser Thr Pro Ser
450                 455                 460
Pro Ser Ser Ser Met Pro Gly Ala Val Thr Ile Asn Gln Ser Gly
465                 470                 475                 480
Asn Gly Ser Val Ile Phe Thr Ala Glu Ser Leu Thr Pro Ser Glu Lys
                485                 490                 495
Leu Gln Val Leu Asn Ser Thr Ser Asn Phe Pro Gly Ala Leu Thr Val
                500                 505                 510
Ser Gly Gly Glu Leu Val Val Thr Glu Gly Ala Thr Leu Thr Thr Gly
                515                 520                 525
Thr Ile Thr Ala Thr Ser Gly Arg Val Thr Leu Gly Ser Gly Ala Ser
                530                 535                 540
Leu Ser Ala Val Ala Gly Ala Ala Asn Asn Asn Tyr Thr Cys Thr Val
545                 550                 555                 560
Ser Lys Leu Gly Ile Asp Leu Glu Ser Phe Leu Thr Pro Asn Tyr Lys
                565                 570                 575
Thr Ala Ile Leu Gly Ala Asp Gly Thr Val Thr Val Asn Ser Gly Ser
                580                 585                 590
Thr Leu Asp Leu Val Met Glu Ser Glu Ala Glu Val Tyr Asp Asn Pro
                595                 600                 605
Leu Phe Val Gly Ser Leu Thr Ile Pro Phe Val Thr Leu Ser Ser Ser
                610                 615                 620
Ser Ala Ser Asn Gly Val Thr Lys Asn Ser Val Thr Ile Asn Asp Ala
625                 630                 635                 640
Asp Ala Ala His Tyr Gly Tyr Gln Gly Ser Trp Ser Ala Asp Trp Thr
                645                 650                 655
Lys Pro Pro Leu Ala Pro Asp Ala Lys Gly Met Val Pro Pro Asn Thr
                660                 665                 670
Asn Asn Thr Leu Tyr Leu Thr Trp Arg Pro Ala Ser Asn Tyr Gly Glu
            675                 680                 685
Tyr Arg Leu Asp Pro Gln Arg Lys Gly Glu Leu Val Pro Asn Ser Leu
690                 695                 700
```

```
Trp Val Ala Gly Ser Ala Leu Arg Thr Phe Thr Asn Gly Leu Lys Glu
705                 710                 715                 720

His Tyr Val Ser Arg Asp Val Gly Phe Val Ala Ser Leu His Ala Leu
                725                 730                 735

Gly Asp Tyr Ile Leu Asn Tyr Thr Gln Asp Asp Arg Asp Gly Phe Leu
            740                 745                 750

Ala Arg Tyr Gly Gly Phe Gln Ala Thr Ala Ala Ser His Tyr Glu Asn
        755                 760                 765

Gly Ser Ile Phe Gly Val Ala Phe Gly Gln Leu Tyr Gly Gln Thr Lys
    770                 775                 780

Ser Arg Met Tyr Tyr Ser Lys Asp Ala Gly Asn Met Thr Met Leu Ser
785                 790                 795                 800

Cys Phe Gly Arg Ser Tyr Val Asp Ile Lys Gly Thr Glu Thr Val Met
                805                 810                 815

Tyr Trp Glu Thr Ala Tyr Gly Tyr Ser Val His Arg Met His Thr Gln
            820                 825                 830

Tyr Phe Asn Asp Lys Thr Gln Lys Phe Asp His Ser Lys Cys His Trp
        835                 840                 845

His Asn Asn Tyr Tyr Ala Phe Val Gly Ala Glu His Asn Phe Leu
    850                 855                 860

Glu Tyr Cys Ile Pro Thr Arg Gln Phe Ala Arg Asp Tyr Glu Leu Thr
865                 870                 875                 880

Gly Phe Met Arg Phe Glu Met Ala Gly Gly Trp Ser Ser Thr Arg
                885                 890                 895

Glu Thr Gly Ser Leu Thr Arg Tyr Phe Ala Arg Gly Ser Gly His Asn
            900                 905                 910

Met Ser Leu Pro Ile Gly Ile Val Ala His Ala Val Ser His Val Arg
        915                 920                 925

Arg Ser Pro Pro Ser Lys Leu Thr Leu Asn Met Gly Tyr Arg Pro Asp
    930                 935                 940

Ile Trp Arg Val Thr Pro His Cys Asn Met Glu Ile Ile Ala Asn Gly
945                 950                 955                 960

Val Lys Thr Pro Ile Gln Gly Ser Pro Leu Ala Arg His Ala Phe Phe
                965                 970                 975

Leu Glu Val His Asp Thr Leu Tyr Ile His His Phe Gly Arg Ala Tyr
            980                 985                 990

Met Asn Tyr Ser Leu Asp Ala Arg Arg Gln Thr Ala His Phe Val
        995                 1000                1005

Ser Met Gly Leu Asn Arg Ile Phe
    1010                1015

<210> SEQ ID NO 70
<211> LENGTH: 878
<212> TYPE: PRT
<213> ORGANISM: Chlamydia trachomatis

<400> SEQUENCE: 70

Met Arg Pro Asp His Met Asn Phe Cys Cys Leu Cys Ala Ala Ile Leu
1               5                   10                  15

Ser Ser Thr Ala Val Leu Phe Gly Gln Asp Pro Leu Gly Glu Thr Ala
                20                  25                  30

Leu Leu Thr Lys Asn Pro Asn His Val Val Cys Thr Phe Phe Glu Asp
            35                  40                  45

Cys Thr Met Glu Ser Leu Phe Pro Ala Leu Cys Ala His Ala Ser Gln
        50                  55                  60
```

-continued

```
Asp Asp Pro Leu Tyr Val Leu Gly Asn Ser Tyr Cys Trp Phe Val Ser
65                  70                  75                  80

Lys Leu His Ile Thr Asp Pro Lys Glu Ala Leu Phe Lys Glu Lys Gly
                85                  90                  95

Asp Leu Ser Ile Gln Asn Phe Arg Phe Leu Ser Phe Thr Asp Cys Ser
            100                 105                 110

Ser Lys Glu Ser Ser Pro Ser Ile Ile His Gln Lys Asn Gly Gln Leu
        115                 120                 125

Ser Leu Arg Asn Asn Gly Ser Met Ser Phe Cys Arg Asn His Ala Glu
    130                 135                 140

Gly Ser Gly Gly Ala Ile Ser Ala Asp Ala Phe Ser Leu Gln His Asn
145                 150                 155                 160

Tyr Leu Phe Thr Ala Phe Glu Glu Asn Ser Ser Lys Gly Asn Gly Gly
                165                 170                 175

Ala Ile Gln Ala Gln Thr Phe Ser Leu Ser Arg Asn Val Ser Pro Ile
            180                 185                 190

Ser Phe Ala Arg Asn Arg Ala Asp Leu Asn Gly Gly Ala Ile Cys Cys
        195                 200                 205

Ser Asn Leu Ile Cys Ser Gly Asn Val Asn Pro Leu Phe Phe Thr Gly
    210                 215                 220

Asn Ser Ala Thr Asn Gly Gly Ala Ile Cys Cys Ile Ser Asp Leu Asn
225                 230                 235                 240

Thr Ser Glu Lys Gly Ser Leu Ser Leu Ala Cys Asn Gln Glu Thr Leu
                245                 250                 255

Phe Ala Ser Asn Ser Ala Lys Glu Lys Gly Gly Ala Ile Tyr Ala Lys
            260                 265                 270

His Met Val Leu Arg Tyr Asn Gly Pro Val Ser Phe Ile Asn Asn Ser
        275                 280                 285

Ala Lys Ile Gly Gly Ala Ile Ala Ile Gln Ser Gly Gly Ser Leu Ser
    290                 295                 300

Ile Leu Ala Gly Glu Gly Ser Val Leu Phe Gln Asn Asn Ser Gln Arg
305                 310                 315                 320

Thr Ser Asp Gln Gly Leu Val Arg Asn Ala Ile Tyr Leu Glu Lys Asp
                325                 330                 335

Ala Ile Leu Ser Ser Leu Glu Ala Arg Asn Gly Asp Ile Leu Phe Phe
            340                 345                 350

Asp Pro Ile Val Gln Glu Ser Ser Lys Glu Ser Pro Leu Pro Ser
        355                 360                 365

Ser Leu Gln Ala Ser Val Thr Ser Pro Thr Pro Thr Ala Ser Pro
370                 375                 380

Leu Val Ile Gln Thr Ser Ala Asn Arg Ser Val Ile Phe Ser Ser Glu
385                 390                 395                 400

Arg Leu Ser Glu Glu Glu Lys Thr Pro Asp Asn Leu Thr Ser Gln Leu
                405                 410                 415

Gln Gln Pro Ile Glu Leu Lys Ser Gly Arg Leu Val Leu Lys Asp Arg
            420                 425                 430

Ala Val Leu Ser Ala Pro Ser Leu Ser Gln Asp Pro Gln Ala Leu Leu
        435                 440                 445

Ile Met Glu Ala Gly Thr Ser Leu Lys Thr Ser Ser Asp Leu Lys Leu
    450                 455                 460

Ala Thr Leu Ser Ile Pro Leu His Ser Leu Asp Thr Glu Lys Ser Val
465                 470                 475                 480

Thr Ile His Ala Pro Asn Leu Ser Ile Gln Lys Ile Phe Leu Ser Asn
                485                 490                 495
```

Ser Gly Asp Glu Asn Phe Tyr Glu Asn Val Glu Leu Leu Ser Lys Glu
            500                 505                 510

Gln Asn Asn Ile Pro Leu Leu Thr Leu Ser Lys Glu Gln Ser His Leu
        515                 520                 525

His Leu Pro Asp Gly Asn Leu Ser Ser His Phe Gly Tyr Gln Gly Asp
    530                 535                 540

Trp Thr Phe Ser Trp Lys Asp Ser Asp Glu Gly His Ser Leu Ile Ala
545                 550                 555                 560

Asn Trp Thr Pro Lys Asn Tyr Val Pro His Pro Glu Arg Gln Ser Thr
                565                 570                 575

Leu Val Ala Asn Thr Leu Trp Asn Thr Tyr Ser Asp Met Gln Ala Val
            580                 585                 590

Gln Ser Met Ile Asn Thr Ile Ala His Gly Gly Ala Tyr Leu Phe Gly
        595                 600                 605

Thr Trp Gly Ser Ala Val Ser Asn Leu Phe Tyr Ala His Asp Ser Ser
    610                 615                 620

Gly Lys Pro Ile Asp Asn Trp His His Arg Ser Leu Gly Tyr Leu Phe
625                 630                 635                 640

Gly Ile Ser Thr His Ser Leu Asp Asp His Ser Phe Cys Leu Ala Ala
                645                 650                 655

Gly Gln Leu Leu Gly Lys Ser Ser Asp Ser Phe Ile Thr Ser Thr Glu
            660                 665                 670

Thr Thr Ser Tyr Ile Ala Thr Val Gln Ala Gln Leu Ala Thr Pro Leu
        675                 680                 685

Met Lys Ile Ser Ala Gln Ala Cys Tyr Asn Glu Ser Ile His Glu Leu
    690                 695                 700

Lys Thr Lys Tyr Arg Ser Phe Ser Lys Glu Gly Phe Gly Ser Trp His
705                 710                 715                 720

Ser Val Ala Val Ser Gly Glu Val Cys Ala Ser Ile Pro Ile Val Ser
                725                 730                 735

Asn Gly Ser Gly Leu Phe Ser Ser Phe Ser Ile Phe Ser Lys Leu Gln
            740                 745                 750

Gly Phe Ser Gly Thr Gln Asp Gly Phe Glu Glu Ser Ser Gly Glu Ile
        755                 760                 765

Arg Ser Phe Ser Ala Ser Ser Phe Arg Asn Ile Ser Leu Pro Met Gly
    770                 775                 780

Ile Thr Phe Glu Lys Lys Ser Gln Lys Thr Arg Asn Tyr Tyr Phe
785                 790                 795                 800

Leu Gly Ala Tyr Ile Gln Asp Leu Lys Arg Asp Val Glu Ser Gly Pro
                805                 810                 815

Val Val Leu Leu Lys Asn Ala Val Ser Trp Asp Ala Pro Met Ala Asn
            820                 825                 830

Leu Asp Ser Arg Ala Tyr Met Phe Arg Leu Thr Asn Gln Arg Ala Leu
        835                 840                 845

His Arg Leu Gln Thr Leu Leu Asn Val Ser Tyr Val Leu Arg Gly Gln
    850                 855                 860

Ser His Ser Tyr Ser Leu Asp Leu Gly Thr Thr Tyr Arg Phe
865                 870                 875

<210> SEQ ID NO 71
<211> LENGTH: 298
<212> TYPE: PRT
<213> ORGANISM: Chlamydia trachomatis

<400> SEQUENCE: 71

```
Met Ala Ser Ile Cys Gly Arg Leu Gly Ser Gly Thr Gly Asn Ala Leu
1               5                   10                  15

Lys Ala Phe Phe Thr Gln Pro Asn Asn Lys Met Ala Arg Val Val Asn
            20                  25                  30

Lys Thr Lys Gly Met Asp Lys Thr Ile Lys Val Ala Lys Ser Ala Ala
        35                  40                  45

Glu Leu Thr Ala Asn Ile Leu Glu Gln Ala Gly Ala Gly Ser Ser
50                  55                  60

Ala His Ile Thr Ala Ser Gln Val Ser Lys Gly Leu Gly Asp Ala Arg
65                  70                  75                  80

Thr Val Val Ala Leu Gly Asn Ala Phe Asn Gly Ala Leu Pro Gly Thr
                85                  90                  95

Val Gln Ser Ala Gln Ser Phe Phe Ser His Met Lys Ala Ser Gln
            100                 105                 110

Lys Thr Gln Glu Gly Asp Glu Gly Leu Thr Ala Asp Leu Cys Val Ser
        115                 120                 125

His Lys Arg Arg Ala Ala Ala Val Cys Ser Ile Ile Gly Gly Ile
    130                 135                 140

Thr Tyr Leu Ala Thr Phe Gly Ala Ile Arg Pro Ile Leu Phe Val Asn
145                 150                 155                 160

Lys Met Leu Ala Lys Pro Phe Leu Ser Ser Gln Thr Lys Ala Asn Met
                165                 170                 175

Gly Ser Ser Val Ser Tyr Ile Met Ala Ala Asn His Ala Ala Ser Val
            180                 185                 190

Val Gly Ala Gly Leu Ala Ile Ser Ala Glu Arg Ala Asp Cys Glu Ala
        195                 200                 205

Arg Cys Ala Arg Ile Ala Arg Glu Glu Ser Leu Leu Glu Val Pro Gly
210                 215                 220

Glu Glu Asn Ala Cys Glu Lys Lys Val Ala Gly Glu Lys Ala Lys Thr
225                 230                 235                 240

Phe Thr Arg Ile Lys Tyr Ala Leu Leu Thr Met Leu Glu Lys Phe Leu
                245                 250                 255

Glu Cys Val Ala Asp Val Phe Lys Leu Val Pro Leu Pro Ile Thr Met
            260                 265                 270

Gly Ile Arg Ala Ile Val Ala Ala Gly Cys Thr Phe Thr Ser Ala Ile
        275                 280                 285

Ile Gly Leu Cys Thr Phe Cys Ala Arg Ala
    290                 295

<210> SEQ ID NO 72
<211> LENGTH: 10
<212> TYPE: PRT
<213> ORGANISM: Chlamydia trachomatis

<400> SEQUENCE: 72

Cys Ser Phe Ile Gly Gly Ile Thr Tyr Leu
1               5                   10

<210> SEQ ID NO 73
<211> LENGTH: 9
<212> TYPE: PRT
<213> ORGANISM: Chlamydia trachomatis

<400> SEQUENCE: 73

Ser Phe Ile Gly Gly Ile Thr Tyr Leu
1               5
```

<210> SEQ ID NO 74
<211> LENGTH: 9
<212> TYPE: PRT
<213> ORGANISM: Chlamydia trachomatis

<400> SEQUENCE: 74

Ser Ile Ile Gly Gly Ile Thr Tyr Leu
1               5

<210> SEQ ID NO 75
<211> LENGTH: 544
<212> TYPE: PRT
<213> ORGANISM: Chlamydia trachomatis

<400> SEQUENCE: 75

Met Val Ala Lys Asn Ile Lys Tyr Asn Glu Glu Ala Arg Lys Lys Ile
1               5                   10                  15

Gln Lys Gly Val Lys Thr Leu Ala Glu Ala Val Lys Val Thr Leu Gly
                20                  25                  30

Pro Lys Gly Arg His Val Val Ile Asp Lys Ser Phe Gly Ser Pro Gln
            35                  40                  45

Val Thr Lys Asp Gly Val Thr Val Ala Lys Glu Val Glu Leu Ala Asp
50                  55                  60

Lys His Glu Asn Met Gly Ala Gln Met Val Lys Glu Val Ala Ser Lys
65                  70                  75                  80

Thr Ala Asp Lys Ala Gly Asp Gly Thr Thr Thr Ala Thr Val Leu Ala
                85                  90                  95

Glu Ala Ile Tyr Thr Glu Gly Leu Arg Asn Val Thr Ala Gly Ala Asn
            100                 105                 110

Pro Met Asp Leu Lys Arg Gly Ile Asp Lys Ala Val Lys Val Val Val
        115                 120                 125

Asp Gln Ile Arg Lys Ile Ser Lys Pro Val Gln His His Lys Glu Ile
130                 135                 140

Ala Gln Val Ala Thr Ile Ser Ala Asn Asn Asp Ala Glu Ile Gly Asn
145                 150                 155                 160

Leu Ile Ala Glu Ala Met Glu Lys Val Gly Lys Asn Gly Ser Ile Thr
                165                 170                 175

Val Glu Glu Ala Lys Gly Phe Glu Thr Val Leu Asp Ile Val Glu Gly
            180                 185                 190

Met Asn Phe Asn Arg Gly Tyr Leu Ser Ser Tyr Phe Ala Thr Asn Pro
        195                 200                 205

Glu Thr Gln Glu Cys Val Leu Glu Asp Ala Leu Val Leu Ile Tyr Asp
    210                 215                 220

Lys Lys Ile Ser Gly Ile Lys Asp Phe Leu Pro Val Leu Gln Gln Val
225                 230                 235                 240

Ala Glu Ser Gly Arg Pro Leu Leu Ile Ile Ala Glu Asp Ile Glu Gly
                245                 250                 255

Glu Ala Leu Ala Thr Leu Val Val Asn Arg Ile Arg Gly Gly Phe Arg
            260                 265                 270

Val Cys Ala Val Lys Ala Pro Gly Phe Gly Asp Arg Arg Lys Ala Met
        275                 280                 285

Leu Glu Asp Ile Ala Ile Leu Thr Gly Gly Gln Leu Ile Ser Glu Glu
    290                 295                 300

Leu Gly Met Lys Leu Glu Asn Ala Asn Leu Ala Met Leu Gly Lys Ala
305                 310                 315                 320

Lys Lys Val Ile Val Ser Lys Glu Asp Thr Thr Ile Val Glu Gly Met

```
                        325                 330                 335
Gly Glu Lys Glu Ala Leu Glu Ala Arg Cys Glu Ser Ile Lys Lys Gln
            340                 345                 350

Ile Glu Asp Ser Ser Ser Asp Tyr Asp Lys Glu Lys Leu Gln Glu Arg
            355                 360                 365

Leu Ala Lys Leu Ser Gly Gly Val Ala Val Ile Arg Val Gly Ala Ala
            370                 375                 380

Thr Glu Ile Glu Met Lys Glu Lys Lys Asp Arg Val Asp Asp Ala Gln
385                 390                 395                 400

His Ala Thr Ile Ala Ala Val Glu Gly Ile Leu Pro Gly Gly Gly
                405                 410                 415

Thr Ala Leu Ile Arg Cys Ile Pro Thr Leu Glu Ala Phe Leu Pro Met
            420                 425                 430

Leu Thr Asn Glu Asp Glu Gln Ile Gly Ala Arg Ile Val Leu Lys Ala
            435                 440                 445

Leu Ser Ala Pro Leu Lys Gln Ile Ala Ala Asn Ala Gly Lys Glu Gly
            450                 455                 460

Ala Ile Ile Phe Gln Gln Val Met Ser Arg Ser Ala Asn Glu Gly Tyr
465                 470                 475                 480

Asp Ala Leu Arg Asp Ala Tyr Thr Asp Met Leu Glu Ala Gly Ile Leu
            485                 490                 495

Asp Pro Ala Lys Val Thr Arg Ser Ala Leu Glu Ser Ala Ala Ser Val
            500                 505                 510

Ala Gly Leu Leu Leu Thr Thr Glu Ala Leu Ile Ala Glu Ile Pro Glu
            515                 520                 525

Glu Lys Pro Ala Ala Ala Pro Ala Met Pro Gly Ala Gly Met Asp Tyr
            530                 535                 540

<210> SEQ ID NO 76
<211> LENGTH: 547
<212> TYPE: PRT
<213> ORGANISM: Chlamydia trachomatis

<400> SEQUENCE: 76

Met Asn Lys Leu Ile Arg Arg Ala Val Thr Ile Phe Ala Val Thr Ser
1               5                   10                  15

Val Ala Ser Leu Phe Ala Ser Gly Val Leu Glu Thr Ser Met Ala Glu
            20                  25                  30

Phe Thr Ser Thr Asn Val Ile Ser Leu Ala Asp Thr Lys Ala Lys Asp
            35                  40                  45

Asn Thr Ser His Lys Ser Lys Lys Ala Arg Lys Asn His Ser Lys Glu
        50                  55                  60

Thr Leu Val Asp Arg Lys Glu Val Ala Pro Val His Glu Ser Lys Ala
65                  70                  75                  80

Thr Gly Pro Lys Gln Asp Ser Cys Phe Gly Arg Met Tyr Thr Val Lys
                85                  90                  95

Val Asn Asp Asp Arg Asn Val Glu Ile Thr Gln Ala Val Pro Glu Tyr
            100                 105                 110

Ala Thr Val Gly Ser Pro Tyr Pro Leu Glu Ile Thr Ala Thr Gly Lys
            115                 120                 125

Arg Asp Cys Ala Asp Val Ile Ile Thr Gln Leu Pro Cys Glu Ala
            130                 135                 140

Glu Phe Val Arg Ser Asp Pro Ala Thr Pro Thr Ala Asp Gly Lys
145                 150                 155                 160

Leu Val Trp Lys Ile Asp Arg Leu Gly Gln Gly Glu Lys Ser Lys Ile
```

```
                        165                 170                 175
Thr Val Trp Val Lys Pro Leu Lys Glu Gly Cys Cys Phe Thr Ala Ala
                180                 185                 190
Thr Val Cys Ala Cys Pro Glu Ile Arg Ser Val Thr Lys Cys Gly Gln
            195                 200                 205
Pro Ala Ile Cys Val Lys Gln Glu Gly Pro Glu Asn Ala Cys Leu Arg
        210                 215                 220
Cys Pro Val Val Tyr Lys Ile Asn Val Val Asn Gln Gly Thr Ala Ile
225                 230                 235                 240
Ala Arg Asn Val Val Glu Asn Pro Val Pro Asp Gly Tyr Ala His
                245                 250                 255
Ser Ser Gly Gln Arg Val Leu Thr Phe Thr Leu Gly Asp Met Gln Pro
            260                 265                 270
Gly Glu His Arg Thr Ile Thr Val Glu Phe Cys Pro Leu Lys Arg Gly
        275                 280                 285
Arg Ala Thr Asn Ile Ala Thr Val Ser Tyr Cys Gly Gly His Lys Asn
        290                 295                 300
Thr Ala Ser Val Thr Thr Val Ile Asn Glu Pro Cys Val Gln Val Ser
305                 310                 315                 320
Ile Ala Gly Ala Asp Trp Ser Tyr Val Cys Lys Pro Val Glu Tyr Val
                325                 330                 335
Ile Ser Val Ser Asn Pro Gly Asp Leu Val Leu Arg Asp Val Val
            340                 345                 350
Glu Asp Thr Leu Ser Pro Gly Val Thr Val Leu Glu Ala Ala Gly Ala
        355                 360                 365
Gln Ile Ser Cys Asn Lys Val Val Trp Thr Val Lys Glu Leu Asn Pro
        370                 375                 380
Gly Glu Ser Leu Gln Tyr Lys Val Leu Val Arg Ala Gln Thr Pro Gly
385                 390                 395                 400
Gln Phe Thr Asn Asn Val Val Val Lys Ser Cys Ser Asp Cys Gly Thr
                405                 410                 415
Cys Thr Ser Cys Ala Glu Ala Thr Thr Tyr Trp Lys Gly Val Ala Ala
            420                 425                 430
Thr His Met Cys Val Val Asp Thr Cys Asp Pro Val Cys Val Gly Glu
        435                 440                 445
Asn Thr Val Tyr Arg Ile Cys Val Thr Ser Arg Gly Ser Ala Glu Asp
        450                 455                 460
Thr Asn Val Ser Leu Met Leu Lys Phe Ser Lys Glu Leu Gln Pro Val
465                 470                 475                 480
Ser Phe Ser Gly Pro Thr Lys Gly Thr Ile Thr Gly Asn Thr Val Val
                485                 490                 495
Phe Asp Ser Leu Pro Arg Leu Gly Ser Lys Glu Thr Val Glu Phe Ser
            500                 505                 510
Val Thr Leu Lys Ala Val Ser Ala Gly Asp Ala Arg Gly Glu Ala Ile
        515                 520                 525
Leu Ser Ser Asp Thr Leu Thr Val Pro Val Ser Asp Thr Glu Asn Thr
        530                 535                 540
His Ile Tyr
545

<210> SEQ ID NO 77
<211> LENGTH: 326
<212> TYPE: PRT
<213> ORGANISM: Chlamydia trachomatis
```

<400> SEQUENCE: 77

```
Met Phe Arg Tyr Thr Leu Ser Arg Ser Leu Phe Phe Ile Leu Ala Leu
1               5                   10                  15

Phe Phe Cys Ser Ala Cys Asp Ser Arg Ser Met Ile Thr His Gly Leu
            20                  25                  30

Ser Gly Arg Asp Ala Asn Glu Ile Val Val Leu Leu Val Ser Lys Gly
        35                  40                  45

Val Ala Ala Gln Lys Val Pro Gln Ala Ala Ser Ser Thr Gly Gly Ser
50                  55                  60

Gly Glu Gln Leu Trp Asp Ile Ser Val Pro Ala Ala Gln Ile Thr Glu
65                  70                  75                  80

Ala Leu Ala Ile Leu Asn Gln Ala Gly Leu Pro Arg Met Lys Gly Thr
                85                  90                  95

Ser Leu Leu Asp Leu Phe Ala Lys Gln Gly Leu Val Pro Ser Glu Met
            100                 105                 110

Gln Glu Lys Ile Arg Tyr Gln Glu Gly Leu Ser Glu Gln Met Ala Thr
        115                 120                 125

Thr Ile Arg Lys Met Asp Gly Ile Val Asp Ala Ser Val Gln Ile Ser
130                 135                 140

Phe Ser Pro Glu Glu Glu Asp Gln Arg Pro Leu Thr Ala Ser Val Tyr
145                 150                 155                 160

Ile Lys His Arg Gly Val Leu Asp Asn Pro Asn Ser Ile Met Val Ser
                165                 170                 175

Lys Ile Lys Arg Leu Val Ala Ser Ala Val Pro Gly Leu Cys Pro Glu
            180                 185                 190

Asn Val Ser Val Val Ser Asp Arg Ala Ser Tyr Ser Asp Ile Thr Ile
        195                 200                 205

Asn Gly Pro Trp Gly Leu Ser Asp Glu Met Asn Tyr Val Ser Val Trp
210                 215                 220

Gly Ile Ile Leu Ala Lys His Ser Leu Thr Lys Phe Arg Leu Val Phe
225                 230                 235                 240

Tyr Phe Leu Ile Leu Leu Leu Phe Ile Leu Ser Cys Gly Leu Leu Trp
                245                 250                 255

Val Ile Trp Lys Thr His Thr Leu Ile Ser Ala Leu Gly Gly Thr Lys
            260                 265                 270

Gly Phe Phe Asp Pro Ala Pro Tyr Ser Gln Leu Ser Phe Thr Gln Asn
        275                 280                 285

Lys Pro Ala Pro Lys Glu Thr Pro Gly Ala Ala Glu Gly Ala Glu Ala
290                 295                 300

Gln Thr Ala Ser Glu Gln Pro Ser Lys Glu Asn Ala Glu Lys Gln Glu
305                 310                 315                 320

Glu Asn Asn Glu Asp Ala
                325

<210> SEQ ID NO 78
<211> LENGTH: 188
<212> TYPE: PRT
<213> ORGANISM: Chlamydia trachomatis

<400> SEQUENCE: 78

Met Arg Lys Thr Ile Phe Lys Ala Phe Asn Leu Leu Phe Ser Leu Leu
1               5                   10                  15

Phe Leu Ser Ser Cys Ser Tyr Pro Cys Arg Asp Trp Glu Cys His Gly
            20                  25                  30

Cys Asp Ser Ala Arg Pro Arg Lys Ser Ser Phe Gly Phe Val Pro Phe
```

```
                35                  40                  45
Tyr Ser Asp Glu Glu Ile Gln Gln Ala Phe Val Glu Asp Phe Asp Ser
             50                  55                  60
Lys Glu Glu Gln Leu Tyr Lys Thr Ser Ala Gln Ser Thr Ser Phe Arg
 65                  70                  75                  80
Asn Ile Thr Phe Ala Thr Asp Ser Tyr Ser Ile Lys Gly Glu Asp Asn
                 85                  90                  95
Leu Thr Ile Leu Ala Ser Leu Val Arg His Leu His Lys Ser Pro Lys
            100                 105                 110
Ala Thr Leu Tyr Ile Glu Gly His Thr Asp Glu Arg Gly Ala Ala Ala
            115                 120                 125
Tyr Asn Leu Ala Leu Gly Ala Arg Arg Ala Asn Ala Val Lys Gln Tyr
        130                 135                 140
Leu Ile Lys Gln Gly Ile Ala Ala Asp Arg Leu Phe Thr Ile Ser Tyr
145                 150                 155                 160
Gly Lys Glu His Pro Val His Pro Gly His Asn Glu Leu Ala Trp Gln
                165                 170                 175
Gln Asn Arg Arg Thr Glu Phe Lys Ile His Ala Arg
            180                 185

<210> SEQ ID NO 79
<211> LENGTH: 432
<212> TYPE: PRT
<213> ORGANISM: Chlamydia trachomatis

<400> SEQUENCE: 79

Met Lys Lys Tyr Phe Tyr Lys Gly Phe Val Gly Ala Leu Leu Leu Ala
 1               5                  10                  15
Cys Gly Ser Thr Asn Leu Ala Phe Ala Gln Ala Ser Ser Met Asp Ser
                20                  25                  30
Gln Leu Trp Ser Val Glu Asp Leu Asp Ser Tyr Leu Ser Ser Lys Gly
            35                  40                  45
Phe Val Glu Thr Arg Lys Arg Asp Gly Val Leu Arg Leu Ala Gly Asp
        50                  55                  60
Val Arg Ala Arg Trp Ile Tyr Ala Lys Glu Asp Leu Glu Thr Thr Gln
 65                  70                  75                  80
Thr Pro Ala Lys Pro Met Leu Pro Thr Asn Arg Tyr Arg Ser Glu Phe
                 85                  90                  95
Asn Leu Tyr Val Asp Tyr Thr Ala Ala Asn Ser Trp Met Thr Ser Lys
            100                 105                 110
Met Asn Trp Val Thr Ile Ala Gly Gly Glu Ser Ser Ala Ala Gly Leu
        115                 120                 125
Asp Ile Asn Arg Ala Phe Leu Gly Tyr Arg Phe Tyr Lys Asn Pro Glu
    130                 135                 140
Thr Gln Ala Glu Val Phe Ala Glu Ile Gly Arg Ser Gly Leu Gly Asp
145                 150                 155                 160
Ile Phe Asp Ser Asp Val Gln Phe Asn Ser Asn Phe Asp Gly Ile His
                165                 170                 175
Leu Tyr Ala Ala Arg Arg Ile Ser Glu Lys Leu Pro Phe Thr Met Ile
            180                 185                 190
Val His Gly Gly Pro Phe Val Val Asn Met Ala Glu Lys Glu Tyr Ala
        195                 200                 205
Trp Val Val Glu Ala Ile Leu Asn Lys Leu Pro Gly Asn Phe Val Val
    210                 215                 220
Lys Thr Ser Val Val Asp Trp Asn Thr Leu Thr Ala Lys Thr Asn Asp
```

```
                225                 230                 235                 240
Pro Ala Asp Ala Ser Ala Ala Gln Pro Ala Lys Pro Asn Thr Lys Tyr
                    245                 250                 255

Asp Tyr Leu Val Trp Gln Trp Leu Val Gly Lys Ser Thr Ala Met Pro
                260                 265                 270

Trp Phe Asn Gly Gln Thr Lys Asn Leu Tyr Thr Tyr Gly Ala Tyr Leu
                275                 280                 285

Phe Asn Pro Leu Ala Glu Ile Pro Glu Asn Trp Lys Gln Ser Thr Thr
            290                 295                 300

Pro Thr Thr Lys Ile Thr Asn Gly Lys Glu Asn His Ala Trp Phe Ile
305                 310                 315                 320

Gly Cys Ser Leu Gly Gly Val Arg Arg Ala Gly Asp Trp Ser Ala Thr
                325                 330                 335

Val Arg Tyr Glu Tyr Val Glu Ala Leu Ala Ile Pro Glu Ile Asp Val
                340                 345                 350

Ala Gly Ile Gly Arg Gly Asn Gln Met Lys Tyr Trp Phe Ala Gln Ala
                355                 360                 365

Ile Lys Gln Gly Leu Asp Pro Lys Glu Ser Asn Gly Phe Thr Asn Tyr
            370                 375                 380

Lys Gly Val Ser Tyr Gln Phe Val Met Gly Leu Thr Asp Ser Val Ser
385                 390                 395                 400

Phe Arg Ala Tyr Ala Ala Tyr Ser Lys Pro Ala Asn Asp Asn Leu Gly
                    405                 410                 415

Ser Asp Phe Thr Tyr Arg Lys Tyr Asp Leu Gly Leu Ile Ser Ser Phe
                420                 425                 430

<210> SEQ ID NO 80
<211> LENGTH: 441
<212> TYPE: PRT
<213> ORGANISM: Chlamydia trachomatis

<400> SEQUENCE: 80

Met Trp Leu Ile Val Ala Ser Thr Leu Leu Ala Cys Leu Ala Met Ala
1               5                   10                  15

Leu Val Phe Lys Ala Tyr Arg His Val Ile Ser Phe Arg Ser Tyr Val
                20                  25                  30

Asn Gln Val Ile Arg Asp Val Arg Leu Ser Val Asp Leu Lys Glu Trp
            35                  40                  45

Ala Val Ala Glu Met Arg Leu Ala Pro Ile Leu Lys Lys Arg Gln Tyr
        50                  55                  60

Arg Arg Lys Tyr Leu Phe Glu Tyr Ile Arg Ile Leu Arg Glu Leu Glu
65                  70                  75                  80

Arg Phe Glu Glu Ala Gly Lys Leu Leu Gly Glu Ala Lys Lys Leu Lys
                85                  90                  95

Leu Ala Gly Ala His Phe Phe Leu Glu Val Ala His Lys Ala Phe Arg
            100                 105                 110

His Gly Ala Tyr Lys Glu Ala Ala His Ala Phe Ser Leu Leu Ser Ala
        115                 120                 125

Glu Leu Met Gly Glu Arg Glu Val Ala Arg Tyr Thr Ile Ser Leu Val
    130                 135                 140

Tyr Leu Gly Glu Val Asp Ala Ala Cys Arg Ile Ile Glu Pro Trp Ile
145                 150                 155                 160

Gly Pro Leu Ala His Gln Glu Val Phe Ile Ser Val Gly His Ile Tyr
                165                 170                 175

Phe Ala Thr Lys Arg Tyr Ala Asp Ala Ile Asp Phe Tyr Arg Arg Ala
```

```
                180                 185                 190
Arg Ser Leu Gly Ser Cys Pro Ile Asp Val Leu Tyr Asn Leu Ala His
            195                 200                 205
Ser Leu Arg Ile Cys Gly Gln Tyr Val Asp Ala Gly Met Leu Phe Arg
            210                 215                 220
Glu Leu Leu Gly Asp Pro Val Tyr Lys Asp Glu Ala Met Phe Asn Ile
225                 230                 235                 240
Gly Leu Cys Glu Gln Lys Leu Gly Asn Ser Lys Lys Ala Leu Leu Ile
                245                 250                 255
Tyr Gln Asn Ser Glu Leu Trp Val Arg Gly Asp Ala Leu Met Met Arg
            260                 265                 270
Tyr Ala Ala Leu Ala Ala Asp Gln Gln Asp Tyr Gln Leu Ala Glu
            275                 280                 285
His Cys Trp Thr Leu Ala Phe Arg Cys Gln Ser Tyr Ala Asp Asp Trp
            290                 295                 300
Asn Cys Cys Val His Tyr Gly Leu Ala Leu Cys His Leu Lys Lys Tyr
305                 310                 315                 320
Ala Glu Ala Glu Lys Val Tyr Leu Arg Val Ile Gln Lys Thr Pro Asp
                325                 330                 335
Cys Leu Val Ala Cys Lys Ala Leu Ala Trp Leu Ala Gly Val Gly His
            340                 345                 350
Ala Thr Met Ile Ser Ala Arg Glu Gly Ile Ala Tyr Ala Lys Arg Ala
            355                 360                 365
Leu Gln Ile Lys Arg Ser Pro Glu Val Leu Glu Leu Ser Ala Cys
            370                 375                 380
Glu Ala Arg Glu Gly Asn Phe Asp Val Ala Tyr Asp Ile Gln Ala Ile
385                 390                 395                 400
Leu Ala Glu Arg Asp Thr Thr Ala Lys Glu Arg Glu Arg Arg Ser Gln
                405                 410                 415
Ile Leu Lys Asn Leu Arg Gln Lys Leu Pro Ile Asp Gln Gln His Ile
                420                 425                 430
Val Glu Val Ser Leu Leu Leu Ala Ala
            435                 440

<210> SEQ ID NO 81
<211> LENGTH: 393
<212> TYPE: PRT
<213> ORGANISM: Chlamydia trachomatis

<400> SEQUENCE: 81

Met Leu Val Glu Ser Gln Leu Gly Leu Glu Asp Val Leu Glu Ala Phe
1               5                   10                  15
Ser Glu Arg Asn Phe Asp Ile Gln Ser Lys Ser Phe Ile Glu Ser Phe
                20                  25                  30
Gln Asp Lys Lys Leu Arg Arg Thr Val Ile Gln Arg Phe Leu His His
            35                  40                  45
Pro Leu Leu His Ile His Asp Ile Ala Arg Ala Ala Tyr Leu Leu Ala
            50                  55                  60
Ala Leu Glu Glu Gly Val Asp Leu Gly Tyr Gln Phe Leu Cys Met His
65                  70                  75                  80
Gln Thr Gln Ser Gly Ala Ala Leu Leu Phe Arg Arg Ala Gly Phe Leu
                85                  90                  95
Trp Gly Gly Leu Pro Tyr Pro Gly Glu His Ala Glu Met Ala Met Leu
                100                 105                 110
Leu Ser Arg Ile Ala Glu Phe Tyr Asp Thr Ser Tyr Glu Gln Val Gln
```

```
                    115                 120                 125
Lys Met Ile Ala Phe Gln His Ala Leu Phe Ser His Glu Arg Asn Ile
    130                 135                 140

Phe Pro Ala Leu Trp Ser Gln Glu Gly Ser Arg Ser Asn Gln Glu Lys
145                 150                 155                 160

Thr Ala Val Ser Lys Leu Leu Phe Cys Gln Lys Glu Ala Arg Ile Glu
                165                 170                 175

Asp Gln Phe Thr Leu Thr Asp Met Ser Leu Gly Phe Trp Met Arg Arg
            180                 185                 190

Thr Pro Ser Phe Ser Ala Tyr Val Ser Gly Ser Gly Cys Lys Ser Gly
        195                 200                 205

Val Gly Ala Phe Leu Ile Gly Asp Val Gly Val Leu Asn Tyr Gly Pro
    210                 215                 220

Cys Val Gly Asp Pro Gly Glu Cys Leu Gly Phe Gly Leu Cys Gly Gln
225                 230                 235                 240

Val Lys Glu Phe Ser Cys Gln Glu Lys Asp Glu Val Ser Ile Ser
                245                 250                 255

Phe Ala Gly Ala Leu Ser Gln Pro Ser Ser Arg Arg Thr Gly Phe Ser
            260                 265                 270

Tyr Leu Gln Asp Ala Leu Phe Ser Thr Asn Ser Cys Tyr Cys Ile Asp
        275                 280                 285

Ile Thr Glu Gln Lys Cys His Val Ala Ser Ser Leu Asp Arg Glu Asn
    290                 295                 300

Gln Asp Ala Phe Phe Ala Ile Phe Cys Lys Gly Ser Gln Cys Gln Val
305                 310                 315                 320

Cys Asn Gly Pro Lys Leu Arg Thr Gly Ser Pro Asp Ser Tyr Lys Gly
                325                 330                 335

Pro Ala Tyr Asp Val Leu Ile Lys Gly Glu Lys Glu Thr Val Arg Ile
            340                 345                 350

Leu Ser Ser Ser Pro His Met Glu Ile Phe Ser Leu Gln Gly Lys Asp
        355                 360                 365

Arg Phe Trp Gly Ser Asn Phe Leu Ile Asn Leu Pro Tyr Thr Gln Asn
    370                 375                 380

Ser Ile Asn Ile Leu Phe Glu Lys Ala
385                 390

<210> SEQ ID NO 82
<211> LENGTH: 316
<212> TYPE: PRT
<213> ORGANISM: Chlamydia trachomatis

<400> SEQUENCE: 82

Met Gly Lys Phe Phe Ala Ser Tyr Leu Leu Ile Leu Ala Pro Phe Phe
1               5                   10                  15

Leu Gln Ser Cys Ser Ala Pro Ser Arg Thr Thr Leu Glu Gly Val Arg
                20                  25                  30

Met Thr Ile Pro Tyr Arg Ile Val Phe Gly Glu Ala Leu Ser Pro Asp
            35                  40                  45

Ala Phe Gln Gln Ala Gln Lys Glu Ile Asp Arg Val Phe Asp His Ile
    50                  55                  60

Asp Gln Thr Phe Asn Asn Trp Asn Pro Leu Ser Glu Ile Ser Arg Ile
65                  70                  75                  80

Asn Arg Thr Thr Lys Gln Thr Pro Ile Pro Leu Ser Pro Ala Leu Phe
                85                  90                  95

Ala Phe Leu Cys Glu Ile Asp His Phe His Ala Phe Ser Asp Gly Arg
```

```
                100              105              110
Phe Asp Pro Thr Leu Gly Ala Leu Lys Ser Leu Trp Leu Leu His Leu
            115              120              125
Lys Ser His Thr Ile Pro Ser Gln Glu Leu Gln His Leu Tyr Lys His
130              135              140
Ser Ser Gly Trp His Leu Ile Ser Leu Asp Lys Thr Gln Gln Thr Leu
145              150              155              160
Arg Lys Leu Ser Pro Leu Val Gln Leu Asp Leu Cys Gly Thr Val Lys
            165              170              175
Gly Phe Ala Val Asp Leu Leu Gly Thr Ala Cys Ala Gln Phe Cys Gln
            180              185              190
Asn Tyr Tyr Val Glu Trp Gly Gly Glu Ile Lys Thr Lys Gly Lys His
            195              200              205
Pro Ser Gly Arg Ser Trp Ala Val Ala Ser Ser Ala Thr Pro Glu Ile
            210              215              220
Leu His Leu His Asp His Ala Ile Ala Thr Ser Gly Ser Gln Tyr Gln
225              230              235              240
Arg Trp His Val Asp Asn Lys Thr Tyr Thr His Ile Leu Asp Pro Leu
            245              250              255
Thr Gly Thr Pro Leu Glu Asp Ser Ser His Pro Ile Leu Ala Val Ser
            260              265              270
Val Ile Asn Glu Ser Cys Ala Phe Ala Asp Ala Met Ala Thr Ala Leu
            275              280              285
Thr Thr Phe Ser Ser Lys Gln Glu Ala Leu Asp Trp Ala Asn Lys Lys
            290              295              300
His Leu Cys Ala Tyr Ile Thr Asp Lys Asn Val Ser
305              310              315

<210> SEQ ID NO 83
<211> LENGTH: 148
<212> TYPE: PRT
<213> ORGANISM: Chlamydia trachomatis

<400> SEQUENCE: 83

Met Phe Gln Pro Glu Thr Val Pro Ser Asn Arg Ser Thr Glu Thr Thr
1               5                   10                  15
Pro Gln Asn Ile Glu Val Tyr Asn Asp Arg Asn Phe Thr Asn His Thr
            20                  25                  30
Thr Glu Asp Val Ile Arg Ile Gly Glu Arg Leu Gln Arg Gln Phe Tyr
        35                  40                  45
Asn Met Thr Glu Glu Ser Arg Val Pro Phe Thr Thr Ser Pro Ser His
50                  55                  60
His Thr Gly Asn Trp Lys Thr Ala Phe Leu Tyr Asn Leu Ser Gln Val
65                  70                  75                  80
Val Ala His Ile Phe Pro Ser Thr Val Gln Pro Ile Arg Val Lys Pro
                85                  90                  95
Thr Arg Ile Pro Pro Ser Pro Thr Pro Pro Glu Gly Thr Thr Thr
            100                 105                 110
Ala Glu Thr Ser Thr Ser Glu Asn Lys Val Thr Thr Ile Ser Lys Glu
            115                 120                 125
Gln Glu Val Thr Thr Lys Pro Leu Leu Val Arg Glu Arg Arg Ser Leu
            130                 135                 140
Leu His Ser Gln
145
```

```
<210> SEQ ID NO 84
<211> LENGTH: 340
<212> TYPE: PRT
<213> ORGANISM: Chlamydia trachomatis

<400> SEQUENCE: 84

Met Ser Ser Lys Leu Val Asn Tyr Leu Arg Leu Thr Phe Leu Ser Phe
1               5                   10                  15

Leu Gly Ile Ala Ser Thr Ser Leu Asp Ala Met Pro Ala Gly Asn Pro
            20                  25                  30

Ala Phe Pro Val Ile Pro Gly Ile Asn Ile Glu Gln Lys Asn Ala Cys
        35                  40                  45

Ser Phe Asp Leu Cys Asn Ser Tyr Asp Val Leu Ser Ala Leu Ser Gly
    50                  55                  60

Asn Leu Lys Leu Cys Phe Cys Gly Asp Tyr Ile Phe Ser Glu Glu Ala
65                  70                  75                  80

Gln Val Lys Asp Val Pro Val Val Thr Ser Val Thr Thr Ala Gly Val
                85                  90                  95

Gly Pro Ser Pro Asp Ile Thr Ser Thr Thr Lys Thr Arg Asn Phe Asp
            100                 105                 110

Leu Val Asn Cys Asn Leu Asn Thr Asn Cys Val Ala Val Ala Phe Ser
        115                 120                 125

Leu Pro Asp Arg Ser Leu Ser Ala Ile Pro Leu Phe Asp Val Ser Phe
    130                 135                 140

Glu Val Lys Val Gly Gly Leu Lys Gln Tyr Tyr Arg Leu Pro Met Asn
145                 150                 155                 160

Ala Tyr Arg Asp Phe Thr Ser Glu Pro Leu Asn Ser Glu Ser Glu Val
                165                 170                 175

Thr Asp Gly Met Ile Glu Val Gln Ser Asn Tyr Gly Phe Val Trp Asp
            180                 185                 190

Val Ser Leu Lys Lys Val Ile Trp Lys Asp Gly Val Ser Phe Val Gly
        195                 200                 205

Val Gly Ala Asp Tyr Arg His Ala Ser Cys Pro Ile Asp Tyr Ile Ile
    210                 215                 220

Ala Asn Ser Gln Ala Asn Pro Glu Val Phe Ile Ala Asp Ser Asp Gly
225                 230                 235                 240

Lys Leu Asn Phe Lys Glu Trp Ser Val Cys Val Gly Leu Thr Thr Tyr
                245                 250                 255

Val Asn Asp Tyr Val Leu Pro Tyr Leu Ala Phe Ser Ile Gly Ser Val
            260                 265                 270

Ser Arg Gln Ala Pro Asp Asp Ser Phe Lys Lys Leu Glu Asp Arg Phe
        275                 280                 285

Thr Asn Leu Lys Phe Lys Val Arg Lys Ile Thr Ser Ser His Arg Gly
    290                 295                 300

Asn Ile Cys Ile Gly Ala Thr Asn Tyr Val Ala Asp Asn Phe Phe Tyr
305                 310                 315                 320

Asn Val Glu Gly Arg Trp Gly Ser Gln Arg Ala Val Asn Val Ser Gly
                325                 330                 335

Gly Phe Gln Phe
            340

<210> SEQ ID NO 85
<211> LENGTH: 560
<212> TYPE: PRT
<213> ORGANISM: Chlamydia trachomatis

<400> SEQUENCE: 85
```

-continued

```
Met Ser Ile Ser Gly Ser Gly Asn Val Ser Pro Ala Thr Pro Asp Phe
1               5                   10                  15

Asp Pro Ser Ile Leu Met Gly Arg Gln Ala Ala Ser Ala His Ala Ala
            20                  25                  30

Lys Glu Ala Ser Gly Ala Ser Lys Ala Thr Glu Thr Ser Ala Ala Glu
        35                  40                  45

Gln Gln Ala Leu Ile Ser Ser Gly Thr Glu Leu Asp Tyr Val Thr Asp
    50                  55                  60

Leu Gln Gln Ser Glu Gly Lys Tyr Lys Lys Thr Leu Asp Lys Thr Ser
65                  70                  75                  80

Lys Ser Pro Lys Thr Lys Leu Lys Gly Asn Phe Ser Lys Val Arg Ala
                85                  90                  95

Gly Thr Lys Gly Phe Leu Thr Gly Phe Gly Thr Arg Ala Ser Arg Ile
            100                 105                 110

Ser Ala Arg Lys Ala Glu Asn Asn Gly Glu Gly Met Ser Met Ile Pro
        115                 120                 125

Ser Gln Met Glu Tyr Val Lys Lys Gly Asn Arg Val Ser Pro Glu
    130                 135                 140

Met Gln Asn Phe Tyr Leu Gly Ala Ser Gly Leu Trp Ser Pro Thr Ser
145                 150                 155                 160

Asp Val Ser Ser Ile Thr Glu Asn Cys Leu Gly Ala Thr Ala Leu Ser
                165                 170                 175

Thr Thr Pro Leu Leu Thr Thr Met Gln Asp Pro Val Ser Ile Glu His
            180                 185                 190

Leu Ser Ser Gly Glu Ile Thr Ala Leu Ala Ser Phe Asn Pro Asn Val
        195                 200                 205

Arg Thr Ala Ser Leu Asn Glu Gln Thr Ile Asn Ala Trp Thr Glu Ala
    210                 215                 220

Arg Leu Gly Gly Glu Met Val Ser Thr Leu Leu Asp Pro Asn Ile Glu
225                 230                 235                 240

Thr Ser Ser Leu Leu Arg Arg Ala Pro Thr Val Ser Asn Glu Gly Met
                245                 250                 255

Val Asp Val Ser Asp Met Gly Asn Gln Thr Thr Ser Leu Ser Met Glu
            260                 265                 270

Gly Leu Val Asn Thr Val Val Asp Asp Pro Ala Ser Ala Glu Glu Glu
        275                 280                 285

Lys Lys Thr Gly Glu Leu Ser Leu Glu Glu Met Ala Ala Met Ala Lys
    290                 295                 300

Met Met Ala Ala Leu Leu Ser Ser Gly Gln Gly Met Ala Val Phe Ile
305                 310                 315                 320

Ala Ser Ser Thr Pro Ser Ser Gly Leu Thr Gln Phe Pro Glu Pro Lys
                325                 330                 335

Phe Ser Gly Thr Ile Pro His His Phe Ser Lys Lys Glu Asp Asn Glu
            340                 345                 350

Thr Ile Trp Gly Leu Asp Ser Gln Ile Gly Ser Ile Ala Phe Asp Thr
        355                 360                 365

Arg Arg Glu Asn Asn Ala Ser Pro Leu Pro Thr Thr Ser Leu His Glu
    370                 375                 380

Glu Ala Ser Tyr Arg Phe Pro Val Gly Glu Ala Pro Leu Asp Val Asn
385                 390                 395                 400

Glu Ile Pro Phe Ala Val Gln His Ser Thr Val Phe Ser Lys Glu Thr
                405                 410                 415

Ala Asn Thr Glu Gln Ala Leu Ile Gln Asn Glu Ser Leu Gly Glu Ile
```

```
                420             425             430
Pro Val Ser Ala Glu Val Val Gly Gln Asp Thr Val Ser Ser Ala Tyr
        435             440             445

Gln Phe Pro Ser His Leu Gly Met Ala Val Leu Ala Ser Val Pro Leu
    450             455             460

Ser Thr Glu Asp Tyr Lys Thr Ala Val Glu His Arg Lys Gly Pro Gly
465             470             475             480

Gly Pro Pro Asp Pro Leu Ile Tyr Gln Tyr Arg Asn Val Ala Val Asp
                485             490             495

Pro Ala Ile Ile Phe Gln Ser Pro Ser Pro Phe Ser Val Ser Ser Arg
            500             505             510

Phe Ser Val Gln Gly Lys Pro Glu Ala Val Ala Val Tyr Asn Asp Asp
        515             520             525

Gln Glu Glu Ala Ala Gly Gly Asn Arg Asp Ser Asp Glu Gly Lys Asp
    530             535             540

Gln Glu Gln Asp Lys Thr Arg Glu Thr Glu Asp Ala Gly Gly Asp Ser
545             550             555             560

<210> SEQ ID NO 86
<211> LENGTH: 236
<212> TYPE: PRT
<213> ORGANISM: Chlamydia trachomatis

<400> SEQUENCE: 86

Met Leu Ser Lys Phe Cys Lys Leu Ser Leu Ser Ala Ile Leu Leu Ile
1               5                   10                  15

Asn Thr Leu Ala Pro Ser Glu Thr Phe Ser Glu Gly Thr Ser Gly
            20                  25                  30

Phe Leu Gly Arg Met Lys Ser Trp Ile Leu Lys Asp Lys Thr Ile Leu
        35                  40                  45

Ser Thr Thr Glu Glu Ser Gln Thr Ser Ala Ile Glu Lys Val Ser Asp
    50                  55                  60

Leu Leu Ser Trp Lys Arg Tyr Asp Tyr Thr Gln Glu Ser Gly Phe Ala
65                  70                  75                  80

Ile Gln Phe Pro Glu Ser Pro Glu His Ser Glu Gln Val Ile Glu Val
                85                  90                  95

Pro Gln Ser Asp Leu Ala Ile Arg Tyr Asp Thr Tyr Val Ala Glu Thr
            100                 105                 110

Pro Ser Asp Ser Thr Val Tyr Val Val Ser Ile Trp Glu Tyr Pro Glu
        115                 120                 125

Lys Ile Asp Ile Ser Arg Pro Glu Leu Asn Leu Gln Glu Gly Phe Ala
    130                 135                 140

Gly Met Leu Tyr Ala Leu Pro Glu Ser Gln Val Leu Tyr Leu Lys Ala
145                 150                 155                 160

Thr Ala Leu Gln Gly His Lys Ala Leu Glu Phe Trp Ile Ala Cys Asp
                165                 170                 175

Asp Val Tyr Phe Arg Gly Met Leu Val Ser Val Asn His Thr Leu Tyr
            180                 185                 190

Gln Val Phe Met Val Tyr Lys Gly Arg Ser Pro Glu Ile Leu Asp Lys
        195                 200                 205

Glu Tyr Ser Thr Phe Ile Gln Ser Phe Lys Val Thr Lys Val Arg Asn
    210                 215                 220

Ser Lys Lys Met Asp Ile Arg Lys Arg Val Ser Leu
225                 230                 235
```

<210> SEQ ID NO 87
<211> LENGTH: 536
<212> TYPE: PRT
<213> ORGANISM: Chlamydia trachomatis

<400> SEQUENCE: 87

```
Met Asn Asp Thr Lys Asn Asn Ile Ser Ser Ser Phe Trp Asn Pro Asn
1               5                   10                  15

Lys Val Val Thr Lys Val Leu Leu Lys Val Ser Glu Thr Gly Ile Glu
            20                  25                  30

Ser Thr Pro Gly Ile Val Lys His Asn Gln Leu Ile Thr Gln Ser Glu
        35                  40                  45

Asn Pro Thr Asp Pro Thr Asp Ala Val Thr Phe Lys Tyr Leu Lys Glu
    50                  55                  60

Asn Tyr Thr Lys Glu Asn Asp Pro Asn Pro Gly Phe Leu Pro Thr Thr
65                  70                  75                  80

Gly Gly Thr Met Thr Gly Asp Ile Asp Met Gln Gly Asn Asn Val Thr
                85                  90                  95

Asp Ile Val Met Tyr Thr Asn Gly Gln Gln Asn Pro Thr Asp Asp Ser
            100                 105                 110

Ala Val Thr Ile Gly Tyr Leu Asn Glu Lys Ala Asp Glu Ile Lys Ser
        115                 120                 125

Asn Asp Gln Ile Thr Thr Ala Val Ala Gly Leu Ser Asn Ile Asn Ser
    130                 135                 140

Gln Ile Ser Thr Leu His Gln Leu Leu Gly Ile Ala Glu Asp Pro Asp
145                 150                 155                 160

Thr Val Thr Asn Pro Asp Leu Leu Lys Thr Ser Gly Gly Thr Val Tyr
                165                 170                 175

Glu Asp Ile Asp Met Ser Ser Asn Thr Val Ser Asp Leu Gly Thr Pro
            180                 185                 190

Thr Asn Lys Asp Thr Lys Ser Ala Ile Asn Val Glu Phe Val Gln Ala
        195                 200                 205

Lys Ile Thr Ser Pro Gln Met Ala Phe Leu Lys Asn Asn Asp Thr Asn
    210                 215                 220

Leu Ser Asn Ile Thr Val Ser Glu Tyr Phe Asn Trp Leu Gln Asp Pro
225                 230                 235                 240

Thr Gln Ala Pro Thr Pro Glu Pro Asp Pro Asp Pro Glu Pro Ala Pro
                245                 250                 255

Glu Pro Glu Pro Asp Thr Ser Asp Ser Ser Gly Ser Gly Ser Glu Asn
            260                 265                 270

Pro Ala Asp Pro Ala Pro Thr Asn Pro Ser Asp Ser Asn Ala Gln Asn
        275                 280                 285

Asn Pro Thr Pro Ser Ser Asn Gly Ala Thr Ala Ser Ile Arg Lys Leu
    290                 295                 300

Ala Ala Thr Thr Thr Thr Val Pro Thr Asp Thr Glu Ile Ala Pro Ala
305                 310                 315                 320

Ala Glu Asp Pro Asn Leu Pro Asn Thr Thr Phe Ser Glu Lys Ser Pro
                325                 330                 335

Leu Trp Glu Glu Phe Phe Ser Phe Ser Asp Ser Ser Arg Ser Glu Met
            340                 345                 350

Val Ile Gln Lys Thr Gly Ile Leu Thr Phe Ser Met Gln Gly Thr Trp
        355                 360                 365

Glu Asn Pro Ser Ser Ser Gln Thr Pro Ser Asp Pro Ile Ser Leu
    370                 375                 380

Glu Leu Thr Val Thr Pro Pro Thr Thr Asp Thr Pro Pro Glu Ser Pro
```

```
                385                 390                 395                 400
Pro Ser Pro Pro Glu Ala Pro Ala Pro Glu Ala Thr Pro Ser Pro Thr
                    405                 410                 415

Asn Asn Asn Leu Thr Ala Ser Ile Thr Lys Thr Phe Ser Arg Lys Tyr
                    420                 425                 430

Asn Leu Ser Ala Thr Pro Ser Pro Thr Pro Thr Thr Pro Thr Glu Pro
                    435                 440                 445

Thr Thr Ile Thr Lys Thr Leu Ser Leu Ser Ser Gly Gln Ser Cys Thr
                    450                 455                 460

Leu Gln Ile Pro Val Gln Ala Thr Arg Ser Val Leu Lys Leu Lys Tyr
465                 470                 475                 480

Val Asn Pro Asn Asn Asn Ser Ser Gly Gly Ser Ser Gly Ser Gly Gly
                    485                 490                 495

Ser Ser Gln Pro Glu Thr Thr Pro Thr Gly Ile Thr Leu Gln Ser Phe
                    500                 505                 510

Ser Trp Ser Leu Val Leu Thr Pro Gly Glu Ile Thr Lys Ala Thr Ser
                    515                 520                 525

Thr Pro Ser Thr Pro Ser Gln Pro
                    530                 535

<210> SEQ ID NO 88
<211> LENGTH: 404
<212> TYPE: PRT
<213> ORGANISM: Chlamydia trachomatis

<400> SEQUENCE: 88

Met Ser Val Gln Gly Ser Ser Ser Leu Lys Tyr Ser Asp Leu Phe Lys
1               5                   10                  15

Pro Pro Glu Pro Thr Ser Ser Thr Asp Ser Ser Lys Glu Pro Pro Lys
                20                  25                  30

Glu Ser Ala Trp Lys Val Val Ser His Ser Arg Gly Arg Arg Arg Ala
                35                  40                  45

Arg Ser Asn Pro Ser Pro His Thr Ser Gln Asn Thr Pro Ser Pro Lys
            50                  55                  60

Asp Ser Ser Leu Val Ala Arg Thr Asp Lys Ala Ala Thr Asp Ile Phe
65                  70                  75                  80

Asn Ser Ala Lys His Lys Ala Ile Glu Thr Thr Lys Arg Ser Asp Gln
                85                  90                  95

Gln Ser Arg Ser Leu His Ile Leu His Leu Leu Ala Glu Asn Pro Glu
                100                 105                 110

Pro Ile Val Phe His Ser Ala His Gln Thr Asn His Asn Asp Pro Gln
                115                 120                 125

Arg Met Leu Cys Asp Ala Ile Leu Gln Ala Asn Arg Ile Ile Thr Met
                130                 135                 140

Arg Ile Phe Asn Ile Gly Ser Pro Glu Ile Ile Arg Ala Leu Ile Arg
145                 150                 155                 160

Ala Val Arg Arg Asn Ile Pro Val Val Ser Ala Trp Asn Phe Pro
                    165                 170                 175

Asn Leu Ser Asn Trp Asp Arg Glu Ser Glu Leu Cys Val Glu Leu Arg
                180                 185                 190

Gly Asn Pro Gln Ile Cys Leu His Lys Lys Thr Thr Leu Ile Asp Asn
                195                 200                 205

Gln Leu Thr Ile Ile Gly Thr Ala Asn Tyr Thr Lys Ser Ser Phe Phe
                210                 215                 220

Lys Asp Ile Asn Leu Thr Ala Leu Ile Gln Asn Pro Ala Leu Tyr Ser
```

```
                225                 230                 235                 240
Leu Ile Leu Ser Asp Thr Arg Gly Ser Val Ser Ile Gly Ser Gln Thr
                245                 250                 255

Ile Ser Tyr Tyr Pro Leu Pro Phe Pro Gln Ser Asn Thr Lys Ile Leu
            260                 265                 270

Pro Ile Ile Gln Glu Ile Gln Lys Ala Gln Arg Thr Ile Lys Ile Ala
        275                 280                 285

Met Asn Ile Phe Ser His Thr Glu Ile Phe Leu Ala Leu Glu Gln Ala
    290                 295                 300

Arg Leu Arg Gly Val Thr Ile Thr Ile Val Ile Asn Lys Lys Glu Ser
305                 310                 315                 320

Ala His Thr Leu Asp Ile Leu His Arg Ile Ser Ala Leu Leu Leu Leu
                325                 330                 335

Lys Ser Val Thr Thr Val Asp Ser Leu His Ala Lys Ile Cys Leu Ile
                340                 345                 350

Asp Asn Gln Thr Leu Ile Phe Gly Ser Pro Asn Trp Thr Tyr His Gly
            355                 360                 365

Met His Lys Asn Leu Glu Asp Leu Leu Ile Val Thr Pro Leu Thr Pro
    370                 375                 380

Lys Gln Ile His Ser Ile Gln Glu Ile Trp Ala Phe Leu Leu Lys Asn
385                 390                 395                 400

Ser Ser Pro Val

<210> SEQ ID NO 89
<211> LENGTH: 245
<212> TYPE: PRT
<213> ORGANISM: Chlamydia trachomatis

<400> SEQUENCE: 89

Met Asp Arg Ser Pro Leu Phe Leu Ile Ile Met Gly Ala Pro Gly Ser
1               5                   10                  15

Gly Lys Gly Thr Gln Ser Lys Leu Leu Ala Ser Gln Leu Ser Leu Leu
            20                  25                  30

His Ile Ser Ser Gly Asp Leu Leu Arg Asp Ala Val Ser Lys Asp Thr
        35                  40                  45

Pro Leu Ser Gln Glu Ile Lys Ser Tyr Leu Asp Gln Gly Lys Leu Leu
    50                  55                  60

Pro Asp Thr Leu Val Trp Lys Leu Val His Glu Lys Leu Asp Glu Phe
65                  70                  75                  80

Gln Gln Asp Thr Leu Leu Arg Arg Leu Ser Phe Leu Ser Arg Ser Glu
                85                  90                  95

Asn Ser Ala Ile Leu Asp Gly Phe Pro Arg Thr Val Thr Gln Ala Lys
            100                 105                 110

Leu Leu His Glu Phe Leu Ser Ser Tyr Phe Pro Asn Tyr Lys Val Ile
        115                 120                 125

Leu Leu Asp Ile Ser Asp Glu Glu Val Leu Asn Arg Leu Thr Ser Arg
    130                 135                 140

Tyr Ile Cys Pro Ala Cys Gln Gly Ile Tyr Asn Glu Gln Gln Gly Phe
145                 150                 155                 160

Ser Ser Cys Pro Lys Cys Ser Val Glu Leu Ile Arg Arg Ser Asp Asp
                165                 170                 175

Thr Leu Glu Val Ile Leu Asp Arg Ile Gln Thr Tyr Lys Gln Glu Thr
            180                 185                 190

Gln Pro Val Leu Asp Tyr Tyr Thr Glu Lys Gln Lys Leu Ile Thr Ile
        195                 200                 205
```

```
Asp Ala Asn Ala Pro Thr Gln Gln Val Phe Gln Ser Ile Leu Asp Ser
    210                 215                 220

Leu Ser Ala Ser Leu Val Tyr Gln Glu Arg Asp Cys Cys Asn Cys Asp
225                 230                 235                 240

Cys Asp Asp Glu Asp
                245

<210> SEQ ID NO 90
<211> LENGTH: 810
<212> TYPE: PRT
<213> ORGANISM: Chlamydia trachomatis

<400> SEQUENCE: 90

Met Thr Lys Pro Ser Phe Leu Tyr Val Ile Gln Pro Phe Ser Val Phe
1               5                   10                  15

Asn Pro Arg Leu Gly Arg Phe Ser Thr Asp Ser Asp Thr Tyr Ile Glu
            20                  25                  30

Glu Glu Asn Arg Leu Ala Ser Phe Ile Glu Ser Leu Pro Leu Glu Ile
        35                  40                  45

Phe Asp Ile Pro Ser Phe Met Glu Thr Ala Ile Ser Asn Ser Pro Tyr
    50                  55                  60

Ile Leu Ser Trp Glu Thr Thr Lys Asp Gly Ala Leu Phe Thr Ile Leu
65                  70                  75                  80

Glu Pro Lys Leu Ser Ala Cys Ala Ala Thr Cys Leu Val Ala Pro Ser
                85                  90                  95

Ile Gln Met Lys Ser Asp Ala Glu Leu Leu Glu Ile Lys Gln Ala
            100                 105                 110

Leu Leu Arg Ser Ser His Asp Gly Val Lys Tyr Arg Ile Thr Arg Glu
        115                 120                 125

Ser Phe Ser Pro Glu Lys Lys Thr Pro Lys Val Ala Leu Val Asp Asp
    130                 135                 140

Asp Ile Glu Leu Ile Arg Asn Val Asp Phe Leu Gly Arg Ala Val Asp
145                 150                 155                 160

Ile Val Lys Leu Asp Pro Ile Asn Ile Leu Asn Thr Val Ser Glu Glu
                165                 170                 175

Asn Ile Leu Asp Tyr Ser Phe Thr Arg Glu Thr Ala Gln Leu Ser Ala
            180                 185                 190

Asp Gly Arg Phe Gly Ile Pro Pro Gly Thr Lys Leu Phe Pro Lys Pro
        195                 200                 205

Ser Phe Asp Val Glu Ile Ser Thr Ser Ile Phe Glu Gly Thr Thr Ser
    210                 215                 220

Phe Thr Arg Ser Phe Ser Ala Ser Val Thr Phe Ser Val Pro Asp Leu
225                 230                 235                 240

Ala Ala Thr Met Pro Leu Gln Ser Pro Pro Met Val Glu Asn Gly Gln
                245                 250                 255

Lys Glu Ile Cys Val Ile Gln Lys His Leu Phe Pro Ser Tyr Ser Pro
            260                 265                 270

Lys Leu Val Asp Ile Val Lys Arg Tyr Lys Arg Glu Ala Lys Ile Leu
        275                 280                 285

Ile Asn Lys Leu Ala Phe Gly Met Leu Trp Arg His Arg Ala Lys Ser
    290                 295                 300

Gln Ile Leu Thr Glu Gly Ser Val Arg Leu Asp Leu Gln Gly Phe Thr
305                 310                 315                 320

Glu Ser Lys Tyr Asn Tyr Gln Ile Gln Val Gly Ser His Thr Ile Ala
                325                 330                 335
```

```
Ala Val Leu Ile Asp Met Asp Ile Ser Lys Ile Gln Ser Lys Ser Glu
            340                 345                 350
Gln Ala Tyr Ala Ile Arg Lys Ile Lys Ser Gly Phe Gln Arg Ser Leu
            355                 360                 365
Asp Asp Tyr His Ile Tyr Gln Ile Glu Arg Lys Gln Thr Phe Ser Phe
            370                 375                 380
Ser Pro Lys His Arg Ser Leu Ser Ser Thr Ser His Ser Glu Asp Ser
385                 390                 395                 400
Asp Leu Asp Leu Ser Glu Ala Ala Phe Ser Gly Ser Leu Thr Cys
            405                 410                 415
Glu Phe Val Lys Lys Ser Thr Gln His Ala Lys Asn Thr Val Thr Cys
            420                 425                 430
Ser Thr Ala Ala His Ser Leu Tyr Thr Leu Lys Glu Asp Asp Ser Ser
            435                 440                 445
Asn Pro Ser Glu Lys Arg Leu Asp Ser Cys Phe Arg Asn Trp Ile Glu
            450                 455                 460
Asn Lys Leu Ser Ala Asn Ser Pro Asp Ser Trp Ser Ala Phe Ile Gln
465                 470                 475                 480
Lys Phe Gly Thr His Tyr Ile Ala Ser Ala Thr Phe Gly Gly Ile Gly
            485                 490                 495
Phe Gln Val Leu Lys Leu Ser Phe Glu Gln Val Glu Asp Leu His Ser
            500                 505                 510
Lys Lys Ile Ser Leu Glu Thr Ala Ala Asn Ser Leu Leu Lys Gly
            515                 520                 525
Ser Val Ser Ser Ser Thr Glu Ser Gly Tyr Ser Ser Tyr Ser Ser Thr
530                 535                 540
Ser Ser Ser His Thr Val Phe Leu Gly Gly Thr Val Leu Pro Ser Val
545                 550                 555                 560
His Asp Glu Arg Leu Asp Phe Lys Asp Trp Ser Glu Ser Val His Leu
            565                 570                 575
Glu Pro Val Pro Ile Gln Val Ser Leu Gln Pro Ile Thr Asn Leu Leu
            580                 585                 590
Val Pro Leu His Phe Pro Asn Ile Gly Ala Ala Glu Leu Ser Asn Lys
            595                 600                 605
Arg Glu Ser Leu Gln Gln Ala Ile Arg Val Tyr Leu Lys Glu His Lys
610                 615                 620
Val Asp Glu Gln Gly Glu Arg Thr Thr Phe Thr Ser Gly Ile Asp Asn
625                 630                 635                 640
Pro Ser Ser Trp Phe Thr Leu Glu Ala Ala His Ser Pro Leu Ile Val
            645                 650                 655
Ser Thr Pro Tyr Ile Ala Ser Trp Ser Thr Leu Pro Tyr Leu Phe Pro
            660                 665                 670
Thr Leu Arg Glu Arg Ser Ser Ala Thr Pro Ile Val Phe Tyr Phe Cys
            675                 680                 685
Val Asp Asn Asn Glu His Ala Ser Gln Lys Ile Leu Asn Gln Ser Tyr
            690                 695                 700
Cys Phe Leu Gly Ser Leu Pro Ile Arg Gln Lys Ile Phe Gly Ser Glu
705                 710                 715                 720
Phe Ala Ser Phe Pro Tyr Leu Ser Phe Tyr Gly Asn Ala Lys Glu Ala
            725                 730                 735
Tyr Phe Asp Asn Thr Tyr Tyr Pro Thr Arg Cys Gly Trp Ile Val Glu
            740                 745                 750
Lys Leu Asn Thr Thr Gln Asp Gln Phe Leu Arg Asp Gly Asp Glu Val
```

```
                   755                 760                 765
Arg Leu Lys His Val Ser Ser Gly Lys Tyr Leu Ala Thr Thr Pro Leu
        770                 775                 780
Lys Asp Thr His Gly Thr Leu Thr Arg Thr Thr Asn Cys Glu Asp Ala
785                 790                 795                 800
Ile Phe Ile Ile Lys Lys Ser Ser Gly Tyr
                805                 810

<210> SEQ ID NO 91
<211> LENGTH: 256
<212> TYPE: PRT
<213> ORGANISM: Chlamydia trachomatis

<400> SEQUENCE: 91

Met Thr Phe Ser Ala Ala Phe Ser Pro Cys Pro Asn Asp Ile Phe Leu
1               5                   10                  15

Phe Arg Ser Phe Leu Glu Lys His Lys Gly Phe Pro Ser Leu Arg Gln
            20                  25                  30

Ile Met Ile Ala Asp Ile Ser Ser Leu Asn Tyr Tyr Ala Leu Glu Thr
        35                  40                  45

Arg Phe Pro Leu Ile Lys Ile Ser Ala Ser Leu Tyr Pro Gln Ile Ala
50                  55                  60

Asp Ser Tyr Asp Val Leu Asn Val Gly Thr Thr Leu Gly Tyr Lys Ile
65                  70                  75                  80

Gly Pro Leu Ile Leu Ser Arg Gln Leu Asp Ser Pro Leu Lys Ser Leu
                85                  90                  95

Ala Thr Pro Gly Glu Thr Thr Thr Ala His Ala Leu Cys Arg Leu Phe
            100                 105                 110

Tyr Pro Arg Ala Glu Leu Val Pro Met Lys Tyr His Glu Ile Ile Pro
        115                 120                 125

Ala Ile Leu Ser Asn Arg Val Asp Gly Gly Ala Val Ile His Glu Glu
130                 135                 140

Arg Phe Ser Phe Pro Lys Asp Leu Cys Ile Val Glu Asp Leu Gly Gln
145                 150                 155                 160

Leu Trp Glu Lys Thr Trp His Leu Pro Leu Pro Leu Gly Cys Ile Val
                165                 170                 175

Ile Ser Lys Lys Val Ser Asp Asp Ser Tyr Leu Leu Asn His Ala
            180                 185                 190

Leu Gln Glu Ser Leu Lys Lys Ser Leu Thr Asp Ser Ala Leu Ala Ile
        195                 200                 205

Gln Lys Ala Ser Glu Tyr Ser Arg Asp Lys Asn Pro Thr Thr Ile Gln
210                 215                 220

His Phe Ile Asp Thr Tyr Val Thr Glu Glu Thr Phe Asn Leu Ser Ser
225                 230                 235                 240

Ile Gly Arg Gln Ala Phe Ser Thr Leu Trp Thr Ala Cys Arg Asn Val
                245                 250                 255

<210> SEQ ID NO 92
<211> LENGTH: 194
<212> TYPE: PRT
<213> ORGANISM: Chlamydia trachomatis

<400> SEQUENCE: 92

Met Phe Lys Arg Pro Ala Lys Asn Phe Phe Asp Glu Val Gln Thr Leu
1               5                   10                  15

Tyr Glu Asp Ser Gly Ala Asn Ser Thr Ser Tyr Ser Ile Tyr Pro Gln
            20                  25                  30
```

```
Arg Thr Glu Arg Leu Glu Asn His Ser Asn Ile Phe Glu Pro Ala Lys
            35                  40                  45

Pro Ala Glu Thr Arg Leu Leu Ser Gln Glu Glu His Ser Gln Trp Thr
 50                  55                  60

Asp Gln Gln Glu Glu Leu Ala Thr Gln Glu Ser Ser Phe Pro Glu Glu
 65                  70                  75                  80

Pro Glu Thr Thr Leu Gly Glu Gly Val Ser Phe Lys Gly Glu Leu Thr
                85                  90                  95

Phe Glu Arg Leu Leu Arg Ile Asp Gly Thr Phe Glu Gly Ile Leu Val
                100                 105                 110

Ser Lys Gly Lys Ile Ile Val Gly Pro Gln Gly Tyr Val Lys Ala Asn
            115                 120                 125

Ile Glu Leu Glu Glu Ala Val Ile Ala Gly Val Val Glu Gly Asn Ile
            130                 135                 140

Thr Val Thr Gly Arg Val Ser Leu Gln Gly Arg Ala Met Val Thr Gly
145                 150                 155                 160

Asp Ile Gln Ala Gly Ser Leu Cys Val Asp Glu Gly Val Arg Leu Cys
                165                 170                 175

Gly Tyr Val Ser Ile Gln Gly Ala Pro Ser Asn Glu Gln Glu Glu Ile
                180                 185                 190

Asp Ser

<210> SEQ ID NO 93
<211> LENGTH: 155
<212> TYPE: PRT
<213> ORGANISM: Chlamydia trachomatis

<400> SEQUENCE: 93

Met Arg Ala Val Leu His Leu Glu His Lys Arg Tyr Phe Gln Asn His
 1                5                 10                  15

Gly His Ile Leu Phe Glu Gly Leu Ala Pro Val Ser Asp Cys Lys Gln
            20                  25                  30

Leu Glu Ala Glu Leu Lys Leu Phe Leu Lys Glu Val Ala Val Val Lys
            35                  40                  45

Asp Arg His Leu Gln Arg Trp Arg Glu Asn Val His Arg Thr Leu Pro
 50                  55                  60

Glu Val Gln Met Ile Val Lys Arg Val Arg Leu Asp His Leu Ala Ala
 65                  70                  75                  80

Glu Leu Thr His Arg Ser Arg Val Ala Leu Val Arg Asp Leu Trp Val
                85                  90                  95

Gln Lys Gln Glu Glu Ile Phe Phe Asp Asp Cys Asp Cys Ser Val Leu
                100                 105                 110

Leu Cys Leu Ser Gly Glu Lys Ala Gly Trp Gly Leu Phe Phe Ser Gly
            115                 120                 125

Glu Tyr Pro Gln Asp Val Phe Asn Trp Gly Ala Gly Asp Thr Ala Ile
            130                 135                 140

Ile Leu Arg Phe Ser Ser Ala Gly Phe Pro Asn
145                 150                 155

<210> SEQ ID NO 94
<211> LENGTH: 442
<212> TYPE: PRT
<213> ORGANISM: Chlamydia trachomatis

<400> SEQUENCE: 94

Met Gln Ala Ala His His His Tyr His Arg Tyr Thr Asp Lys Leu His
```

```
            1               5                   10                  15
Arg Gln Asn His Lys Lys Asp Leu Ile Ser Pro Lys Pro Thr Glu Gln
                20                  25                  30

Glu Ala Cys Asn Thr Ser Ser Leu Ser Lys Glu Leu Ile Pro Leu Ser
                35                  40                  45

Glu Gln Arg Gly Leu Leu Ser Pro Ile Cys Asp Phe Ile Ser Glu Arg
    50                  55                  60

Pro Cys Leu His Gly Val Ser Val Arg Asn Leu Lys Gln Ala Leu Lys
65                  70                  75                  80

Asn Ser Ala Gly Thr Gln Ile Ala Leu Asp Trp Ser Ile Leu Pro Gln
                85                  90                  95

Trp Phe Asn Pro Arg Val Ser His Ala Pro Lys Leu Ser Ile Arg Asp
                100                 105                 110

Phe Gly Tyr Ser Ala His Gln Thr Val Thr Glu Ala Thr Pro Pro Cys
                115                 120                 125

Trp Gln Asn Cys Phe Asn Pro Ser Ala Ala Val Thr Ile Tyr Asp Ser
                130                 135                 140

Ser Tyr Gly Lys Gly Val Phe Gln Ile Ser Tyr Thr Leu Val Arg Tyr
145                 150                 155                 160

Trp Arg Glu Asn Ala Ala Thr Ala Gly Asp Ala Met Met Leu Ala Gly
                165                 170                 175

Ser Ile Asn Asp Tyr Pro Ser Arg Gln Asn Ile Phe Ser Gln Phe Thr
                180                 185                 190

Phe Ser Gln Asn Phe Pro Asn Glu Arg Val Ser Leu Thr Ile Gly Gln
                195                 200                 205

Tyr Ser Leu Tyr Ala Ile Asp Gly Thr Leu Tyr Asn Asn Asp Gln Gln
                210                 215                 220

Leu Gly Phe Ile Ser Tyr Ala Leu Ser Gln Asn Pro Thr Ala Thr Tyr
225                 230                 235                 240

Ser Ser Gly Ser Leu Gly Ala Tyr Leu Gln Val Ala Pro Thr Ala Ser
                245                 250                 255

Thr Ser Leu Gln Ile Gly Phe Gln Asp Ala Tyr Asn Ile Ser Gly Ser
                260                 265                 270

Ser Ile Lys Trp Ser Asn Leu Thr Lys Asn Arg Tyr Asn Phe His Gly
                275                 280                 285

Phe Ala Ser Trp Ala Pro Arg Cys Cys Leu Gly Ser Gly Gln Tyr Ser
                290                 295                 300

Val Leu Leu Tyr Val Thr Arg Gln Val Pro Glu Gln Met Glu Gln Thr
305                 310                 315                 320

Met Gly Trp Ser Val Asn Ala Ser Gln His Ile Ser Ser Lys Leu Tyr
                325                 330                 335

Val Phe Gly Arg Tyr Ser Gly Val Thr Gly His Val Phe Pro Ile Asn
                340                 345                 350

Arg Thr Tyr Ser Phe Gly Met Ala Ser Ala Asn Leu Phe Asn Arg Asn
                355                 360                 365

Pro Gln Asp Leu Phe Gly Ile Ala Cys Ala Phe Asn Asn Val His Leu
                370                 375                 380

Ser Ala Ser Pro Asn Thr Lys Arg Lys Tyr Glu Thr Val Ile Glu Gly
385                 390                 395                 400

Phe Ala Thr Ile Gly Cys Gly Pro Tyr Leu Ser Phe Ala Pro Asp Phe
                405                 410                 415

Gln Leu Tyr Leu Tyr Pro Ala Leu Arg Pro Asn Lys Gln Ser Ala Arg
                420                 425                 430
```

```
Val Tyr Ser Val Arg Ala Asn Leu Ala Ile
        435                 440

<210> SEQ ID NO 95
<211> LENGTH: 975
<212> TYPE: PRT
<213> ORGANISM: Chlamydia trachomatis

<400> SEQUENCE: 95

Met Asn Arg Val Ile Glu Ile His Ala His Tyr Asp Gln Arg Gln Leu
1               5                   10                  15

Ser Gln Ser Pro Asn Thr Asn Phe Leu Val His His Pro Tyr Leu Thr
            20                  25                  30

Leu Ile Pro Lys Phe Leu Leu Gly Ala Leu Ile Val Tyr Ala Pro Tyr
        35                  40                  45

Ser Phe Ala Glu Met Glu Leu Ala Ile Ser Gly His Lys Gln Gly Lys
    50                  55                  60

Asp Arg Asp Thr Phe Thr Met Ile Ser Ser Cys Pro Glu Gly Thr Asn
65                  70                  75                  80

Tyr Ile Ile Asn Arg Lys Leu Ile Leu Ser Asp Phe Ser Leu Leu Asn
                85                  90                  95

Lys Val Ser Ser Gly Gly Ala Phe Arg Asn Leu Ala Gly Lys Ile Ser
            100                 105                 110

Phe Leu Gly Lys Asn Ser Ser Ala Ser Ile His Phe Lys His Ile Asn
        115                 120                 125

Ile Asn Gly Phe Gly Ala Gly Val Phe Ser Glu Ser Ser Ile Glu Phe
    130                 135                 140

Thr Asp Leu Arg Lys Leu Val Ala Phe Gly Ser Glu Ser Thr Gly Gly
145                 150                 155                 160

Ile Phe Thr Ala Lys Glu Asp Ile Ser Phe Lys Asn Asn His His Ile
                165                 170                 175

Ala Phe Arg Asn Asn Ile Thr Lys Gly Asn Gly Val Ile Gln Leu
            180                 185                 190

Gln Gly Asp Met Lys Gly Ser Val Ser Phe Val Asp Gln Arg Gly Ala
        195                 200                 205

Ile Ile Phe Thr Asn Asn Gln Ala Val Thr Ser Ser Ser Met Lys His
    210                 215                 220

Ser Gly Arg Gly Gly Ala Ile Ser Gly Asp Phe Ala Gly Ser Arg Ile
225                 230                 235                 240

Leu Phe Leu Asn Asn Gln Gln Ile Thr Phe Glu Gly Asn Ser Ala Val
                245                 250                 255

His Gly Gly Ala Ile Tyr Asn Lys Asn Gly Leu Val Glu Phe Leu Gly
            260                 265                 270

Asn Ala Gly Pro Leu Ala Phe Lys Glu Asn Thr Thr Ile Ala Asn Gly
        275                 280                 285

Gly Ala Ile Tyr Thr Ser Asn Phe Lys Ala Asn Gln Gly Thr Ser Pro
    290                 295                 300

Ile Leu Phe Ser Gln Asn His Ala Asn Lys Lys Gly Gly Ala Ile Tyr
305                 310                 315                 320

Ala Gln Tyr Val Asn Leu Glu Gln Asn Gln Asp Thr Ile Arg Phe Glu
                325                 330                 335

Lys Asn Thr Ala Lys Glu Gly Gly Ala Ile Thr Ser Ser Gln Cys
            340                 345                 350

Ser Ile Thr Ala His Asn Thr Ile Ile Phe Ser Asp Asn Ala Ala Gly
        355                 360                 365
```

-continued

```
Asp Leu Gly Gly Gly Ala Ile Leu Glu Gly Lys Lys Pro Ser Leu
    370                 375                 380

Thr Leu Ile Ala His Ser Gly Asn Ile Ala Phe Ser Gly Asn Thr Met
385                 390                 395                 400

Leu His Ile Thr Lys Lys Ala Ser Leu Asp Arg His Asn Ser Ile Leu
                405                 410                 415

Ile Lys Glu Ala Pro Tyr Lys Ile Gln Leu Ala Ala Asn Lys Asn His
            420                 425                 430

Ser Ile His Phe Phe Asp Pro Val Met Ala Leu Ser Ala Ser Ser Ser
        435                 440                 445

Pro Ile Gln Ile Asn Ala Pro Glu Tyr Glu Thr Pro Phe Phe Ser Pro
    450                 455                 460

Lys Gly Met Ile Val Phe Ser Gly Ala Asn Leu Leu Asp Asp Ala Arg
465                 470                 475                 480

Glu Asp Val Ala Asn Arg Thr Ser Ile Phe Asn Gln Pro Val His Leu
                485                 490                 495

Tyr Asn Gly Thr Leu Ser Ile Glu Asn Gly Ala His Leu Ile Val Gln
            500                 505                 510

Ser Phe Lys Gln Thr Gly Gly Arg Ile Ser Leu Ser Pro Gly Ser Ser
    515                 520                 525

Leu Ala Leu Tyr Thr Met Asn Ser Phe Phe His Gly Asn Ile Ser Ser
530                 535                 540

Lys Glu Pro Leu Glu Ile Asn Gly Leu Ser Phe Gly Val Asp Ile Ser
545                 550                 555                 560

Pro Ser Asn Leu Gln Ala Glu Ile Arg Ala Gly Asn Ala Pro Leu Arg
                565                 570                 575

Leu Ser Gly Ser Pro Ser Ile His Asp Pro Glu Gly Leu Phe Tyr Glu
            580                 585                 590

Asn Arg Asp Thr Ala Ala Ser Pro Tyr Gln Met Glu Ile Leu Leu Thr
    595                 600                 605

Ser Asp Lys Ile Val Asp Ile Ser Lys Phe Thr Thr Asp Ser Leu Val
610                 615                 620

Thr Asn Lys Gln Ser Gly Phe Gln Gly Ala Trp His Phe Ser Trp Gln
625                 630                 635                 640

Pro Asn Thr Ile Asn Asn Thr Lys Gln Lys Ile Leu Arg Ala Ser Trp
                645                 650                 655

Leu Pro Thr Gly Glu Tyr Val Leu Glu Ser Asn Arg Val Gly Arg Ala
            660                 665                 670

Val Pro Asn Ser Leu Trp Ser Thr Phe Leu Leu Gln Thr Ala Ser
    675                 680                 685

His Asn Leu Gly Asp His Leu Cys Asn Asn Arg Ser Leu Ile Pro Thr
690                 695                 700

Ser Tyr Phe Gly Val Leu Ile Gly Gly Thr Gly Ala Glu Met Ser Thr
705                 710                 715                 720

His Ser Ser Glu Glu Ser Phe Ile Ser Arg Leu Gly Ala Thr Gly
                725                 730                 735

Thr Ser Ile Ile Arg Leu Thr Pro Ser Leu Thr Leu Ser Gly Gly Gly
            740                 745                 750

Ser His Met Phe Gly Asp Ser Phe Val Ala Asp Leu Pro Glu His Ile
    755                 760                 765

Thr Ser Glu Gly Ile Val Gln Asn Val Gly Leu Thr His Val Trp Gly
770                 775                 780

Pro Leu Thr Val Asn Ser Thr Leu Cys Ala Ala Leu Asp His Asn Ala
785                 790                 795                 800
```

```
Met Val Arg Ile Cys Ser Lys Lys Asp His Thr Tyr Gly Lys Trp Asp
                805                 810                 815

Thr Phe Gly Met Arg Gly Thr Leu Gly Ala Ser Tyr Thr Phe Leu Glu
            820                 825                 830

Tyr Asp Gln Thr Met Arg Val Phe Ser Phe Ala Asn Ile Glu Ala Thr
        835                 840                 845

Asn Ile Leu Gln Arg Ala Phe Thr Glu Thr Gly Tyr Asn Pro Arg Ser
    850                 855                 860

Phe Ser Lys Thr Lys Leu Leu Asn Ile Ala Ile Pro Ile Gly Ile Gly
865                 870                 875                 880

Tyr Glu Phe Cys Leu Gly Asn Ser Ser Phe Ala Leu Leu Gly Lys Gly
                885                 890                 895

Ser Ile Gly Tyr Ser Arg Asp Ile Lys Arg Glu Asn Pro Ser Thr Leu
            900                 905                 910

Ala His Leu Ala Met Asn Asp Phe Ala Trp Thr Thr Asn Gly Cys Ser
        915                 920                 925

Val Pro Thr Ser Ala His Thr Leu Ala Asn Gln Leu Ile Leu Arg Tyr
    930                 935                 940

Lys Ala Cys Ser Leu Tyr Ile Thr Ala Tyr Thr Ile Asn Arg Glu Gly
945                 950                 955                 960

Lys Asn Leu Ser Asn Ser Leu Ser Cys Gly Gly Tyr Val Gly Phe
                965                 970                 975

<210> SEQ ID NO 96
<211> LENGTH: 696
<212> TYPE: PRT
<213> ORGANISM: Chlamydia trachomatis

<400> SEQUENCE: 96

Met Ile Asp Lys Ile Ile Arg Thr Ile Leu Val Leu Ser Leu Phe Leu
1               5                   10                  15

Leu Tyr Trp Ser Ser Asp Leu Leu Glu Lys Asp Val Lys Ser Ile Lys
            20                  25                  30

Arg Glu Leu Lys Ala Leu His Glu Asp Val Leu Glu Leu Val Arg Ile
        35                  40                  45

Ser His Gln Gln Lys Asn Trp Val Gln Ser Thr Asp Phe Ser Val Ser
    50                  55                  60

Pro Glu Ile Ser Val Leu Lys Asp Cys Gly Asp Pro Ala Phe Pro Asn
65                  70                  75                  80

Leu Leu Cys Glu Asp Pro Tyr Val Glu Lys Val Pro Ser Leu Leu
                85                  90                  95

Lys Glu Gly Phe Val Pro Lys Gly Ile Leu Arg Thr Ala Gln Val Gly
            100                 105                 110

Arg Pro Asp Asn Leu Ser Pro Phe Asn Gly Phe Val Asn Ile Val Arg
        115                 120                 125

Phe Tyr Glu Leu Cys Val Pro Asn Leu Ala Val Glu His Val Gly Lys
    130                 135                 140

Tyr Glu Glu Phe Ala Pro Ser Leu Ala Leu Lys Ile Glu Glu His Tyr
145                 150                 155                 160

Val Glu Asp Gly Ser Gly Asp Lys Glu Phe His Ile Tyr Leu Arg Pro
                165                 170                 175

Asn Met Phe Trp Glu Pro Ile Asp Pro Thr Leu Phe Pro Lys Asn Ile
            180                 185                 190

Thr Leu Ala Asp Ser Phe Leu Arg Pro His Pro Val Thr Ala His Asp
        195                 200                 205
```

-continued

```
Val Lys Phe Tyr Tyr Asp Val Met Asn Pro Tyr Val Ala Glu Met
    210                 215                 220
Arg Ala Val Ala Met Arg Ser Tyr Phe Glu Asp Met Val Ser Val Arg
225                 230                 235                 240
Val Glu Asn Asp Leu Lys Leu Ile Val Arg Trp Arg Ala His Thr Val
                245                 250                 255
Arg Asn Glu Gln Gly Glu Glu Lys Lys Val Leu Tyr Ser Ala Phe
                260                 265                 270
Ala Asn Thr Leu Ala Leu Gln Pro Leu Pro Cys Phe Val Tyr Gln His
                275                 280                 285
Phe Ala Asn Gly Glu Lys Ile Val Pro Glu Asp Ser Asp Pro Asp Thr
290                 295                 300
Tyr Arg Lys Asp Ser Val Trp Ala Gln Asn Phe Ser Ser His Trp Ala
305                 310                 315                 320
Tyr Asn Tyr Ile Val Ser Cys Gly Ala Phe Arg Phe Ala Gly Met Asp
                325                 330                 335
Asp Glu Lys Ile Thr Leu Val Arg Asn Pro Asn Tyr His Asn Pro Phe
                340                 345                 350
Ala Ala Leu Val Glu Lys Arg Tyr Ile Tyr Met Lys Asp Ser Thr Asp
                355                 360                 365
Ser Leu Phe Gln Asp Phe Lys Ala Gly Lys Val Asp Ile Ala Tyr Phe
370                 375                 380
Pro Pro Asn His Val Asp Asn Leu Ala Ser Phe Met Gln Thr Ser Ala
385                 390                 395                 400
Tyr Lys Glu Gln Ala Ala Arg Gly Glu Ala Ile Leu Glu Lys Asn Ser
                405                 410                 415
Ser Asp Arg Ser Tyr Ser Tyr Ile Gly Trp Asn Cys Leu Ser Leu Phe
                420                 425                 430
Phe Asn Asn Arg Ser Val Arg Gln Ala Met Asn Met Leu Ile Asp Arg
                435                 440                 445
Asp Arg Ile Ile Glu Gln Cys Leu Asp Gly Arg Gly Val Ser Val Ser
                450                 455                 460
Gly Pro Phe Ser Leu Cys Ser Pro Ser Tyr Asn Arg Asp Val Glu Gly
465                 470                 475                 480
Trp Gln Tyr Ser Pro Glu Glu Ala Ala Arg Lys Leu Glu Glu Glu Gly
                485                 490                 495
Trp Ile Asp Ala Asp Gly Asp Gly Ile Arg Glu Lys Val Ile Asp Gly
                500                 505                 510
Val Val Val Pro Phe Arg Phe Arg Leu Cys Tyr Tyr Val Lys Ser Val
                515                 520                 525
Thr Ala Arg Thr Ile Ala Glu Tyr Val Ala Thr Val Cys Lys Glu Val
                530                 535                 540
Gly Ile Glu Cys Cys Leu Leu Gly Leu Asp Met Ala Asp Tyr Ser Gln
545                 550                 555                 560
Ala Leu Glu Glu Lys Asn Phe Asp Ala Ile Leu Ser Gly Trp Cys Leu
                565                 570                 575
Gly Thr Pro Pro Glu Asp Pro Arg Ala Leu Trp His Ser Glu Gly Ala
                580                 585                 590
Leu Glu Lys Gly Ser Ala Asn Ala Val Gly Phe Cys Asn Glu Glu Ala
                595                 600                 605
Asp Arg Ile Ile Glu Gln Leu Ser Tyr Glu Tyr Asp Ser Asn Lys Arg
                610                 615                 620
Gln Ala Leu Tyr His Arg Phe His Glu Val Ile His Glu Glu Ser Pro
```

```
                   625                 630                 635                 640
Tyr Ala Phe Leu Tyr Ser Arg Gln Tyr Ser Leu Val Tyr Lys Glu Phe
                    645                 650                 655

Val Lys Asn Ile Phe Val Pro Thr Glu His Gln Asp Leu Ile Pro Gly
                    660                 665                 670

Ala Gln Asp Glu Thr Val Asn Leu Ser Met Leu Trp Val Asp Lys Glu
                675                 680                 685

Glu Gly Arg Cys Ser Ala Ile Ser
            690                 695

<210> SEQ ID NO 97
<211> LENGTH: 194
<212> TYPE: PRT
<213> ORGANISM: Chlamydia trachomatis

<400> SEQUENCE: 97

Met Leu Lys Met Phe Trp Leu Asn Ser Leu Val Phe Phe Ser Leu Leu
1               5                   10                  15

Leu Ser Ala Cys Gly Tyr Thr Val Leu Ser Pro His Tyr Val Glu Lys
                20                  25                  30

Lys Phe Ser Leu Ser Glu Gly Ile Tyr Val Cys Pro Ile Glu Gly Asp
            35                  40                  45

Ser Leu Gly Asp Leu Val Ser Ser Leu Ser Tyr Glu Leu Glu Lys Arg
    50                  55                  60

Gly Leu His Thr Arg Ser Gln Gly Thr Ser Ser Gly Tyr Val Leu Lys
65                  70                  75                  80

Val Ser Leu Phe Asn Glu Thr Asp Glu Asn Ile Gly Phe Ala Tyr Thr
                85                  90                  95

Pro Gln Lys Pro Asp Glu Lys Pro Val Lys His Phe Ile Val Ser Asn
            100                 105                 110

Glu Gly Arg Leu Ala Leu Ser Ala Lys Val Gln Leu Ile Lys Asn Arg
        115                 120                 125

Thr Gln Glu Ile Leu Val Glu Lys Cys Leu Arg Lys Ser Val Thr Phe
    130                 135                 140

Asp Phe Gln Pro Asp Leu Gly Thr Ala Asn Ala His Gln Leu Ala Leu
145                 150                 155                 160

Gly Gln Phe Glu Met His Asn Glu Ala Ile Lys Ser Ala Ser Arg Ile
                165                 170                 175

Leu Tyr Ser Gln Leu Ala Glu Thr Ile Val Gln Gln Val Tyr Tyr Asp
            180                 185                 190

Leu Phe

<210> SEQ ID NO 98
<211> LENGTH: 167
<212> TYPE: PRT
<213> ORGANISM: Chlamydia trachomatis

<400> SEQUENCE: 98

Met Ser Arg Gln Asn Ala Glu Glu Asn Leu Lys Asn Phe Ala Lys Glu
1               5                   10                  15

Leu Lys Leu Pro Asp Val Ala Phe Asp Gln Asn Asn Thr Cys Ile Leu
                20                  25                  30

Phe Val Asp Gly Glu Phe Ser Leu His Leu Thr Tyr Glu Glu His Ser
            35                  40                  45

Asp Arg Leu Tyr Val Tyr Ala Pro Leu Leu Asp Gly Leu Pro Asp Asn
    50                  55                  60
```

-continued

```
Pro Gln Arg Arg Leu Ala Leu Tyr Glu Lys Leu Leu Glu Gly Ser Met
 65                  70                  75                  80

Leu Gly Gly Gln Met Ala Gly Gly Val Gly Val Ala Thr Lys Glu
                 85                  90                  95

Gln Leu Ile Leu Met His Cys Val Leu Asp Met Lys Tyr Ala Glu Thr
            100                 105                 110

Asn Leu Leu Lys Ala Phe Ala Gln Leu Phe Ile Glu Thr Val Val Lys
        115                 120                 125

Trp Arg Thr Val Cys Ser Asp Ile Ser Ala Gly Arg Glu Pro Thr Val
    130                 135                 140

Asp Thr Met Pro Gln Met Pro Gly Gly Gly Ile Gln Pro
145                 150                 155                 160

Pro Pro Ala Gly Ile Arg Ala
                165

<210> SEQ ID NO 99
<211> LENGTH: 144
<212> TYPE: PRT
<213> ORGANISM: Chlamydia trachomatis

<400> SEQUENCE: 99

Met Lys Asn Asn Ser Ala Gln Lys Ile Ile Asp Ser Ile Lys Gln Ile
  1               5                  10                  15

Leu Ser Ile Tyr Lys Ile Asp Phe Glu Pro Ser Phe Gly Ala Thr Leu
             20                  25                  30

Thr Asp Asp Asn Asp Leu Asp Tyr Gln Met Leu Ile Glu Lys Thr Gln
         35                  40                  45

Glu Lys Ile Gln Glu Leu Asp Lys Arg Ser Gln Glu Ile Leu Gln Gln
     50                  55                  60

Thr Gly Met Thr Arg Glu Gln Met Glu Val Phe Ala Asn Asn Pro Asp
 65                  70                  75                  80

Asn Phe Ser Pro Glu Glu Trp Arg Ala Leu Glu Asn Ile Arg Ser Ser
                 85                  90                  95

Cys Asn Glu Tyr Lys Lys Glu Thr Glu Glu Leu Ile Lys Glu Val Thr
            100                 105                 110

Asn Asp Ile Gly His Ser Ser His Lys Ser Pro Thr Pro Lys Lys Thr
        115                 120                 125

Lys Ser Ser Ser Gln Lys Lys Ser Lys Lys Asn Trp Ile Pro Leu
    130                 135                 140

<210> SEQ ID NO 100
<211> LENGTH: 307
<212> TYPE: PRT
<213> ORGANISM: Chlamydia trachomatis

<400> SEQUENCE: 100

Met Arg Lys Ile Ile Leu Cys Ser Pro Arg Gly Phe Cys Ala Gly Val
  1               5                  10                  15

Ile Arg Ala Ile Gln Thr Val Glu Val Ala Leu Glu Lys Trp Gly Arg
             20                  25                  30

Pro Ile Tyr Val Lys His Glu Ile Val His Asn Arg His Val Val Asp
         35                  40                  45

Lys Leu Arg Glu Lys Gly Ala Ile Phe Ile Glu Asp Leu Gln Glu Val
     50                  55                  60

Pro Arg Asn Ser Arg Val Ile Phe Ser Ala His Gly Val Pro Pro Ser
 65                  70                  75                  80

Val Arg Glu Glu Ala Glu Glu Arg Gly Leu Ile Ala Ile Asp Ala Thr
```

```
                  85                  90                  95
Cys Gly Leu Val Thr Lys Val His Ser Ala Val Lys Met Tyr Ala Lys
                100                 105                 110

Lys Gly Tyr His Ile Ile Leu Ile Gly Lys Arg Lys His Val Glu Ile
            115                 120                 125

Ile Gly Ile Arg Gly Glu Ala Pro Asp Gln Ile Thr Val Val Glu Asn
        130                 135                 140

Ile Ala Glu Val Glu Ala Leu Pro Phe Ser Ala Gln Asp Pro Leu Phe
145                 150                 155                 160

Tyr Val Thr Gln Thr Thr Leu Ser Met Asp Asp Ala Ala Asp Ile Val
                165                 170                 175

Ala Ala Leu Lys Ala Arg Tyr Pro Arg Ile Phe Thr Leu Pro Ser Ser
            180                 185                 190

Ser Ile Cys Tyr Ala Thr Gln Asn Arg Gln Gly Ala Leu Arg Asn Ile
        195                 200                 205

Leu Pro Gln Val Asp Phe Val Tyr Val Ile Gly Asp Thr Gln Ser Ser
    210                 215                 220

Asn Ser Asn Arg Leu Arg Glu Val Ala Glu Arg Arg Gly Val Thr Ala
225                 230                 235                 240

Arg Leu Val Asn His Pro Asp Glu Val Thr Glu Ile Leu Gln Tyr
                245                 250                 255

Ser Gly Asn Ile Gly Ile Thr Ala Gly Ala Ser Thr Pro Glu Asp Val
            260                 265                 270

Val Gln Ala Cys Leu Met Lys Leu Gln Glu Leu Ile Pro Asp Leu Ser
        275                 280                 285

Ile Glu Met Asp Leu Phe Val Glu Asp Thr Val Phe Gln Leu Pro
    290                 295                 300

Lys Glu Leu
305

<210> SEQ ID NO 101
<211> LENGTH: 283
<212> TYPE: PRT
<213> ORGANISM: Chlamydia trachomatis

<400> SEQUENCE: 101

Met Glu Leu Asn Lys Thr Ser Glu Ser Leu Phe Ser Ala Lys Ile Asp
1               5                   10                  15

His Asn His Pro Arg Thr Glu Ala His Glu Pro Arg Asp Gln Arg Glu
            20                  25                  30

Val Arg Val Phe Ser Leu Glu Gly Arg Ser Thr Arg Gln Glu Lys
        35                  40                  45

Ala Asp Arg Met Pro Gly Arg Thr Ser Ser Arg Gln Glu Ser Ser Lys
    50                  55                  60

Gly Ser Glu Glu Gly Ala Val His Glu Ser Thr Ala Gly Val Ser Ser
65                  70                  75                  80

Lys Glu Glu Glu Glu Ser Lys Gly Asp Gly Phe Phe Thr Gly Gly Asn
                85                  90                  95

Pro Thr Ser Gly Met Ala Leu Val Glu Thr Pro Met Ala Val Val Ser
            100                 105                 110

Glu Ala Met Val Glu Thr Ser Thr Met Thr Val Ser Gln Val Asp Leu
        115                 120                 125

Gln Trp Val Glu Gln Leu Val Thr Ser Thr Val Glu Ser Leu Leu Val
    130                 135                 140

Ala Asp Ile Asp Gly Lys Gln Leu Val Glu Ile Val Leu Asp Asn Ser
```

```
                145                 150                 155                 160
Asn Thr Val Pro Ala Ala Phe Cys Gly Ala Asn Leu Thr Leu Val Gln
                    165                 170                 175

Thr Gly Glu Glu Ile Ser Val Ser Phe Ser Asn Phe Val Asp Gln Ala
                180                 185                 190

Gln Leu Thr Glu Ala Thr Gln Leu Val Gln Gln Asn Pro Lys Gln Leu
            195                 200                 205

Val Ser Leu Val Glu Ser Leu Lys Ala Arg Gln Leu Asn Leu Thr Glu
        210                 215                 220

Leu Val Gly Asn Val Ala Val Ser Leu Pro Thr Ile Glu Lys Ile
225                 230                 235                 240

Glu Thr Pro Leu His Met Ile Ala Ala Thr Ile Arg His His Asp Gln
                    245                 250                 255

Glu Gly Asp Gln Glu Gly Glu Gly Arg Gln Asp Gln His Gln Gly Gln
                260                 265                 270

His Gln Glu Lys Lys Val Glu Glu Ala His Ile
            275                 280

<210> SEQ ID NO 102
<211> LENGTH: 242
<212> TYPE: PRT
<213> ORGANISM: Chlamydia trachomatis

<400> SEQUENCE: 102

Met Lys Val Lys Ile Asn Asp Gln Phe Ile Cys Ile Ser Pro Tyr Ile
1               5                   10                  15

Ser Ala Arg Trp Asn Gln Ile Ala Phe Ile Glu Ser Cys Asp Gly Gly
                20                  25                  30

Thr Glu Gly Gly Ile Thr Leu Lys Leu His Leu Ile Asp Gly Glu Thr
            35                  40                  45

Val Ser Ile Pro Asn Leu Gly Gln Ala Ile Val Asp Glu Val Phe Gln
        50                  55                  60

Glu His Leu Leu Tyr Leu Glu Ser Thr Ala Pro Gln Lys Asn Lys Glu
65                  70                  75                  80

Glu Glu Lys Ile Ser Ser Leu Leu Gly Ala Val Gln Gln Met Ala Lys
                85                  90                  95

Gly Cys Glu Val Gln Val Phe Ser Gln Lys Gly Leu Val Ser Met Leu
                100                 105                 110

Leu Gly Gly Ala Gly Ser Ile Asn Val Leu Leu Gln His Ser Pro Glu
            115                 120                 125

His Lys Asp His Pro Asp Leu Pro Thr Asp Leu Leu Glu Arg Ile Ala
        130                 135                 140

Gln Met Met Arg Ser Leu Ser Ile Gly Pro Thr Ser Ile Leu Ala Lys
145                 150                 155                 160

Pro Glu Pro His Cys Asn Cys Leu His Cys Gln Ile Gly Arg Ala Thr
                    165                 170                 175

Val Glu Glu Glu Asp Ala Gly Val Ser Asp Glu Asp Leu Thr Phe Arg
                180                 185                 190

Ser Trp Asp Ile Ser Gln Ser Gly Glu Lys Met Tyr Thr Val Thr Asp
            195                 200                 205

Pro Leu Asn Pro Glu Glu Gln Phe Asn Val Tyr Leu Gly Thr Pro Ile
        210                 215                 220

Gly Cys Thr Cys Gly Gln Pro Tyr Cys Glu His Val Lys Ala Val Leu
225                 230                 235                 240

Tyr Thr
```

```
<210> SEQ ID NO 103
<211> LENGTH: 433
<212> TYPE: PRT
<213> ORGANISM: Chlamydia trachomatis

<400> SEQUENCE: 103

Met Leu Ile Phe Ala Leu Ser Phe Gly Ala Asp Ala Cys Leu Cys Ala
1               5                   10                  15

Ala Asp Leu Ser Lys Ala Lys Val Glu Ala Ser Val Gly Asp Arg Ala
            20                  25                  30

Ala Phe Ser Pro Phe Thr Gly Glu Ile Lys Gly Asn Arg Val Arg Leu
        35                  40                  45

Arg Leu Ala Pro His Thr Asp Ser Phe Ile Ile Lys Glu Leu Ser Lys
    50                  55                  60

Gly Asp Cys Leu Ala Val Leu Gly Glu Ser Lys Asp Tyr Tyr Val Val
65                  70                  75                  80

Ala Ala Pro Glu Gly Val Arg Gly Tyr Val Phe Arg Thr Phe Val Leu
                85                  90                  95

Asp Asn Val Ile Glu Gly Glu Lys Val Asn Val Arg Leu Glu Pro Ser
            100                 105                 110

Thr Ser Ala Pro Ile Leu Ala Arg Leu Ser Lys Gly Thr Val Val Lys
        115                 120                 125

Thr Leu Gly Ala Ala Gln Gly Lys Trp Ile Glu Ile Ala Leu Pro Lys
130                 135                 140

Gln Cys Val Phe Tyr Val Ala Lys Asn Phe Val Lys Asn Val Gly Ala
145                 150                 155                 160

Leu Asp Leu Tyr Asn Gln Lys Glu Gly Gln Lys Lys Leu Ala Leu Asp
                165                 170                 175

Leu Leu Ser Ser Ala Met Asp Phe Ala Asp Ala Glu Leu Gln Lys Lys
            180                 185                 190

Ile Glu Asp Ile Asp Leu Asp Ala Ile Tyr Lys Lys Met Asn Leu Ala
        195                 200                 205

Gln Ser Glu Glu Phe Lys Asp Val Pro Gly Leu Gln Ser Leu Val Gln
    210                 215                 220

Lys Ala Leu Glu Arg Val Gln Glu Ala Phe Leu Ala Lys Ser Leu Glu
225                 230                 235                 240

Lys Ser Ser Val Lys Val Pro Glu Ile Arg His Lys Val Leu Glu Glu
                245                 250                 255

Ile Ala Val Val Ser Pro Ala Val Glu Glu Thr Pro Val Thr Lys
            260                 265                 270

Thr Glu Glu Gln Lys Val Thr Thr Val Pro Val Pro Ala Pro Ala Val
        275                 280                 285

Val Thr Glu Pro Ala Gln Asp Leu Ser Ser Val Lys Gly Ser Leu Leu
    290                 295                 300

Ser His Tyr Ile Arg Lys Lys Gly Phe Val Lys Ala Ser Pro Val Ile
305                 310                 315                 320

Glu Gly Arg Glu Ser Phe Glu Arg Ser Leu Phe Ala Val Trp Leu Ser
                325                 330                 335

Leu Gln Pro Glu Glu Ile Arg His Gln Leu Thr Met Glu Ser Phe Tyr
            340                 345                 350

Arg Asp Glu Gln Lys Lys Lys Arg Val Leu Thr Gly Glu Leu Glu Val
        355                 360                 365

Tyr Pro His Ile Val Lys Asn Asn Pro Gly Asp Tyr Leu Leu Lys Asn
    370                 375                 380
```

```
Gly Glu Asp Val Val Ala Phe Val Tyr Ala Thr Ser Ile Asp Leu Ser
385                 390                 395                 400

Lys Trp Leu Gly Lys Ser Val Val Leu Glu Cys Val Ser Arg Pro Asn
            405                 410                 415

Asn His Phe Ala Phe Pro Ala Tyr Ile Val Leu Ser Val Lys Glu Gly
            420                 425                 430

Ala

<210> SEQ ID NO 104
<211> LENGTH: 6
<212> TYPE: PRT
<213> ORGANISM: Artificial Sequence
<220> FEATURE:
<223> OTHER INFORMATION: Linker sequence

<400> SEQUENCE: 104

Gly Ser Gly Gly Gly Gly
1               5

<210> SEQ ID NO 105
<211> LENGTH: 619
<212> TYPE: PRT
<213> ORGANISM: Chlamydia trachomatis

<400> SEQUENCE: 105

Met Thr Ile Ile Tyr Phe Val Leu Ala Ala Leu Ala Leu Gly Phe Leu
1               5                   10                  15

Ile Leu Ile His Glu Leu Gly His Leu Leu Ala Ala Lys Ala Val Gly
            20                  25                  30

Met Ser Val Glu Ser Phe Ser Ile Gly Phe Gly Pro Ala Leu Val Arg
        35                  40                  45

Lys Lys Met Gly Ser Val Glu Tyr Arg Ile Gly Ala Ile Pro Phe Gly
    50                  55                  60

Gly Tyr Val Arg Ile Lys Gly Met Asp Arg Asn Asp Lys Asp Asn Ser
65                  70                  75                  80

Gly Asp Lys Glu Lys Thr Val Tyr Asp Ile Pro Glu Gly Phe Phe Ser
            85                  90                  95

Lys Ser Pro Trp Lys Arg Ile Phe Val Leu Ala Ala Gly Pro Leu Ala
            100                 105                 110

Asn Leu Leu Val Ala Ile Phe Val Phe Gly Ile Leu Tyr Phe Ser Gly
            115                 120                 125

Gly Arg Thr Lys Ser Phe Ser Glu Tyr Thr Ser Ile Val Gly Trp Val
130                 135                 140

His Pro Ser Leu Glu Gln Gln Gly Leu His Ala Gly Asp Gln Ile Phe
145                 150                 155                 160

Phe Cys Asn Gly Gln Pro Tyr Ser Gly His Lys Met Ala Phe Ser Ser
            165                 170                 175

Ser Leu Leu Glu Arg Lys Leu Ser Leu Gln Gly Gln His Pro Ala Tyr
            180                 185                 190

Phe Ser Glu Ser Glu Ala Phe Ser Leu Glu Ala Pro Phe Asn Pro Asn
        195                 200                 205

Met Glu Gly Val Pro Cys Leu Gly Ala Ser Tyr Leu Leu Tyr Arg Gly
    210                 215                 220

Ser Asp Pro Leu Pro Glu Lys Ser Pro Leu Val Asp Ala Gly Leu Ser
225                 230                 235                 240

Glu Gly Asp Arg Leu Val Trp Met Asp Gly Leu Leu Val Phe Ser Gly
            245                 250                 255
```

```
Ala Gln Val Ser Gln Met Leu Asn Glu Lys Gln Ser Phe Leu Arg Val
            260                 265                 270

Glu Arg Gln Gly Lys Val Val Phe Val Arg Gln Ala Arg Val Leu Ala
            275                 280                 285

Gly Asp Leu Thr Leu Thr Pro Tyr Phe Lys Asn Glu Leu Ile Asp Cys
            290                 295                 300

Gln Tyr Glu Ala Gly Leu Lys Gly Lys Trp Ala Ser Leu Tyr Thr Leu
305                 310                 315                 320

Pro Tyr Ile Ile Asn Gly Asp Gly Phe Val Glu Ser Lys Val Lys Leu
                325                 330                 335

Leu Asn Asp Glu Arg Val Ser Leu Asp Tyr Asn Leu Glu Leu Gly Asp
            340                 345                 350

Lys Ile Val Ala Val Asp Gly Ile Pro Val Met Ser Asn Ala Asp Ile
            355                 360                 365

Leu Arg Leu Val Gln Asp His Arg Val Ser Leu Ile Phe Gln Arg Met
            370                 375                 380

Ser Pro Glu Gln Leu Thr Val Leu Glu Gln Lys Ala Ala Asp Gln Ala
385                 390                 395                 400

Phe Ile Asn Ser Tyr Asp Met Asp Asp Leu Leu Arg Val Ala Glu Ser
                405                 410                 415

Val Gly Glu Glu Arg Glu Val Ser Arg Leu Gly Asp Tyr Arg Leu Val
            420                 425                 430

Thr Arg Val Gln Pro Arg Pro Trp Ala His Ile Tyr Ser Glu Ala Leu
            435                 440                 445

Leu Asp Lys Gln Arg Ala Leu Ala Ser Lys Phe Arg Asp Glu Gln Glu
            450                 455                 460

Arg Arg Tyr Tyr Leu Glu Arg Ile Glu Ala Glu Lys Gln Arg Ile Ser
465                 470                 475                 480

Leu Gly Ile Pro Leu Lys Asp Leu Ala Val Gln Tyr Asn Pro Asp Pro
                485                 490                 495

Trp Val Leu Met Glu Glu Ser Val Ser Asp Ser Leu Lys Thr Val Lys
            500                 505                 510

Ala Leu Gly Met Gly Arg Val Ser Pro Gln Trp Leu Ser Gly Pro Val
            515                 520                 525

Gly Ile Val Arg Ile Leu His Thr Gly Trp Ser Val Gly Ile Pro Glu
            530                 535                 540

Ala Leu Ala Trp Ile Gly Leu Ile Ser Val Asn Leu Ala Val Leu Asn
545                 550                 555                 560

Leu Leu Pro Ile Pro Val Leu Asp Gly Gly Tyr Ile Leu Leu Cys Leu
                565                 570                 575

Trp Glu Ile Leu Ser Arg Arg Arg Leu Asn Met Arg Leu Val Glu Lys
            580                 585                 590

Ala Leu Val Pro Phe Met Ile Leu Leu Val Leu Phe Phe Val Phe Leu
            595                 600                 605

Thr Leu Gln Asp Leu Ser Arg Val Phe Val Gly
        610                 615

<210> SEQ ID NO 106
<211> LENGTH: 13
<212> TYPE: PRT
<213> ORGANISM: Chlamydia trachomatis

<400> SEQUENCE: 106

Ser Pro Leu Val Asp Ala Gly Leu Ser Glu Gly Asp Arg
1               5                   10
```

-continued

<210> SEQ ID NO 107
<211> LENGTH: 694
<212> TYPE: PRT
<213> ORGANISM: Chlamydia trachomatis

<400> SEQUENCE: 107

Met Ser Asp Gln Glu Phe Gly Leu Asp Ala Ile Arg Asn Ile Gly Ile
1               5                   10                  15

Met Ala His Ile Asp Ala Gly Lys Thr Thr Thr Glu Arg Ile Leu
            20                  25                  30

Phe Tyr Ala Gly Arg Thr His Lys Ile Gly Glu Val His Glu Gly Gly
        35                  40                  45

Ala Thr Met Asp Trp Met Glu Gln Glu Gln Arg Gly Ile Thr Ile
    50                  55                  60

Thr Ser Ala Ala Thr Thr Val Phe Trp Leu Gly Ala Lys Ile Asn Ile
65                  70                  75                  80

Ile Asp Thr Pro Gly His Val Asp Phe Thr Ile Glu Val Glu Arg Ser
                85                  90                  95

Leu Arg Val Leu Asp Gly Ala Val Ala Val Phe Asp Ala Val Ser Gly
            100                 105                 110

Val Glu Pro Gln Ser Glu Thr Val Trp Arg Gln Ala Asn Lys Tyr Gly
        115                 120                 125

Val Pro Arg Ile Ala Phe Val Asn Lys Met Asp Arg Met Gly Ala Asn
    130                 135                 140

Tyr Phe Gly Ala Ile Glu Ser Met Arg Glu Lys Leu Gly Ala Asn Ala
145                 150                 155                 160

Ile Pro Val His Cys Pro Ile Gly Ser Glu Ser Gln Phe Val Gly Met
                165                 170                 175

Val Asp Leu Ile Ser Gln Lys Thr Leu Tyr Phe Leu Glu Glu Thr Leu
            180                 185                 190

Gly Ala Lys Trp Glu Glu Arg Glu Ile Pro Glu Asp Leu Gln Glu Gln
        195                 200                 205

Cys Ala Thr Leu Arg Met Gln Leu Leu Glu Glu Leu Ala Thr Val Asp
    210                 215                 220

Glu Ser Asn Glu Ala Phe Met Glu Lys Val Leu Glu Asn Pro Asp Ser
225                 230                 235                 240

Ile Thr Glu Glu Glu Ile His Thr Val Met Arg Lys Gly Val Ile Glu
                245                 250                 255

Gly Lys Ile Asn Pro Val Leu Cys Gly Ser Ala Phe Lys Asn Lys Gly
            260                 265                 270

Val Gln Gln Leu Leu Asp Val Ile Val Lys Trp Leu Pro Ser Pro Leu
        275                 280                 285

Asp Arg Gly Asn Val Arg Gly Ile Asn Leu Lys Thr Gly Glu Glu Val
    290                 295                 300

Ser Leu Lys Pro Ser Lys Asp Gly Pro Leu Ala Ala Leu Ala Phe Lys
305                 310                 315                 320

Ile Met Thr Asp Pro Tyr Val Gly Arg Ile Thr Phe Ile Arg Ile Tyr
                325                 330                 335

Ser Gly Thr Leu Lys Lys Gly Ser Ala Ile Leu Asn Ser Thr Lys Asp
            340                 345                 350

Lys Lys Glu Arg Ile Ser Arg Leu Leu Glu Met His Ala Asn Glu Arg
        355                 360                 365

Thr Asp Arg Asp Glu Phe Thr Val Gly Asp Ile Gly Ala Cys Val Gly
    370                 375                 380

```
Leu Lys Phe Ser Val Thr Gly Asp Thr Leu Cys Asp Glu Asn Gln Glu
385                 390                 395                 400

Ile Val Leu Glu Arg Ile Glu Ala Pro Glu Pro Val Ile Asp Met Ala
            405                 410                 415

Ile Glu Pro Lys Ser Lys Gly Asp Arg Glu Lys Leu Ala Gln Ala Leu
            420                 425                 430

Ser Ala Leu Ser Glu Glu Asp Pro Thr Phe Arg Val Ser Thr Asn Glu
            435                 440                 445

Glu Thr Gly Gln Thr Ile Ile Ser Gly Met Gly Glu Leu His Leu Asp
450                 455                 460

Ile Leu Arg Asp Arg Met Ile Arg Glu Phe Arg Val Glu Ala Asn Val
465                 470                 475                 480

Gly Lys Pro Gln Val Ser Tyr Lys Glu Thr Ile Thr Lys Thr Ser Asn
            485                 490                 495

Ser Glu Thr Lys Tyr Val Lys Gln Ser Gly Arg Gly Gln Tyr Ala
            500                 505                 510

His Val Cys Leu Glu Ile Glu Pro Asn Glu Pro Gly Lys Gly Asn Glu
            515                 520                 525

Val Val Ser Lys Ile Val Gly Val Ile Pro Lys Glu Tyr Ile Pro
530                 535                 540

Ala Val Ile Lys Gly Val Glu Glu Gly Leu Asn Ser Gly Val Leu Ala
545                 550                 555                 560

Gly Tyr Gly Leu Val Asp Val Lys Val Ser Ile Val Phe Gly Ser Tyr
            565                 570                 575

His Glu Val Asp Ser Ser Glu Met Ala Phe Lys Ile Cys Gly Ser Met
            580                 585                 590

Ala Val Lys Glu Ala Cys Arg Lys Ala Leu Pro Val Ile Leu Glu Pro
            595                 600                 605

Ile Met Lys Val Thr Val Ile Thr Pro Glu Asp His Leu Gly Asp Val
            610                 615                 620

Ile Gly Asp Leu Asn Arg Arg Gly Lys Ile Leu Gly Gln Glu Ser
625                 630                 635                 640

Ser Arg Asn Met Ala Gln Val Ser Ala Glu Val Pro Leu Ser Glu Met
            645                 650                 655

Phe Gly Tyr Met Thr Ser Leu Arg Ser Leu Thr Ser Gly Arg Ala Thr
            660                 665                 670

Ser Thr Met Glu Pro Ala Phe Phe Ala Lys Val Pro Gln Lys Ile Gln
            675                 680                 685

Glu Glu Ile Val Lys Lys
            690

<210> SEQ ID NO 108
<211> LENGTH: 13
<212> TYPE: PRT
<213> ORGANISM: Chlamydia trachomatis

<400> SEQUENCE: 108

Met Gly Ala Asn Tyr Phe Gly Ala Ile Glu Ser Met Arg
1               5                   10

<210> SEQ ID NO 109
<211> LENGTH: 11
<212> TYPE: PRT
<213> ORGANISM: Chlamydia trachomatis

<400> SEQUENCE: 109
```

```
Thr Gly Glu Glu Val Ser Leu Lys Pro Ser Lys
1               5                  10
```

<210> SEQ ID NO 110
<211> LENGTH: 16
<212> TYPE: PRT
<213> ORGANISM: Chlamydia trachomatis

<400> SEQUENCE: 110

```
Leu Ala Gln Ala Leu Ser Ala Leu Ser Glu Glu Asp Pro Thr Phe Arg
1               5                   10                  15
```

<210> SEQ ID NO 111
<211> LENGTH: 18
<212> TYPE: PRT
<213> ORGANISM: Chlamydia trachomatis

<400> SEQUENCE: 111

```
Val Leu Glu Asn Pro Asp Ser Ile Thr Glu Glu Ile His Thr Val
1               5                   10                  15

Met Arg
```

<210> SEQ ID NO 112
<211> LENGTH: 487
<212> TYPE: PRT
<213> ORGANISM: Chlamydia trachomatis

<400> SEQUENCE: 112

```
Met Ser Leu Ser Ser Ser Ser Ser Asp Ser Ser Asn Leu Lys Asn
1               5                   10                  15

Val Leu Ser Gln Val Ile Ala Ser Thr Pro Gln Gly Val Pro Asn Ala
                20                  25                  30

Asp Lys Leu Thr Asp Asn Gln Val Lys Gln Val Gln Gln Thr Arg Gln
            35                  40                  45

Asn Arg Asp Asp Leu Ser Met Glu Ser Asp Val Ala Val Ala Gly Thr
        50                  55                  60

Ala Gly Lys Asp Arg Ala Ala Ser Ala Ser Gln Ile Glu Gly Gln Glu
65                  70                  75                  80

Leu Ile Glu Gln Gln Gly Leu Ala Ala Gly Lys Glu Thr Ala Ser Ala
                85                  90                  95

Asp Ala Thr Ser Leu Thr Gln Ser Ser Lys Gly Ala Ser Ser Gln
            100                 105                 110

Gln Cys Ile Glu Asp Thr Ser Lys Ser Leu Glu Leu Ser Ser Leu Ser
        115                 120                 125

Ser Leu Ser Ser Val Asp Ala Thr His Leu Gln Glu Ile Gln Ser Ile
130                 135                 140

Val Ser Ser Ala Met Gly Ala Thr Asn Glu Leu Ser Leu Thr Asn Leu
145                 150                 155                 160

Glu Thr Pro Gly Leu Pro Lys Pro Ser Thr Thr Pro Arg Gln Glu Val
                165                 170                 175

Met Glu Ile Ser Leu Ala Leu Ala Lys Ala Ile Thr Ala Leu Gly Glu
            180                 185                 190

Ser Thr Gln Ala Ala Leu Glu Asn Phe Gln Ser Thr Gln Ser Gln Ser
        195                 200                 205

Ala Asn Met Asn Lys Met Ser Leu Glu Ser Gln Gly Leu Lys Ile Asp
    210                 215                 220

Lys Glu Arg Glu Glu Phe Lys Lys Met Gln Glu Ile Gln Gln Lys Ser
225                 230                 235                 240
```

Gly Thr Asn Ser Thr Met Asp Thr Val Asn Lys Val Met Ile Gly Val
               245                 250                 255

Thr Val Ala Ile Thr Val Ile Ser Val Val Ser Ala Leu Phe Thr Cys
            260                 265                 270

Gly Leu Gly Leu Ile Gly Thr Ala Ala Gly Ala Thr Ala Ala Ala
        275                 280                 285

Ala Gly Ala Thr Ala Ala Ala Thr Thr Ala Thr Ser Val Ala Thr Thr
290                 295                 300

Val Ala Thr Gln Val Thr Met Gln Ala Val Val Gln Val Val Lys Gln
305                 310                 315                 320

Ala Ile Ile Gln Ala Val Lys Gln Ala Ile Val Gln Ala Ile Lys Gln
            325                 330                 335

Gly Ile Lys Gln Gly Ile Lys Gln Ala Ile Lys Gln Ala Val Lys Ala
            340                 345                 350

Ala Val Lys Thr Leu Ala Lys Asn Val Gly Lys Ile Phe Ser Ala Gly
            355                 360                 365

Lys Asn Ala Val Ser Lys Ser Phe Pro Lys Leu Ser Lys Val Ile Asn
        370                 375                 380

Thr Leu Gly Ser Lys Trp Val Thr Leu Gly Val Gly Ala Leu Thr Ala
385                 390                 395                 400

Val Pro Gln Leu Val Ser Gly Ile Thr Ser Leu Gln Leu Ser Asp Met
                405                 410                 415

Gln Lys Glu Leu Ala Gln Ile Gln Lys Glu Val Gly Ala Leu Thr Ala
                420                 425                 430

Gln Ser Glu Met Met Lys Ala Phe Thr Leu Phe Trp Gln Gln Ala Ser
            435                 440                 445

Lys Ile Ala Ala Lys Gln Thr Glu Ser Pro Ser Glu Thr Gln Gln Gln
        450                 455                 460

Ala Ala Lys Thr Gly Ala Gln Ile Ala Lys Ala Leu Ser Ala Ile Ser
465                 470                 475                 480

Gly Ala Leu Ala Ala Ala Ala
            485

<210> SEQ ID NO 113
<211> LENGTH: 22
<212> TYPE: PRT
<213> ORGANISM: Chlamydia trachomatis

<400> SEQUENCE: 113

Ala Ala Ser Ala Ser Gln Ile Glu Gly Gln Glu Leu Ile Glu Gln Gln
1               5                   10                  15

Gly Leu Ala Ala Gly Lys
            20

<210> SEQ ID NO 114
<211> LENGTH: 16
<212> TYPE: PRT
<213> ORGANISM: Chlamydia trachomatis

<400> SEQUENCE: 114

Glu Thr Ala Ser Ala Asp Ala Thr Ser Leu Thr Gln Ser Ala Ser Lys
1               5                   10                  15

<210> SEQ ID NO 115
<211> LENGTH: 13
<212> TYPE: PRT
<213> ORGANISM: Chlamydia trachomatis

<400> SEQUENCE: 115

```
Gly Ala Ser Ser Gln Gln Cys Ile Glu Asp Thr Ser Lys
1               5                   10
```

```
<210> SEQ ID NO 116
<211> LENGTH: 14
<212> TYPE: PRT
<213> ORGANISM: Chlamydia trachomatis

<400> SEQUENCE: 116
```

```
Gln Thr Glu Ser Pro Ser Glu Thr Gln Gln Gln Ala Ala Lys
1               5                   10
```

```
<210> SEQ ID NO 117
<211> LENGTH: 439
<212> TYPE: PRT
<213> ORGANISM: Chlamydia trachomatis

<400> SEQUENCE: 117
```

```
Met Thr Thr Gly Val Arg Gly Asp Asn Ala Pro Asp Pro Ser Leu Leu
1               5                   10                  15

Ala Gln Leu Thr Gln Asn Ala Asn Ser Ala Ser Ala Ala Ser Thr Gly
                20                  25                  30

Lys Asn Gly Gln Val Ala Gly Ala Lys Gln Glu Asn Val Asp Ala Ser
            35                  40                  45

Phe Glu Asp Leu Leu Gln Asp Ala Gln Gly Thr Gly Ser Lys Lys
    50                  55                  60

Ala Thr Ala Asn Gln Thr Ser Lys Ser Gly Lys Ser Glu Lys Ala Gln
65                  70                  75                  80

Ala Ser Ser Gly Thr Ser Thr Thr Ser Val Ala Gln Ala Ser Gln
                85                  90                  95

Thr Ala Thr Ala Gln Ala Val His Gly Ala Arg Asp Ser Gly Phe Asn
                100                 105                 110

Ser Asp Gly Ser Ala Thr Leu Pro Ser Pro Thr Gly Thr Glu Val Asn
            115                 120                 125

Gly Val Val Leu Arg Lys Gly Met Gly Thr Leu Ala Leu Met Gly Leu
        130                 135                 140

Ile Met Thr Leu Leu Ala Gln Ala Ser Ala Lys Ser Trp Ser Ser Ser
145                 150                 155                 160

Phe Gln Gln Gln Asn Gln Ala Ile Gln Asn Gln Val Ala Met Ala Pro
                165                 170                 175

Glu Ile Gly Asn Ala Ile Arg Thr Gln Ala Asn His Gln Ala Gln Ala
            180                 185                 190

Thr Glu Leu Gln Ala Gln Gln Ser Leu Ile Ser Gly Ile Thr Asn Ile
        195                 200                 205

Val Gly Phe Ala Val Ser Val Gly Gly Gly Ile Leu Ser Ala Ser Lys
    210                 215                 220

Ser Leu Gly Gly Leu Lys Ser Ala Ala Phe Thr Asn Glu Thr Ala Ser
225                 230                 235                 240

Ala Thr Thr Ser Ala Thr Ser Leu Ala Lys Thr Ala Thr Ser Ala
                245                 250                 255

Leu Asp Asp Val Ala Gly Thr Ala Thr Ala Val Gly Ala Lys Ala Thr
            260                 265                 270

Ser Gly Ala Ala Ser Ala Ala Ser Ala Ala Thr Lys Leu Thr Gln
        275                 280                 285

Asn Met Ala Glu Ser Ala Ser Lys Thr Leu Ser Gln Thr Ala Ser Lys
    290                 295                 300
```

```
Ser Ala Gly Gly Leu Phe Gly Gln Ala Leu Asn Thr Pro Ser Trp Ser
305                 310                 315                 320

Glu Lys Val Ser Arg Gly Met Asn Val Val Lys Thr Gln Gly Thr Arg
                325                 330                 335

Ala Ala Lys Phe Ala Gly Arg Ala Leu Ser Ser Ala Met Asn Ile Ser
            340                 345                 350

Gln Met Val His Gly Leu Thr Ala Gly Ile Asp Gly Ile Val Gly Gly
        355                 360                 365

Val Ile Gly Ala Gln Val Ala Gln Glu Gln Arg Met Ala Gly Met Ala
370                 375                 380

Glu Ala Arg Ala Glu Glu Leu Lys Ser Leu Asn Ser Val Gln Ala Gln
385                 390                 395                 400

Tyr Ala Ser Gln Ala Gln Gln Leu Gln Glu Gln Ser Gln Gln Ser Phe
                405                 410                 415

Asn Ser Ala Leu Gln Thr Leu Gln Ser Ile Ser Asp Ser Ala Leu Gln
            420                 425                 430

Thr Thr Ala Ser Met Phe Asn
            435

<210> SEQ ID NO 118
<211> LENGTH: 26
<212> TYPE: PRT
<213> ORGANISM: Chlamydia trachomatis

<400> SEQUENCE: 118

Asp Ser Gly Phe Asn Ser Asp Gly Ser Ala Thr Leu Pro Ser Pro Thr
1               5                   10                  15

Gly Thr Glu Val Asn Gly Val Val Leu Arg
            20                  25

<210> SEQ ID NO 119
<211> LENGTH: 21
<212> TYPE: PRT
<213> ORGANISM: Chlamydia trachomatis

<400> SEQUENCE: 119

Ser Ala Ala Phe Thr Asn Glu Thr Ala Ser Ala Thr Thr Ser Ala Thr
1               5                   10                  15

Ser Ser Leu Ala Lys
            20

<210> SEQ ID NO 120
<211> LENGTH: 15
<212> TYPE: PRT
<213> ORGANISM: Chlamydia trachomatis

<400> SEQUENCE: 120

Ala Thr Ser Gly Ala Ala Ser Ala Ala Ser Ser Ala Ala Thr Lys
1               5                   10                  15

<210> SEQ ID NO 121
<211> LENGTH: 19
<212> TYPE: PRT
<213> ORGANISM: Chlamydia trachomatis

<400> SEQUENCE: 121

Thr Ala Thr Ser Ala Leu Asp Asp Val Ala Gly Thr Ala Thr Ala Val
1               5                   10                  15

Gly Ala Lys
```

```
<210> SEQ ID NO 122
<211> LENGTH: 11
<212> TYPE: PRT
<213> ORGANISM: Chlamydia trachomatis

<400> SEQUENCE: 122

Leu Thr Gln Asn Met Ala Glu Ser Ala Ser Lys
1               5                   10

<210> SEQ ID NO 123
<211> LENGTH: 18
<212> TYPE: PRT
<213> ORGANISM: Chlamydia trachomatis

<400> SEQUENCE: 123

Ser Ala Gly Gly Leu Phe Gly Gln Ala Leu Asn Thr Pro Ser Trp Ser
1               5                   10                  15

Glu Lys

<210> SEQ ID NO 124
<211> LENGTH: 282
<212> TYPE: PRT
<213> ORGANISM: Chlamydia trachomatis

<400> SEQUENCE: 124

Met Glu Phe Ser Cys Thr Leu Thr Leu Lys Glu Leu Leu Glu Ser Gly
1               5                   10                  15

Ala His Phe Gly His Gln Thr Ser Arg Trp Asn Pro Arg Met Lys Pro
                20                  25                  30

Phe Ile Phe Glu Glu Lys Asn Gly Leu Tyr Ile Ile Asp Leu Ala Lys
        35                  40                  45

Thr Leu Ala Gln Leu Lys Lys Ala Val Ala Cys Ile Gln Thr Thr Ile
    50                  55                  60

Gly Gln Glu Lys Ser Ile Leu Phe Val Gly Thr Lys Lys Gln Ala Lys
65                  70                  75                  80

Gln Ile Ile Arg Glu Ala Ala Ile Glu Cys Gly Glu Phe Phe Ala Ser
                85                  90                  95

Glu Arg Trp Leu Gly Gly Met Leu Thr Asn Met Ala Thr Ile Arg Asn
            100                 105                 110

Ser Val Lys Thr Leu Asn Arg Ile Glu Leu Asp Leu Glu Ala Ser Asn
        115                 120                 125

Ser Gly Leu Thr Lys Lys Glu Leu Ala Leu Ala Lys Arg His Arg
    130                 135                 140

Lys Leu Leu Asn Asn Leu Glu Gly Val Arg His Met Asn Ser Leu Pro
145                 150                 155                 160

Gly Leu Leu Ile Val Ile Asp Pro Gly Tyr Glu Arg Ile Ala Val Ala
                165                 170                 175

Glu Ala Gly Lys Leu Gly Ile Pro Val Met Ala Leu Val Asp Thr Asn
            180                 185                 190

Cys Asp Pro Thr Pro Ile Asn His Val Ile Pro Cys Asn Asp Ser
        195                 200                 205

Met Lys Ser Ile Arg Leu Ile Val Asn Val Leu Lys Asp Ala Val Ile
    210                 215                 220

Asp Ala Lys Lys Arg Leu Gly Val Glu Ile Leu Ser Pro Val Arg Pro
225                 230                 235                 240

Ala Glu Arg Pro Ala Glu Glu Ala Val Glu Glu Leu Pro Leu Pro Thr
                245                 250                 255

Gly Glu Ala Gln Asp Glu Ala Ser Ser Lys Glu Gly Val Leu Leu Trp
```

```
                    260                 265                 270
Ala Asp Ile Asp Asn Cys Glu Ala Leu Lys
            275                 280

<210> SEQ ID NO 125
<211> LENGTH: 14
<212> TYPE: PRT
<213> ORGANISM: Chlamydia trachomatis

<400> SEQUENCE: 125

Ile Glu Leu Asp Leu Glu Ala Ser Asn Ser Gly Leu Thr Lys
1               5                   10

<210> SEQ ID NO 126
<211> LENGTH: 133
<212> TYPE: PRT
<213> ORGANISM: Chlamydia trachomatis

<400> SEQUENCE: 126

Met Gln Gln Pro Pro Thr Leu Trp Ser Gln Thr Cys Arg Tyr Ser Pro
1               5                   10                  15

Met Arg Met Ala Leu Asp Lys Lys Arg Leu Thr Leu Phe Val Glu
            20                  25                  30

Lys Arg Met Phe Arg Ser Gln Lys Pro Lys Lys Asn Lys Cys Cys Leu
        35                  40                  45

Trp Leu Arg Gly Val Leu Phe Gly Gly Phe Leu Ala Thr Leu Leu Thr
    50                  55                  60

Ser Leu Phe Leu Pro Lys Ser Gly Met Gln Ile Arg Lys Leu Leu
65                  70                  75                  80

Arg Val Lys Thr Ser Gly Thr Lys Lys Gly Arg Ala Leu Leu Lys Asn
                85                  90                  95

Ser Lys His His Thr Arg Glu Phe Ala Glu Gln Thr Lys Leu Leu Ala
            100                 105                 110

Lys Asn Ile Ser Lys Glu Ile Gln Asp Phe Thr Gln Ser Ile Ile Asp
        115                 120                 125

Glu Ser Arg Arg Asp
    130

<210> SEQ ID NO 127
<211> LENGTH: 14
<212> TYPE: PRT
<213> ORGANISM: Chlamydia trachomatis

<400> SEQUENCE: 127

Glu Ile Gln Asp Phe Thr Gln Ser Ile Ile Asp Glu Ser Arg
1               5                   10

<210> SEQ ID NO 128
<211> LENGTH: 21
<212> TYPE: PRT
<213> ORGANISM: Chlamydia trachomatis

<400> SEQUENCE: 128

Leu Leu Glu Gly Ser Met Leu Gly Gly Gln Met Ala Gly Gly Gly Val
1               5                   10                  15

Gly Val Ala Thr Lys
            20

<210> SEQ ID NO 129
<211> LENGTH: 15
<212> TYPE: PRT
```

<213> ORGANISM: Chlamydia trachomatis

<400> SEQUENCE: 129

Asp Leu Ala Glu Ala Ser Ser Glu Thr Gly Glu Ala Leu Trp Arg
1 5 10 15

<210> SEQ ID NO 130
<211> LENGTH: 17
<212> TYPE: PRT
<213> ORGANISM: Chlamydia trachomatis

<400> SEQUENCE: 130

Glu Val Glu Leu Ala Asp Lys His Glu Asn Met Gly Ala Gln Met Val
1 5 10 15

Lys

<210> SEQ ID NO 131
<211> LENGTH: 12
<212> TYPE: PRT
<213> ORGANISM: Chlamydia trachomatis

<400> SEQUENCE: 131

Asn Val Thr Ala Gly Ala Asn Pro Met Asp Leu Lys
1 5 10

<210> SEQ ID NO 132
<211> LENGTH: 26
<212> TYPE: PRT
<213> ORGANISM: Chlamydia trachomatis

<400> SEQUENCE: 132

Glu Ile Ala Gln Val Ala Thr Ile Ser Ala Asn Asn Asp Ala Glu Ile
1 5 10 15

Gly Asn Leu Ile Ala Glu Ala Met Glu Lys
20 25

<210> SEQ ID NO 133
<211> LENGTH: 10
<212> TYPE: PRT
<213> ORGANISM: Chlamydia trachomatis

<400> SEQUENCE: 133

Asn Gly Ser Ile Thr Val Glu Glu Ala Lys
1 5 10

<210> SEQ ID NO 134
<211> LENGTH: 11
<212> TYPE: PRT
<213> ORGANISM: Chlamydia trachomatis

<400> SEQUENCE: 134

Gln Ile Glu Asp Ser Ser Ser Asp Tyr Asp Lys
1 5 10

<210> SEQ ID NO 135
<211> LENGTH: 12
<212> TYPE: PRT
<213> ORGANISM: Chlamydia trachomatis

<400> SEQUENCE: 135

Glu Gly Ala Ile Ile Phe Gln Gln Val Met Ser Arg
1 5 10

<210> SEQ ID NO 136

```
-continued

<211> LENGTH: 10
<212> TYPE: PRT
<213> ORGANISM: Chlamydia trachomatis

<400> SEQUENCE: 136

Ser Ala Asn Glu Gly Tyr Asp Ala Leu Arg
1               5                   10

<210> SEQ ID NO 137
<211> LENGTH: 14
<212> TYPE: PRT
<213> ORGANISM: Chlamydia trachomatis

<400> SEQUENCE: 137

Phe Ser Thr Asp Ser Asp Thr Tyr Ile Glu Glu Glu Asn Arg
1               5                   10

<210> SEQ ID NO 138
<211> LENGTH: 19
<212> TYPE: PRT
<213> ORGANISM: Chlamydia trachomatis

<400> SEQUENCE: 138

Leu Gln Asp Asp Asp Tyr Met Glu Gly Leu Ser Glu Thr Ala Ala Ala
1               5                   10                  15

Glu Leu Arg

<210> SEQ ID NO 139
<211> LENGTH: 11
<212> TYPE: PRT
<213> ORGANISM: Chlamydia trachomatis

<400> SEQUENCE: 139

Phe Ala Thr Ser Asp Leu Asn Asp Leu Tyr Arg
1               5                   10

<210> SEQ ID NO 140
<211> LENGTH: 16
<212> TYPE: PRT
<213> ORGANISM: Chlamydia trachomatis

<400> SEQUENCE: 140

Leu Gly Phe Pro Leu Asp Asp Glu Thr Leu Ser Gln Val Thr Leu Arg
1               5                   10                  15

<210> SEQ ID NO 141
<211> LENGTH: 42
<212> TYPE: PRT
<213> ORGANISM: Chlamydia trachomatis

<400> SEQUENCE: 141

Trp Asp Val Thr Ala Ala Ala Pro Val Val Ala Val Ala Gly Ala Ala
1               5                   10                  15

Ala Ala Gly Asp Ala Pro Ala Ser Ala Glu Pro Thr Glu Phe Ala Val
                20                  25                  30

Ile Leu Glu Asp Val Pro Ser Asp Lys Lys
        35                  40

<210> SEQ ID NO 142
<211> LENGTH: 12
<212> TYPE: PRT
<213> ORGANISM: Chlamydia trachomatis

<400> SEQUENCE: 142
```

Ser Tyr Ser Leu Gly Glu Ala Ile Asp Ile Leu Lys
1               5                   10

<210> SEQ ID NO 143
<211> LENGTH: 12
<212> TYPE: PRT
<213> ORGANISM: Chlamydia trachomatis

<400> SEQUENCE: 143

Asp Tyr Ser Ser Ile Asp Asn Thr Pro Glu Glu Lys
1               5                   10

<210> SEQ ID NO 144
<211> LENGTH: 16
<212> TYPE: PRT
<213> ORGANISM: Chlamydia trachomatis

<400> SEQUENCE: 144

Gly Ile Thr Ile Asn Ala Ser His Val Glu Tyr Glu Thr Ala Asn Arg
1               5                   10                  15

<210> SEQ ID NO 145
<211> LENGTH: 26
<212> TYPE: PRT
<213> ORGANISM: Chlamydia trachomatis

<400> SEQUENCE: 145

Ile Asp Met Ile Ser Glu Glu Asp Ala Glu Leu Val Asp Leu Val Glu
1               5                   10                  15
Met Glu Leu Val Glu Leu Leu Glu Glu Lys
            20                  25

<210> SEQ ID NO 146
<211> LENGTH: 19
<212> TYPE: PRT
<213> ORGANISM: Chlamydia trachomatis

<400> SEQUENCE: 146

Glu Ile Asp Lys Pro Phe Leu Met Pro Ile Glu Asp Val Phe Ser Ile
1               5                   10                  15
Ser Gly Arg

<210> SEQ ID NO 147
<211> LENGTH: 11
<212> TYPE: PRT
<213> ORGANISM: Chlamydia trachomatis

<400> SEQUENCE: 147

Glu Thr Ile Val Thr Gly Val Glu Met Phe Arg
1               5                   10

<210> SEQ ID NO 148
<211> LENGTH: 10
<212> TYPE: PRT
<213> ORGANISM: Chlamydia trachomatis

<400> SEQUENCE: 148

Ala Gly Glu Asn Val Gly Leu Leu Leu Arg
1               5                   10

<210> SEQ ID NO 149
<211> LENGTH: 10
<212> TYPE: PRT
<213> ORGANISM: Chlamydia trachomatis

```
<400> SEQUENCE: 149

Lys Phe Ser Glu Val Glu Ser Glu Ile Lys
1               5                   10

<210> SEQ ID NO 150
<211> LENGTH: 9
<212> TYPE: PRT
<213> ORGANISM: Chlamydia trachomatis

<400> SEQUENCE: 150

Phe Ser Glu Val Glu Ser Glu Ile Lys
1               5

<210> SEQ ID NO 151
<211> LENGTH: 16
<212> TYPE: PRT
<213> ORGANISM: Chlamydia trachomatis

<400> SEQUENCE: 151

Ile Ile Pro Glu Pro Thr Ala Ala Ala Leu Ala Tyr Gly Ile Asp Lys
1               5                   10                  15

<210> SEQ ID NO 152
<211> LENGTH: 18
<212> TYPE: PRT
<213> ORGANISM: Chlamydia trachomatis

<400> SEQUENCE: 152

Glu Ser Leu Ser Ser Thr Glu Asn Ser Ser Ala Ile Glu Glu Glu
1               5                   10                  15

Ile Arg

<210> SEQ ID NO 153
<211> LENGTH: 9
<212> TYPE: PRT
<213> ORGANISM: Chlamydia trachomatis

<400> SEQUENCE: 153

Glu Val Ala Pro Val His Glu Ser Lys
1               5

<210> SEQ ID NO 154
<211> LENGTH: 12
<212> TYPE: PRT
<213> ORGANISM: Chlamydia trachomatis

<400> SEQUENCE: 154

Ser Asp Pro Ala Thr Thr Pro Thr Ala Asp Gly Lys
1               5                   10

<210> SEQ ID NO 155
<211> LENGTH: 19
<212> TYPE: PRT
<213> ORGANISM: Chlamydia trachomatis

<400> SEQUENCE: 155

Thr Ser Gly Pro Glu Asn Thr Ser Gly Gly Ala Ala Ala Ala Leu Asn
1               5                   10                  15

Ser Leu Arg

<210> SEQ ID NO 156
<211> LENGTH: 20
<212> TYPE: PRT
<213> ORGANISM: Chlamydia trachomatis
```

```
<400> SEQUENCE: 156

Thr Ser Gly Pro Glu Asn Thr Ser Asp Gly Ala Ala Ala Ala Ala Leu
1               5                   10                  15

Asn Ser Leu Arg
            20

<210> SEQ ID NO 157
<211> LENGTH: 9
<212> TYPE: PRT
<213> ORGANISM: Chlamydia trachomatis

<400> SEQUENCE: 157

Val Gly Gln Asp Thr Asp Phe Asp Arg
1               5

<210> SEQ ID NO 158
<211> LENGTH: 10
<212> TYPE: PRT
<213> ORGANISM: Chlamydia trachomatis

<400> SEQUENCE: 158

Leu Val Leu Gln Val Glu Thr Asp Gly Arg
1               5                   10

<210> SEQ ID NO 159
<211> LENGTH: 18
<212> TYPE: PRT
<213> ORGANISM: Chlamydia trachomatis

<400> SEQUENCE: 159

Leu Glu Leu Gly Met Asp Leu Ser Gln Phe Gly Val Gly Leu Asp Asn
1               5                   10                  15

Val Lys

<210> SEQ ID NO 160
<211> LENGTH: 20
<212> TYPE: PRT
<213> ORGANISM: Chlamydia trachomatis

<400> SEQUENCE: 160

Gly Met Gln Ser Glu Ile Asp Gly Gln Ser Ala Pro Leu Thr Asp Thr
1               5                   10                  15

Glu Tyr Glu Lys
            20

<210> SEQ ID NO 161
<211> LENGTH: 14
<212> TYPE: PRT
<213> ORGANISM: Chlamydia trachomatis

<400> SEQUENCE: 161

Tyr Gln Glu Gly Leu Ser Glu Gln Met Ala Thr Thr Ile Arg
1               5                   10

<210> SEQ ID NO 162
<211> LENGTH: 20
<212> TYPE: PRT
<213> ORGANISM: Chlamydia trachomatis

<400> SEQUENCE: 162

Glu Thr Pro Gly Ala Ala Glu Gly Ala Glu Ala Gln Thr Ala Ser Glu
1               5                   10                  15
```

-continued

```
Gln Pro Ser Lys
            20

<210> SEQ ID NO 163
<211> LENGTH: 17
<212> TYPE: PRT
<213> ORGANISM: Chlamydia trachomatis

<400> SEQUENCE: 163

Glu Glu Ala Gln Leu Ser Gln Glu Ile Ser Ser Ile Phe Leu Gly Leu
1               5                   10                  15

Lys

<210> SEQ ID NO 164
<211> LENGTH: 22
<212> TYPE: PRT
<213> ORGANISM: Chlamydia trachomatis

<400> SEQUENCE: 164

Ser Gly Glu Thr Glu Asp Thr Thr Ile Ala Asp Leu Ala Val Ala Phe
1               5                   10                  15

Asn Thr Gly Gln Ile Lys
            20

<210> SEQ ID NO 165
<211> LENGTH: 22
<212> TYPE: PRT
<213> ORGANISM: Chlamydia trachomatis

<400> SEQUENCE: 165

Leu Met Ala Ile Glu Glu Glu Met Gly Pro Glu Ala Leu Phe Gln Asp
1               5                   10                  15

Ser Asn Pro Phe Ser Lys
            20

<210> SEQ ID NO 166
<211> LENGTH: 19
<212> TYPE: PRT
<213> ORGANISM: Chlamydia trachomatis

<400> SEQUENCE: 166

Glu Gln Met Glu Val Phe Ala Asn Asn Pro Asp Asn Phe Ser Pro Glu
1               5                   10                  15

Glu Trp Arg

<210> SEQ ID NO 167
<211> LENGTH: 18
<212> TYPE: PRT
<213> ORGANISM: Chlamydia trachomatis

<400> SEQUENCE: 167

Gln Thr Ser Pro Met Ala Gly Val Phe Gly Asn Leu Asp Val Asn Glu
1               5                   10                  15

Ala Arg

<210> SEQ ID NO 168
<211> LENGTH: 16
<212> TYPE: PRT
<213> ORGANISM: Chlamydia trachomatis

<400> SEQUENCE: 168

Ala Thr Leu Glu Glu Ser Met Pro Met Leu Glu Asn Leu Glu Glu Arg
1               5                   10                  15
```

-continued

```
<210> SEQ ID NO 169
<211> LENGTH: 11
<212> TYPE: PRT
<213> ORGANISM: Chlamydia trachomatis

<400> SEQUENCE: 169

Met Glu Gly Asp Glu Ala Gln Gly Pro Ser Arg
1               5                   10

<210> SEQ ID NO 170
<211> LENGTH: 15
<212> TYPE: PRT
<213> ORGANISM: Chlamydia trachomatis

<400> SEQUENCE: 170

Gly Ala Asp Gly Thr Tyr Asp Ile Pro Leu Val Asp Asp Trp Arg
1               5                   10                  15

<210> SEQ ID NO 171
<211> LENGTH: 12
<212> TYPE: PRT
<213> ORGANISM: Chlamydia trachomatis

<400> SEQUENCE: 171

Ile Pro Asn Ser Gln Gln Val Glu Gly Ile Leu Arg
1               5                   10

<210> SEQ ID NO 172
<211> LENGTH: 13
<212> TYPE: PRT
<213> ORGANISM: Chlamydia trachomatis

<400> SEQUENCE: 172

Tyr Gln Leu Gln Asn Met Asp Val Glu Ala Gly Phe Arg
1               5                   10

<210> SEQ ID NO 173
<211> LENGTH: 491
<212> TYPE: PRT
<213> ORGANISM: Chlamydia trachomatis

<400> SEQUENCE: 173

Met Tyr Arg Lys Ser Ala Leu Glu Leu Arg Asp Ala Val Val Asn Arg
1               5                   10                  15

Glu Leu Ser Val Thr Ala Ile Thr Glu Tyr Phe Tyr His Arg Ile Glu
                20                  25                  30

Ser His Asp Glu Gln Ile Gly Ala Phe Leu Ser Leu Cys Lys Glu Arg
            35                  40                  45

Ala Leu Leu Arg Ala Ser Arg Ile Asp Asp Lys Leu Ala Lys Gly Asp
        50                  55                  60

Pro Ile Gly Leu Leu Ala Gly Ile Pro Ile Gly Val Lys Asp Asn Ile
65                  70                  75                  80

His Ile Thr Gly Val Lys Thr Thr Cys Ala Ser Lys Met Leu Glu Asn
                85                  90                  95

Phe Val Ala Pro Phe Asp Ser Thr Val Val Arg Arg Ile Glu Met Glu
            100                 105                 110

Asp Gly Ile Leu Leu Gly Lys Leu Asn Met Asp Glu Phe Ala Met Gly
        115                 120                 125

Ser Thr Thr Arg Tyr Ser Ala Phe His Pro Thr Asn Asn Pro Trp Asp
    130                 135                 140
```

```
Leu Glu Arg Val Pro Gly Gly Ser Ser Gly Gly Ser Ala Ala Ala Val
145                 150                 155                 160

Ser Ala Arg Phe Cys Pro Ile Ala Leu Gly Ser Asp Thr Gly Gly Ser
                165                 170                 175

Ile Arg Gln Pro Ala Ala Phe Cys Gly Val Val Gly Phe Lys Pro Ser
            180                 185                 190

Tyr Gly Ala Val Ser Arg Tyr Gly Leu Val Ala Phe Gly Ser Ser Leu
        195                 200                 205

Asp Gln Ile Gly Pro Leu Thr Thr Val Val Glu Asp Val Ala Leu Ala
210                 215                 220

Met Asp Ala Phe Ala Gly Arg Asp Pro Lys Asp Ser Thr Thr Arg Asp
225                 230                 235                 240

Phe Phe Lys Gly Thr Phe Ser Gln Ala Leu Ser Leu Glu Val Pro Lys
                245                 250                 255

Leu Ile Gly Val Pro Arg Gly Phe Leu Asp Gly Leu Gln Glu Asp Cys
            260                 265                 270

Lys Glu Asn Phe Phe Glu Ala Leu Ala Val Met Glu Arg Glu Gly Ser
        275                 280                 285

Arg Ile Ile Asp Val Asp Leu Ser Val Leu Lys His Ala Val Pro Val
290                 295                 300

Tyr Tyr Ile Val Ala Ser Ala Glu Ala Ala Thr Asn Leu Ala Arg Phe
305                 310                 315                 320

Asp Gly Val Arg Tyr Gly His Arg Cys Ala Gln Ala Asp Asn Met His
                325                 330                 335

Glu Met Tyr Ala Arg Ser Arg Lys Glu Gly Phe Gly Lys Glu Val Thr
            340                 345                 350

Arg Arg Ile Leu Leu Gly Asn Tyr Val Leu Ser Ala Glu Arg Gln Asn
        355                 360                 365

Ile Phe Tyr Lys Lys Gly Met Ala Val Arg Ala Arg Leu Ile Asp Ala
370                 375                 380

Phe Gln Ala Ala Phe Glu Arg Cys Asp Val Ile Ala Met Pro Val Cys
385                 390                 395                 400

Ala Thr Pro Ala Ile Arg Asp Gln Asp Val Leu Asp Pro Val Ser Leu
                405                 410                 415

Tyr Leu Gln Asp Val Tyr Thr Val Ala Val Asn Leu Ala Tyr Leu Pro
            420                 425                 430

Ala Ile Ser Val Pro Ser Gly Leu Ser Lys Glu Gly Leu Pro Leu Gly
        435                 440                 445

Val Gln Phe Ile Gly Glu Arg Gly Ser Asp Gln Gln Ile Cys Gln Val
450                 455                 460

Gly Tyr Ser Phe Gln Glu His Ser Gln Ile Lys Gln Leu Tyr Pro Lys
465                 470                 475                 480

Ala Val Asn Gly Leu Phe Asp Gly Gly Ile Glu
                485                 490

<210> SEQ ID NO 174
<211> LENGTH: 16
<212> TYPE: PRT
<213> ORGANISM: Chlamydia trachomatis

<400> SEQUENCE: 174

Val Pro Gly Gly Ser Ser Gly Gly Ser Ala Ala Ala Val Ser Ala Arg
1               5                   10                  15

<210> SEQ ID NO 175
<211> LENGTH: 488
```

```
<212> TYPE: PRT
<213> ORGANISM: Chlamydia trachomatis

<400> SEQUENCE: 175

Met Gly Ile Ala His Thr Glu Trp Glu Ser Val Ile Gly Leu Glu Val
1               5                   10                  15

His Val Glu Leu Asn Thr Glu Ser Lys Leu Phe Ser Pro Ala Arg Asn
                20                  25                  30

His Phe Gly Asp Glu Pro Asn Thr Asn Ile Ser Pro Val Cys Thr Gly
            35                  40                  45

Met Pro Gly Ser Leu Pro Val Leu Asn Lys Asp Ala Val Arg Lys Ala
        50                  55                  60

Val Leu Phe Gly Cys Ala Val Glu Gly Asp Val Ala Leu Phe Ser Arg
65              70                  75                  80

Phe Asp Arg Lys Ser Tyr Phe Tyr Pro Asp Ser Pro Arg Asn Phe Gln
                85                  90                  95

Ile Thr Gln Tyr Glu His Pro Ile Val Arg Gly Gly Cys Ile Arg Ala
            100                 105                 110

Val Val Glu Gly Glu Lys Thr Phe Glu Leu Ala Gln Thr His Leu
        115                 120                 125

Glu Asp Asp Ala Gly Met Leu Lys His Phe Gly Asp Phe Ala Gly Val
130                 135                 140

Asp Tyr Asn Arg Ala Gly Val Pro Leu Ile Glu Ile Val Ser Lys Pro
145                 150                 155                 160

Cys Met Phe Ser Ala Glu Asp Ala Val Ala Tyr Ala Asn Ala Leu Val
                165                 170                 175

Ser Ile Leu Gly Tyr Ile Gly Ile Ser Asp Cys Asn Met Glu Glu Gly
            180                 185                 190

Ser Ile Arg Phe Asp Val Asn Ile Ser Val Arg Pro Arg Gly Ser Arg
        195                 200                 205

Glu Leu Arg Asn Lys Val Glu Ile Lys Asn Met Asn Ser Phe Thr Phe
210                 215                 220

Met Ala Gln Ala Leu Glu Ala Glu Lys Arg Arg Gln Ile Glu Glu Tyr
225                 230                 235                 240

Leu Ser Tyr Pro Asn Glu Asp Pro Lys Lys Val Val Pro Ala Ala Thr
                245                 250                 255

Tyr Arg Trp Asp Pro Glu Lys Lys Lys Thr Val Leu Met Arg Leu Lys
            260                 265                 270

Glu Arg Ala Glu Asp Tyr Met Tyr Phe Val Glu Pro Asp Leu Pro Val
        275                 280                 285

Leu Gln Ile Thr Glu Thr Tyr Ile Asp Glu Val Arg Gln Thr Leu Pro
290                 295                 300

Glu Leu Pro His Ser Lys Tyr Met Arg Tyr Ile Thr Asp Phe Asp Ile
305                 310                 315                 320

Ala Glu Asp Leu Ala Met Ile Leu Val Gly Asp Arg His Thr Ala His
                325                 330                 335

Phe Phe Glu Thr Ala Thr Met Ser Cys Lys Asn Tyr Arg Ala Leu Ser
            340                 345                 350

Asn Trp Ile Thr Val Glu Phe Ala Gly Arg Cys Lys Ala Arg Gly Lys
        355                 360                 365

Thr Leu Pro Phe Thr Gly Ile Leu Pro Glu Trp Val Ala Gln Leu Val
    370                 375                 380

Asn Phe Ile Asp Arg Gly Val Ile Thr Gly Lys Ile Ala Lys Glu Ile
385                 390                 395                 400
```

```
Ala Asp Arg Met Val Ser Ser Phe Gly Glu Ser Pro Glu Asp Ile Leu
            405                 410                 415

Arg Arg His Pro Ser Leu Leu Pro Met Thr Asp His Ala Leu Arg
            420                 425                 430

Ala Ile Val Lys Glu Val Val Ala Gln Asn Thr Ala Ser Val Ala Asp
            435                 440                 445

Tyr Lys Asn Gly Lys Ala Lys Ala Leu Gly Phe Leu Val Gly Gln Ile
        450                 455                 460

Met Lys Arg Thr Glu Gly Lys Ala Pro Pro Lys Arg Val Asn Glu Leu
465                 470                 475                 480

Leu Leu Ala Ala Met Arg Asp Met
                485

<210> SEQ ID NO 176
<211> LENGTH: 14
<212> TYPE: PRT
<213> ORGANISM: Chlamydia trachomatis

<400> SEQUENCE: 176

Glu Val Val Ala Gln Asn Thr Ala Ser Val Ala Asp Tyr Lys
1               5                   10

<210> SEQ ID NO 177
<211> LENGTH: 363
<212> TYPE: PRT
<213> ORGANISM: Chlamydia trachomatis

<400> SEQUENCE: 177

Met Thr Pro Val Thr Pro Val Pro Gln Ser Pro Gln Gln Val Lys
1               5                   10                  15

Gly Leu Leu Ser Arg Phe Leu Thr Ala Pro Asp Arg His Pro Lys Leu
            20                  25                  30

Arg Tyr Val Tyr Asp Ile Ala Leu Ile Ala Ile Ser Ile Leu Cys Ile
            35                  40                  45

Val Ser Ile Ile Leu Trp Thr Gln Gly Ser Gly Leu Ala Leu Phe Ala
        50                  55                  60

Ile Ala Pro Ala Leu Ala Ile Gly Ala Leu Gly Val Thr Leu Leu Val
65                  70                  75                  80

Ser Asp Leu Ala Glu Ser Gln Lys Ser Lys Glu Ile Ala Asp Thr Val
            85                  90                  95

Ala Ala Val Ser Leu Pro Phe Ile Leu Thr Gly Thr Ala Ala Gly Leu
            100                 105                 110

Met Phe Ser Ala Ile Ala Val Gly Gly Gly Ala Val Ile Leu Ala Asn
            115                 120                 125

Pro Leu Phe Leu Met Gly Ser Met Thr Leu Gly Phe Ala Leu Met Ser
        130                 135                 140

Leu His Arg Val Thr Tyr Gln Tyr Leu Ser Asn Arg Glu Gln Trp Lys
145                 150                 155                 160

Gln Gln Lys Lys Leu Glu Gln Val Glu Leu Ala Ala Trp Glu Ser His
            165                 170                 175

Leu Pro Lys Glu Ser Lys Ser Ser Ala Leu Glu Glu Val Arg Tyr Ser
            180                 185                 190

Pro Arg Leu Met Lys Arg Gly Lys Thr Trp Lys Arg Ala Ile Arg
        195                 200                 205

Arg Lys Asn Tyr Thr Pro Ile Pro Leu Val Asp Lys Thr Leu Gln Thr
        210                 215                 220

Met Gln Pro Asp Ala Leu Phe Ser Ser Thr Thr Thr His Ser Thr Asp
```

```
                225                 230                 235                 240
Ser Glu Gln Ile Leu Thr Ser Val Ser Pro Gln Ser Ser Asp Thr Glu
                245                 250                 255

Ser Ser Ser Ser Ser Ser Phe His Thr Pro Pro Asn Ser Asp Lys Glu
                260                 265                 270

Leu Ser Asp Ser Asn Ser Ser Asp Ser Ser Ser Ser Glu Tyr Met
            275                 280                 285

Asp Ala Leu Glu Thr Val Ala Ala Gly Asp Val Ser Gly Ile Thr Pro
            290                 295                 300

Pro Ser Lys Pro Ser Ser Ser Pro Lys Thr Thr Arg Arg Val Val Lys
305                 310                 315                 320

Leu Ser Arg Ser Glu Arg Asn Ala Gln His His Arg Asn Lys Asp Gln
                325                 330                 335

Glu Gln Arg Gln Asp Ser Ser Glu Ser Ser Glu Asp Ser Ser Ser
            340                 345                 350

Asp Ser Ser Gln Lys Lys Lys Pro Ser Arg Lys
            355                 360

<210> SEQ ID NO 178
<211> LENGTH: 18
<212> TYPE: PRT
<213> ORGANISM: Chlamydia trachomatis

<400> SEQUENCE: 178

Gln Asp Ser Ser Glu Ser Ser Glu Glu Asp Ser Ser Asp Ser Ser
1               5                   10                  15

Gln Lys

<210> SEQ ID NO 179
<211> LENGTH: 666
<212> TYPE: PRT
<213> ORGANISM: Chlamydia trachomatis

<400> SEQUENCE: 179

Met Glu Ser Leu Ser Val Arg Ser Thr Ile Pro Leu Pro Leu Gly Ala
1               5                   10                  15

Lys Lys Leu Ser Ala Asp Arg Tyr Arg Phe Ser Leu Phe Ser Ser Gln
                20                  25                  30

Ala Gln Gln Val Thr Leu Val Leu Asp Pro Leu Ser Glu Ile His
            35                  40                  45

Glu Ile Pro Leu Ser Ser Thr Asp His Arg Thr Gly Ala Ile Trp His
50                  55                  60

Ile Glu Ile Ala Gly Ile Ser Ser Glu Trp Ser Tyr Ala Tyr Lys Leu
65                  70                  75                  80

Arg Gly Thr Asp Leu Ser Ser Gln Lys Phe Ala Thr Asp Ser Tyr Ile
                85                  90                  95

Ala Asp Pro Tyr Ser Lys Asn Ile Tyr Ser Pro Gln Leu Phe Gly Ser
            100                 105                 110

Pro Lys Gln Glu Lys Asp Tyr Ala Phe Ser Tyr Leu Lys His Glu Asp
        115                 120                 125

Phe Asp Trp Glu Gly Asp Thr Pro Leu His Leu Pro Lys Glu Asn Tyr
    130                 135                 140

Phe Ile Tyr Glu Met His Val Arg Ser Phe Thr Arg Asp Pro Ser Ser
145                 150                 155                 160

Gln Val Ser His Pro Gly Thr Phe Leu Gly Ile Ile Glu Lys Ile Asp
                165                 170                 175
```

-continued

```
His Leu Lys Gln Leu Gly Val His Ala Val Glu Leu Leu Pro Ile Phe
            180                 185                 190
Glu Phe Asp Glu Thr Val His Pro Phe Lys Asn Gln Asp Phe Pro His
        195                 200                 205
Leu Cys Asn Tyr Trp Gly Tyr Ser Ser Val Asn Phe Phe Cys Pro Ser
    210                 215                 220
Arg Arg Tyr Thr Tyr Gly Ala Asp Pro Cys Ala Pro Ala Arg Glu Phe
225                 230                 235                 240
Lys Thr Leu Val Lys Ala Leu His Arg Ala Gly Ile Glu Val Ile Leu
                245                 250                 255
Asp Val Val Phe Asn His Thr Gly Phe Glu Gly Thr Ser Cys Pro Leu
            260                 265                 270
Pro Trp Ile Asp Leu Glu Ser Tyr Tyr Met Val Asn Asp His Gly Asp
        275                 280                 285
Leu Met Asn Phe Ser Gly Cys Gly Asn Thr Val Asn Thr Asn Thr Pro
    290                 295                 300
Thr Thr Leu Lys Trp Ile Leu Asp Ala Leu Arg Tyr Trp Val Gln Glu
305                 310                 315                 320
Met His Val Asp Gly Phe Arg Phe Asp Leu Ala Ser Val Phe Ser Arg
                325                 330                 335
Asp Pro Gln Gly Val Pro Leu Pro Leu Thr Pro Ile Leu Gln Ala Ile
            340                 345                 350
Ser Ser Asp Ser Ile Leu Ser Glu Thr Lys Leu Ile Ala Glu Pro Trp
        355                 360                 365
Asp Ala Gly Gly Leu Tyr Gln Leu Gly His Phe Pro Ser Ile Ser Thr
    370                 375                 380
Arg Trp Ser Glu Trp Asn Gly Cys Tyr Arg Asp His Val Lys Ala Phe
385                 390                 395                 400
Leu Asn Gly Asp Ala His Gln Val Ser Ser Phe Ala Ser Arg Ile Ser
                405                 410                 415
Gly Ser His Asp Ile Tyr Pro Asn Gly Lys Pro Thr Asn Ser Ile Asn
            420                 425                 430
Tyr Ile Cys Ser His Asp Gly Phe Thr Leu Tyr Asp Thr Val Ala Tyr
        435                 440                 445
Asn Asp Lys His Asn Glu Glu Asn Gly Glu Tyr Asn Arg Asp Gly Thr
    450                 455                 460
Ser Ala Asn Tyr Ser Tyr Asn Phe Gly Cys Glu Gly Glu Thr Thr Asp
465                 470                 475                 480
Pro Thr Ile Cys Ala Leu Arg Glu Arg Gln Met Lys Asn Phe Phe Leu
                485                 490                 495
Ala Leu Phe Leu Ser Gln Gly Ile Pro Met Ile Gln Ser Gly Asp Glu
            500                 505                 510
Tyr Gly His Thr Ala Tyr Gly Asn Asn Asn His Trp Cys Leu Asp Thr
        515                 520                 525
Lys Ile Asn Tyr Phe Leu Trp Asp Arg Leu Ala Glu Arg Lys Glu Leu
    530                 535                 540
Phe Ser Phe Leu Cys Gln Val Ile Ala Leu Arg Lys Ala Tyr Thr Glu
545                 550                 555                 560
Leu Phe Asn Thr Ser Phe Leu Ser Glu Asp Thr Ile Thr Trp Leu Asn
                565                 570                 575
Thr Lys Gly Ser Pro Arg Glu Trp Gly Ala Asp His Tyr Leu Ala Phe
            580                 585                 590
Glu Leu Lys His Leu Asn Tyr Ser Leu Phe Val Ala Phe Tyr Ser Gly
        595                 600                 605
```

```
Asn Glu Arg Ile Glu Ile Ser Leu Pro Lys Pro Arg Lys Glu His Leu
    610                 615                 620

Ala Tyr Glu Lys Ile Val Asp Ser Thr Thr Gly Phe Phe Ser Gln Ile
625                 630                 635                 640

Leu Ser Pro Lys Leu Ser Leu Glu Pro Tyr Ser Ser Leu Val Ala Ile
                645                 650                 655

Ser Arg Arg Lys Thr Ser Leu Glu Ser Arg
            660                 665

<210> SEQ ID NO 180
<211> LENGTH: 17
<212> TYPE: PRT
<213> ORGANISM: Chlamydia trachomatis

<400> SEQUENCE: 180

Ala Ala Asp Gln Ala Phe Ile Asn Ser Tyr Asp Met Asp Asp Leu Leu
1               5                   10                  15

Arg

<210> SEQ ID NO 181
<211> LENGTH: 365
<212> TYPE: PRT
<213> ORGANISM: Chlamydia trachomatis

<400> SEQUENCE: 181

Met Ser Ile Glu Val Arg Ile Pro Asn Ile Ala Glu Ser Ile Ser Glu
1               5                   10                  15

Val Thr Ile Ser Ala Leu Leu Ile Pro Ser Gly Asp Leu Val Gln Glu
                20                  25                  30

Asn Gln Gly Ile Leu Glu Ile Glu Ser Asp Lys Val Asn Gln Leu Ile
            35                  40                  45

Tyr Ala Pro Cys Ser Gly Arg Val Glu Trp Ser Val Ser Val Gly Asp
    50                  55                  60

Thr Val Ala Val Gly Ser Val Val Gly Ile Ile Ser Glu Ala Glu Lys
65                  70                  75                  80

Ser Gln Asp Thr Ala Pro Ile His Glu Gln Met Pro Phe Ser Leu Val
                85                  90                  95

Glu Gln Glu Ser Asp Ala Gln Ile Ile Ala Phe Pro Ser Ser Val Arg
            100                 105                 110

Gln Asp Pro Pro Ala Glu Gly Lys Thr Phe Val Pro Leu Lys Glu Ile
        115                 120                 125

Gln Pro Ala Ser Ser Asp His Arg Glu Ser Arg Glu Ser Met Ser Ala
    130                 135                 140

Ile Arg Lys Thr Ile Ser Arg Arg Leu Val Gln Ser Leu His Asp Ser
145                 150                 155                 160

Ala Met Leu Thr Thr Phe Asn Glu Ile His Met Gly Pro Leu Ile Ala
                165                 170                 175

Leu Arg Lys Glu Arg Gln Glu Asp Phe Val Ala Lys Tyr Gly Val Lys
            180                 185                 190

Leu Gly Phe Met Ser Phe Phe Val Arg Ala Val Val Asp Ser Leu Lys
        195                 200                 205

Lys Tyr Pro Arg Val Asn Ala Tyr Ile Glu Asp Asn Glu Ile Val Tyr
    210                 215                 220

Arg His Tyr Tyr Asp Ile Ser Ile Ala Ile Gly Thr Asp Arg Gly Leu
225                 230                 235                 240

Val Val Pro Val Ile Arg Asn Cys Asp Gln Leu Ser Ser Gly Glu Ile
```

```
                      245                 250                 255
Glu Leu Gln Leu Ala Asp Leu Ala Ser Arg Ala Arg Glu Gly Lys Leu
            260                 265                 270

Ala Ile His Glu Leu Glu Gly Gly Phe Thr Ile Thr Asn Gly Gly
        275                 280                 285

Val Tyr Gly Ser Leu Leu Ser Thr Pro Ile Ile Asn Pro Pro Gln Val
        290                 295                 300

Gly Ile Leu Gly Met His Lys Ile Glu Lys Arg Pro Val Val Arg Glu
305                 310                 315                 320

Asp Ala Ile Val Ile Ala Asp Met Met Tyr Val Ala Met Ser Tyr Asp
                325                 330                 335

His Arg Ile Ile Asp Gly Lys Glu Ala Val Gly Phe Leu Val Asn Val
            340                 345                 350

Lys Glu Gln Leu Glu Gln Pro Glu Leu Leu Leu Lys Met
            355                 360                 365

<210> SEQ ID NO 182
<211> LENGTH: 13
<212> TYPE: PRT
<213> ORGANISM: Chlamydia trachomatis

<400> SEQUENCE: 182

Val Asn Ala Tyr Ile Glu Asp Asn Glu Ile Val Tyr Arg
1               5                   10

<210> SEQ ID NO 183
<211> LENGTH: 129
<212> TYPE: PRT
<213> ORGANISM: Chlamydia trachomatis

<400> SEQUENCE: 183

Met Ile Gln Glu Ser Val Ala Thr Gly Arg Arg Lys Gln Ala Val Ser
1               5                   10                  15

Ser Val Arg Leu Arg Ser Gly Asn Gly Lys Ile Asp Val Asn Gly Lys
            20                  25                  30

Thr Leu Glu Gln Tyr Phe Pro Leu Glu Val Gln Arg Ala Thr Ile Leu
        35                  40                  45

Ala Pro Leu Arg Met Leu Gly Asp Val Asn Ser Phe Asp Leu Ile Ile
    50                  55                  60

Arg Val Ser Gly Gly Gly Val Gln Gly Gln Val Ile Ala Thr Arg Leu
65                  70                  75                  80

Gly Leu Ala Arg Ala Val Leu Gln Glu Lys Glu Asp Met Lys Gln Glu
                85                  90                  95

Leu Lys Ala Gln Gly Phe Leu Thr Arg Asp Pro Arg Lys Lys Glu Arg
            100                 105                 110

Lys Lys Tyr Gly Arg Lys Lys Ala Arg Lys Ser Phe Gln Phe Ser Lys
        115                 120                 125

Arg

<210> SEQ ID NO 184
<211> LENGTH: 14
<212> TYPE: PRT
<213> ORGANISM: Chlamydia trachomatis

<400> SEQUENCE: 184

Val Ser Gly Gly Gly Val Gln Gly Gln Val Ile Ala Thr Arg
1               5                   10
```

<210> SEQ ID NO 185
<211> LENGTH: 348
<212> TYPE: PRT
<213> ORGANISM: Chlamydia trachomatis

<400> SEQUENCE: 185

Met Thr Thr Ile Phe Asp Leu Leu Gly Lys Asp Ala Asp Tyr Leu Leu
1               5                   10                  15

Asn His Lys Cys Val Ile Lys Lys Glu Ala Leu Thr Leu Pro Ser Gly
            20                  25                  30

Asp Leu Val Ser Arg Val Phe Ala Glu Ser Asp Arg Asn Asn Arg Val
        35                  40                  45

Leu Arg Ser Leu Gln Gln Met Phe Ser Cys Gly Arg Leu Gly Gly Thr
    50                  55                  60

Gly Tyr Leu Ser Ile Leu Pro Val Asp Gln Gly Val Glu His Thr Ala
65                  70                  75                  80

Gly Ala Ser Phe Ala Lys Asn Pro Met Tyr Phe Asp Pro Glu Asn Ile
                85                  90                  95

Val Arg Leu Ala Met Glu Ala Gly Cys Ser Ala Val Ala Ser Ser Tyr
            100                 105                 110

Gly Val Leu Ser Ile Leu Ala Arg Arg Tyr Ala His Lys Ile Pro Phe
        115                 120                 125

Leu Leu Lys Leu Asn His Asn Glu Leu Leu Ser Tyr Pro Thr Thr Tyr
    130                 135                 140

His Gln Ile Phe Phe Ser Gln Val Glu Asp Ala Tyr Asn Met Gly Ala
145                 150                 155                 160

Val Ala Val Gly Ala Thr Ile Tyr Phe Gly Ser Glu Ser Ser Ser Glu
                165                 170                 175

Glu Ile Val Ala Val Ala Glu Ala Phe Ala Arg Ala Arg Glu Leu Gly
            180                 185                 190

Leu Ala Thr Val Leu Trp Cys Tyr Leu Arg Asn Pro His Phe Val Val
        195                 200                 205

Asn Asn Val Asp Tyr His Thr Ala Ala Asp Leu Thr Gly Gln Ala Asp
    210                 215                 220

His Leu Gly Ala Thr Leu Gly Ala Asp Ile Val Lys Gln Lys Leu Pro
225                 230                 235                 240

Thr Leu Gln Gly Gly Phe Lys Thr Ile Asn Phe Ser Lys Thr Asp Asp
                245                 250                 255

Leu Val Tyr Ser Glu Leu Ser Ser Asn His Pro Ile Asp Leu Cys Arg
            260                 265                 270

Tyr Gln Val Leu Asn Ser Tyr Cys Gly Lys Val Gly Leu Ile Asn Ser
        275                 280                 285

Gly Gly Pro Ser Gly Gln Asp Asp Phe Ala Glu Ala Val Lys Thr Ala
    290                 295                 300

Val Ile Asn Lys Arg Ala Gly Gly Met Gly Leu Ile Leu Gly Arg Lys
305                 310                 315                 320

Ala Phe Gln Arg Pro Phe Ser Glu Gly Val Arg Leu Leu Asn Leu Ile
                325                 330                 335

Gln Asp Ile Tyr Leu Asp Pro Thr Ile Ser Ile Ser
            340                 345

<210> SEQ ID NO 186
<211> LENGTH: 20
<212> TYPE: PRT
<213> ORGANISM: Chlamydia trachomatis

<400> SEQUENCE: 186

```
Val Gly Leu Ile Asn Ser Gly Gly Pro Ser Gly Gln Asp Asp Phe Ala
1               5                  10                 15

Glu Ala Val Lys
            20
```

<210> SEQ ID NO 187
<211> LENGTH: 77
<212> TYPE: PRT
<213> ORGANISM: Chlamydia trachomatis

<400> SEQUENCE: 187

```
Met Ser Leu Glu Asp Asp Val Lys Ala Ile Ile Val Asp Gln Leu Gly
1               5                  10                 15

Val Ser Pro Glu Asp Val Lys Val Asp Ser Ser Phe Ile Glu Asp Leu
            20                 25                 30

Asn Ala Asp Ser Leu Asp Leu Thr Glu Leu Ile Met Thr Leu Glu Glu
        35                 40                 45

Lys Phe Ala Phe Glu Ile Ser Glu Asp Asp Ala Glu Gln Leu Arg Thr
    50                 55                 60

Val Gly Asp Val Ile Lys Tyr Ile Gln Glu Arg Gln Asn
65                  70                 75
```

<210> SEQ ID NO 188
<211> LENGTH: 15
<212> TYPE: PRT
<213> ORGANISM: Chlamydia trachomatis

<400> SEQUENCE: 188

```
Ala Ile Ile Val Asp Gln Leu Gly Val Ser Pro Glu Asp Val Lys
1               5                  10                 15
```

<210> SEQ ID NO 189
<211> LENGTH: 100
<212> TYPE: PRT
<213> ORGANISM: Chlamydia trachomatis

<400> SEQUENCE: 189

```
Met Ala Thr Met Thr Lys Lys Leu Ile Ser Thr Ile Ser Gln Asp
1               5                  10                 15

His Lys Ile His Pro Asn His Val Arg Thr Val Ile Gln Asn Phe Leu
            20                 25                 30

Asp Lys Met Thr Asp Ala Leu Val Gln Gly Asp Arg Leu Glu Phe Arg
        35                 40                 45

Asp Phe Gly Val Leu Gln Val Val Glu Arg Lys Pro Lys Val Gly Arg
    50                 55                 60

Asn Pro Lys Asn Ala Ala Val Pro Ile His Ile Pro Ala Arg Arg Ala
65                  70                 75                 80

Val Lys Phe Thr Pro Gly Lys Arg Met Lys Arg Leu Ile Glu Thr Pro
                85                 90                 95

Thr Lys Ser Ser
            100
```

<210> SEQ ID NO 190
<211> LENGTH: 10
<212> TYPE: PRT
<213> ORGANISM: Chlamydia trachomatis

<400> SEQUENCE: 190

```
Met Thr Asp Ala Leu Val Gln Gly Asp Arg
1               5                  10
```

<210> SEQ ID NO 191
<211> LENGTH: 327
<212> TYPE: PRT
<213> ORGANISM: Chlamydia trachomatis

<400> SEQUENCE: 191

Met Ser Ser Gln Phe Asp Gln Leu Lys Leu Trp Ser Val Leu Val Gly
1               5                   10                  15

Asp Thr Gly Asp Pro Ala Leu Ile Lys Thr Leu Gly Val Gln Asp Ala
            20                  25                  30

Thr Thr Asn Pro Ser Leu Ile Leu Lys Val Ala Gln Glu Pro Lys Tyr
        35                  40                  45

Gln Ser Met Leu Thr Glu Ala Ile Ser Trp Gly Ile Arg Gln Asn Gly
    50                  55                  60

Asp Asp Val Gln Thr Leu Thr Phe Val Leu Asp Lys Ile Gln Val Asn
65                  70                  75                  80

Leu Gly Leu Glu Ile Leu Lys His Val Pro Gly Arg Val Ser Leu Glu
                85                  90                  95

Ile Asp Ala Arg Leu Ser Phe Asn Thr Glu Ala Met Val Gln Arg Ala
            100                 105                 110

Ile Phe Leu Ser Gln Leu Phe Glu Lys Met Gly Gly Asp Lys Lys Arg
        115                 120                 125

Leu Leu Val Lys Ile Pro Gly Thr Trp Glu Gly Ile Cys Ala Ala Glu
130                 135                 140

Val Leu Glu Ser Gln Gly Ile Ala Cys Asn Val Thr Leu Ile Phe Asn
145                 150                 155                 160

Leu Val Gln Ala Ile Ala Ala Lys Ala Lys Val Thr Leu Val Ser
                165                 170                 175

Pro Phe Val Gly Arg Ile Tyr Asp Trp Trp Ile Ala Ala Tyr Gly Ala
            180                 185                 190

Glu Gly Tyr Ser Ile Glu Ala Asp Pro Gly Val Ala Ser Val Ala Asn
        195                 200                 205

Ile Tyr Ser Tyr Tyr Lys Lys Phe Asp Ile Pro Thr Gln Ile Met Ala
    210                 215                 220

Ala Ser Phe Arg Thr Lys Glu Gln Val Leu Ala Leu Ala Gly Cys Asp
225                 230                 235                 240

Phe Leu Thr Ile Ser Pro Lys Leu Leu Glu Glu Leu Lys Lys Asp Gln
                245                 250                 255

Gln Pro Val Glu Arg Lys Leu Ser Val Glu Glu Ala Lys Lys Leu Asp
            260                 265                 270

Ile Gln Pro Val Glu Leu Ser Glu Ser Val Phe Arg Phe Leu Met Asn
        275                 280                 285

Glu Asp Ala Met Ala Thr Glu Lys Leu Ala Glu Gly Ile Arg Ile Phe
    290                 295                 300

Ser Gly Asp Thr Gln Ile Leu Glu Ser Ala Val Thr Glu Phe Ile Arg
305                 310                 315                 320

Gln Ile Ala Ala Gln Glu Ala
                325

<210> SEQ ID NO 192
<211> LENGTH: 16
<212> TYPE: PRT
<213> ORGANISM: Chlamydia trachomatis

<400> SEQUENCE: 192

```
Leu Trp Ser Val Leu Val Gly Asp Thr Gly Asp Pro Ala Leu Ile Lys
1               5                   10                  15
```

<210> SEQ ID NO 193
<211> LENGTH: 124
<212> TYPE: PRT
<213> ORGANISM: Chlamydia trachomatis

<400> SEQUENCE: 193

```
Met Pro Leu Thr Asp Glu Glu Ile Ala Asn Phe Lys Thr Arg Leu Leu
1               5                   10                  15

Glu Met Lys Ala Lys Leu Ser His Thr Leu Glu Gly Asn Ala Gln Glu
            20                  25                  30

Val Lys Lys Pro Asn Glu Ala Thr Gly Tyr Ser Gln His Gln Ala Asp
        35                  40                  45

Gln Gly Thr Asp Thr Phe Asp Arg Thr Ile Ser Leu Glu Val Thr Thr
    50                  55                  60

Lys Glu Tyr Lys Leu Leu Arg Gln Ile Asp Arg Ala Leu Glu Lys Ile
65                  70                  75                  80

Glu Glu Ala Ser Tyr Gly Ile Cys Asp Val Ser Gly Glu Glu Ile Pro
                85                  90                  95

Leu Ala Arg Leu Met Ala Ile Pro Tyr Ala Thr Met Thr Val Lys Ser
            100                 105                 110

Gln Glu Lys Phe Glu Lys Gly Leu Leu Ser Gly Asn
        115                 120
```

<210> SEQ ID NO 194
<211> LENGTH: 11
<212> TYPE: PRT
<213> ORGANISM: Chlamydia trachomatis

<400> SEQUENCE: 194

```
Pro Leu Thr Asp Glu Glu Ile Ala Asn Phe Lys
1               5                   10
```

<210> SEQ ID NO 195
<211> LENGTH: 621
<212> TYPE: PRT
<213> ORGANISM: Chlamydia trachomatis

<400> SEQUENCE: 195

```
Met Arg Arg Ser Val Cys Tyr Val Thr Pro Ser Val Ala Arg Ala Gly
1               5                   10                  15

Gln Ile Ser Thr Trp Arg Phe Glu Tyr Ser Ser Ala Asn Phe Leu Pro
            20                  25                  30

Glu Gly Thr Leu Leu Lys Phe Asp Leu Gly Ile Asp Gly Arg Pro Ile
        35                  40                  45

Asp Trp Glu Ile Pro Ser Thr Asp Leu Ser Gln Pro Cys Asn Thr Ile
    50                  55                  60

Tyr Leu Glu Thr Pro Ser Glu Asp Ile Val Ala Ala Lys Ala Val Tyr
65                  70                  75                  80

Ala Pro Gly Gly Tyr Ile Pro Thr Phe Glu Phe Thr Leu Pro Cys Asp
                85                  90                  95

Val Glu Ala Gly Asp Thr Phe Ser Ile Ile Leu Gly Ser Ser Pro Asn
            100                 105                 110

Phe Pro Gln Glu Asp Ser Ser Gly Asn Gly Ala Gln Leu Phe Thr Gln
        115                 120                 125

Arg Arg Lys Pro Phe Ser Leu Tyr Val Asp Pro Ser Gly Lys Gly Ser
    130                 135                 140
```

-continued

```
Phe Glu Asp Pro Asp Ile Phe Thr Met Asp Ile Arg Gly Asn Val Leu
145                 150                 155                 160

Lys Asn Ile Arg Ile Phe Ala Pro Ser Tyr Val Ile Lys Asn Lys Arg
            165                 170                 175

Phe Asp Ile Thr Val Arg Phe Glu Asp Glu Phe Gly Asn Leu Thr Asn
            180                 185                 190

Phe Ser Pro Glu Glu Thr His Ile Glu Leu Ser Tyr Glu His Leu Arg
            195                 200                 205

Glu Asn Leu Asn Trp Gln Leu Phe Ile Pro Glu Thr Gly Phe Val Ile
210                 215                 220

Leu Pro Asn Leu Tyr Phe Asn Glu Pro Gly Ile Tyr Arg Ile Gln Leu
225                 230                 235                 240

Arg Asn Gln Ala Thr Lys Glu Val Phe Thr Ser Ala Pro Ile Lys Cys
            245                 250                 255

Phe Ala Glu Thr Ser Ser His Leu Leu Trp Gly Leu Leu His Gly Glu
            260                 265                 270

Ser Glu Arg Val Asp Ser Glu Gly Asn Ile Glu Ser Cys Leu Arg Tyr
            275                 280                 285

Phe Arg Asp Asp Cys Ala Leu Asn Phe Ala Thr Ser Ser Phe Glu
290                 295                 300

Ile Gln Asp Gly Leu Thr Pro Glu Thr Ile Lys Thr Ile Asn Gln Thr
305                 310                 315                 320

Val Ala Asp Phe Asn Glu Glu Asp Arg Phe Ile Ala Leu Ser Gly Ala
            325                 330                 335

Gln Tyr Leu Ser Glu Glu Pro Gly Glu Gly Ile Arg Glu Val Leu Leu
            340                 345                 350

Met Lys Glu Pro Lys Ser Pro Gly Lys His Lys Glu Cys Lys Leu Phe
            355                 360                 365

Pro Leu Ser Lys Leu Tyr Lys Gln Ser Thr Ser His Glu Leu Ile Ser
370                 375                 380

Ile Pro Ser Phe Thr Ala Ser Lys Lys Phe Gly Tyr Asn Phe Asn Asn
385                 390                 395                 400

Phe His Pro Glu Phe Glu Arg Val Val Glu Ile Tyr Asn Ala Trp Gly
            405                 410                 415

Cys Ser Glu Arg Thr Glu Ala Glu Gly Asn Pro Phe Pro Ile Lys Gly
            420                 425                 430

Ser Ile Asp Ser Glu Asn Pro Glu Gly Thr Val Leu Ser Ala Leu Lys
            435                 440                 445

Arg Asn Leu Arg Phe Gly Phe Val Ala Gly Gly Leu Asp Asp Arg Asn
450                 455                 460

Leu Tyr Asn His Phe Phe Asp Ser Asp Gln Gln Tyr Ser Pro Gly
465                 470                 475                 480

Leu Thr Ala Val Ile Cys Asn Lys Tyr Ser Arg Asp Ser Leu Leu Glu
            485                 490                 495

Ala Leu Tyr Gln Arg Gln Cys Tyr Ala Thr Thr Gly Gln Arg Ile Ile
            500                 505                 510

Val Asn Phe Gln Ile Thr Ser Ala Pro Met Gly Ser Glu Leu Ser Thr
            515                 520                 525

Ala Ile Lys Pro Gly Leu Val Ile Asn Arg His Ile Ser Gly Tyr Val
            530                 535                 540

Ala Gly Thr Ala Lys Ile Ala Ser Ile Glu Ile Arg Asn Glu Asp
545                 550                 555                 560

Ile Leu His Thr Phe His Pro Asp Gly Asn Asn Phe Glu Tyr Glu Tyr
```

```
                    565                 570                 575
Asp Asp Leu Ser Pro Phe Ala Gln Val Thr Leu Lys Asp Pro Gln Asn
            580                 585                 590

Gly Ala Pro Phe Ala Phe Tyr Tyr Leu Arg Val Thr Gln Glu Asn Gly
        595                 600                 605

Ala Met Ala Trp Ser Ser Pro Ile Trp Ile Asp Leu Asn
    610                 615                 620

<210> SEQ ID NO 196
<211> LENGTH: 14
<212> TYPE: PRT
<213> ORGANISM: Chlamydia trachomatis

<400> SEQUENCE: 196

Gly Ser Phe Glu Asp Pro Asp Ile Phe Thr Met Asp Ile Arg
1               5                   10

<210> SEQ ID NO 197
<211> LENGTH: 86
<212> TYPE: PRT
<213> ORGANISM: Chlamydia trachomatis

<400> SEQUENCE: 197

Met Ser Gln Asn Lys Asn Ser Ala Phe Met Gln Pro Val Asn Val Ser
1               5                   10                  15

Ala Asp Leu Ala Ala Ile Val Gly Ala Gly Pro Met Pro Arg Thr Glu
            20                  25                  30

Ile Ile Lys Lys Met Trp Asp Tyr Ile Lys Lys Asn Gly Leu Gln Asp
        35                  40                  45

Pro Thr Asn Lys Arg Asn Ile Asn Pro Asp Asp Lys Leu Ala Lys Val
    50                  55                  60

Phe Gly Thr Glu Lys Pro Ile Asp Met Phe Gln Met Thr Lys Met Val
65                  70                  75                  80

Ser Gln His Ile Ile Lys
                85

<210> SEQ ID NO 198
<211> LENGTH: 10
<212> TYPE: PRT
<213> ORGANISM: Chlamydia trachomatis

<400> SEQUENCE: 198

Asn Gly Leu Gln Asp Pro Thr Asn Lys Arg
1               5                   10

<210> SEQ ID NO 199
<211> LENGTH: 144
<212> TYPE: PRT
<213> ORGANISM: Chlamydia trachomatis

<400> SEQUENCE: 199

Met Ile Lys Leu Glu Cys Leu Gln Asp Pro Ser Pro Arg Lys Arg Arg
1               5                   10                  15

Thr Lys Leu Leu Gly Arg Gly Pro Ser Ser Gly His Gly Lys Thr Ser
            20                  25                  30

Gly Arg Gly His Lys Gly Asp Gly Ser Arg Ser Gly Tyr Lys Arg Arg
        35                  40                  45

Phe Gly Tyr Glu Gly Gly Val Pro Leu Tyr Arg Arg Val Pro Thr
    50                  55                  60

Arg Gly Phe Ser His Thr Arg Phe Asp Lys Cys Val Glu Glu Ile Thr
```

```
                    65                  70                  75                  80
Thr Gln Arg Leu Asn Glu Ile Phe Asp Asn Gly Ala Glu Val Ser Leu
                        85                  90                  95

Glu Ala Leu Lys Glu Arg Lys Val Ile His Arg Glu Thr Ser Arg Val
                100                 105                 110

Lys Val Ile Leu Lys Gly Ala Leu Asp Lys Lys Leu Val Trp Lys Asp
            115                 120                 125

Ala Ala Ile Val Leu Ser Glu Gly Val Lys Ser Leu Ile Glu Ala Val
        130                 135                 140

<210> SEQ ID NO 200
<211> LENGTH: 17
<212> TYPE: PRT
<213> ORGANISM: Chlamydia trachomatis

<400> SEQUENCE: 200

Leu Asn Glu Ile Phe Asp Asn Gly Ala Glu Val Ser Leu Glu Ala Leu
1               5                   10                  15

Lys

<210> SEQ ID NO 201
<211> LENGTH: 165
<212> TYPE: PRT
<213> ORGANISM: Chlamydia trachomatis

<400> SEQUENCE: 201

Met Thr Leu Ser Arg Asn Ser His Lys Glu Asp Gln Leu Glu Glu Lys
1               5                   10                  15

Val Leu Val Val Asn Arg Cys Cys Lys Val Val Lys Gly Gly Arg Lys
                20                  25                  30

Phe Ser Phe Ser Ala Leu Ile Leu Val Gly Asp Arg Lys Gly Arg Leu
            35                  40                  45

Gly Phe Gly Phe Ala Lys Ala Asn Glu Leu Thr Asp Ala Ile Arg Lys
        50                  55                  60

Gly Gly Asp Ala Ala Arg Lys Asn Leu Val Ser Ile Asn Ser Leu Glu
65                  70                  75                  80

Gly Gly Ser Ile Pro His Glu Val Leu Val Asn His Asp Gly Ala Glu
                85                  90                  95

Leu Leu Leu Lys Pro Ala Lys Pro Gly Thr Gly Ile Val Ala Gly Ser
            100                 105                 110

Arg Ile Arg Leu Ile Leu Glu Met Ala Gly Val Lys Asp Ile Val Ala
        115                 120                 125

Lys Ser Leu Gly Ser Asn Asn Pro Met Asn Gln Val Lys Ala Ala Phe
    130                 135                 140

Lys Ala Leu Leu Thr Leu Ser Cys Lys Asp Asp Ile Met Lys Arg Arg
145                 150                 155                 160

Ala Val Ile Asn Asp
                165

<210> SEQ ID NO 202
<211> LENGTH: 12
<212> TYPE: PRT
<213> ORGANISM: Chlamydia trachomatis

<400> SEQUENCE: 202

Ser Leu Gly Ser Asn Asn Pro Met Asn Gln Val Lys
1               5                   10
```

```
<210> SEQ ID NO 203
<211> LENGTH: 183
<212> TYPE: PRT
<213> ORGANISM: Chlamydia trachomatis

<400> SEQUENCE: 203

Met Ser Arg Lys Ala Arg Asp Pro Ile Val Leu Pro Gln Gly Val Glu
1               5                   10                  15

Val Ser Ile Gln Asn Asp Glu Ile Ser Val Lys Gly Pro Lys Gly Ser
            20                  25                  30

Leu Thr Gln Val Leu Ala Lys Glu Val Glu Ile Ala Val Lys Gly Asn
        35                  40                  45

Glu Val Phe Val Thr Pro Ala Ala His Val Val Asp Arg Pro Gly Arg
    50                  55                  60

Ile Gln Gly Leu Tyr Trp Ala Leu Ile Ala Asn Met Val Lys Gly Val
65                  70                  75                  80

His Thr Gly Phe Glu Lys Arg Leu Glu Met Ile Gly Val Gly Phe Arg
                85                  90                  95

Ala Ala Val Gln Gly Ser Leu Leu Asp Leu Ser Ile Gly Val Ser His
            100                 105                 110

Pro Thr Lys Met Pro Ile Pro Thr Gly Leu Glu Val Ser Val Glu Lys
        115                 120                 125

Asn Thr Leu Ile Ser Ile Lys Gly Ile Asn Lys Gln Leu Val Gly Glu
    130                 135                 140

Phe Ala Ala Cys Val Arg Ala Lys Arg Pro Glu Pro Tyr Lys Gly
145                 150                 155                 160

Lys Gly Ile Arg Tyr Glu Asn Glu Tyr Val Arg Arg Lys Ala Gly Lys
                165                 170                 175

Ala Ala Lys Thr Gly Lys Lys
            180

<210> SEQ ID NO 204
<211> LENGTH: 13
<212> TYPE: PRT
<213> ORGANISM: Chlamydia trachomatis

<400> SEQUENCE: 204

Met Pro Ile Pro Thr Gly Leu Glu Val Ser Val Glu Lys
1               5                   10

<210> SEQ ID NO 205
<211> LENGTH: 111
<212> TYPE: PRT
<213> ORGANISM: Chlamydia trachomatis

<400> SEQUENCE: 205

Met Lys Arg Arg Ser Val Cys Val Gly Asp Thr Val Tyr Val Leu Ala
1               5                   10                  15

Gly Asn Asp Lys Gly Lys Gln Gly Lys Val Leu Arg Cys Leu Lys Asp
            20                  25                  30

Lys Val Val Val Glu Gly Ile Asn Val Arg Val Lys Asn Ile Lys Arg
        35                  40                  45

Ser Gln Glu Asn Pro Lys Gly Lys Arg Ile Asn Ile Glu Ala Pro Leu
    50                  55                  60

His Ile Ser Asn Val Arg Leu Ser Ile Asp Asn Gln Pro Ala Arg Leu
65                  70                  75                  80

Phe Val Lys Val Arg Glu Lys Gly Arg Glu Leu Trp Asn Lys His Ser
                85                  90                  95
```

```
Asp Gly Ser Ser Ser Leu Tyr Arg Ser Val Arg Glu Arg Lys Gly
            100                 105                 110

<210> SEQ ID NO 206
<211> LENGTH: 10
<212> TYPE: PRT
<213> ORGANISM: Chlamydia trachomatis

<400> SEQUENCE: 206

His Ser Asp Gly Ser Ser Leu Tyr Arg
1               5                   10

<210> SEQ ID NO 207
<211> LENGTH: 111
<212> TYPE: PRT
<213> ORGANISM: Chlamydia trachomatis

<400> SEQUENCE: 207

Met Phe Lys Ala Thr Ala Arg Tyr Ile Arg Val Gln Pro Arg Lys Ala
1               5                   10                  15

Arg Leu Ala Ala Gly Leu Met Arg Asn Arg Ser Val Val Glu Ala Gln
            20                  25                  30

Gln Gln Leu Ser Phe Ser Gln Met Lys Ala Gly Arg Cys Leu Lys Lys
        35                  40                  45

Val Leu Asp Gly Ala Ile Ala Asn Ala Glu Ser Asn Glu Asn Ile Lys
    50                  55                  60

Arg Glu Asn Leu Cys Val Leu Glu Val Arg Val Asp Val Gly Pro Met
65                  70                  75                  80

Phe Lys Arg Met Lys Ser Lys Ser Arg Gly Gly Arg Ala Pro Ile Leu
                85                  90                  95

Lys Arg Thr Ser His Leu Thr Val Ile Val Gly Glu Arg Gly Gln
            100                 105                 110

<210> SEQ ID NO 208
<211> LENGTH: 16
<212> TYPE: PRT
<213> ORGANISM: Chlamydia trachomatis

<400> SEQUENCE: 208

Val Leu Asp Gly Ala Ile Ala Asn Ala Glu Ser Asn Glu Asn Ile Lys
1               5                   10                  15

<210> SEQ ID NO 209
<211> LENGTH: 284
<212> TYPE: PRT
<213> ORGANISM: Chlamydia trachomatis

<400> SEQUENCE: 209

Met Phe Lys Lys Phe Lys Pro Val Thr Pro Gly Thr Arg Gln Leu Ile
1               5                   10                  15

Leu Pro Ser Phe Asp Glu Leu Thr Thr Gln Gly Glu Leu Lys Gly Ser
            20                  25                  30

Ser Ser Arg Arg Ser Val Arg Pro Asn Lys Lys Leu Ser Phe Phe Lys
        35                  40                  45

Lys Ser Ser Gly Gly Arg Asp Asn Leu Gly His Ile Ser Cys Arg His
    50                  55                  60

Arg Gly Gly Gly Val Arg Arg His Tyr Arg Val Ile Asp Phe Lys Arg
65                  70                  75                  80

Asn Lys Asp Gly Ile Glu Ala Lys Val Ala Ser Val Glu Tyr Asp Pro
                85                  90                  95
```

-continued

```
Asn Arg Ser Ala Tyr Ile Ala Leu Leu Asn Tyr Val Asp Gly Glu Lys
            100                 105                 110
Arg Tyr Ile Leu Ala Pro Lys Gly Ile Lys Arg Gly Asp Arg Val Ile
        115                 120                 125
Ser Gly Glu Gly Ser Pro Phe Lys Thr Gly Cys Cys Met Thr Leu Lys
130                 135                 140
Ser Ile Pro Leu Gly Leu Ser Val His Asn Val Glu Met Arg Pro Gly
145                 150                 155                 160
Ser Gly Gly Lys Leu Val Arg Ser Ala Gly Leu Ser Ala Gln Ile Ile
                165                 170                 175
Ala Lys Thr Ala Gly Tyr Val Thr Leu Lys Met Pro Ser Gly Glu Phe
            180                 185                 190
Arg Met Leu Asn Glu Met Cys Arg Ala Thr Val Gly Glu Val Ser Asn
        195                 200                 205
Ala Asp His Asn Leu Cys Val Asp Gly Lys Ala Gly Arg Arg Arg Trp
210                 215                 220
Lys Gly Ile Arg Pro Thr Val Arg Gly Thr Ala Met Asn Pro Val Asp
225                 230                 235                 240
His Pro His Gly Gly Gly Glu Gly Arg His Asn Gly Tyr Ile Ser Gln
                245                 250                 255
Thr Pro Trp Gly Lys Val Thr Lys Gly Leu Lys Thr Arg Asp Lys Arg
            260                 265                 270
Lys Ser Asn Lys Trp Ile Val Lys Asp Arg Arg Lys
        275                 280

<210> SEQ ID NO 210
<211> LENGTH: 17
<212> TYPE: PRT
<213> ORGANISM: Chlamydia trachomatis

<400> SEQUENCE: 210

Gly Thr Ala Met Asn Pro Val Asp His Pro His Gly Gly Gly Glu Gly
1               5                   10                  15
Arg

<210> SEQ ID NO 211
<211> LENGTH: 222
<212> TYPE: PRT
<213> ORGANISM: Chlamydia trachomatis

<400> SEQUENCE: 211

Met Val Leu Leu Ser Lys Phe Asp Phe Ser Gly Lys Glu Ser Gly Lys
1               5                   10                  15
Phe Glu Leu Pro Asp Ala Phe Phe Thr Glu Gly Lys Glu Gln Ser Val
            20                  25                  30
Lys Asp Tyr Leu Val Ala Ile Gln Ala Asn Lys Arg Gln Trp Ser Ala
        35                  40                  45
Cys Thr Arg Gly Arg Ser Glu Val Ser His Ser Thr Lys Lys Pro Phe
    50                  55                  60
Arg Gln Lys Gly Thr Gly Asn Ala Arg Gln Gly Cys Leu Ala Ala Pro
65                  70                  75                  80
Gln Phe Arg Gly Gly Gly Ile Val Phe Gly Pro Lys Pro Lys Phe Asp
                85                  90                  95
Gln His Ile Arg Ile Asn Lys Lys Glu Arg Arg Ala Ala Ile Arg Leu
            100                 105                 110
Leu Leu Ala Gln Lys Ile Gln Thr Gly Lys Leu Ile Val Ala Glu Asn
        115                 120                 125
```

```
Ser Val Phe Val Ser Ser Leu Asp Ala Pro Lys Thr Lys Glu Ala Leu
    130                 135                 140

Arg Phe Leu Lys Glu Cys Asn Val Glu Cys Arg Gly Val Leu Phe Val
145                 150                 155                 160

Asp Gly Leu Ala His Val Gly Ser Asn Glu Asn Leu Arg Leu Ser Val
                165                 170                 175

Arg Asn Leu Ser Ala Val Arg Gly Phe Thr Tyr Gly Glu Asn Ile Ser
            180                 185                 190

Gly Tyr Asp Ile Ala Ala Ala Arg Asn Ile Val Val Ser Glu Lys Ala
        195                 200                 205

Leu Glu Leu Leu Val Glu Ser Leu Val Ser Thr Thr Lys Asp
    210                 215                 220

<210> SEQ ID NO 212
<211> LENGTH: 17
<212> TYPE: PRT
<213> ORGANISM: Chlamydia trachomatis

<400> SEQUENCE: 212

Leu Ile Val Ala Glu Asn Ser Val Phe Val Ser Ser Leu Asp Ala Pro
1               5                   10                  15

Lys

<210> SEQ ID NO 213
<211> LENGTH: 17
<212> TYPE: PRT
<213> ORGANISM: Chlamydia trachomatis

<400> SEQUENCE: 213

Gly Phe Thr Tyr Gly Glu Asn Ile Ser Gly Tyr Asp Ile Ala Ala Ala
1               5                   10                  15

Arg

<210> SEQ ID NO 214
<211> LENGTH: 232
<212> TYPE: PRT
<213> ORGANISM: Chlamydia trachomatis

<400> SEQUENCE: 214

Met Ser Thr Pro Ser Ser Asn Asn Ser Lys Lys Pro Ser Ala Ser Phe
1               5                   10                  15

Asn Lys Lys Ser Arg Ser Arg Leu Ala Glu Ile Ala Ala Gln Lys Lys
            20                  25                  30

Ala Lys Ala Glu Asp Leu Glu Gln Lys Tyr Pro Val Pro Thr Glu Glu
        35                  40                  45

Glu Thr Lys Gln Val Leu Met Asp Ile Leu Gln Gly Leu Ser Asn Gly
    50                  55                  60

Leu Thr Leu Gln Gln Ile Leu Gly Leu Ser Asp Val Leu Leu Glu Glu
65                  70                  75                  80

Ile Tyr Thr Val Ala Tyr Thr Phe Tyr Ser Gln Gly Lys Tyr Gln Glu
                85                  90                  95

Ala Ile Gly Leu Phe Gln Ile Leu Thr Ala Ser Lys Pro Gln Cys Tyr
            100                 105                 110

Lys Tyr Ile Leu Gly Leu Ser Ser Cys Tyr His Gln Leu Lys Met Tyr
        115                 120                 125

Asp Glu Ala Ala Phe Gly Phe Phe Leu Ala Phe Asp Ala Gln Pro Glu
    130                 135                 140
```

```
Asn Pro Ile Pro Pro Tyr Tyr Ile Ala Asp Ser Leu Met Lys Leu Asn
145                 150                 155                 160

Gln Pro Glu Glu Ser Gln Asp Phe Leu Asp Ile Thr Ile Asp Met Cys
            165                 170                 175

Lys Asn Lys Pro Glu Tyr Lys Val Leu Lys Asp Arg Cys Ser Ile Met
        180                 185                 190

Lys Gln Ser Leu Asp Ala Val Leu Lys Lys Glu Lys Ser Ala Lys Gly
    195                 200                 205

Ser Glu Thr Gln Ala Ser Ser Pro Lys Asn Thr Lys Ala Lys Lys Ala
210                 215                 220

Ala Ser Asn Lys Lys Lys Ala Lys
225                 230
```

<210> SEQ ID NO 215
<211> LENGTH: 10
<212> TYPE: PRT
<213> ORGANISM: Chlamydia trachomatis

<400> SEQUENCE: 215

```
Tyr Pro Val Pro Thr Glu Glu Glu Thr Lys
1               5                   10
```

<210> SEQ ID NO 216
<211> LENGTH: 19
<212> TYPE: PRT
<213> ORGANISM: Chlamydia trachomatis

<400> SEQUENCE: 216

```
Leu Asn Gln Pro Glu Glu Ser Gln Asp Phe Leu Asp Ile Thr Ile Asp
1               5                   10                  15

Met Cys Lys
```

<210> SEQ ID NO 217
<211> LENGTH: 234
<212> TYPE: PRT
<213> ORGANISM: Chlamydia trachomatis

<400> SEQUENCE: 217

```
Met Arg Lys Ala Leu Tyr Thr His Ala Met Leu Gln Lys His Thr Arg
1               5                   10                  15

Ile Ala Val Ala Leu Ser Gly Gly Lys Asp Ser Leu Ser Leu Leu
            20                  25                  30

Met Leu Lys Ala Ile Ser Gly Arg Gly Phe Pro Glu Leu Thr Ile His
        35                  40                  45

Ala Ile His Ile Gly Gly Lys Tyr Ser Cys Gly Ala Ala Val Ser Gly
    50                  55                  60

Asn Tyr Leu Ser Ser Ile Cys Asp Lys Ile Gln Val Pro Leu Ile Ser
65                  70                  75                  80

Ile Pro Ser Pro Tyr Glu Thr Glu Asn Pro Glu Cys Tyr Thr Cys Ser
                85                  90                  95

Arg Ile Arg Arg Arg Leu Leu Phe Asp Thr Ala Lys Ala Val Gly Ala
            100                 105                 110

Thr Ala Val Ala Phe Gly His His Arg Asp Asp Val Val Gln Thr Thr
        115                 120                 125

Leu Met Asn Leu Leu His Lys Ala Glu Phe Ala Gly Met Leu Pro Ile
    130                 135                 140

Val Asp Met Val Asn Phe Gly Ile Thr Ile Leu Arg Pro Leu Ile Phe
145                 150                 155                 160
```

```
Ile Pro Glu Asp Leu Ile Arg Lys Phe Ala Lys Glu Ser Gly Phe Ala
            165                 170                 175

Arg Ile Thr Cys Arg Cys Pro Val Ile Ser Leu Arg Thr Lys Thr Glu
        180                 185                 190

Glu Ala Leu Lys Thr Leu Glu Thr Ile Phe Pro Gln Ala Arg His Asn
    195                 200                 205

Ile Ala Leu Ala Val Arg Glu Thr Gly Leu Ser Lys Ala Asn Arg Val
210                 215                 220

Glu Gln Tyr Asp Ser Leu Leu Thr Glu Ala
225                 230

<210> SEQ ID NO 218
<211> LENGTH: 19
<212> TYPE: PRT
<213> ORGANISM: Chlamydia trachomatis

<400> SEQUENCE: 218

Asn Ala Gly Gly Ile Glu Gly Thr Glu Tyr Pro Leu Leu Ala Asp Pro
1               5                   10                  15

Ser Phe Lys

<210> SEQ ID NO 219
<211> LENGTH: 17
<212> TYPE: PRT
<213> ORGANISM: Chlamydia trachomatis

<400> SEQUENCE: 219

Ile Ser Glu Ala Phe Gly Val Leu Asn Pro Gly Gly Ser Leu Ala Leu
1               5                   10                  15

Arg

<210> SEQ ID NO 220
<211> LENGTH: 11
<212> TYPE: PRT
<213> ORGANISM: Chlamydia trachomatis

<400> SEQUENCE: 220

His Ala Val Ile Asn Asp Leu Pro Leu Gly Arg
1               5                   10

<210> SEQ ID NO 221
<211> LENGTH: 231
<212> TYPE: PRT
<213> ORGANISM: Chlamydia trachomatis

<400> SEQUENCE: 221

Met Met Glu Val Phe Met Asn Phe Leu Asp Gln Leu Asp Leu Ile Ile
1               5                   10                  15

Gln Asn Lys His Met Leu Glu His Thr Phe Tyr Val Lys Trp Ser Lys
            20                  25                  30

Gly Glu Leu Thr Lys Glu Gln Leu Gln Ala Tyr Ala Lys Asp Tyr Tyr
        35                  40                  45

Leu His Ile Lys Ala Phe Pro Lys Tyr Leu Ser Ala Ile His Ser Arg
    50                  55                  60

Cys Asp Asp Leu Glu Ala Arg Lys Leu Leu Asp Asn Leu Met Asp
65                  70                  75                  80

Glu Glu Asn Gly Tyr Pro Asn His Ile Asp Leu Trp Lys Gln Phe Val
                85                  90                  95

Phe Ala Leu Gly Val Thr Pro Glu Glu Leu Glu Ala His Glu Pro Ser
            100                 105                 110
```

```
Glu Ala Ala Lys Ala Lys Val Ala Thr Phe Met Arg Trp Cys Thr Gly
            115                 120                 125

Asp Ser Leu Ala Ala Gly Val Ala Ala Leu Tyr Ser Tyr Glu Ser Gln
        130                 135                 140

Ile Pro Arg Ile Ala Arg Glu Lys Ile Arg Gly Leu Thr Glu Tyr Phe
145                 150                 155                 160

Gly Phe Ser Asn Pro Glu Asp Tyr Ala Tyr Phe Thr Glu His Glu Glu
                165                 170                 175

Ala Asp Val Arg His Ala Arg Glu Glu Lys Ala Leu Ile Glu Met Leu
            180                 185                 190

Leu Lys Asp Asp Ala Asp Lys Val Leu Glu Ala Ser Gln Glu Val Thr
        195                 200                 205

Gln Ser Leu Tyr Gly Phe Leu Asp Ser Phe Leu Asp Pro Gly Thr Cys
    210                 215                 220

Cys Ser Cys His Gln Ser Tyr
225                 230

<210> SEQ ID NO 222
<211> LENGTH: 23
<212> TYPE: PRT
<213> ORGANISM: Chlamydia trachomatis

<400> SEQUENCE: 222

Gln Phe Val Phe Ala Leu Gly Val Thr Pro Glu Glu Leu Glu Ala His
1               5                   10                  15

Glu Pro Ser Glu Ala Ala Lys
            20

<210> SEQ ID NO 223
<211> LENGTH: 213
<212> TYPE: PRT
<213> ORGANISM: Chlamydia trachomatis

<400> SEQUENCE: 223

Ala Lys Asn Ala Leu Ile Ser Leu Arg Asp Ala Ile Leu Asn Lys Asn
1               5                   10                  15

Ser Ser Pro Thr Asp Ser Leu Ser Gln Leu Glu Ala Ser Thr Ser Thr
            20                  25                  30

Ser Thr Val Thr Arg Val Ala Ala Lys Asp Tyr Asp Lys Ala Lys Ser
        35                  40                  45

Asn Phe Asp Thr Ala Lys Ser Gly Leu Glu Asn Ala Lys Thr Leu Ala
50                  55                  60

Glu Tyr Glu Thr Lys Met Ala Asp Leu Met Ala Leu Gln Asp Met
65                  70                  75                  80

Glu Ala Asn Ser Asp Pro Ser Asn Asp His Thr Glu Glu Leu Asn Asn
            85                  90                  95

Ile Lys Lys Ala Leu Glu Ala Gln Lys Asp Thr Ile Asp Lys Leu Asn
        100                 105                 110

Lys Leu Val Thr Leu Gln Asn Gln Asn Lys Ser Leu Thr Glu Ala Leu
    115                 120                 125

Lys Thr Thr Asp Ser Ala Asp Gln Ile Pro Ala Ile Asn Ser Arg Leu
130                 135                 140

Glu Ile Asn Lys Asn Ser Ala His Gln Ile Ile Lys Glu Leu Lys Glu
145                 150                 155                 160

Gln Ile Ser Asn Tyr Lys Ala Val Leu Thr Asp Val Glu Lys Val Ile
                165                 170                 175
```

```
Lys Glu Phe Ser Glu Ala Gly Ile Lys Leu Gly Gln Ala Leu Gln Ser
            180                 185                 190

Ile Val Asp Ala Gly Asp Gln Ser Gln Ala Ala Val Leu Gln Ala Arg
                195                 200                 205

Gln Ser Asn Ser Pro
            210

<210> SEQ ID NO 224
<211> LENGTH: 22
<212> TYPE: PRT
<213> ORGANISM: Chlamydia trachomatis

<400> SEQUENCE: 224

Asn Ser Ser Pro Thr Asp Ser Leu Ser Gln Leu Glu Ala Ser Thr Ser
1               5                   10                  15

Thr Ser Thr Val Thr Arg
                20

<210> SEQ ID NO 225
<211> LENGTH: 15
<212> TYPE: PRT
<213> ORGANISM: Chlamydia trachomatis

<400> SEQUENCE: 225

Ser Gly Leu Glu Asn Ala Thr Thr Leu Ala Glu Tyr Glu Thr Lys
1               5                   10                  15

<210> SEQ ID NO 226
<211> LENGTH: 829
<212> TYPE: PRT
<213> ORGANISM: Chlamydia trachomatis

<400> SEQUENCE: 226

Met Gly Ile Arg Leu Val Ile Asp Lys Gly Pro Leu Ser Gly Thr Val
1               5                   10                  15

Leu Ile Leu Glu Asn Gly Thr Ser Trp Ser Leu Gly Ser Asp Gly Lys
                20                  25                  30

Ala Ser Asp Ile Leu Leu Gln Asp Glu Lys Leu Ala Pro Ser Gln Ile
            35                  40                  45

Arg Ile Thr Leu Lys Asp Gly Glu Tyr Tyr Leu Glu Asn Leu Asp Ala
        50                  55                  60

Leu Arg Pro Val Ser Val Asp Gly Thr Val Ile Thr Ala Pro Val Leu
65                  70                  75                  80

Leu Lys Asp Gly Val Ser Phe Val Met Gly Ser Cys Gln Val Ser Phe
                85                  90                  95

Phe Lys Gly Glu Glu Val Glu Gly Asp Ile Glu Leu Ser Phe Gln Thr
            100                 105                 110

Glu Gly Gly Asn Glu Gly Glu Pro Ala Ala Gln Gly Ser Ser Ser Val
        115                 120                 125

Ser Ser Glu Ala Pro Lys Lys Glu Thr Gly Asn Pro Ser Leu Pro Ser
    130                 135                 140

Glu Ala Lys Ala Ser Gly Glu Val Ser Ser Ala Ile Ala Lys Glu
145                 150                 155                 160

Gln Glu Leu Ala Ala Ser Phe Leu Ala Ser Val Glu Lys Glu Pro Gly
                165                 170                 175

Thr Pro Lys Glu Val Ser Glu Pro Lys Val Ser Ser Gln Glu Gly Gln
            180                 185                 190

Thr Pro Ser Val Thr Gly Glu Lys Lys Asp Leu Glu Leu Pro Leu Ala
        195                 200                 205
```

Ser Gln Glu Gln Pro Lys Gln Thr Thr Pro Ser Gly Ser Gly Glu Pro
    210                 215                 220

Thr Gln Ser Gln Asn Ala Ser Met Glu Glu Asn Arg Thr Ser Pro Asp
225                 230                 235                 240

Gln Asn Gln Gln Pro Gln Leu Ser Ser Ala Ser Glu Ser Gly Ser Gln
                245                 250                 255

Ser Pro Glu Asn Gln Glu Gln Gln Pro Ser Gln Thr Pro Pro Pro Ser
            260                 265                 270

Pro Glu Thr Pro Glu Pro Ser Gly Glu Pro Asn Ser Ala Thr Glu Glu
        275                 280                 285

Asn Ser Pro Ser Pro Met Glu Lys Ala Ser Val Thr Glu Glu Gly Ser
    290                 295                 300

Ser Gly Thr Ser Glu Glu Lys Glu Gly Glu Glu Asp Thr Ala Glu
305                 310                 315                 320

Ser Ala Ala Asn Glu Glu Pro Lys Ala Glu Ala Ser Gln Glu Glu Glu
                325                 330                 335

Lys Lys Glu Glu Asp Lys Gly Glu Val Leu Ala Pro Phe Asn Val Gln
            340                 345                 350

Asp Leu Phe Arg Phe Asp Gln Gly Ile Phe Pro Ala Glu Ile Glu Asp
        355                 360                 365

Leu Ala Gln Lys Gln Val Ala Val Asp Leu Thr Gln Pro Ser Arg Phe
    370                 375                 380

Leu Leu Lys Val Leu Ala Gly Ala Asn Ile Gly Ala Glu Phe His Leu
385                 390                 395                 400

Asp Ser Gly Lys Thr Tyr Ile Val Gly Ser Asp Pro Gln Val Ala Asp
                405                 410                 415

Ile Val Leu Ser Asp Met Ser Ile Ser Arg Gln His Ala Lys Ile Ile
            420                 425                 430

Ile Gly Asn Asp Asn Ser Val Leu Ile Glu Asp Leu Gly Ser Lys Asn
        435                 440                 445

Gly Val Ile Val Glu Gly Arg Lys Ile Glu His Gln Ser Thr Leu Ser
    450                 455                 460

Ala Asn Gln Val Val Ala Leu Gly Thr Thr Leu Phe Leu Leu Val Asp
465                 470                 475                 480

Tyr Ala Ala Pro Ser Asp Thr Val Met Ala Thr Ile Ser Ser Glu Asp
                485                 490                 495

Tyr Gly Leu Phe Gly Arg Pro Gln Ser Pro Glu Glu Ile Ala Ala Arg
            500                 505                 510

Ala Ala Glu Glu Glu Glu Lys Arg Lys Arg Ala Thr Leu Pro Thr
        515                 520                 525

Gly Ala Phe Ile Leu Thr Leu Phe Ile Gly Gly Leu Ala Leu Leu Phe
    530                 535                 540

Gly Ile Gly Thr Ala Ser Leu Phe His Thr Lys Glu Val Val Ser Ile
545                 550                 555                 560

Asp Gln Ile Asp Leu Ile His Asp Ile Glu His Val Ile Gln Gln Phe
                565                 570                 575

Pro Thr Val Arg Phe Thr Phe Asn Lys Asn Asn Gly Gln Leu Phe Leu
            580                 585                 590

Ile Gly His Val Arg Asn Ser Ile Asp Lys Ser Glu Leu Leu Tyr Lys
        595                 600                 605

Val Asp Ala Leu Ser Phe Val Lys Ser Val Asp Asn Val Ile Asp
    610                 615                 620

Asp Glu Ala Val Trp Gln Glu Met Asn Ile Leu Leu Ser Lys Asn Pro

```
                    625                 630                 635                 640
Glu Phe Lys Gly Ile Ser Met Gln Ser Pro Glu Pro Gly Ile Phe Val
                645                 650                 655

Ile Ser Gly Tyr Leu Lys Thr Glu Glu Gln Ala Ala Cys Leu Ala Asp
                660                 665                 670

Tyr Leu Asn Leu His Phe Asn Tyr Leu Ser Leu Leu Asp Asn Lys Val
                675                 680                 685

Ile Ile Glu Ser Gln Val Met Lys Ala Leu Ala Gly His Leu Val Gln
                690                 695                 700

Ser Gly Phe Ala Asn Val His Val Ser Phe Thr Asn Gly Glu Ala Val
705                 710                 715                 720

Leu Thr Gly Tyr Ile Asn Asn Lys Asp Ala Asp Lys Phe Arg Thr Val
                725                 730                 735

Val Gln Glu Leu Gln Asp Ile Ala Gly Ile Arg Ala Val Lys Asn Phe
                740                 745                 750

Val Val Leu Leu Pro Ala Glu Glu Gly Val Ile Asp Leu Asn Met Arg
                755                 760                 765

Tyr Pro Gly Arg Tyr Arg Val Thr Gly Phe Ser Lys Cys Gly Asp Ile
                770                 775                 780

Ser Ile Asn Val Val Asn Gly Arg Ile Leu Thr Arg Gly Asp Ile
785                 790                 795                 800

Leu Asp Gly Met Thr Val Thr Ser Ile Gln Ser His Cys Ile Phe Leu
                805                 810                 815

Glu Arg Glu Gly Leu Lys Tyr Lys Ile Glu Tyr Asn Lys
                820                 825

<210> SEQ ID NO 227
<211> LENGTH: 15
<212> TYPE: PRT
<213> ORGANISM: Chlamydia trachomatis

<400> SEQUENCE: 227

Val Ser Ser Gln Glu Gly Gln Thr Pro Ser Val Thr Gly Glu Lys
1               5                   10                  15

<210> SEQ ID NO 228
<211> LENGTH: 14
<212> TYPE: PRT
<213> ORGANISM: Chlamydia trachomatis

<400> SEQUENCE: 228

Gly Glu Val Leu Ala Pro Phe Asn Val Gln Asp Leu Phe Arg
1               5                   10

<210> SEQ ID NO 229
<211> LENGTH: 16
<212> TYPE: PRT
<213> ORGANISM: Chlamydia trachomatis

<400> SEQUENCE: 229

Ala Ser Val Thr Glu Glu Gly Ser Ser Gly Thr Ser Glu Glu Glu Lys
1               5                   10                  15

<210> SEQ ID NO 230
<211> LENGTH: 16
<212> TYPE: PRT
<213> ORGANISM: Chlamydia trachomatis

<400> SEQUENCE: 230

Glu Gly Glu Glu Asp Thr Ala Glu Ser Ala Ala Asn Glu Glu Pro Lys
```

-continued

```
1               5                   10                  15
```

<210> SEQ ID NO 231
<211> LENGTH: 16
<212> TYPE: PRT
<213> ORGANISM: Chlamydia trachomatis

<400> SEQUENCE: 231

```
Phe Asp Gln Gly Ile Phe Pro Ala Glu Ile Glu Asp Leu Ala Gln Lys
1               5                   10                  15
```

<210> SEQ ID NO 232
<211> LENGTH: 22
<212> TYPE: PRT
<213> ORGANISM: Chlamydia trachomatis

<400> SEQUENCE: 232

```
Thr Tyr Ile Val Gly Ser Asp Pro Gln Val Ala Asp Ile Val Leu Ser
1               5                   10                  15

Asp Met Ser Ile Ser Arg
            20
```

<210> SEQ ID NO 233
<211> LENGTH: 373
<212> TYPE: PRT
<213> ORGANISM: Chlamydia trachomatis

<400> SEQUENCE: 233

```
Met Ala Val Ala Ala Glu Pro Ser Ser Asn Trp Leu Lys Ala Arg Asp
1               5                   10                  15

Glu Leu Leu Ser Ser Leu Gln Glu Gln Lys Glu Gly Met Phe Ser Phe
            20                  25                  30

Pro Val Phe Pro Lys Gln Glu Cys Glu Gln Lys Leu Lys Asp Lys Phe
        35                  40                  45

His Met Glu Glu Val Glu Leu Ser Phe Glu Ser Arg Gly Leu Leu Ser
    50                  55                  60

Val Ala Ala Ala Val Gln Glu Tyr Gly Glu His Ile Leu Leu Gln Pro
65                  70                  75                  80

Phe Leu Ala Asn Pro Phe Glu Ser Arg Glu Phe Tyr Ile Val Ser Ser
                85                  90                  95

Glu Glu Asp Leu Gln Ala Leu Ile Arg Thr Ile Phe Asn Asp Ser Ser
            100                 105                 110

Leu Ala Ser Tyr Phe Tyr Glu Lys Asp Arg Leu Leu Gly Phe His Tyr
        115                 120                 125

Tyr Phe Val Ala Glu Ile Cys Lys Leu Leu Gln Glu Ser Pro Trp Ile
    130                 135                 140

Pro Ser Met Ser Val Lys Val Thr Gly Asp Val Ala Phe Ser Ala Arg
145                 150                 155                 160

Ala Leu Glu Gly Glu Tyr His Val Ile Gln Val Ser Cys Arg Leu Asp
                165                 170                 175

Gly Ser Cys Ile Arg Phe Ser Ile Leu Val Pro Glu Thr Thr Ala Gln
            180                 185                 190

Ser Ala Cys Arg Phe Leu Glu Glu Lys Asp Gln Ala Phe Asp Met Gln
        195                 200                 205

Lys Val Asp Leu Gln Thr Pro Ile Thr Leu Ala Val Glu Val Gly Phe
    210                 215                 220

Cys Gln Ile Ser Glu Glu Asp Trp His Gln Val Val Pro Gly Ser Phe
225                 230                 235                 240
```

```
Ile Leu Leu Asp Ala Cys Leu Tyr Asp Pro Asp Thr Gly Asp Ala Gly
                245                 250                 255

Ala Phe Leu Ser Ile Gln Arg Thr Arg Phe Phe Gly Gly Arg Phe Leu
            260                 265                 270

Asp Lys Gln Ser Gly Ala Phe Lys Ile Thr Gly Leu Gln Glu Met Gln
        275                 280                 285

Pro Glu Asp Ala Pro Glu Pro Ser Glu Gly Gly Pro Ala Thr Pro
    290                 295                 300

Leu Pro Ser Ala Thr Lys Ile Val Ala Glu Val Ala Arg Tyr Ser Leu
305                 310                 315                 320

Ser Val Gly Glu Phe Leu Lys Leu Gly Pro Gly Ser Val Leu Gln Phe
                325                 330                 335

Asp Gly Val His Pro Thr Leu Gly Val Asp Ile Ile Leu Asn Gly Ala
            340                 345                 350

Lys Val Gly Arg Gly Asn Ile Ile Ala Leu Gln Asp Val Leu Gly Ile
        355                 360                 365

Arg Val Leu Glu Val
    370

<210> SEQ ID NO 234
<211> LENGTH: 16
<212> TYPE: PRT
<213> ORGANISM: Chlamydia trachomatis

<400> SEQUENCE: 234

Glu Phe Tyr Ile Val Ser Ser Glu Glu Asp Leu Gln Ala Leu Ile Arg
1               5                   10                  15

<210> SEQ ID NO 235
<211> LENGTH: 245
<212> TYPE: PRT
<213> ORGANISM: Chlamydia trachomatis

<400> SEQUENCE: 235

Met Met Lys Lys Arg Val Lys Arg Val Leu Phe Lys Ile Ser Gly Glu
1               5                   10                  15

Ala Leu Ser Asp Gly Asp Ser Ser Asn Arg Ile Ser Glu Glu Arg Leu
            20                  25                  30

Ser Arg Leu Ile Ala Glu Leu Lys Val Val Arg Asn Ala Asp Val Glu
        35                  40                  45

Val Ala Leu Val Ile Gly Gly Gly Asn Ile Leu Arg Gly Leu Ser Gln
    50                  55                  60

Ser Gln Ser Leu Gln Ile Asn Arg Val Ser Ala Asp Gln Met Gly Met
65                  70                  75                  80

Leu Ala Thr Leu Ile Asn Gly Met Ala Leu Ala Asp Ala Leu Lys Thr
                85                  90                  95

Glu Asp Val Pro Asn Leu Leu Thr Ser Thr Leu Ser Cys Pro Gln Leu
            100                 105                 110

Ala Glu Leu Tyr Asn Pro Gln Lys Ala Ser Asp Ala Leu Ser Gln Gly
        115                 120                 125

Lys Val Val Ile Cys Thr Met Gly Ala Gly Ala Pro Tyr Leu Thr Thr
    130                 135                 140

Asp Thr Gly Ala Ala Leu Arg Ala Cys Glu Leu Lys Val Asp Val Leu
145                 150                 155                 160

Leu Lys Ala Thr Met His Val Asp Gly Val Tyr Asp Gln Asp Pro Arg
                165                 170                 175

Glu Cys Ala Asp Ala Val Arg Tyr Asp His Ile Ser Tyr Arg Asp Phe
```

```
                180                 185                 190
Leu Ser Gln Gly Leu Gly Ala Ile Asp Pro Ala Ala Ile Ser Leu Cys
        195                 200                 205

Met Glu Ala Gly Ile Pro Ile Lys Met Phe Ser Phe Ala Arg His Ser
        210                 215                 220

Leu Glu Glu Ala Val Phe Asn Thr Val Gly Thr Val Ile Ser Ser Thr
225                 230                 235                 240

Glu Gly Gly Gln Leu
                245

<210> SEQ ID NO 236
<211> LENGTH: 14
<212> TYPE: PRT
<213> ORGANISM: Chlamydia trachomatis

<400> SEQUENCE: 236

Ile Ser Gly Glu Ala Leu Ser Asp Gly Asp Ser Ser Asn Arg
1               5                   10

<210> SEQ ID NO 237
<211> LENGTH: 12
<212> TYPE: PRT
<213> ORGANISM: Chlamydia trachomatis

<400> SEQUENCE: 237

Gly Leu Ser Gln Ser Gln Ser Leu Gln Ile Asn Arg
1               5                   10

<210> SEQ ID NO 238
<211> LENGTH: 114
<212> TYPE: PRT
<213> ORGANISM: Chlamydia trachomatis

<400> SEQUENCE: 238

Met Tyr Ser Arg Leu Phe Phe Ser Ile Leu Phe Phe Leu Gly Cys Cys
1               5                   10                  15

Pro Ala Leu Phe Ala Asp Thr Asp Ser Pro Gln Arg Ala Thr Phe Gly
            20                  25                  30

Gln Pro Ala Val Met Leu Gly Ile Ala Ile Val Phe Phe Tyr Phe Ile
        35                  40                  45

Leu Trp Arg Pro Glu Gln Lys Arg Arg Gln Ala Met Glu Lys Arg Lys
    50                  55                  60

Ser Glu Leu Ala Val Gly Asp Lys Val Thr Ala Met Gly Ile Val Gly
65                  70                  75                  80

Thr Ile Ala Glu Ile Arg Glu His Thr Val Ile Leu Asn Ile Ala Ser
                85                  90                  95

Gly Lys Ile Glu Ile Leu Lys Ala Ala Ile Ser Glu Ile Leu Lys Ala
            100                 105                 110

Glu Lys

<210> SEQ ID NO 239
<211> LENGTH: 14
<212> TYPE: PRT
<213> ORGANISM: Chlamydia trachomatis

<400> SEQUENCE: 239

Val Thr Ala Met Gly Ile Val Gly Thr Ile Ala Glu Ile Arg
1               5                   10
```

```
<210> SEQ ID NO 240
<211> LENGTH: 190
<212> TYPE: PRT
<213> ORGANISM: Chlamydia trachomatis

<400> SEQUENCE: 240

Met Val Arg Val Ser Thr Ser Glu Phe Arg Val Gly Leu Arg Val Lys
1               5                   10                  15

Ile Asp Gly Gln Pro Tyr Val Ile Leu Gln Asn Asp Phe Val Lys Pro
            20                  25                  30

Gly Lys Gly Gln Ala Phe Asn Arg Ile Lys Val Lys Asn Phe Leu Thr
        35                  40                  45

Gly Arg Val Ile Glu Lys Thr Phe Lys Ser Gly Glu Ser Ile Glu Thr
    50                  55                  60

Ala Asp Val Arg Glu Gln Gln Met Arg Leu Leu Tyr Thr Asp Gln Glu
65                  70                  75                  80

Gly Ala Thr Phe Met Asp Asp Glu Thr Phe Glu Gln Glu Leu Ile Phe
                85                  90                  95

Trp Asp Lys Leu Glu Asn Val Arg Gln Trp Leu Leu Glu Asp Thr Ile
            100                 105                 110

Tyr Thr Leu Val Leu Tyr Asn Gly Asp Val Ile Ser Val Glu Pro Pro
        115                 120                 125

Ile Phe Met Glu Leu Thr Ile Ala Glu Thr Ala Pro Gly Val Arg Gly
    130                 135                 140

Asp Thr Ala Ser Gly Arg Val Leu Lys Pro Ala Thr Thr Asn Thr Gly
145                 150                 155                 160

Ala Lys Ile Met Val Pro Ile Phe Ile Glu Glu Gly Glu Val Val Lys
                165                 170                 175

Val Asp Thr Arg Thr Gly Ser Tyr Glu Ser Arg Val Ser Lys
            180                 185                 190

<210> SEQ ID NO 241
<211> LENGTH: 14
<212> TYPE: PRT
<213> ORGANISM: Chlamydia trachomatis

<400> SEQUENCE: 241

Ile Met Val Pro Ile Phe Ile Glu Glu Gly Glu Val Val Lys
1               5                   10

<210> SEQ ID NO 242
<211> LENGTH: 562
<212> TYPE: PRT
<213> ORGANISM: Chlamydia trachomatis

<400> SEQUENCE: 242

Met Asp Ile Pro Glu Gln Gly Ser Asn Thr Pro Glu Val Glu Gln Ala
1               5                   10                  15

Ala Cys Cys Asn Gln Glu Ala Ala Glu Asn Asp Arg Ala Lys Asp Glu
            20                  25                  30

Leu Ser Ser Ser Glu Ile Ser Ala Glu Ala Val Gln Ser Cys Glu Ser
        35                  40                  45

Met Glu Ala Phe Glu Gln Val Val Ala Glu Arg Ser Ser Ile Glu Glu
    50                  55                  60

Lys Ile Leu Phe Ala Leu Glu Gln Met Gly Val Leu Leu Lys Gly Ala
65                  70                  75                  80

Asp Gln Asn Ser Asp Leu Lys Leu Phe Trp Asn Val Arg Lys Phe Cys
                85                  90                  95
```

-continued

```
Leu Pro Leu Phe Gln Gln Leu Glu Asp Pro Val Gln Arg Ala Asn Leu
            100                 105                 110
Trp Gly Cys Tyr Thr Glu Leu Thr Arg Glu Gly Arg His Ile Lys Thr
        115                 120                 125
Leu Gln Asp Glu Glu Gly Ala Phe Leu Val Gly Gln Ile Glu Leu Ala
    130                 135                 140
Ile Ser Cys Leu Glu Ser Gly Val Gln Gly Phe Phe Ser Lys Thr Glu
145                 150                 155                 160
Lys Glu Glu Ile Ser Glu Glu Asp Arg Ala Ala Leu Glu Ile Pro Ser
                165                 170                 175
Leu Ser Ala His Lys Asp Phe Tyr Leu Ser Thr His Ala Asp Leu Arg
            180                 185                 190
Trp Leu Gly Ser Phe Ser Ser Gln Ile Ile Asn Leu Arg Lys Glu Leu
        195                 200                 205
Met Asn Ile Ser Met Arg Met Arg Leu Lys Ser Gln Phe Phe Gln Lys
    210                 215                 220
Leu Ser Val Leu Gly Asn Lys Val Phe Pro Arg Arg Lys Glu Leu Thr
225                 230                 235                 240
Glu Lys Val Ser Glu Leu Phe Ala Gln Asp Val Glu Ala Phe Val Glu
                245                 250                 255
Arg Tyr Phe Ser Arg Ala Ser Arg Glu Ser Leu Lys Lys Ser Val Phe
            260                 265                 270
Phe Leu Arg Lys Glu Ile Lys Arg Leu Gln Gln Ala Lys Tyr Leu
        275                 280                 285
Ser Ile Ser Ser Gly Val Phe Ser Ser Thr Arg Leu Gly Leu Ser Gln
    290                 295                 300
Cys Trp Asp Gln Leu Lys Gly Leu Glu Lys Glu Ile Arg Gln Glu Gln
305                 310                 315                 320
Ser Arg Leu Ala Ala Thr Ser Ala Glu Asn Met Lys Glu Val Gln Gly
                325                 330                 335
Arg Leu Asp Gln Val Glu Val Leu Gln Glu Asn Glu Glu Val His
            340                 345                 350
Lys Ile Arg Lys Glu Ile Glu Ala Ile Ser Lys His Ile Arg Gly Ile
        355                 360                 365
Ser Leu Val His Asp Asp Val Val Leu Leu Lys Gly Arg Ile Gln Thr
    370                 375                 380
Leu Leu Gly Glu Val Arg Glu Arg Glu Ala Val Ile Glu Lys Glu Met
385                 390                 395                 400
Lys Glu Leu Gln Ala Lys Ala Glu Arg Ala Arg Ala Glu Ala Ile Gln
                405                 410                 415
Ala Leu Glu Asn Glu Val Gln Ser Phe Cys Asp Gln Cys Asn Glu Gly
            420                 425                 430
Asp Leu Pro Glu Gly Ala Lys Glu Arg Cys Gln Glu Leu Lys Glu Ala
        435                 440                 445
Val Gln Lys Met Ala Tyr Leu Pro Tyr Ala Lys Lys Val Ala Leu Asp
    450                 455                 460
Asn Gln Ile Asn Ala Ala Gln Arg Ser Val Leu Ala Arg Leu Glu Glu
465                 470                 475                 480
Gln Met Leu Ala Cys Pro Asp Ala Lys Glu Lys Val Leu Asn Met Arg
                485                 490                 495
Gln Val Leu Glu Gln Arg Met Leu Arg Arg Lys Glu Leu Lys Ala Lys
            500                 505                 510
Phe Glu Cys Asp Lys Lys Leu Leu Gly Gly Ser Gly Leu Asp Phe Asp
        515                 520                 525
```

-continued

```
Arg Ala Leu Gln Tyr Ser Ala Met Val Glu Glu Asp Arg Lys Ala Leu
        530                 535                 540

Glu Glu Leu Asp Ala Ala Ile Ile Glu Leu Lys Arg Gln Ile Gln Gln
545                 550                 555                 560

Phe Val

<210> SEQ ID NO 243
<211> LENGTH: 12
<212> TYPE: PRT
<213> ORGANISM: Chlamydia trachomatis

<400> SEQUENCE: 243

Val Ala Leu Asp Asn Gln Ile Asn Ala Ala Gln Arg
1               5                   10

<210> SEQ ID NO 244
<211> LENGTH: 150
<212> TYPE: PRT
<213> ORGANISM: Chlamydia trachomatis

<400> SEQUENCE: 244

Met Met Lys Thr Lys His Glu Tyr Ser Phe Gly Val Ile Pro Ile Arg
1               5                   10                  15

Phe Phe Gly Thr Pro Asp Arg Ser Thr Leu Lys Ala Cys Phe Val Cys
                20                  25                  30

His Thr Asp Gly Lys His Trp Gly Phe Pro Lys Gly His Ala Glu Glu
            35                  40                  45

Lys Glu Gly Pro Gln Glu Ala Ala Glu Arg Glu Leu Val Glu Glu Thr
        50                  55                  60

Gly Leu Gly Ile Val Asn Phe Phe Pro Lys Ile Phe Val Glu Asn Tyr
65                  70                  75                  80

Ser Phe Asn Asp Lys Glu Glu Ile Phe Val Arg Lys Glu Val Thr Tyr
                85                  90                  95

Phe Leu Ala Glu Val Lys Gly Glu Val His Ala Asp Pro Asp Glu Ile
                100                 105                 110

Cys Asp Val Gln Trp Leu Ser Phe Gln Glu Gly Leu Arg Leu Leu Ile
            115                 120                 125

Phe Pro Glu Ile Arg Asn Ile Val Thr Glu Ala Asp Lys Phe Val Gln
        130                 135                 140

Ser Tyr Leu Phe Ala Ser
145                 150

<210> SEQ ID NO 245
<211> LENGTH: 16
<212> TYPE: PRT
<213> ORGANISM: Chlamydia trachomatis

<400> SEQUENCE: 245

Glu Leu Val Glu Glu Thr Gly Leu Gly Ile Val Asn Phe Phe Pro Lys
1               5                   10                  15

<210> SEQ ID NO 246
<211> LENGTH: 346
<212> TYPE: PRT
<213> ORGANISM: Chlamydia trachomatis
```

```
<400> SEQUENCE: 246

Met Lys Tyr Ser Leu Gln Ile Glu Asp Leu His Ile Glu Gly Tyr Glu
1               5                   10                  15

Gln Val Leu Lys Val Thr Cys Glu Ser Val Gln Leu Ala Val Ile
            20                  25                  30

Ala Ile His Gln Thr Lys Val Gly Pro Ala Leu Gly Gly Ile Arg Ala
        35                  40                  45

Phe Pro Tyr Leu Gln Phe Glu Asp Gly Leu Gln Asp Ala Leu Arg Leu
    50                  55                  60

Ser Lys Ala Met Thr Tyr Lys Ala Leu Leu Ser Ser Thr Glu Thr Gly
65                  70                  75                  80

Gly Gly Lys Ser Val Ile Phe Leu Pro Lys Gly Met Thr Ser Pro Thr
                85                  90                  95

Glu Gly Met Leu Arg Ala Phe Gly Gln Ala Val Asn Ser Leu Gln Gly
            100                 105                 110

Lys Tyr Ile Ala Ala Glu Asp Val Gly Val Ser Val Gln Asp Val Met
        115                 120                 125

Ile Ile Arg Glu Glu Thr Pro Tyr Val Cys Gly Leu Val Thr Val Ser
130                 135                 140

Gly Asp Pro Ser Ile Tyr Thr Ala His Gly Val Phe Leu Cys Ile Gln
145                 150                 155                 160

Glu Thr Ala Asp Tyr Leu Cys Lys Thr Asp Ile Arg Gly Lys Arg Val
                165                 170                 175

Ala Val Gln Gly Leu Gly Ala Val Gly Arg Lys Leu Val His Glu Leu
            180                 185                 190

Phe Phe Ala Gly Ala Glu Leu Ile Val Tyr Asp Thr Arg Lys Asp Leu
        195                 200                 205

Leu Asp Glu Val Val Thr Leu Tyr Gly Ala Gln Val Asp Glu Asn Ile
210                 215                 220

Ile Ser Ala Asp Cys Asp Ile Leu Cys Pro Cys Ala Leu Gly Gly Ile
225                 230                 235                 240

Ile Asn Ser Met Ser Ile Asp Gln Leu Arg Cys Arg Ala Ile Val Gly
                245                 250                 255

Ala Thr Asn Asn Gln Leu Glu Asn Pro Ala Ile Gly Arg Glu Leu Val
            260                 265                 270

Ala Arg Gly Ile Leu Tyr Ala Pro Asp Tyr Leu Ala Asn Ala Gly Gly
        275                 280                 285

Leu Leu Asn Val Ala Gly Ser Val Gly Arg Ala Tyr Ser Pro Lys Glu
    290                 295                 300

Val Leu Ser Lys Val Glu Gly Leu Pro Lys Ile Leu Arg Lys Leu Tyr
305                 310                 315                 320

Glu Gln Gly Ala Lys Glu Asn Arg Asp Thr Gly Thr Leu Ala Asp Ala
                325                 330                 335

Ile Val Glu Glu Arg Leu Ala Val Tyr Ala
            340                 345

<210> SEQ ID NO 247
<211> LENGTH: 17
<212> TYPE: PRT
<213> ORGANISM: Chlamydia trachomatis

<400> SEQUENCE: 247

Ala Ile Val Gly Ala Thr Asn Asn Gln Leu Glu Asn Pro Ala Ile Gly
1               5                   10                  15

Arg
```

-continued

<210> SEQ ID NO 248
<211> LENGTH: 64
<212> TYPE: PRT
<213> ORGANISM: Chlamydia trachomatis

<400> SEQUENCE: 248

Met Pro Lys Met Lys Ser Asn Lys Ser Val Ala Ala Arg Phe Lys Leu
1               5                   10                  15

Thr Gly Ser Gly Gln Leu Lys Arg Thr Arg Pro Gly Lys Arg His Lys
            20                  25                  30

Leu Ser Lys Arg Ser Ser Gln Gln Lys Arg Asn Leu Ser Lys Gln Pro
        35                  40                  45

Leu Val Asp Gln Gly Gln Val Gly Met Tyr Lys Arg Met Met Leu Val
    50                  55                  60

<210> SEQ ID NO 249
<211> LENGTH: 13
<212> TYPE: PRT
<213> ORGANISM: Chlamydia trachomatis

<400> SEQUENCE: 249

Gln Pro Leu Val Asp Gln Gly Gln Val Gly Met Tyr Lys
1               5                   10

<210> SEQ ID NO 250
<211> LENGTH: 913
<212> TYPE: PRT
<213> ORGANISM: Chlamydia trachomatis

<400> SEQUENCE: 250

Met Ala Lys Asp Lys Lys Thr Asn Pro Glu Ser Lys Lys Ser Phe Pro
1               5                   10                  15

Thr Ala Phe Phe Phe Leu Leu Phe Gly Val Ile Phe Gly Val Val Thr
            20                  25                  30

Val Gln Asn Phe Ser Ala Lys Lys Ala Ser Val Gly Phe Ser His
            35                  40                  45

Gln Leu Glu His Leu Val Asn Leu Lys Leu Leu Ile Pro Glu Glu Ser
    50                  55                  60

Arg Lys Thr Ala Leu Asn Asp Asn Leu Val Ser Phe Ser Gly Arg Phe
65              70                  75                  80

Arg Glu Val Val Pro Ala Glu Gly Gln Val Arg Tyr Gln Tyr Leu Asp
                85                  90                  95

Leu Ile Glu Arg Lys His Gln Ile Asp Phe Glu Leu Glu Glu Ala Ser
            100                 105                 110

Lys Ser Leu Thr Val Leu Ser Lys Glu Val Arg Asn Ala Ile Thr Trp
        115                 120                 125

Phe Ser Ala Ile Ser Gly Met Pro Ile Pro Glu Ala Gly Tyr Thr Ile
    130                 135                 140

Ser Pro Arg Thr Asp Val Gly Leu Ser Val Leu Glu Pro Leu Val Val
145                 150                 155                 160

Tyr Gly Pro Val Asp Ala Gln Ile Val Asn Leu Ala Ala Leu Glu Asn
                165                 170                 175

Arg Val Arg Ser Leu Pro Lys Ser Thr Glu Ser Leu Arg Val Phe Gly
            180                 185                 190

Ser Asp Leu Tyr Ala Leu Ile Gly Lys Tyr Leu Ser Pro Ala Leu Gly
        195                 200                 205

Ile Gly Ser Glu Ser Leu Lys Lys Glu Ile Lys Asp Leu His Gln Gln
    210                 215                 220

```
Val Glu Asn Ser Leu Thr Gln Val Ile Glu Gly Asp Gln Ala Val Ala
225                 230                 235                 240

Leu Tyr Lys Thr Val Leu Glu Thr Leu His Arg Ile Ser Leu Ala Leu
            245                 250                 255

Val Ser Pro Glu Glu Gly Thr Arg Phe His Gln Leu Arg Ser Val Arg
        260                 265                 270

Leu Tyr Arg Glu Asp Phe Asn Arg Cys Val Lys Leu Leu Gly Glu Ser
    275                 280                 285

Asp Glu Thr Gln Val Gln Leu Asp Lys Leu Arg Gly Glu Leu Val Gln
290                 295                 300

Ala Val Trp Tyr Phe Asn Asn Gln Glu Leu Ser Ser Arg Ala Leu Glu
305                 310                 315                 320

Lys Gln Asp Pro Glu Val Phe Ser Arg Trp Phe Glu Gly Ala Lys Gln
                325                 330                 335

Glu Trp Ala Ala Phe Ser Ser Asn Lys Ser Leu Ser Phe Arg Ala Pro
            340                 345                 350

Asp Gln Pro Arg Asn Leu Val Leu Glu Lys Thr Phe Arg Ser Glu Glu
        355                 360                 365

Pro Thr Pro His Tyr Ser Gly Tyr Leu Phe Thr Phe Met Pro Ile Ile
    370                 375                 380

Leu Val Leu Leu Phe Ile Tyr Phe Ile Phe Ser Arg Gln Val Lys Gly
385                 390                 395                 400

Met Asn Gly Ser Ala Met Ser Phe Gly Lys Ser Pro Ala Arg Leu Leu
                405                 410                 415

Ala Lys Gly Gln Asn Lys Val Thr Phe Ala Asp Val Ala Gly Ile Glu
            420                 425                 430

Glu Ala Lys Glu Glu Leu Val Glu Ile Val Asp Phe Leu Lys Asn Pro
        435                 440                 445

Thr Lys Phe Thr Ser Leu Gly Gly Arg Ile Pro Lys Gly Ile Leu Leu
    450                 455                 460

Ile Gly Ala Pro Gly Thr Gly Lys Thr Leu Ile Ala Lys Ala Val Ala
465                 470                 475                 480

Gly Glu Ala Asp Arg Pro Phe Phe Ser Ile Ala Gly Ser Asp Phe Val
                485                 490                 495

Glu Met Phe Val Gly Val Gly Ala Ser Arg Ile Arg Asp Met Phe Glu
            500                 505                 510

Gln Ala Lys Arg Asn Ala Pro Cys Ile Ile Phe Ile Asp Glu Ile Asp
        515                 520                 525

Ala Val Gly Arg His Arg Gly Ala Gly Ile Gly Gly Gly His Asp Glu
    530                 535                 540

Arg Glu Gln Thr Leu Asn Gln Leu Leu Val Glu Met Asp Gly Phe Gly
545                 550                 555                 560

Thr Asn Glu Gly Val Ile Leu Met Ala Ala Thr Asn Arg Pro Asp Val
                565                 570                 575

Leu Asp Lys Ala Leu Leu Arg Pro Gly Arg Phe Asp Arg Arg Val Val
            580                 585                 590

Val Asn Leu Pro Asp Ile Lys Gly Arg Phe Glu Ile Leu Ala Val His
        595                 600                 605

Ala Lys Arg Ile Lys Leu Asp Pro Thr Val Asp Leu Met Ala Val Ala
    610                 615                 620

Arg Ser Thr Pro Gly Ala Ser Gly Ala Asp Leu Glu Asn Leu Leu Asn
625                 630                 635                 640

Glu Ala Ala Leu Leu Ala Ala Arg Lys Asp Arg Thr Ala Val Thr Ala
                645                 650                 655
```

```
Val Glu Val Ala Glu Ala Arg Asp Lys Val Leu Tyr Gly Lys Glu Arg
            660                 665                 670

Arg Ser Leu Glu Met Asp Ala Gln Glu Lys Lys Thr Thr Ala Tyr His
        675                 680                 685

Glu Ser Gly His Ala Ile Val Gly Leu Cys Val Glu His Ser Asp Pro
    690                 695                 700

Val Asp Lys Val Thr Ile Ile Pro Arg Gly Leu Ser Leu Gly Ala Thr
705                 710                 715                 720

His Phe Leu Pro Glu Lys Asn Lys Leu Ser Tyr Trp Lys Lys Glu Leu
                725                 730                 735

Tyr Asp Gln Leu Ala Val Leu Met Gly Gly Arg Ala Ala Glu Gln Ile
            740                 745                 750

Phe Leu Gly Asp Val Ser Ser Gly Ala Gln Gln Asp Ile Ala Gln Ala
        755                 760                 765

Thr Lys Ile Val Arg Ser Met Ile Cys Glu Trp Gly Met Ser Asp His
    770                 775                 780

Leu Gly Thr Val Ala Tyr Asp Glu Arg Ser Glu Ala Ala Pro Thr Gly
785                 790                 795                 800

Tyr Gly Ser Cys His Glu Lys Asn Tyr Ser Glu Glu Thr Ala Lys Ala
                805                 810                 815

Ile Asp Asn Glu Leu Lys Thr Leu Leu Asp Ala Ala Tyr Gln Arg Ala
            820                 825                 830

Leu Asp Ile Ile Asn Ser His Lys Glu Glu Leu Glu Leu Met Thr Gln
        835                 840                 845

Met Leu Ile Glu Phe Glu Thr Leu Asp Ser Lys Asp Val Lys Glu Ile
    850                 855                 860

Met Asp His Ser Trp Asp Ala Asp Lys Lys Gln Ala Arg Met Lys Glu
865                 870                 875                 880

Glu Gly Met Leu Tyr Lys Lys Ile Ser Glu Asp Leu Pro Pro Pro
                885                 890                 895

Pro Gln Glu Asn Val Gln Asp Gly Thr Ser Leu Lys Phe Asn Thr Ser
            900                 905                 910

Thr

<210> SEQ ID NO 251
<211> LENGTH: 13
<212> TYPE: PRT
<213> ORGANISM: Chlamydia trachomatis

<400> SEQUENCE: 251

Ile Ser Leu Ala Leu Val Ser Pro Glu Glu Gly Thr Arg
1               5                   10

<210> SEQ ID NO 252
<211> LENGTH: 7
<212> TYPE: PRT
<213> ORGANISM: Chlamydia trachomatis

<400> SEQUENCE: 252

Ser Thr Pro Gly Ala Ser Gly
1               5

<210> SEQ ID NO 253
<211> LENGTH: 695
<212> TYPE: PRT
<213> ORGANISM: Chlamydia trachomatis
```

-continued

<400> SEQUENCE: 253

```
Met Ala Phe Glu Thr Phe Ser Val Ala Leu Asp Lys Asp Lys Thr Leu
1               5                   10                  15

Ile Phe Glu Thr Gly Lys Ile Ala Arg Gln Ala Ser Gly Ala Val Leu
            20                  25                  30

Val Lys Met Asn Glu Thr Trp Val Phe Ser Ser Ala Cys Ala Ala Ser
        35                  40                  45

Leu Ser Glu Ala Val Asp Phe Leu Pro Phe Arg Val Asp Tyr Gln Glu
    50                  55                  60

Lys Phe Ser Ser Ala Gly Arg Thr Ser Gly Gly Phe Leu Lys Arg Glu
65                  70                  75                  80

Gly Arg Pro Ser Glu Arg Glu Ile Leu Val Ser Arg Leu Met Asp Arg
                85                  90                  95

Ser Leu Arg Pro Ser Phe Pro Asn Arg Leu Met Gln Asp Ile Gln Val
            100                 105                 110

Leu Ser Tyr Val Trp Ser Tyr Asp Gly Lys Thr Leu Pro Asp Pro Leu
        115                 120                 125

Ala Ile Cys Gly Ala Ser Ala Ala Leu Ala Ile Ser Glu Val Pro Gln
    130                 135                 140

Asn Cys Ile Val Ala Gly Val Arg Val Gly Leu Val Gly Gly Lys Trp
145                 150                 155                 160

Val Ile Asn Pro Thr Arg Asp Glu Leu Ser Ala Ser Lys Leu Asp Leu
                165                 170                 175

Val Met Ala Gly Thr Ala Ser Ala Val Leu Met Ile Glu Gly His Cys
            180                 185                 190

Asp Phe Leu Thr Glu Glu Gln Val Leu Glu Ala Ile Ala Phe Gly Gln
        195                 200                 205

Thr Tyr Ile Ala Lys Ile Cys Asp Ala Ile Glu Ala Trp Gln Lys Ala
    210                 215                 220

Ile Gly Lys Gln Lys Asn Phe Ser Ala Val Leu Asp Met Pro Glu Asp
225                 230                 235                 240

Val Gln Asn Val Val Ser Asp Phe Ile Arg Glu Lys Phe Glu Lys Ala
                245                 250                 255

Leu Ser Phe Arg Asp Lys Glu Ala Leu Glu Gln Ala Ser Lys Glu Leu
            260                 265                 270

Glu Glu Ser Val Ile Ala Asn Leu Val Gln Glu Asn Ser Asp Phe
        275                 280                 285

Ser Leu Leu Asn Val Lys Ala Ala Phe Lys Thr Ala Lys Ser Asn Gln
    290                 295                 300

Met Arg Ala Leu Ile Gln Asp Leu Gly Ile Arg Val Asp Gly Arg Thr
305                 310                 315                 320

Thr Thr Glu Ile Arg Pro Ile Ser Ile Glu Thr Pro Phe Leu Pro Arg
                325                 330                 335

Thr His Gly Ser Cys Leu Phe Thr Arg Gly Glu Thr Gln Ser Met Ala
            340                 345                 350

Val Cys Thr Leu Gly Gly Glu Asn Met Ala Gln Arg Phe Glu Asp Leu
        355                 360                 365

Asn Gly Asp Gly Ala Ala Arg Phe Tyr Leu Gln Tyr Phe Phe Pro Pro
    370                 375                 380

Phe Ser Val Gly Glu Val Gly Arg Ile Gly Ser Pro Gly Arg Arg Glu
385                 390                 395                 400

Ile Gly His Gly Lys Leu Ala Glu Lys Ala Leu Ser His Val Leu Pro
                405                 410                 415
```

```
Glu Thr Ser Arg Phe Pro Tyr Ile Ile Arg Leu Glu Ser Asn Ile Thr
            420                 425                 430

Glu Ser Asn Gly Ser Ser Met Ala Ser Val Cys Gly Gly Cys Leu
            435                 440                 445

Ala Leu Met Asp Ala Gly Val Pro Ile Lys Ala Pro Val Ala Gly Ile
450                 455                 460

Ala Met Gly Leu Ile Leu Asp Arg Asp Gln Ala Ile Ile Leu Ser Asp
465                 470                 475                 480

Ile Ser Gly Ile Glu Asp His Leu Gly Asp Met Asp Phe Lys Val Ala
                485                 490                 495

Gly Thr Ala Lys Gly Ile Thr Ala Phe Gln Met Asp Ile Lys Ile Glu
            500                 505                 510

Gly Ile Thr His Lys Ile Met Glu Gln Ala Leu Ala Gln Ala Lys Gln
            515                 520                 525

Gly Arg Ser His Ile Leu Asn Leu Met Thr Gln Val Leu Ala Ser Pro
            530                 535                 540

Lys Gly Thr Val Ser Lys Tyr Ala Pro Arg Ile Glu Thr Met Gln Ile
545                 550                 555                 560

Asn Thr Ser Lys Ile Ala Thr Val Ile Gly Pro Gly Lys Gln Ile
                565                 570                 575

Arg Gln Ile Ile Glu Arg Ser Gly Ala Gln Val Asp Ile Asn Asp Asp
            580                 585                 590

Gly Val Ile Asn Ile Ala Ala Ser Thr Gln Glu Ser Ile Asn Lys Ala
            595                 600                 605

Lys Glu Leu Ile Glu Gly Leu Thr Gly Glu Val Glu Val Gly Lys Val
            610                 615                 620

Tyr Asn Gly Arg Val Thr Ser Ile Ala Thr Phe Gly Val Phe Val Glu
625                 630                 635                 640

Val Leu Pro Gly Lys Glu Gly Leu Cys His Ile Ser Glu Leu Ser Lys
                645                 650                 655

Gln Lys Val Asp Asn Ile Ser Asp Phe Val Lys Glu Gly Asp Lys Leu
            660                 665                 670

Ala Val Lys Leu Leu Ser Ile Asn Glu Lys Gly Gln Leu Lys Leu Ser
            675                 680                 685

His Lys Ala Thr Leu Glu Asp
            690                 695

<210> SEQ ID NO 254
<211> LENGTH: 10
<212> TYPE: PRT
<213> ORGANISM: Chlamydia trachomatis

<400> SEQUENCE: 254

Asp Lys Glu Ala Leu Glu Gln Ala Ser Lys
1               5                   10

<210> SEQ ID NO 255
<211> LENGTH: 24
<212> TYPE: PRT
<213> ORGANISM: Chlamydia trachomatis

<400> SEQUENCE: 255

Glu Leu Glu Glu Ser Val Ile Ala Asn Leu Val Gln Glu Glu Asn Ser
1               5                   10                  15

Asp Phe Ser Leu Leu Asn Val Lys
            20
```

<210> SEQ ID NO 256
<211> LENGTH: 867
<212> TYPE: PRT
<213> ORGANISM: Chlamydia trachomatis

<400> SEQUENCE: 256

| Met | Glu | Lys | Phe | Ser | Asp | Ala | Val | Ser | Glu | Ala | Leu | Glu | Lys | Ala | Phe |
|---|---|---|---|---|---|---|---|---|---|---|---|---|---|---|---|
| 1 | | | | 5 | | | | | 10 | | | | | 15 | |
| Glu | Leu | Ala | Lys | Asn | Ser | Lys | His | Ser | Tyr | Val | Thr | Glu | Asn | His | Leu |
| | | | 20 | | | | | 25 | | | | | 30 | | |
| Leu | Lys | Ser | Leu | Leu | Gln | Asn | Pro | Gly | Ser | Leu | Phe | Cys | Leu | Val | Ile |
| | | | 35 | | | | | 40 | | | | | 45 | | |
| Lys | Asp | Val | His | Gly | Asn | Leu | Gly | Leu | Leu | Thr | Ser | Ala | Val | Asp | Asp |
| | 50 | | | | | 55 | | | | | 60 | | | | |
| Ala | Leu | Arg | Arg | Glu | Pro | Thr | Val | Val | Glu | Gly | Thr | Ala | Val | Ala | Ser |
| 65 | | | | | 70 | | | | | 75 | | | | | 80 |
| Pro | Ser | Pro | Ser | Leu | Gln | Gln | Leu | Leu | Leu | Asn | Ala | His | Gln | Glu | Ala |
| | | | | 85 | | | | | 90 | | | | | 95 | |
| Arg | Ser | Met | Gly | Asp | Glu | Tyr | Leu | Ser | Gly | Asp | His | Leu | Leu | Leu | Ala |
| | | | 100 | | | | | 105 | | | | | 110 | | |
| Phe | Trp | Arg | Ser | Thr | Lys | Glu | Pro | Phe | Ala | Ser | Trp | Arg | Lys | Thr | Val |
| | | | 115 | | | | | 120 | | | | | 125 | | |
| Lys | Thr | Thr | Ser | Glu | Ala | Leu | Lys | Glu | Leu | Ile | Thr | Lys | Leu | Arg | Gln |
| | 130 | | | | | 135 | | | | | 140 | | | | |
| Gly | Ser | Arg | Met | Asp | Ser | Pro | Ser | Ala | Glu | Glu | Asn | Leu | Lys | Gly | Leu |
| 145 | | | | | 150 | | | | | 155 | | | | | 160 |
| Glu | Lys | Tyr | Cys | Lys | Asn | Leu | Thr | Val | Leu | Ala | Arg | Glu | Gly | Lys | Leu |
| | | | | 165 | | | | | 170 | | | | | 175 | |
| Asp | Pro | Val | Ile | Gly | Arg | Asp | Glu | Glu | Ile | Arg | Arg | Thr | Ile | Gln | Val |
| | | | 180 | | | | | 185 | | | | | 190 | | |
| Leu | Ser | Arg | Arg | Thr | Lys | Asn | Asn | Pro | Met | Leu | Ile | Gly | Glu | Pro | Gly |
| | | | 195 | | | | | 200 | | | | | 205 | | |
| Val | Gly | Lys | Thr | Ala | Ile | Ala | Glu | Gly | Leu | Ala | Leu | Arg | Ile | Val | Gln |
| | 210 | | | | | 215 | | | | | 220 | | | | |
| Gly | Asp | Val | Pro | Glu | Ser | Leu | Lys | Glu | Lys | His | Leu | Tyr | Val | Leu | Asp |
| 225 | | | | | 230 | | | | | 235 | | | | | 240 |
| Met | Gly | Ala | Leu | Ile | Ala | Gly | Ala | Lys | Tyr | Arg | Gly | Glu | Phe | Glu | Glu |
| | | | | 245 | | | | | 250 | | | | | 255 | |
| Arg | Leu | Lys | Ser | Val | Leu | Lys | Gly | Val | Glu | Ala | Ser | Glu | Gly | Glu | Cys |
| | | | 260 | | | | | 265 | | | | | 270 | | |
| Ile | Leu | Phe | Ile | Asp | Glu | Val | His | Thr | Leu | Val | Gly | Ala | Gly | Ala | Thr |
| | | | 275 | | | | | 280 | | | | | 285 | | |
| Asp | Gly | Ala | Met | Asp | Ala | Ala | Asn | Leu | Leu | Lys | Pro | Ala | Leu | Ala | Arg |
| | 290 | | | | | 295 | | | | | 300 | | | | |
| Gly | Thr | Leu | His | Cys | Ile | Gly | Ala | Thr | Thr | Leu | Asn | Glu | Tyr | Gln | Lys |
| 305 | | | | | 310 | | | | | 315 | | | | | 320 |
| Tyr | Ile | Glu | Lys | Asp | Ala | Ala | Leu | Glu | Arg | Arg | Phe | Gln | Pro | Ile | Phe |
| | | | | 325 | | | | | 330 | | | | | 335 | |
| Val | Thr | Glu | Pro | Ser | Leu | Glu | Asp | Ala | Val | Phe | Ile | Leu | Arg | Gly | Leu |
| | | | 340 | | | | | 345 | | | | | 350 | | |
| Arg | Glu | Lys | Tyr | Glu | Ile | Phe | His | Gly | Val | Arg | Ile | Thr | Glu | Gly | Ala |
| | | | 355 | | | | | 360 | | | | | 365 | | |
| Leu | Asn | Ala | Ala | Val | Val | Leu | Ser | Arg | Tyr | Ile | Thr | Asp | Arg | Phe |
| | 370 | | | | | 375 | | | | | 380 | | | | |

```
Leu Pro Asp Lys Ala Ile Asp Leu Ile Asp Glu Ala Ala Ser Leu Ile
385                 390                 395                 400

Arg Met Gln Ile Gly Ser Leu Pro Leu Pro Ile Asp Glu Lys Glu Arg
            405                 410                 415

Glu Leu Ser Ala Leu Ile Val Lys Gln Glu Ala Ile Lys Arg Glu Gln
            420                 425                 430

Ala Pro Ala Tyr Gln Glu Glu Ala Glu Asp Met Gln Lys Ala Ile Asp
            435                 440                 445

Arg Val Lys Glu Glu Leu Ala Ala Leu Arg Leu Arg Trp Asp Glu Glu
        450                 455                 460

Lys Gly Leu Ile Thr Gly Leu Lys Glu Lys Lys Asn Ala Leu Glu Asn
465                 470                 475                 480

Leu Lys Phe Ala Glu Glu Ala Glu Arg Thr Ala Asp Tyr Asn Arg
                485                 490                 495

Val Ala Glu Leu Arg Tyr Ser Leu Ile Pro Ser Leu Glu Glu Glu Ile
            500                 505                 510

His Leu Ala Glu Glu Ala Leu Asn Gln Arg Asp Gly Arg Leu Leu Gln
            515                 520                 525

Glu Glu Val Asp Glu Arg Leu Ile Ala Gln Val Ala Asn Trp Thr
        530                 535                 540

Gly Ile Pro Val Gln Lys Met Leu Glu Gly Glu Ser Glu Lys Leu Leu
545                 550                 555                 560

Val Leu Glu Glu Ser Leu Glu Arg Val Val Gly Gln Pro Phe Ala
                565                 570                 575

Ile Ala Ala Val Ser Asp Ser Ile Arg Ala Ala Arg Val Gly Leu Ser
            580                 585                 590

Asp Pro Gln Arg Pro Leu Gly Val Phe Leu Phe Leu Gly Pro Thr Gly
        595                 600                 605

Val Gly Lys Thr Glu Leu Ala Lys Ala Leu Ala Glu Leu Leu Phe Asn
    610                 615                 620

Lys Glu Glu Ala Met Ile Arg Phe Asp Met Thr Glu Tyr Met Glu Lys
625                 630                 635                 640

His Ser Val Ser Lys Leu Ile Gly Ser Pro Pro Gly Tyr Val Gly Tyr
                645                 650                 655

Glu Glu Gly Gly Ser Leu Ser Glu Ala Leu Arg Arg Arg Pro Tyr Ser
            660                 665                 670

Val Val Leu Phe Asp Glu Ile Glu Lys Ala Asp Lys Glu Val Phe Asn
        675                 680                 685

Ile Leu Leu Gln Ile Phe Asp Asp Gly Ile Leu Thr Asp Ser Lys Lys
            690                 695                 700

Arg Lys Val Asn Cys Lys Asn Ala Leu Phe Ile Met Thr Ser Asn Ile
705                 710                 715                 720

Gly Ser Gln Glu Leu Ala Asp Tyr Cys Thr Lys Lys Gly Thr Ile Val
                725                 730                 735

Asp Lys Glu Ala Val Leu Ser Val Val Ala Pro Ala Leu Lys Asn Tyr
            740                 745                 750

Phe Ser Pro Glu Phe Ile Asn Arg Ile Asp Ile Leu Pro Phe Val
        755                 760                 765

Pro Leu Thr Thr Glu Asp Ile Val Lys Ile Val Gly Ile Gln Met Asn
    770                 775                 780

Arg Val Ala Leu Arg Leu Leu Glu Arg Lys Ile Ser Leu Thr Trp Asp
785                 790                 795                 800

Asp Ser Leu Val Leu Phe Leu Ser Glu Gln Gly Tyr Asp Ser Ala Phe
                805                 810                 815
```

```
Gly Ala Arg Pro Leu Lys Arg Leu Ile Gln Gln Lys Val Val Thr Met
            820                 825                 830

Leu Ser Lys Ala Leu Leu Lys Gly Asp Ile Lys Pro Gly Met Ala Val
        835                 840                 845

Glu Leu Thr Met Ala Lys Asp Val Val Val Phe Lys Ile Lys Thr Asn
850                 855                 860

Pro Ala Val
865

<210> SEQ ID NO 257
<211> LENGTH: 26
<212> TYPE: PRT
<213> ORGANISM: Chlamydia trachomatis

<400> SEQUENCE: 257

Ala Gln Thr Ala Ser Glu Thr Ser Gly Ser Ser Ser Ser Ser Gly Asn
1               5                   10                  15

Asp Ser Val Ser Ser Pro Ser Ser Arg
            20                  25

<210> SEQ ID NO 258
<211> LENGTH: 16
<212> TYPE: PRT
<213> ORGANISM: Chlamydia trachomatis

<400> SEQUENCE: 258

Ser Asp Gln Gln Ile Ser Leu Leu Val Leu Pro Thr Asp Ser Ser Lys
1               5                   10                  15

<210> SEQ ID NO 259
<211> LENGTH: 17
<212> TYPE: PRT
<213> ORGANISM: Chlamydia trachomatis

<400> SEQUENCE: 259

Val Gly Gly Gly Ser Ala Gly Thr Ala Gly Thr Val Gln Met Asn Val
1               5                   10                  15

Lys

<210> SEQ ID NO 260
<211> LENGTH: 20
<212> TYPE: DNA
<213> ORGANISM: Artificial Sequence
<220> FEATURE:
<223> OTHER INFORMATION: Immunostimulatory oligonucleotide

<400> SEQUENCE: 260
tccatgacgt tcctgacgtt                                           20

<210> SEQ ID NO 261
<211> LENGTH: 9
<212> TYPE: PRT
<213> ORGANISM: Chlamydia trachomatis

<400> SEQUENCE: 261

Asn Val Leu Leu Met Val Ser Gln Gly
1               5

<210> SEQ ID NO 262
<211> LENGTH: 9
<212> TYPE: PRT
<213> ORGANISM: Chlamydia trachomatis
```

```
<400> SEQUENCE: 262

Asp Val Val Arg Phe Ile Val Leu Lys
1               5

<210> SEQ ID NO 263
<211> LENGTH: 9
<212> TYPE: PRT
<213> ORGANISM: Chlamydia trachomatis

<400> SEQUENCE: 263

Leu Ser His Arg Ser Gly Glu Thr Glu
1               5

<210> SEQ ID NO 264
<211> LENGTH: 9
<212> TYPE: PRT
<213> ORGANISM: Chlamydia trachomatis

<400> SEQUENCE: 264

Ser Gly Glu Thr Glu Asp Thr Thr Ile
1               5

<210> SEQ ID NO 265
<211> LENGTH: 9
<212> TYPE: PRT
<213> ORGANISM: Chlamydia trachomatis

<400> SEQUENCE: 265

Ile Ala Asp Leu Ala Val Ala Phe Asn
1               5

<210> SEQ ID NO 266
<211> LENGTH: 9
<212> TYPE: PRT
<213> ORGANISM: Chlamydia trachomatis

<400> SEQUENCE: 266

Leu Ala Val Ala Phe Asn Thr Gly Gln
1               5

<210> SEQ ID NO 267
<211> LENGTH: 9
<212> TYPE: PRT
<213> ORGANISM: Chlamydia trachomatis

<400> SEQUENCE: 267

Val Ala Phe Asn Thr Gly Gln Ile Lys
1               5

<210> SEQ ID NO 268
<211> LENGTH: 9
<212> TYPE: PRT
<213> ORGANISM: Chlamydia trachomatis

<400> SEQUENCE: 268

Phe Asn Thr Gly Gln Ile Lys Thr Gly
1               5

<210> SEQ ID NO 269
<211> LENGTH: 9
<212> TYPE: PRT
<213> ORGANISM: Chlamydia trachomatis
```

```
<400> SEQUENCE: 269

Thr Gly Gln Ile Lys Thr Gly Ser Leu
1               5

<210> SEQ ID NO 270
<211> LENGTH: 9
<212> TYPE: PRT
<213> ORGANISM: Chlamydia trachomatis

<400> SEQUENCE: 270

Tyr Asn Arg Leu Met Ala Ile Glu Glu
1               5

<210> SEQ ID NO 271
<211> LENGTH: 9
<212> TYPE: PRT
<213> ORGANISM: Chlamydia trachomatis

<400> SEQUENCE: 271

Arg Ile Ala Lys Tyr Asn Arg Leu Met
1               5

<210> SEQ ID NO 272
<211> LENGTH: 9
<212> TYPE: PRT
<213> ORGANISM: Chlamydia trachomatis

<400> SEQUENCE: 272

Leu Tyr Glu Lys Leu Leu Glu Gly Ser
1               5

<210> SEQ ID NO 273
<211> LENGTH: 9
<212> TYPE: PRT
<213> ORGANISM: Chlamydia trachomatis

<400> SEQUENCE: 273

Gly Ser Met Leu Gly Gly Gln Met Ala
1               5

<210> SEQ ID NO 274
<211> LENGTH: 9
<212> TYPE: PRT
<213> ORGANISM: Chlamydia trachomatis

<400> SEQUENCE: 274

Gly Gly Gly Val Gly Val Ala Thr Lys
1               5

<210> SEQ ID NO 275
<211> LENGTH: 9
<212> TYPE: PRT
<213> ORGANISM: Chlamydia trachomatis

<400> SEQUENCE: 275

Gly Gly Val Gly Val Ala Thr Lys Glu
1               5
```